(12) United States Patent
Wild et al.

(10) Patent No.: US 7,892,564 B2
(45) Date of Patent: *Feb. 22, 2011

(54) RECOMBINANT INFECTIOUS LARYNGOTRACHEITIS VIRUS AND USES THEREOF

(75) Inventors: Martha A. Wild, San Diego, CA (US); Mark D. Cochran, Carlsbad, CA (US)

(73) Assignee: Schering-Plough Animal Health Corp., Summit, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 12/363,134

(22) Filed: Jan. 30, 2009

(65) Prior Publication Data

US 2009/0191239 A1 Jul. 30, 2009

Related U.S. Application Data

(60) Division of application No. 12/047,787, filed on Mar. 13, 2008, now Pat. No. 7,501,491, which is a division of application No. 11/342,171, filed on Jan. 27, 2006, now Pat. No. 7,364,893, which is a division of application No. 10/836,383, filed on Apr. 30, 2004, now Pat. No. 7,045,598, which is a division of application No. 09/994,064, filed on Nov. 6, 2001, now Pat. No. 6,984,728, which is a division of application No. 08/468,190, filed on Jun. 6, 1995, now abandoned, which is a continuation of application No. 08/410,121, filed on Mar. 23, 1995, now abandoned, which is a continuation-in-part of application No. 08/126,597, filed on Sep. 24, 1993, now abandoned.

(51) Int. Cl.
*A61K 39/245* (2006.01)

(52) U.S. Cl. ............... 424/229.1; 435/320.1; 435/435; 435/235.1

(58) Field of Classification Search ................ None
See application file for complete search history.

(56) References Cited

U.S. PATENT DOCUMENTS

| | | | |
|---|---|---|---|
| 4,769,331 A | 9/1988 | Roizman et al. | |
| 4,877,737 A | 10/1989 | Shih | |
| 4,980,162 A | 12/1990 | Honda et al. | |
| 5,047,237 A | 9/1991 | Cochran et al. | |
| 5,182,210 A | 1/1993 | Binns et al. | |
| 5,187,087 A | 2/1993 | Sondermeijer et al. | |
| 5,223,424 A | 6/1993 | Cochran et al. | |
| 5,231,023 A | 7/1993 | Morgan | |
| 5,240,703 A | 8/1993 | Cochran et al. | |
| 5,252,717 A | 10/1993 | Velicer | |
| 5,279,965 A | 1/1994 | Keeler, Jr. | |
| 5,310,671 A | 5/1994 | Binns et al. | |
| 5,869,312 A | 2/1999 | Cochran et al. | |
| 5,906,821 A | 5/1999 | Griffin et al. | |
| 5,928,648 A | 7/1999 | Cochran | |
| 5,965,138 A | 10/1999 | Cochran et al. | |
| 6,033,904 A | 3/2000 | Cochran et al. | |
| 6,123,949 A | 9/2000 | Cochran et al. | |
| 6,221,361 B1 | 4/2001 | Cochran et al. | |
| 6,328,975 B1 | 12/2001 | Cochran et al. | |
| 6,497,882 B1 | 12/2002 | Cochran et al. | |
| 7,364,893 B2 * | 4/2008 | Wild et al. | ............... 435/235.1 |

FOREIGN PATENT DOCUMENTS

| | | |
|---|---|---|
| CA | 2050850 | 3/1992 |
| EP | 0 431 668 B1 | 6/1991 |
| EP | 0 473 210 B1 | 3/1992 |
| EP | 0 477 056 A1 | 3/1992 |
| WO | WO 87/04429 | 7/1987 |
| WO | WO 88/07088 | 9/1988 |
| WO | WO 89/01040 | 2/1989 |
| WO | WO 90/02802 | 3/1990 |
| WO | WO 90/02803 | 3/1990 |
| WO | WO 91/02053 | 2/1991 |
| WO | WO 92/01040 | 1/1992 |
| WO | WO 92/02053 | 2/1992 |
| WO | WO 92/02802 | 2/1992 |
| WO | WO 92/03547 | 3/1992 |
| WO | WO 92/03554 | 3/1992 |
| WO | WO 93/14194 | 7/1993 |
| WO | WO 95/03070 | 2/1995 |

OTHER PUBLICATIONS

Fuchs et al., "In vitro and in vivo relevance of infectious laryngotracheitis virus gJ proteins that are expressed from spliced and nonspliced mRNAs," Journal of Virology, vol. 79 No. 2, pp. 705-716 (Jan. 2005).*

(Continued)

*Primary Examiner*—Ali R. Salimi

(57) ABSTRACT

The present invention provides a recombinant, attenuated infectious laryngotracheitis virus comprising the infectious laryngotracheitis viral genome which contains a deletion in the glycoprotein gG gene. This attenuated virus is useful as a vaccine against infectious laryngotracheitis virus.

The present invention also provides a recombinant, attenuated infectious laryngotracheitis virus comprising the infectious laryngotracheitis viral genome which contains a deletion in the US2 gene, UL47-like gene, ORF4 gene or glycoprotein g60 gene.

The present invention also provides a method for distinguishing chickens or other poultry vaccinated with a recombinant infectious laryngotracheitis virus which produces no glycoprotein gG from those infected with a naturally-occurring infectious laryngotracheitis virus.

9 Claims, 35 Drawing Sheets

OTHER PUBLICATIONS

Andreasen, J., et al., "Studies of infectious laryngotracheitis vaccines: Immunity in broilers," *Avian Diseases* 33:516-23 (1989).

Andreasen, J., et al., "Studies of infectious laryngotracheitis vaccines: Immunity in vayers," *Avian Diseases* 33:524-30 (1989).

Andreasen, J., et al., "Differentiation of vaccine strains and Georgia field isolates of infectious laryngotracheitis virus by their restriction endonuclease fragment patterns," *Avian Diseases* 34:646-56(1990).

Colle, et al., "Open reading frames encoding a protein kinase, homolog of glycoprotein gX of pseudorabies virus and a novel glycoprotein map within the unique short segment of equine herpesvirus type 1.," *Virology* 188:545-57 (1992).

Davison, S., et al., "Laryngotracheitis in chickens: The length of the preinfectious periods," *Avian Diseases* 33:18-23 (1989).

Davison, S., et al., "Laryngotracheitis in chickens: Infections studies and the efficacy of a tissue-culture vaccine in chicks less than four weeks old," *Avian Diseases* 33:24-29 (1989).

Finkelstein, A., et al., "Live recombinant vaccines for poultry," *Trends in Biotechnology* 7:273-77 (1989).

Griffin, A., et al., "The neucleotide sequence of the glycoprotein gB gene of infectious laryntracheitis virus: Analysis and evolutionary relationship to the homologous gene from other herpesviruses," *J. Gen. Virology* 72:393-98 (1991).

Griffin, A., et al., The complete sequence of the capsid p40 gene from infectious laryngotracheitis virus, *Nucleic Acids Res.* 18:3664 (1991).

Griffin, A., et al., "Identification of 21 genes of infectious laryngotracheitis virus random sequencing of genomic DNA," *J. Gen. Virology* 70:3085-89 (1989).

Griffin, A., "Analysis of the nucleotide sequence of DNA from the region of the thymidine kinase gene of infectious laryngotracheitis virus: Potential evolutionary relationships between the herpesvirus subfamilies," *J. Gen. Virology* 71:841-50 (1990).

Griffin, H., "Attenuated Salmonella as live vaccines: Prospects for multivalent poultry vaccines," *World's Poultry Science Journal* 47:131-40 (1991).

Guo, et al., "Construction of recombinant avian infectious laryngotracheitis virus express the β-galactosidase gene and DNA sequencing of the insertion region," *Virology* 202:771-81 (1994).

Guy, J., et al., "Virulence of infectious laryngotracheitis viruses: Comparison of modified-live vaccine viruses and North Carolina field isolates," *Avian Diseases* 34:106-13 (1990).

Guy, J., et al., "Increased virulence of modified-live infections laryngotracheitis vaccine virus following bird-to-bird passage," *Avian Diseases* 35:348-55 (1991).

Guy, J., et al., "Restriction endonuclease analysis of infections laryngotracheitis viruses: Comparison of modified-live vaccine and North Carolina field isolates," *Avian Diseases* 33:316-23 (1989).

Hanson, et al., Disease of Poultry, Ninth Edition, M.S. Hofstad Ed., pp. 485-495, Iowa State University Press (1991).

Hughes, et al., "Latency and reactivation of infectious laryngotracheitis vaccine virus," *Arch. Virol.* 121:213-18 (1991).

Izuchi, et al., "Studies on a live virus vaccine against infectious laryngotracheitis of chickens, I. Biological properties of attenuated strain C7," *Avian Diseases* 27:918-926. (1983).

Johnson, M., et al., "Gallid herpesvirus 1 (infectious laryngotracheitis virus): Cloning and physical maps of the SA-2 strain," *Arch Virol.* 119:181-198 (1991).

Johnson, et al., "Sequence characteristics of a gene in infections laryngotracheitis virus homologous to glycoprotein D of herpes simplex virus," *The Journal of Sequencing and Mapping* 5:191-94 (1995).

Johnson, et al., "Nucleotide sequence of infectious laryngotracheitis virus (gallid herpesvirus 1) ICP4 gene," *Virus Research* 35:193-204 (1995).

Johnson, et al., "Molecular evolution of infectious laryngotracheitis virus (ILTV; gallid herpesvirus 1): An ancient example of the Alphaherpesviridae?" *Veterinary Microbiology* 46:221-31 (1995).

Keam, L., et al., "Detection of infectious laryngotracheitis virus in chickens using a non-radioactive DNA probe," *Avian Diseases* 35:257-262 (1991).

Keeler, C., et al., "Identification of the thymidine kinase gene of infectious laryngotracheitis virus," *Avian Diseases* 35:920-929 (1991).

Key, D., et al., Abstract From the 65$^{th}$ Northeast Conference on Avian Disease, Jun. 9-11, University of Delaware, Newark, Delaware (1993).

Kingsley, et al., Abstract From the 65$^{th}$ Northeastern Conference on Avian Diseases, Jun. 9-11, University of Delaware, Newark, Delaware (1993).

Kongsuwan, K., et al., "Nucleotide sequence of the gene encoding infectious laryngotracheitis virus glycoprotein B," *Virology* 184:404-410 (1991).

Kongsuwan, K., et al., "Use of lambda gtII and monoclonal antibodies to map the gene for the 60,000 Dalton glycoprotein of infectious laryngotracheitis virus," *Virus Genes* 7:297-303 (1993).

Kongsuwan, K., et al., "Identification on an infectious laryngotracheitis virus gene encoding an immunogenic protein with a predicted M(r) of 32 kilodaltons," *Virus Research* 29:125-140 (1993).

Kotiw, M., et al., "Differentiation of infectious laryngotracheitis virus strain using restriction endonucleases," *Avian Diseases* 26:718-731 (1982).

Kotiw, M., et al., "Differentiation between virulent and avirulent strains of infectious laryngotracheitis virus by DNA: DNA hybridization using a cloned DNA marker," *Vet. Microbiology* 11: 319-330 (1986).

Leib, D. et al., "Restriction endonuclease patterns of some European and American isolates of avian infectious laryngotracheitis virus," *Avian Diseases* 30:835-837 (1986).

Leib, D., et al., "Genome isomerism in two alphaherpesviruses: Herpesvirus Saimiri-1 (Herpesvirus tamarinus) and avian infectious laryngotracheitis virus," *Arch Virology* 93:287-294 (1987).

Nazerian, et al., "Protection against Marek's disease by fowlpox virus recombinant expressing the glycoprotein B of Marek's disease virus," *J. Virology* 66(3):1409-1413 (1992).

Petrovskis, et al., "DNA sequence of the gene for pseudorabies virus gp50, a glycoprotein gB gene by the polymerase chain reaction," *J. Virol.* 59(2):216-223 (1986).

Poulsen, D., et al., "Identification of the infectious laryngotracheitis virus glycoprotein gB gene by the polymerase chain reaction," *Virus Genes* 5:335-347 (1991).

Purves, et al., "Herpes simplex virus 1 protein kinase is encoded by open reading frame US3 which is not essential for virus growth in cell culture," *J. Virology* 61:2896-2901 (1987).

Prideaux, et al., "Infectious laryngotracheitis virus growth, DNA replication, and protein synthesis," *Arch. Virol.* 123:181-192 (1991).

Reilly, et al., "Cosmid library of the turkey herpesvirus genome constructed from nanogram quantities of viral DNA associated with an excess of cellular DNA," *Journal of Virological Methods* 41: 323-332 (1993).

Ross, L., et al., "Properties and evolutionary relationships of the Marek's disease virus homologues of protein kinase, glycoprotein I of herpes simplex virus," *J. Gen. Virology* 72:939-947 (1991).

Ross, L., et al., "DNA sequence and organization of genes in a 5.5 kbp EcoRI fragment mapping in the short unique segment of Marek's disease virus (strain RB1B)," *J. Gen. Virology* 72:949-954 (1991).

Saif, et al., AVMA 130$^{th}$ Annual Meeting, Jul. 17-21, Minneapolis, MN. (1993).

Sakaguchi, et al., "Sequence determination and genetic content of an 8.9-kb restriction fragment in the short unique region and the internal inverted repeat of Marek's disease virus type 1 DNA," *Virus Genes* 6(4):365-378 (1992).

Sanchez-Martinez, et al., "Evaluation of a test based on baculovirus expressed glycoprotein G for detection of herpes simplex virus type specific antibodies," *J. of Infectious Disease* 164:1196-1199 (1991).

Schnitzlein, W. et al., "Generation of thymidine kinase-deficient mutant of infectious laryngotracheitis virus," *Virology* 209:304-314 (1995).

Sharma, et al., "A plaque system for study of infectious laryngotracheitis virus in adult chicken kidney cultures," *Avian Diseases* 13:268-279 (1969).

Sheppard, et al., "Identification of an infectious laryngotracheitis virus equivalent to the herpes simplex virus type 2 major DNA binding protein (ICP8)," *Acta. Virol.* 34:443-448 (1990).

Shirley, et al., "Detection of DNA from infectious laryngotracheitis virus b colourimetric analysis of polymerase chain reactions," *J. Virological Methods* 30:251-260 (1990).

Van Zijl et al., "Regeneration of herpesviruses from molecularly cloned subgenomic fragments," *J. Virology* 62:2191-2195 (1988).

Wark, et al., "The development and evaluation of a cell vaccine against infectious laryngotracheitis virus," *Journal of Biological Standardization* 7:73-80 (1979).

Weber, et al., "Rapid identification of nonessential genes of herpes simplex virus type 1 by Tn5 mutagenesis," *Science* 236:576-579 (1987).

Wild et al., "A genomic map of infectious laryngotracheitis virus and the sequence and organization of genes present in the unique short and flanking regions," *Virus Genes* 12:107-116 (1996).

York, et al., "Immunogenic glycoproteins of infectious laryngotracheitis herpesvirus," *Virology* 161:340-347 (1990).

York, et al., "Humoral and cell-medicated immune responses to the glycoproteins of infections laryngotracheitis herpesvirus," *Arch. Viro.* 115:289-97 (1990).

Zelnik, et al., "The complete sequence and gene organization of the short unique region of herpesvirus of turkeys," *J. Gen. Virol.* 74:2151-62 (1993).

Altschul, et al., "Gapped BLAST and PSI-BLAST", *Nucleic Acids Res.* 25:3389-3402 (1997).

Barker et al. "Identification of three genes nonessential for growth in cell culture near the right terminus of the unique sequences of long component of herpes simplex virus 1", *Virology*. 177(2):684-91 (1990).

Cardona et al., "Characterization of a recombinant fowlpox virus expressing the native hexon of hemorrhagic enteritis virus," *Virus Genes*, col. 22 No. 3, pp. 353-361 (Jun. 2001).

Grose, C. "Glycoproteins of varicella-zoster virus and their herpes simplex virus homologs", *Rev Infect Dis.*, 13 Suppl 11:S960-3 (1991).

Jucker et al., "Characterization of the haemorrhagic enteritis virus genome and the sequence of the putative penton bases and core protein genes", *Journal of General Virology*, 77:469-479 (1996).

Kongsuwan et al., "Nucleotide sequence analysis of an infectious laryngotracheitis virus gene corresponding to the US3 of HSV-1 and a unique gene encoding a 67 kDa protein", *Archives of Virology*, 140:27-39; © Springer-Verlag, Austria (1995).

Mettenleiter et al., "Isolation of a viable herpesvirus (pseudorabies virus) mutant specifically lacking all four known nonessential glycoproteins", *Virology*, 179(1):498-503 (1990).

Mutalib, A., "Studies on Transmissibility of a tissue-culture-modified larynotracheitis virus", *Journal of Veterinary Diagnostic Investigation*, 4(4):412-415 (1992).

\* cited by examiner

FIGURE 1A

```
CCCGTGCCCC TAAAGGCCGC CGAGAAAGCT AAGTCCAAAT GTGACGTCGG 50
AGGTCTCGAC ATGGTCGCCA ACCCTCCAAA TGCTACCCGC CGGCCCACGC 100
AACGCGGGCT TTTATAAAGA TGGCGCGCGA GACAATAACA CTTACTCATC 150
CGCGTACGCG TTTATTATTG TCAATATTTG TGTGGTTATT ATTACTGCTA 200
CCGCCCTTGT TTCTGCAAGG CCCTCGCCGC GGCCCAGGCC ACTATTCCGG 250
CAGCGGCCGC CGACGCGGCG AGCGTCGCCG CTAACGTCGG CGCCGCGGGG 300
AGCGGGGTTT CTTCGACTTA AATAGACTCC CGAGAAAAAA TTTTGGCTGC 350
CGTTCGCCAT CATCCGAGTC GGAAACACAG TATGCGGCCG AGTTAGGTTT 400
TACTTTTAAA AACTTTACCG TGCTGTACGG CCAGGGCGTT CTCAGGCTCG 450
AAGGGGCAAG AGTTGTCCAG ACTGATGGGT GACTCAGAGA CAGCGTTGTC 500
TTGTCTCCGT TTACCAAAAA TATTTCCACT CCTCTCTCAA AATTTTTACC 550
TCCGGTTTCG GTAATTAGGA AAGTTTTTGG CGCAGGGAGG TTTAAAGCTG 600
CCATGCATAT GTCAGCGGTA CCCAGCACCC ACAAATGGAA CTCTTTTGCG 650
GCATACGCGC CAGATGACAA ATGGTAAAAC CCTGCGTCCA AGCCGCTCCA 700
CTCGGGACTT ACTCCAGGCG GGTCGCCCCC CTCACCGAAC CGAATCACGG 750
GTCTGCACAT CCTGGGAAGG GAAAACAGCT CCCCGGAAAC TTCGTACAGA 800
GATGCCGGGC GCACGATTAC CGATAATGTA CTCGGACGAT CGTAACTCGC 850
CATAGTTTTC ACTGCGTGAA CCAATTCTTT CCATCCAGAA TCCGAGAGCT 900
CAAATCTAGA ATTAGGTAGT TTGTAGTGCG AATCGACCGC AGAAACTATA 950
GTCACTTTTA CAGGCGCCAT CGCCGCTCAG ACTCCACCCC GCTATGATGT 1000
CAGAAATATA ACGCTCTTAT TCTAGCAGAG TCAGGCCAAT ATATACAGCT 1050
TAGAGAAGAT GCGGTTTCGG CGCATCTGTT CACGCTCTAG GGCAGAAAAA 1100
CGAAGAAGAA CAACCGAGAA TCCGCTTACC TCAAAACGCG TTTGCGTATT 1150
GGATAGTTTC TCACGGACAA TGTCATTGCG CCCCTATGCA GAAATTTTGC 1200
CGACCGCGGA AGGCGTCGAG CGCCTCGCCG AACTTGTTAG TGTGACAATG 1250
ACAGAACGCG CGGAACCTGT GACAGAGAAT ACAGCTGTAA ACAGTATCCC 1300
CCCGGCTAAC GAGAACGGGC AGAACTTCGC ATATGCAGGC GATGGGCCCT 1350
CGACTACTGA AAAAGTTGAC GGCTCGCATA CAGACTTCGA TGAAGCATCG 1400
AGCGACTACG CCGGCCCTGT CCCGCTCGCG CAAACTAGAT TGAAGCATTC 1450
GGATGAATTT CTTCAGCACT TCCGAGTTTT AGACGATTTG GTGGAGGGGG 1500
CTTACGGGTT TATCTGCGGC GTCCGTCGCT ACACCGAGGA AGAGCAACGT 1550
CGAAGAGGGG TTAACAGTAC TAACCAGGGG AAATCAAAAT GTAAGCGCCT 1600
GATAGCTAAA TATGTGAAAA ATGGAACAAG GGCGGCCTCT CAGCTGGAAA 1650
ATGAAATTTT GGTTCTCGGG CGCCTAAATC ACGAGAATGT TCTCAAGATC 1700
CAGGAAATCC TTCGGTACCC GGATAATACG TACATGTTAA CGCAGAGGTA 1750
```

FIGURE 1B

```
TCAGTTCGAC TTGTACAGCT ACATGTACGA TGAAGCGTTC GACTGGAAAG 1800
ACAGTCCAAT GCTTAAACAG ACTAGACGCA TCATGAAGCA GCTCATGTCA 1850
GCGGTCTCGT ATATCCATTC AAAGAAACTG ATTCACAGGG ACATCAAACT 1900
CGAAAATATT TTCTTAAACT GCGACGGCAA GACAGTGCTG GGCGACTTTG 1950
GAACTGTCAC GCCTTTTGAA AATGAGCGGG AGCCCTTCGA ATATGGATGG 2000
GTGGGGACCG TGGCTACTAA CTCTCCCGAG ATACTCGCCA GGGATTCGTA 2050
CTGTGAAATT ACAGACATTT GGAGCTGCGG AGTAGTATTG CTGGAAATGG 2100
TAAGCCATGA ATTTTGCCCG ATCGGCGATG GCGGGGGAAA TCCGCACCAG 2150
CAATTGCTGA AAGTTATCGA CTCTCTCTCA GTTTGTGATG AAGAGTTCCC 2200
AGACCCCCCG TGTAATCTGT ACAATTATTT GCATTATGCG AGCATCGATC 2250
GCGCCGGACA TACGGTCCCG TCGCTCATAC GGAACCTCCA CCTTCCGGCG 2300
GATGTGGAAT ACCCTCTAGT TAAAATGCTT ACTTTTGACT GGCGTTTGAG 2350
ACCCAGCGCG GCCGAAGTAT TGGCAATGCC ACTGTTTTCG GCTGAAGAGG 2400
AACGGACCAT AACAATTATT CATGGAAAAC ATAAACCCAT CCGACCCGAA 2450
ATCCGTGCGC GGGTGCCACG GTCCATGAGT GAAGGTTAAT AATAAAGGAC 2500
GGAGATAGAG AACTGAAGCG TCAGATTTTT TTAAAAAAAT AAATGATCGA 2550
GAACTTATGA TTTGTCTTTC TTGAATGACC TTGCCCCATC GATTAACGAA 2600
AAGACCTTTC GCGCGTCGAT TCTGCTCGGT CTTTGTGATA CATTATAGTG 2650
AGACTAAACT CGACCGATAT AACAAGACAA TGTTACTCTA TAGACCGGAC 2700
TCAACCATGC GGCATAGCGG AGGCGACGCA AATCACAGAG GGATAAGGCC 2750
GAGGCGGAAA TCTATTGGAG CGTTTAGCGC GCGCGAAAAG ACTGGAAAAC 2800
GAAATGCGCT GACGGAAAGC AGCTCCTCCT CCGACATGCT AGATCCGTTT 2850
TCCACGGATA AGGAATTTGG CGGTAAGTGG ACGGTAGACG GACCTGCCGA 2900
CATTACTGCC GAGGTCCTTT CTCAGGCATG GGACGTTCTC CAATTAGTGA 2950
AGCATGAAGA TGCGGAGGAG GAGAGAGTGA CTTATGAGTC CAAACCGACC 3000
CCGATACAGC CGTTCAATGC CTGGCCGGAC GGGCCGAGTT GGAACGCGCA 3050
GGATTTTACT CGAGCGCCAA TAGTTTATCC CTCTGCGGAG GTATTGGACG 3100
CAGAGGCGTT GAAAGTAGGG GCATTCGTTA GCCGAGTTTT ACAATGTGTA 3150
CCGTTCACGC GATCAAAGAA AAGCGTTACG GTGCGGGATG CGCAGTCGTT 3200
TTTGGGGGAC TCGTTCTGGA GAATAATGCA GAACGTTTAC ACGGTTTGCT 3250
TACGACAGCA CATAACTCGA CTCAGGCACC CTTCCAGCAA AAGCATTGTT 3300
AACTGCAACG ACCCTCTATG GTACGCCTAC GCGAATCAAT TTCACTGGAG 3350
AGGAATGCGC GTGCCGTCGC TTAAATTAGC CTCTCCCCCG GAGGAGAATA 3400
TTCAACACGG CCCAATGGCC GCCGTTTTTA GAAACGCGGG GGCTGGTCTG 3450
TTCCTGTGGC CTGCCATGCG CGCAGCCTTT GAAGAGCGCG ACAAGCGACT 3500
```

FIGURE 1C

```
GTTAAGAGCA TGCCTGTCTT CACTCGATAT CATGGACGCA GCCGTCCTCG 3550
CGTCGTTTCC ATTTTACTGG CGCGGCGTCC AAGACACCTC GCGCTTCGAG 3600
CCTGCGCTGG GCTGTTTGTC AGAGTACTTT GCACTAGTGG TGTTACTGGC 3650
CGAGACGGTC TTAGCGACCA TGTTCGACCA CGCACTGGTA TTCATGAGGG 3700
CGCTGGCAGA CGGCAATTTC GATGACTATG ACGAAACTAG ATATATAGAC 3750
CCCGTTAAAA ACGAGTACCT GAACGGAGCC GAGGGTACTC TGTTACGGGG 3800
CATAGTGGCC TCCAACACCG CTCTGGCGGT GGTTTGCGCA AACACCTATT 3850
CGACGATAAG AAAACTCCCG TCCGTGGCAA CTAGCGCGTG CAATGTTGCC 3900
TACAGGACCG AAACGCTGAA AGCGAGGCGC CCTGGCATGA GCGACATATA 3950
CCGGATATTA CAAAAAGAGT TTTTCTTTTA CATTGCGTGG CTCCAGAGGG 4000
TTGCAACACA CGCAAATTTC TGTTTAAACA TTCTGAAGAG AAGCGTGGAT 4050
ACGGGCCCCC GCCATTTTTG TTCAGGGCCA GCTCGGAGAA GCGGCTGCAG 4100
CAGTTAAATA AAATGCTCTG CCCCCTTCTC GTGCCGATTC AATATGAAGA 4150
CTTTTCGAAG GCCATGGGGT CTGAGCTCAA GAGGGAAAAG TTAGAGACAT 4200
TCGTTAAAGC TATTTCCAGC GACAGGGACC CGAGGGGGTC CTTAAGATTT 4250
CTCATTTCGG ACCATGCAAG GGAAATTATT GCAGACGGAG TACGGTTTAA 4300
GCCGGTGATA GACGAGCCGG TTCGGGCTTC AGTTGCGCTG AGTACCGCTG 4350
CCGCTGGGAA AGTGAAAGCG CGACGCTTAA CCTCAGTTCG CGCGCCCGTA 4400
CCGCCCGCAG GCGCCGTTTC CGCGCGCCGG AAATCGGAAA TATGATAAAA 4450
ATGCTTGGCA TTTGCGGGCG AAGAGGCGTG ATCTGAAGGG CTCCACAATG 4500
ACGTAACTGA GCTACGCATC CCTATAAAGT GTACSCGCTG ACCGCTAGCC 4550
CATACAGTGT TACAGGAGGG GAGAGAGACA ACTTCAGCTC GAAGTCTGAA 4600
GAGACATCAT GAGCGGCTTC AGTAACATAG GATCGATTGC CACCGTTTCC 4650
CTAGTATGCT CGCTTTTGTG CGCATCTGTA TTAGGGGCGC CGGTACTGGA 4700
CGGGCTCGAG TCGAGCCCTT TCCCGTTCGG GGGCAAAATT ATAGCCCAGG 4750
CGTGCAACCG CACCACGATT GAGGTGACGG TCCCGTGGAG CGACTACTCT 4800
GGTCGCACCG AAGGAGTGTC AGTCGAGGTG AAATGGTTCT ACGGGAATAG 4850
TAATCCCGAA AGCTTCGTGT TCGGGGTGGA TAGCGAAACG GGCAGTGGAC 4900
ACGAGGACCT GTCTACGTGC TGGGCTCTAA TCCATAATCT GAACGCGTCT 4950
GTGTGCAGGG CGTCTGACGC CGGGATACCT GATTTCGACA AGCAGTGCGA 5000
AAAAGTGCAG AGAAGACTGC GCTCCGGGGT GGAACTTGGT AGTTACGTGT 5050
CTGGCAATGG ATCCCTGGTG CTGTACCCAG GGATGTACGA TGCCGGCATC 5100
TACGCCTACC AGCTCTCAGT GGGTGGGAAG GGATATACCG GGTCTGTTTA 5150
TCTAGACGTC GGACCAAACC CCGGATGCCA CGACCAGTAT GGGTACACCT 5200
ATTACAGCCT GGCCGACGAG GCGTCAGACT TATCATCTTA TGACGTAGCC 5250
```

FIGURE 1D

```
TCGCCCGAAC TCGACGGTCC TATGGAGGAA GATTATTCCA ATTGTCTAGA 5300
CATGCCCCCG CTACGCCCAT GGACAACCGT TTGTTCGCAT GACGTCGAGG 5350
AGCAGGAAAA CGCCACGGAC GAGCTTTACC TATGGGACGA GGAATGCGCC 5400
GGTCCGCTGG ACGAGTACGT CGACGAAAGG TCAGAGACGA TGCCCAGGAT 5450
GGTTGTCTTT TCACCGCCCT CTACGCTCCA GCAGTAGCCA CCCGAGAGTG 5500
TTTTTTGTGA GCGCCCACGC AACATACCTA ACTGCTTCAT TTCTGATCAA 5550
TTATTGCGTA TTGAATAAAT AAACAGTACA AAAGCATCAG GTGTGGTTTG 5600
CGTGTCTGTG CTAAACCATG GCGTGTGCGG GTGAAACCGT AAATTACGTG 5650
ATAATAAATA GCATAGGAGT TGGCGTGCAG CGTATTTCGC CGAGAGATGG 5700
GGACAATGTT AGTGTTGCGC CTTTTCCTAC TTGCAGTAGC GGACGCGGCG 5750
TTGCCGACCG GCAGATTCTG CCGAGTTTGG AAGGTGCCTC CGGGAGGAAC 5800
CATCCAAGAG AACCTGGCGG TGCTCGCGGA ATCGCCGGTC ACGGACACG 5850
CGACATATCC GCCGCCTGAA GGCGCCGTCA GCTTTCAGAT TTTTGCGGAC 5900
ACCCCTACTT TGCGCATTCG CTACGGGCCT ACGGAGGACG AACTTGCACT 5950
GGAGCGCGGG ACGTCCGCCT CAGACGCGGA CAACGTGACA TTTTCGCTGT 6000
CATATCGCCC GCGCCCAGAA ATTCACGGAG CATACTTCAC CATAGGGGTA 6050
TTCGCTACTG GCCAGAGCAC GGAAAGCAGC TATTCGGTCA TCAGTCGGGT 6100
CTTAGTTAAC GCCTCTCTGG AACGGTCCGT GCGCCTGGAA ACGCCGTGCG 6150
ATGAAAATTT TTTGCAGAAC GAGCCTACAT GGGGCTCGAA GCGTTGGTTA 6200
GGCCCCCCGT CGCCTTATGT GCGAGATAAC GATGTCGCCG TGTTGACAAA 6250
AGCGCAGTAC ATTGGGGAGT GCTACTCCAA CTCGGCGGCC CAGACGGGGC 6300
TCACGTCTCT CAACATGACC TTTTTCTATT CGCCTAAAAG AATAGTAAAC 6350
GTCACGTGGA CAACCGGCGG CCCCTCCCCC TCGCGCATAA CGGTATACTC 6400
GTCGCGGGAG AACGGGCAGC CCGTGTTGAG GAACGTTTCT GACGGGTTCT 6450
TGGTTAAGTA CACTCCCGAC ATTGACGGCC GGGCCATGAT AAACGTTATT 6500
GCCAATTATT CGCCGGCGGA CTCCGGCAGC GTCCTCGCGT TTACGGCCTT 6550
TAGGGAAGGA AAACTCCCAT CCGCGATTCA ACTGCACCGG ATAGATATGT 6600
CCGGGACTGA GCCGCCGGGG ACTGAAACGA CCTTCGACTG TCAAAAAATG 6650
ATAGAAACCC CGTACCGAGC GCTCGGGAGC AATGTTCCCA GGGACGACTC 6700
TATCCGTCCG GGGGCCACTC TGCCTCCGTT CGATACCGCA GCACCTGATT 6750
TCGATACAGG TACTTCCCCG ACCCCACTA CCGTGCCAGA GCCAGCCATT 6800
ACTACACTCA TACCGCGCAG CACTAGCGAT ATGGGATTCT TCTCCACGGC 6850
ACGTGCTACC GGATCAGAAA CTCTTTCGGT ACCCGTCCAG GAAACGGATA 6900
GAACTCTTTC GACAACTCCT CTTACCCTTC CACTGACTCC CGGTGAGTCA 6950
GAAAATACAC TGTTTCCTAC GACCGCGCCG GGGATTTCTA CCGAGACCCC 7000
```

FIGURE 1E

```
GAGCGCGGCA CATGAAACTA CACAGACCCA GAGTGCAGAA ACGGTGGTCT 7050
TTACTCAGAG TCCGAGTACC GAGTCGGAAA CCGCGCGGTC CCAGAGTCAG 7100
GAACCGTGGT ATTTTACTCA GACTCCGAGT ACTGAACAGG CGGCTCTTAC 7150
TCAGACGCAG ATCGCAGAAA CGGAGGCGTT GTTTACTCAG ACTCCGAGTG 7200
CTGAACAGAT GACTTTTACT CAGACTCCGG GTGCAGAAAC CGAGGCACCT 7250
GCCCAGACCC CGAGCACGAT ACCCGAGATA TTTACTCAGT CTCGTAGCAC 7300
GCCCCCCGAA ACCGCTCGCG CTCCGAGCGC GGCGCCGGAG GTTTTTACAC 7350
AGAGTTCGAG TACGGTAACG GAGGTGTTTA CTCAGACCCC GAGCACGGTA 7400
CCGAAAACTA CTCTGAGTTC GAGTACTGAA CCGGCGATTT TTACTCGGAC 7450
TCAGAGCGCG GGAACTGAGG CCTTTACTCA GACTTCGAGT GCCGAGCCGG 7500
ACACTATGCG AACTCAGAGT ACTGAAACAC ACTTTTTCAC TCAGGCCCCG 7550
AGTACGGTAC CGAAAGCTAC TCAGACTCCG AGTACAGAGC CGGAGGTGTT 7600
GACTCAGAGT CCGAGTACCG AACCTGTGCC TTTCACCCGG ACTCTGGGCG 7650
CAGAGCCGGA AATTACTCAG ACCCCGAGCG CGGCACCGGA GGTTTATACT 7700
CGGAGTTCGA GTACGATGCC AGAAACTGCA CAGAGCACAC CCCTGGCCTC 7750
GCAAAACCCT ACCAGTTCGG GAACCGGGAC GCATAATACT GAACCGAGGA 7800
CTTATCCAGT GCAAACGACA CCACATACCC AGAAACTCTA CACAGAAAAT 7850
AAGACTTTAT CGTTTCCTAC TGTTGTTTCA GAATTCCATG AGATGTCGAC 7900
GGCAGAGTCG CAGACGCCCC TATTGGACGT CAAAATTGTA GAGGTGAAGT 7950
TTTCAAACGA TGGCGAAGTA ACGGCGACTT GCGTTTCCAC CGTCAAATCT 8000
CCCTATAGGG TAGAAACTAA TTGGAAAGTA GACCTCGTAG ATGTAATGGA 8050
TGAAATTTCT GGGAACAGTC CCGCCGGGGT TTTTAACAGT AATGAGAAAT 8100
GGCAGAAACA GCTGTACTAC AGAGTAACCG ATGGAAGAAC ATCGGTCCAG 8150
CTAATGTGCC TGTCGTGCAC GAGCCATTCT CCGGAACCTT ACTGTCTTTT 8200
CGACACGTCT CTTATAGCGA GGGAAAAAGA TATCGCGCCA GAGTTATACT 8250
TTACCTCTGA TCCGCAAACG GCATACTGCA CAATAACTCT GCCGTCCGGC 8300
GTTGTTCCGA GATTCGAATG GAGCCTTAAT AATGTTTCAC TGCCGGAATA 8350
TTTGACGGCC ACGACCGTTG TTTCGCATAC CGCTGGCCAA AGTACAGTGT 8400
GGAAGAGCAG CGCGAGAGCA GGCGAGGCGT GGATTTCTGG CCGGGGAGGC 8450
AATATATACG AATGCACCGT CCTCATCTCA GACGGCACTC GCGTTACTAC 8500
GCGAAAGGAG AGGTGCTTAA CAAACACATG GATTGCGGTG GAAAACGGTG 8550
CTGCTCAGGC GCAGCTGTAT TCACTCTTTT CTGGACTTGT GTCAGGATTA 8600
TGCGGGAGCA TATCTGCTTT GTACGCAACG CTATGGACCG CCATTTATTT 8650
TTGAGGAATG CTTTTTGGAC TATCGTACTG CTTTCTTCCT TCGCTAGCCA 8700
GAGCACCGCC GCCGTCACGT ACGACTACAT TTTAGGCCGT CGCGCGCTCG 8750
```

FIGURE 1F

```
ACGCGCTAAC CATACCGGCG GTTGGCCCGT ATAACAGATA CCTCACTAGG 8800
GTATCAAGAG GCTGCGACGT TGTCGAGCTC AACCCGATTT CTAACGTGGA 8850
CGACATGATA TCGGCGGCCA AAGAAAAAGA GAAGGGGGGC CCTTTCGAGG 8900
CCTCCGTCGT CTGGTTCTAC GTGATTAAGG GCGACGACGG CGAGGACAAG 8950
TACTGTCCAA TCTATAGAAA AGAGTACAGG GAATGTGGCG ACGTACAACT 9000
GCTATCTGAA TGCGCCGTTC AATCTGCACA GATGTGGGCA GTGGACTATG 9050
TTCCTAGCAC CCTTGTATCG CGAAATGGCG CGGGACTGAC TATATTCTCC 9100
CCCACTGCTG CGCTCTCTGG CCAATACTTG CTGACCCTGA AAATCGGGAG 9150
ATTTGCGCAA ACAGCTCTCG TAACTCTAGA AGTTAACGAT CGCTGTTTAA 9200
AGATCGGGTC GCAGCTTAAC TTTTTACCGT CGAAATGCTG GACAACAGAA 9250
CAGTATCAGA CTGGATTTCA AGGCGAACAC CTTTATCCGA TCGCAGACAC 9300
CAATACACGA CACGCGGACG ACGTATATCG GGGATACGAA GATATTCTGC 9350
AGCGCTGGAA TAATTTGCTG AGGAAAAAGA ATCCTAGCGC GCCAGACCCT 9400
CGTCCAGATA GCGTCCCGCA AGAAATTCCC GCTGTAACCA AGAAAGCGGA 9450
AGGGCGCACC CCGGACGCAG AAAGCAGCGA AAAGAAGGCC CCTCCAGAAG 9500
ACTCGGAGGA CGACATGCAG GCAGAGGCTT CTGGAGAAAA TCCTGCCGCC 9550
CTCCCCGAAG ACGACGAAGT CCCCGAGGAC ACCGAGCACG ATGATCCAAA 9600
CTCGGATCCT GACTATTACA ATGACATGCC CGCCGTGATC CCGGTGGAGG 9650
AGACTACTAA AAGTTCTAAT GCCGTCTCCA TGCCCATATT CGCGGCGTTC 9700
GTAGCCTGCG CGGTCGCGCT CGTGGGGCTA CTGGTTTGGA GCATCGTAAA 9750
ATGCGCGCGT AGCTAATCGA GCCTAGAATA GGTGGTTTCT TCCTACATGC 9800
CACGCCTCAC GCTCATAATA TAAATCACAT GGAATAGCAT ACCAATGCCT 9850
ATTCATTGGG ACGTTCGAAA AGCATGGCAT CGCTACTTGG AACTCTGGCT 9900
CTCCTTGCCG CGACGCTCGC ACCCTTCGGC GCGATGGGAA TCGTGATCAC 9950
TGGAAATCAC GTCTCCGCCA GGATTGACGA CGATCACATC GTGATCGTCG 10000
CGCCTCGCCC CGAAGCTACA ATTCAACTGC AGCTATTTTT CATGCCTGGC 10050
CAGAGACCCC ACAAACCCTA CTCAGGAACC GTCCGCGTCG CGTTTCGGTC 10100
TGATATAACA AACCAGTGCT ACCAGGAACT TAGCGAGGAG CGCTTTGAAA 10150
ATTGCACTCA TCGATCGTCT TCTGTTTTTG TCGGCTGTAA AGTGACCGAG 10200
TACACGTTCT CCGCCTCGAA CAGACTAACC GGACCTCCAC ACCCGTTTAA 10250
GCTCACTATA CGAAATCCTC GTCCGAACGA CAGCGGGATG TTCTACGTAA 10300
TTGTTCGGCT AGACGACACC AAAGAACCCA TTGACGTCTT CGCGATCCAA 10350
CTATCGGTGT ATCAATTCGC GAACACCGCC GCGACTCGCG GACTCTATTC 10400
CAAGGCTTCG TGTCGCACCT TCGGATTACC TACCGTCCAA CTTGAGGCCT 10450
ATCTCAGGAC CGAGGAAAGT TGGCGCAACT GGCAAGCGTA CGTTGCCACG 10500
```

FIGURE 1G

```
GAGGCCACGA CGACCAGCGC CGAGGCGACA ACCCCGACGC CCGTCACTGC 10550
AACCAGCGCC TCCGAACTTG AAGCGGAACA CTTTACCTTT CCCTGGCTAG 10600
AAAATGGCGT GGATCATTAC GAACCGACAC CCGCAAACGA AAATTCAAAC 10650
GTTACTGTCC GTCTCGGGAC AATGAGCCCT ACGCTAATTG GGGTAACCGT 10700
GGCTGCCGTC GTGAGCGCAA CGATCGGCCT CGTCATTGTA ATTTCCATCG 10750
TCACCAGAAA CATGTGCACC CCGCACCGAA AATTAGACAC GGTCTCGCAA 10800
GACGACGAAG AACGTTCCCA AACTAGAAGG GAATCGCGAA AATTTGGACC 10850
CATGGTTGCG TGCGAAATAA ACAAGGGCGC TGACCAGGAT AGTGAACTTG 10900
TGGAACTGGT TGCGATTGTT AACCCGTCTG CGCTAAGCTC GCCCGACTCA 10950
ATAAAAATGT GATTAAGTCT GAATGTGGCT CTCCAATCAT TTCGATTCTC 11000
TAATCTCCCA ATCCTCTCAA AAGGGGCAGT ATCGGACACG GACTGGGAGG 11050
GGCGTACTAC ACGATAGTTA TATGGTACAG CAGAGGCCTC TGAACACTTA 11100
GGAGGAGAAT TCAGCCGGGG AGAGCCCTG TTGAGTAGGC TTGGGAGCAT 11150
ATTGCAGGAT GAACATGTTA GTGATAGTTC TCGCCTCTTG TCTTGCGCGC 11200
CTAACTTTTG CGACGCGACA CGTCCTCTTT TTGGAAGGCA CTCAGGCTGT 11250
CCTCGGGGAA GATGATCCCA GAAACGTTCC GGAAGGGACT GTAATCAAAT 11300
GGACAAAAGT CCTGCGGAAC GCGTGCAAGA TGAAGGCGGC CGATGTCTGC 11350
TCTTCGCCTA ACTATTGCTT TCATGATTTA ATTTACGACG GAGGAAAGAA 11400
AGACTGCCCG CCCGCGGGAC CCCTGTCTGC AAACCTGGTA ATTTTACTAA 11450
AGCGCGGCGA AAGCTTCGTC GTGCTGGGTT CTGGGCTACA CAACAGCAAT 11500
ATAACTAATA TCATGTGGAC AGAGTACGGA GGCCTGCTCT TTGATCCTGT 11550
AACTCGTTCG GACGAGGGAA TCTATTTTCG ACGGATCTCT CAGCCAGATC 11600
TGGCCATGGA AACTACATCG TACAACGTCA GCGTTCTTTC GCACGTAGAC 11650
GAGAAGGCTC CAGCACCGCA CGAGGTGGAG ATAGACACCA TCAAGCCGTC 11700
AGAGGCCCAC GCGCACGTGG AATTACAAAT GCTGCCGTTT CATGAACTCA 11750
ACGACAACAG CCCCACCTAT GTGACCCCTG TTCTTAGAGT CTTCCCACCG 11800
ACCGAGCACG TAAAATTTAA CGTTACGTAT TCGTGGTATG GGTTTGATGT 11850
CAAAGAGGAG TGCGAAGAAG TGAAACTGTT CGAGCCGTGC GTATACCATC 11900
CTACAGACGG CAAATGTCAG TTTCCCGCAA CCAACCAGAG ATGCCTCATA 11950
GGATCTGTCT TGATGGCGGA ATTCTTGGGC GCGGCCTCTT TGCTGGATTG 12000
TTCCCGCGAT ACTCTAGAAG ACTGCCACGA AAATCGCGTG CCGAACCTAC 12050
GGTTCGATTC GCGACTCTCC GAGTCACGCG CAGGCCTGGT GATCAGTCCT 12100
CTTATAGCCA TCCCCAAAGT TTTGATTATA GTCGTTTCCG ACGGAGACAT 12150
TTTGGGATGG AGCTACACGG TGCTCGGGAA ACGTAACAGT CCGCGCGTAG 12200
TAGTCGAAAC GCACATGCCC TCGAAGGTCC CGATGAACAA AGTAGTAATT 12250
```

FIGURE 1H

```
GGCAGTCCCG GACCAATGGA CGAAACGGGT AACTATAAAA TGTACTTCGT 12300
CGTCGCGGGG GTGGCCGCGA CGTGCGTAAT TCTTACATGC GCTCTGCTTG 12350
TGGGGAAAAA GAAGTGCCCC GCGCACCAAA TGGGTACTTT TTCCAAGACC 12400
GAACCATTGT ACGCGCCGCT CCCCAAAAAC GAGTTTGAGG CCGGCGGGCT 12450
TACGGACGAT GAGGAAGTGA TTTATGACGA AGTATACGAA CCCCTATTTC 12500
GCGGCTACTG TAAGCAGGAA TTCCGCGAAG ATGTGAATAC CTTTTTCGGT 12550
GCGGTCGTGG AGGGAGAAAG GGCCTTAAAC TTTAAATCCG CCATCGCATC 12600
AATGGCAGAT CGCATCCTGG CAAATAAAAG CGGCAGAAGG AATATGGATA 12650
GCTATTAGTT GGTCATGCCT TTTAAGACCA GAGGGGCCGA AGACGCGGCC 12700
GCGGGCAAGA ACAGGTTTAA GAAATCGAGA AATCGGGAAA TCTTACCGAC 12750
CAGACTGCGT GGCACCGGTA AGAAAACTGC CGGATTGTCC AATTATACCC 12800
AGCCTATTCC CTGGAACCCT AAATTCTGCA GCGCGCGCGG GGAATCTGAC 12850
AACCACGCGT GTAAAGACAC TTTTTATCGC AGGACGTGCT GCGCATCGCG 12900
CTCTACCGTT TCCAGTCAAC CCGATTCCCC CCACACACCC ATGCCTACTG 12950
AGTATGGGCG CGTGCCCTCC GCAAAGCGCA AAAAACTATC ATCTTCAGAC 13000
TSSGAGGGCG CGCACCAACC CCTAGTATCC TGTAAACTTC CGGATTCTCA 13050
AGCAGCACCG GCGCGAACCT ATAGTTCTGC GCAAAGATAT ACTGTTGACG 13100
AGGTTTCGTC GCCAACTCCG CCAGGCGTCG ACGCTGTTGC GGACTTAGAA 13150
ACGCGCGCGG AACTTCCTGG CGCTACGACG GAACAAACGG AAAGTAAAAA 13200
TAAGCTCCCC AACCAACAAT CGCGCCTGAA GCCGAAACCC ACAAACGAGC 13250
ACGTCGGAGG GGAGCGGTGC CCCTCCGAAG GCACGGTCGA GGCGCCATCG 13300
CTCGGCATCC TCTCGCGCGT CGGGGCAGCG ATAGCAAACG AGCTGGCTCG 13350
TATGCGGAGG GCGTGTCTTC CGCTCGCCGC GTCGGCGGCC GCTGCCGGAA 13400
TAGTGGCCTG GGCCGCGGCG AGGGCCTTGC AGAAACAAGG GCGGTAGCAG 13450
TAATAATAAC CACACAAATA TTG 13473
```

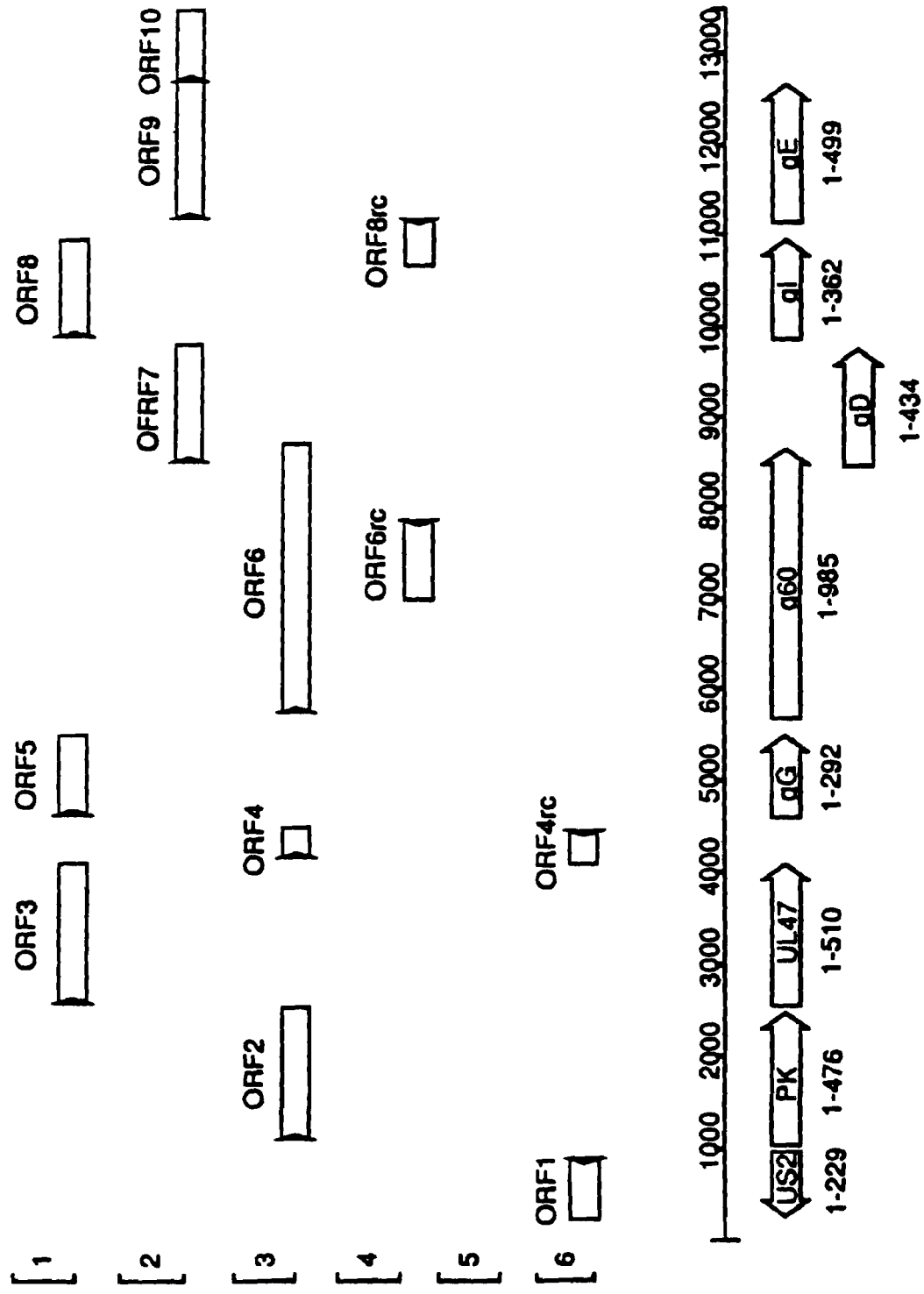

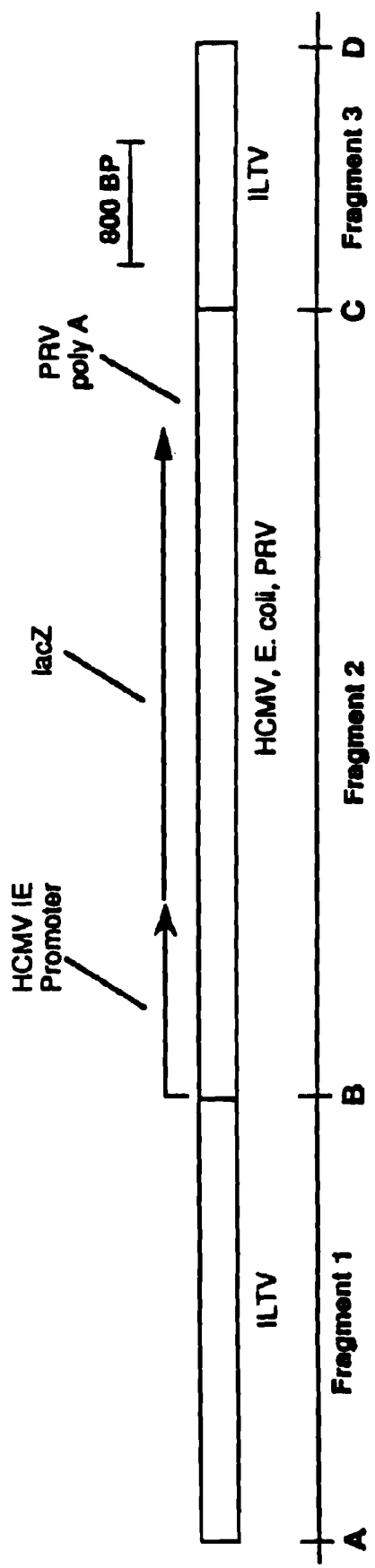

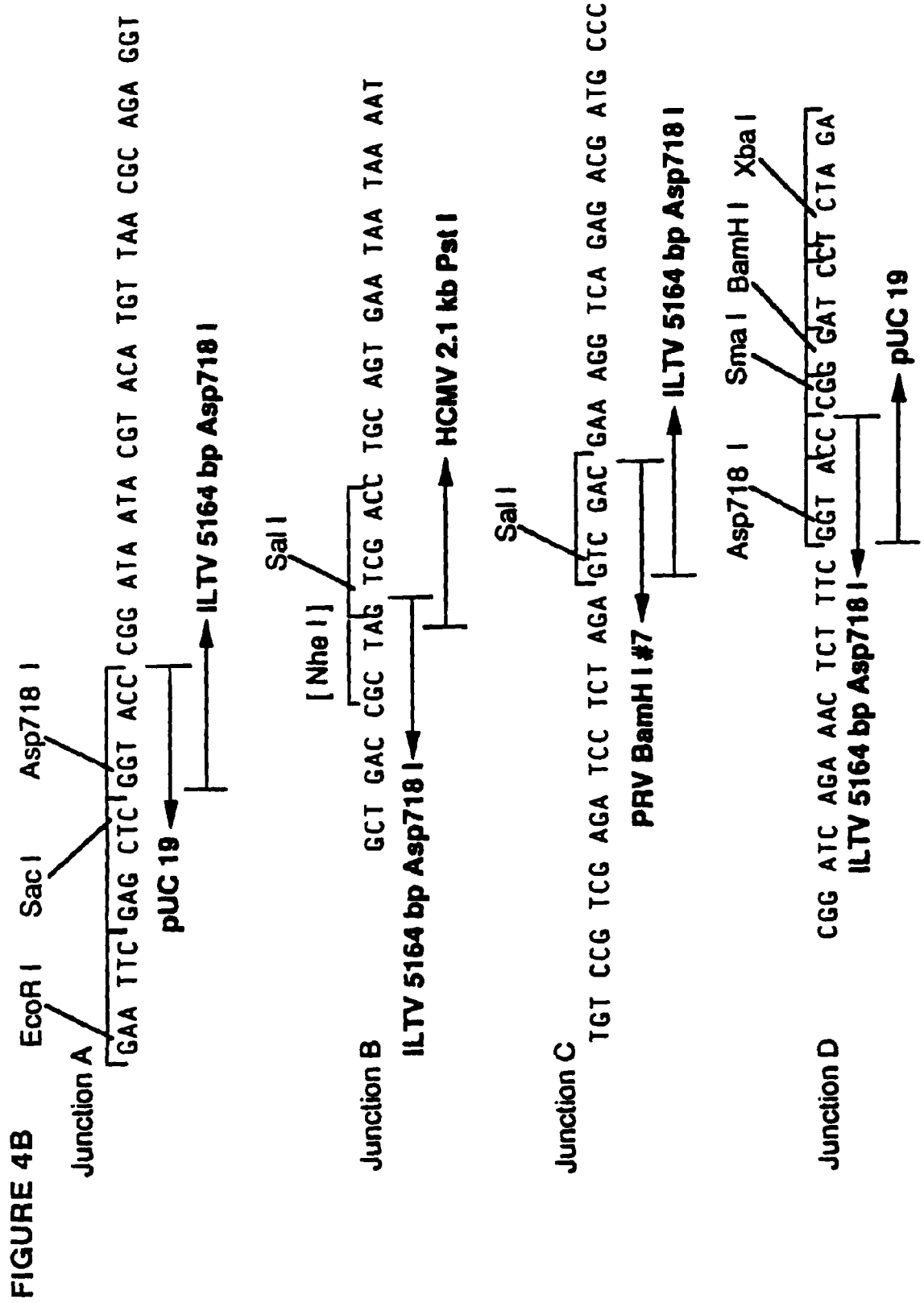

| DNA | Origin | Sites | Size |
| --- | --- | --- | --- |
| Vector | pSP 64/65 | Hind III—Hind III | ~3002 BP |
| Fragment 1 | ILTV 2.4 kb Hind III | Hind III—Bcl I | ~1087 BP |
| Fragment 2 | PRV, E. coli, HCMV | Sal I—Sal I | ~5017 BP |
| Fragment 3 | ILTV 2.4 kb Hind III | Bcl I—Hind III | ~700 BP |

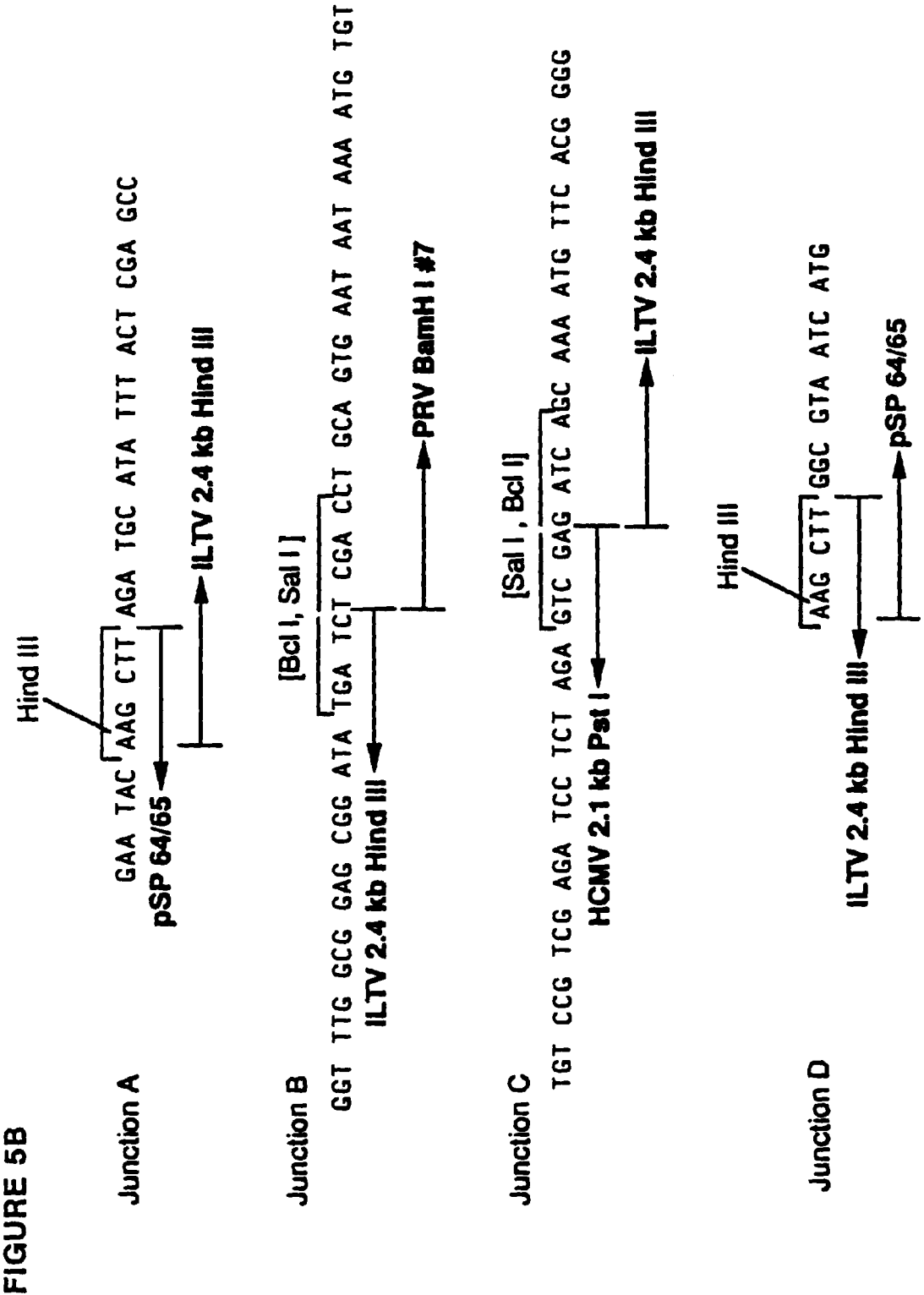

| DNA | Origin | Sites | Size |
|---|---|---|---|
| Vector | pSP 18/19 | Asp718 I—Asp718 I | ~2958 BP |
| Fragment 1 | ILTV 2.5 kb Asp718 I | Asp718 I—Dra I | ~2300 BP |
| Fragment 2 | PRV, E. coli, HSV-1 | Xba I—Xba I | ~3039 BP |
| Fragment 3 | ILTV 1097 bp Asp718 I | Xba I—Asp718 I | ~ 809 BP |

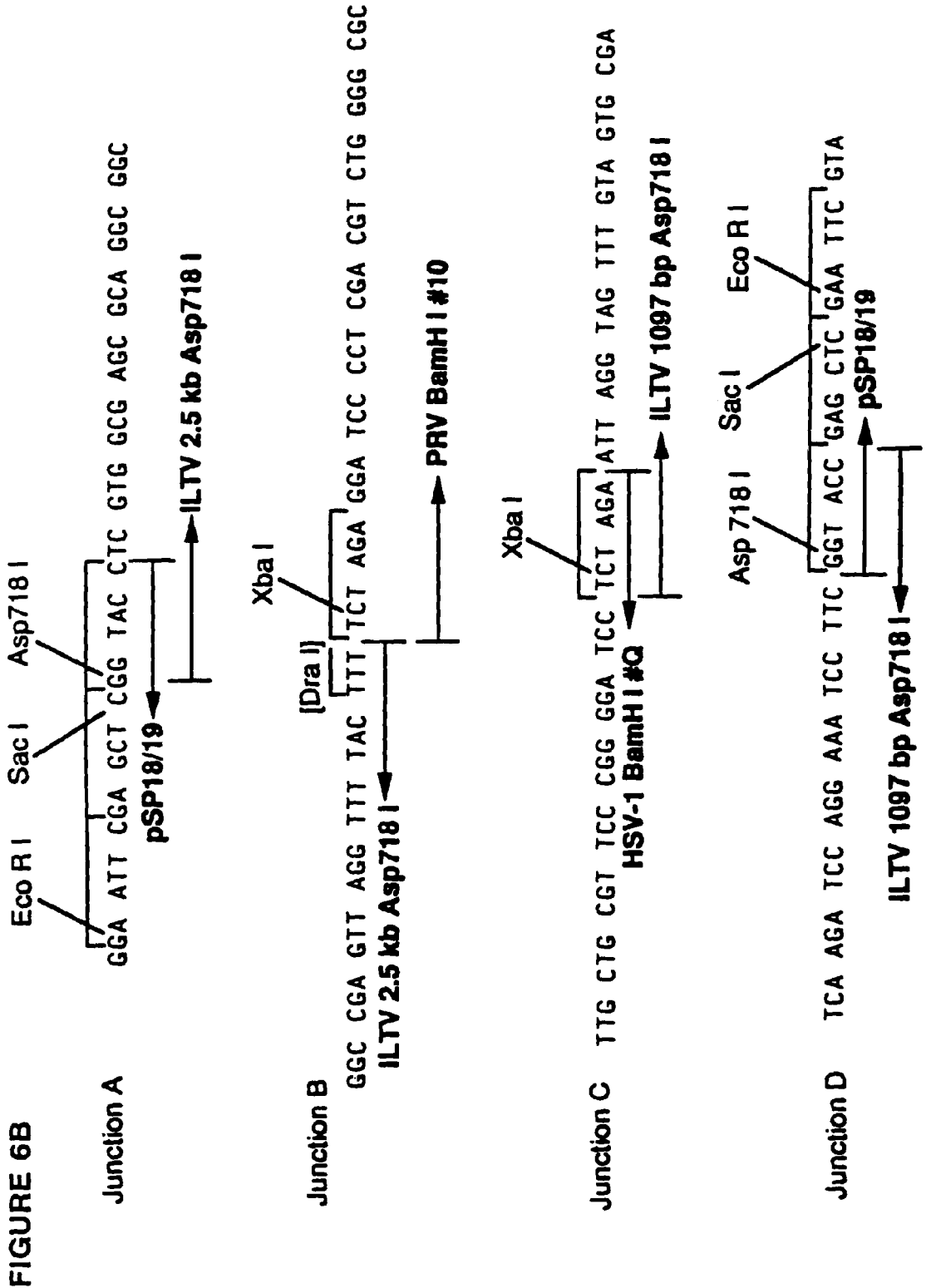

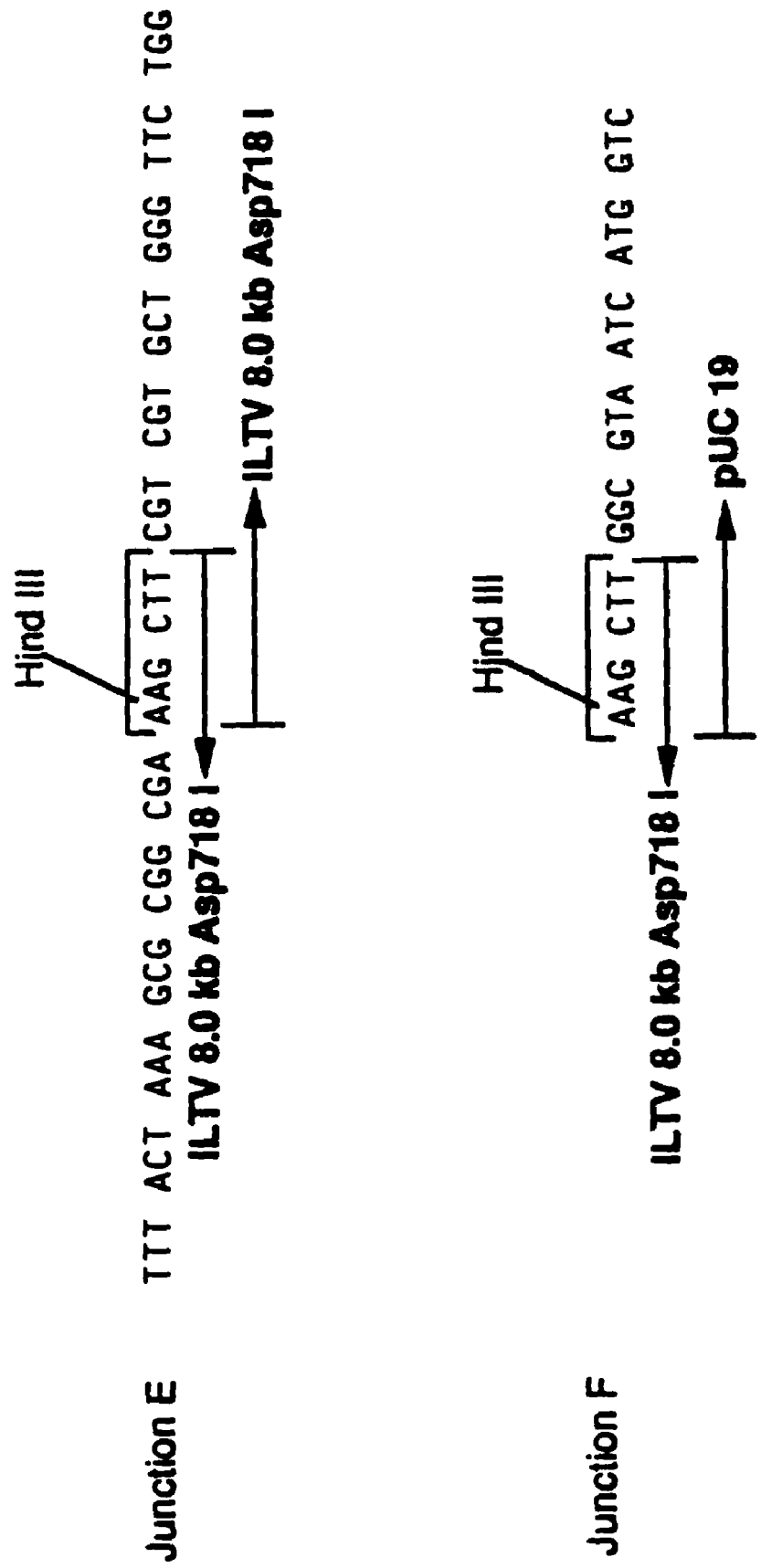

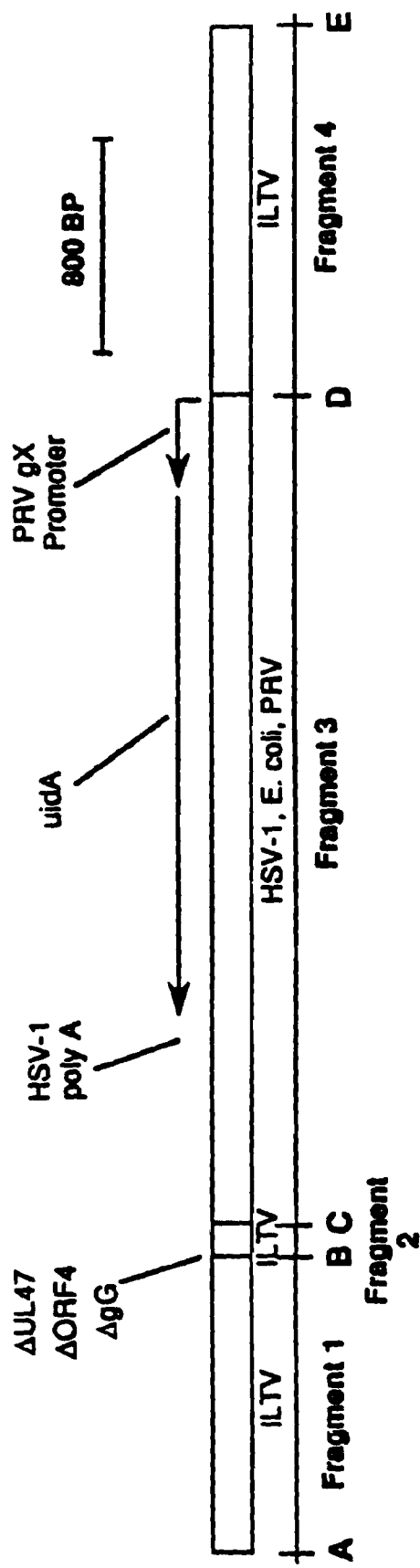

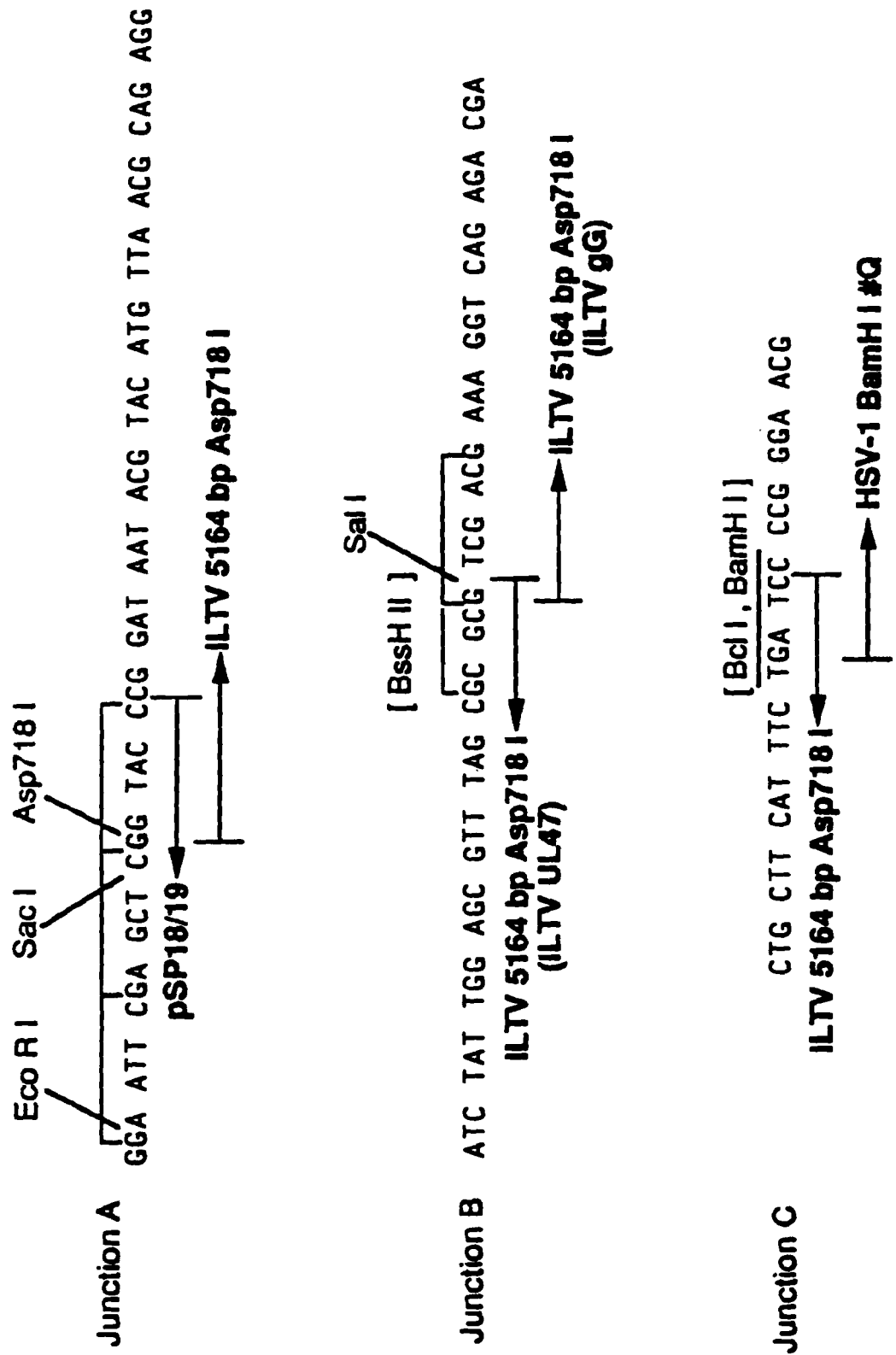

| DNA | Origin | Sites | Size |
| --- | --- | --- | --- |
| Vector | pUC19 | Asp718 I—BamH I | ~2677 BP |
| Fragment 1 | ILTV 5164 bp Asp718I | Asp718 I—Nhe I | ~2830 BP |
| Fragment 2 | PRV, E. coli, HSV-1 | Sal I—Sal I | ~3051 BP |
| Fragment 3 | ILTV 4545 bp BamH I | Sal I—BamH I | ~1709 BP |

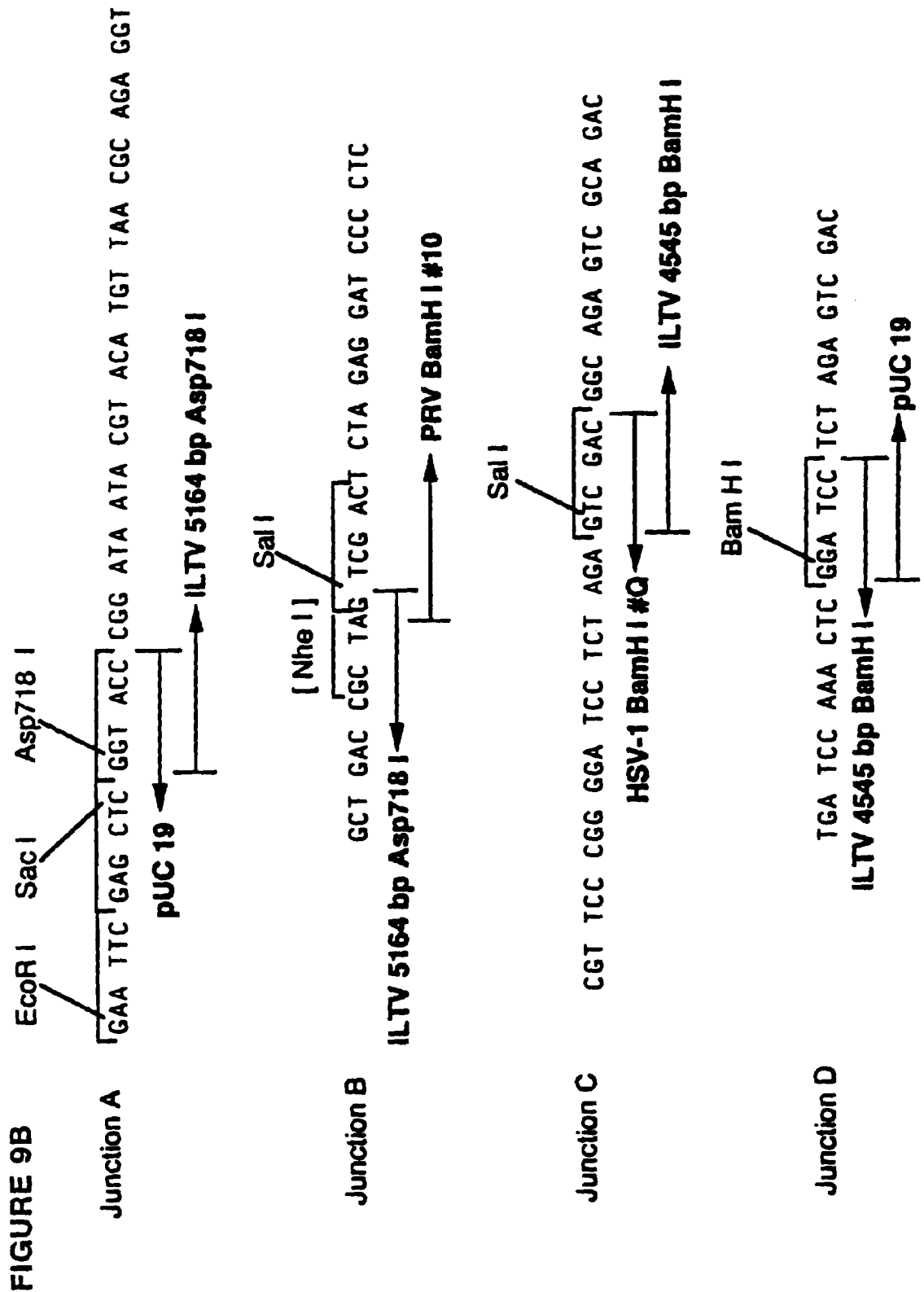

| DNA | Origin | Sites | Size |
| --- | --- | --- | --- |
| Vector | pSP 71 | Xma I—Sma I | ~3066 BP |
| Fragment 1 | PRV BamH I #10 | Sal I—EcoR I† | ~ 422 BP |
| Fragment 2 | pRAJ 260 | EcoR I†—Xma I† | ~1826 BP |
| Fragment 3 | HSV-1 BamH I #Q | Xma I—Xma I | ~ 784 BP |

†Restriction enzyme site introduced by PCR cloning

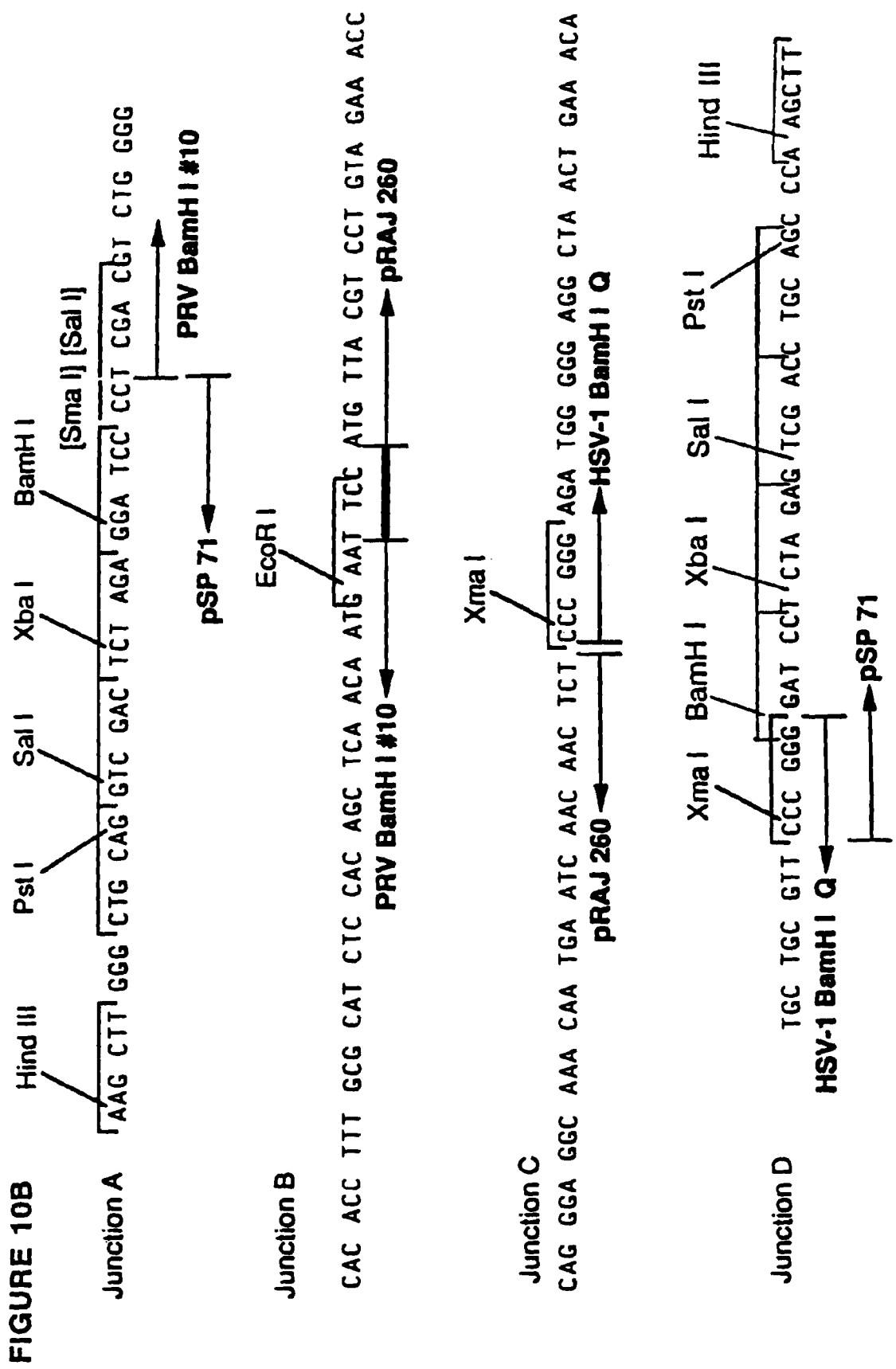

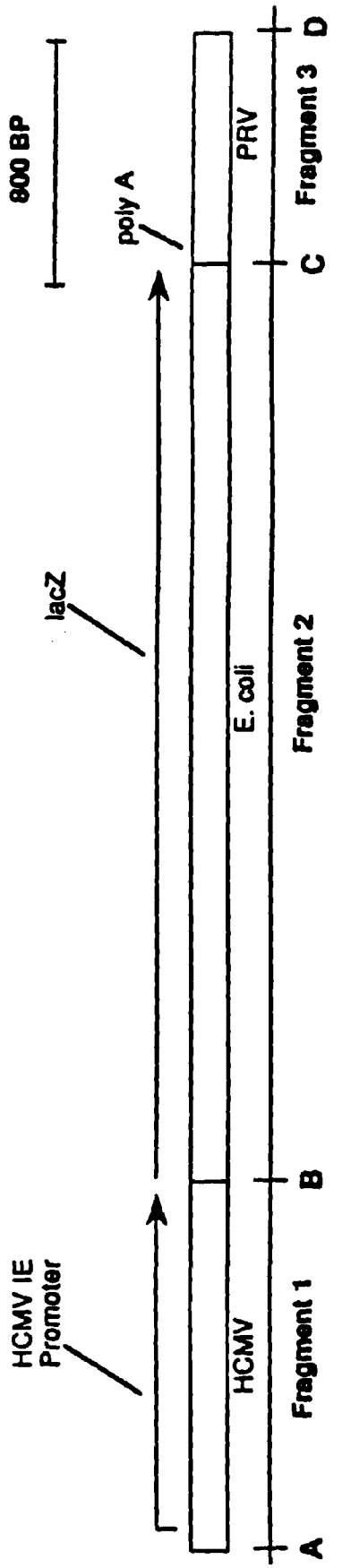

FIGURE 17

```
ILT 277  QHGPMAAVFRNAGAGLFLWPAMRAAFEERDKRLLRACLSSLDIMDAAVLASF
             ||  ||||||::  ::|:  ||::||  ::    .    .::||:||.|
HSV 351  QSGPDAAVFRSSLGSLLYWPGVRALLDRDCRVAARYAGRMTYLATGALLARF
           .:::|||||  :||:|||::|   -    |:.|    ||.|         ||||
EHV 531  LRTPNSAVFRAFFGSLVYWAELRLLALRDPASINCRYVGFHLQTSEIYLLARA
           :|.|  ::  ||  ::|||.|||:|||   ||  . .:|:|||||||:|
MDV 472  MRDPMASAARASYGSLAYWPELRCALGSENKRIVRYAIVAMLQAEIYLLTRI
```

US 7,892,564 B2

RECOMBINANT INFECTIOUS LARYNGOTRACHEITIS VIRUS AND USES THEREOF

This application is a divisional of U.S. Ser. No. 12/047,787, filed on Mar. 13, 2008, now U.S. Pat. No. 7,501,491, which is a divisional of U.S. Ser. No. 11/342,171, filed on Jan. 27, 2006, now U.S. Pat. No. 7,364,893, which is a divisional of U.S. Ser. No. 10/836,383, filed on Apr. 30, 2004, now U.S. Pat. No. 7,045,598, which is a divisional of U.S. Ser. No. 09/994,064 filed Nov. 6, 2001, now U.S. Pat. No. 6,984,728, which is a divisional of U.S. Ser. No. 08/468,190 filed Jun. 6, 1995, now abandoned, which is a continuation of U.S. Ser. No. 08/410,121 filed Mar. 23, 1995, now abandoned, which is a continuation-in-part of U.S. Ser. No. 08/126,597 filed Sep. 24, 1993, now abandoned, the contents of all of which are hereby incorporated by reference in their entireties into this application.

Within this application several publications are referenced by arabic numerals within parentheses. Full citations for these publications may be found at the end of the specification preceding the claims. The disclosures of these publications are hereby incorporated by reference into this application in order to more fully describe the state of the art to which this invention pertains.

BACKGROUND OF THE INVENTION

Infectious laryngotracheitis virus is a herpesvirus that causes a respiratory illness of varying virulence in chickens. Live attenuated ILTV vaccines are available to protect against the disease, but several reports have implicated vaccine viruses in the possible recurrence and spread of the disease (65 and 72), limiting vaccination to use in uninfected birds early in an outbreak. In order to design a more efficacious, attenuated vaccine, the genomic organization of the ILTV virus has been studied.

The ability to isolate viral DNA and clone this isolated DNA into bacterial plasmids has greatly expanded the approaches available to make viral vaccines. The methods used to make the present invention involve modifying cloned viral DNA sequences by insertions, deletions and single or multiple base changes. The modified DNA is then reinserted into the viral genome to render the virus non-pathogenic. The resulting live virus may then be used in a vaccine to elicit an immune response in a host animal and to protect the animal against a disease.

One group of animal viruses, the herpesviruses or Herpetoviridae, is an example of a class of viruses amenable to this approach. These viruses contain 100,000 to 200,000 base pairs of DNA as their genetic material. Importantly, several regions of the genome have been identified that are nonessential for the replication of virus in vitro in cell culture. Modifications in these regions of the DNA may lower the pathogenicity of the virus, i.e. attenuate the virus. For example, inactivation of the thymidine kinase gene renders human herpes simplex virus non-pathogenic (1), and pseudorabies virus of swine non-pathogenic (2).

Removal of part of the repeat region renders human herpes simplex virus non-pathogenic (3, 4). A repeat region has been identified in Marek's disease virus that is associated with viral oncogenicity (5). A region in herpesvirus saimiri has similarly been correlated with oncogenicity (6). Removal of part of the repeat region renders pseudorabies virus non-pathogenic (U.S. Pat. No. 4,877,737, issued Oct. 31, 1989). A region in pseudorabies virus has been shown to be deleted in naturally-occurring vaccine strains (7, 8) and it has been shown that these deletions are at least partly responsible for the lack of pathogenicity of these strains.

It is generally agreed that herpesviruses contain non-essential regions of DNA in various parts of the genome. Some of these regions are associated with virulence of the virus, and modification of them leads to a less-pathogenic virus, from which a vaccine may be derived.

Infectious laryngotracheitis virus (ILTV), an alpha herpesvirus (9), is an important pathogen of poultry in the USA, Europe, and Australia, responsible for egg production losses and death (10). It causes an acute disease of chickens which is characterized by respiratory depression, gasping and expectoration of bloody exudate. Viral replication is limited to cells of the respiratory tract wherein infection of the trachea gives rise to tissue erosion and hemorrhage.

In chickens, no drug has been effective in reducing the degree of lesion formation or in decreasing clinical signs. Vaccination of birds with various modified forms of the ILT virus derived by cell passage and/or tedious regimes of administration have been used to confer acceptable protection in susceptible chickens. Due to the limited degree of attenuation of current ILTV vaccines care must be taken to assure that the correct level of virus is maintained; enough to provide protection, but not enough to cause disease in the flock (11-21). Furthermore, these viruses may revert back to virulence, causing disease rather than providing protection against it.

ILTV has been analyzed at the molecular level. Restriction maps of the ILTV genome have been reported (22-26). The DNA sequence of several genes have been identified, i.e., thymidine kinase (27, 28), glycoprotein gB (27, 29, 30), ribonucleotide reductase (27, 31), capsid p40 (31, 32).

Furthermore, Shepard, et al. (53) disclosed that several genes located in the unique long region of the infectious laryngotracheitis virus genomic DNA are non-essential for viral replication.

Applicants have unexpectedly found that the unique short region of the ILT virus genomic DNA contains genes that are associated with ILTV virulence and that a deletion in those genes leads to an attenuated ILTV. Particularly, it was found that a deletion in the glycoprotein G (gG) gene of the ILT virus results in an attenuated virus, which is useful as a vaccine against subsequent attack by a virulent ILTV strains.

Applicants also found that a deletion in the glycoprotein I (gI) gene of the unique short region also attenuates the ILTV. Furthermore, it is contemplated that a deletion in the US2 gene, the UL-47 like gene, and the glycoprotein g60 gene of the unique short region will also attenuate the ILTV.

ILTV can become latent in healthy animals which makes them potential carriers of the virus. For this reason, it is clearly advantageous to be able to distinguish animals vaccinated with non-virulent virus from animals infected with disease-causing wild-type or naturally-occurring virus. The development of differential vaccines and companion diagnostic tests has proven valuable in the management of pseudorabies disease (55). A similar differential marker vaccine would be of great value in the management of ILTV caused disease. The construction of differential diagnostics has focused on the deletion of glycoproteins. Theoretically, the glycoprotein chosen to be the diagnostic marker should have the following characteristics: (1) the glycoprotein and its gene should be non-essential for the production of infectious virus in tissue culture; (2) the glycoprotein should elicit a major serological response in the animal; and (3) the glycoprotein should not be one that makes a significant contribution to the protective immunity.

The ILT virus has been shown to specify at least four major glycoproteins as identified by monoclonal antibodies ($M_r$=205K, 115K, 90K and 60K). Three glycoproteins seem to be antigenically related ($M_r$=205K, U115K, and 90K) (34-36).

Three major ILT virus glycoproteins, gB (29, 30), gC (27, 51), and g60 (34, 53) have been described in the literature. These three genes have been sequenced and two of the ILTV genes have been shown to be homologous to the HSV glycoproteins gB, and gC.

Of these, it is known that the ILTV gB gene is an essential gene and would not be appropriate as deletion marker genes. Furthermore, the gC gene of herpesviruses has been shown to make a significant contribution to protective immunity as a target of neutralizing antibody (56) and as a target of cell-mediated immunity (57). Therefore, the gC gene is not desirable as a deletion marker gene.

As to other glycoprotein encoding genes cited above, it is not known whether or not they would be suitable candidates for deletion in order to construct a recombinant ILT virus which can be used as a diagnostic vaccine.

Applicants have unexpectedly found that there are two glycoprotein encoding genes located within the unique short region of the ILT viral genome which could be safely deleted in order to construct a recombinant ILT virus that can be used as a diagnostic vaccine. These are the glycoprotein gG gene and the glycoprotein gI gene. By genetically engineering an ILT virus with a deletion in the glycoprotein G gene or the glycoprotein I gene, a ILT virus is produced which does not express any glycoprotein G or glycoprotein I. None of the prior arts teach or suggest that these two genes in the unique short region of the virus are appropriate candidates for deletion in order to create a diagnostic ILT virus vaccine. Although several of the herpesviruses have been genetically engineered, no examples of recombinant ILTV have been reported.

The ability to engineer DNA viruses with large genomes, such as vaccinia virus and the herpesviruses, has led to the finding that these recombinant viruses can be used as vectors to deliver vaccine antigens and therapeutic agents for animals. The herpesviruses are attractive candidates for development as vectors because their host range is primarily limited to a single target species (37) and they have the capacity for establishing latent infection (38) that could provide for stable in vivo expression of a foreign gene. Although several herpesvirus species have been engineered to express foreign gene products, recombinant infectious laryngotracheitis viruses expressing foreign gene products have not been constructed. The infectious laryngotracheitis viruses described above may be used as vectors for the delivery of vaccine antigens from microorganisms causing important poultry diseases. Other viral antigens which may be included in a multivalent vaccine with an ILTV vector include infectious bronchitis virus (IBV), Newcastle disease virus (NDV), infectious bursal disease virus (IBDV), and Marek's disease virus (MDV). Such multivalent recombinant viruses would protect against ILT disease as well as other diseases. Similarly the infectious laryngotracheitis viruses may be used as vectors for the delivery of therapeutic agents. The therapeutic agent that is delivered by a viral vector of the present invention must be a biological molecule that is a by-product of ILTV replication. This limits the therapeutic agent in the first analysis to either DNA. RNA or protein. There are examples of therapeutic agents from each of these classes of compounds in the form of anti-sense DNA, anti-sense RNA (39), ribozymes (40), suppressor tRNAs (41), interferon-inducing double stranded RNA and numerous examples of protein therapeutics, from hormones, e.g. insulin, to lymphokines. e.g., interferons and interleukins, to natural opiates. The discovery of these therapeutic agents and the elucidation of their structure and function does not necessarily allow one to use them in a viral vector delivery system, however, because of the experimentation necessary to determine whether an appropriate insertion site exists.

ILTV is classified as an alpha herpesvirus with a type D genome (78) composed of a unique long region and a unique short region flanked by inverted repeats. A genomic restriction map of an Australian ILTV isolate (SA-2) was described by Johnson et al. (66). Using this map, Guo et al. (62) isolated and sequenced a DNA fragment from the USDA challenge strain which appeared to be derived from the unique short region. Applicants map the USDA challenge strain of ILTV, and reports characteristics of the putative genes present in the unique short region. The map disclosed herewith indicates that the sequence identified by Guo et al. (62) is part of the short repeat sequence, and is not from the unique short. Other reports (69 and 70) describe the sequences of two genes, one homologous to PRV gG and the other unlike other reported herpesvirus genes. These two genes were mapped to the unique long region of SA-2. However, these sequences are identical to sequences identified in this application as being from the unique short region. The data in this application indicate that the overall organization of the short region of ILTV is similar to other herpesviruses.

SUMMARY OF THE INVENTION

The present invention provides a recombinant, attenuated infectious laryngotracheitis virus comprising the infectious laryngotracheitis viral genome which contains a deletion in the glycoprotein gG gene. This attenuated virus is useful as a vaccine against infectious laryngotracheitis virus.

The present invention also provides a recombinant, attenuated infectious laryngotracheitis virus comprising the infectious laryngotracheitis viral genome which contains a deletion in the US2 gene, UL47-like gene. ORF4 gene or glycoprotein g60 gene.

The present invention also provides a method for distinguishing chickens or other poultry vaccinated with a recombinant infectious laryngotracheitis virus which produces no glycoprotein gG from those infected with a naturally-occurring infectious laryngotracheitis virus.

BRIEF DESCRIPTION OF THE FIGURES

FIGS. 1A-1H:

The nucleotide sequence of 13,473 base pairs of contiguous DNA from the unique short region of the ILT virus (SEQ ID NO: 1). This sequence contains the entire 13,098 base pair unique short region as well as 273 base pairs of repeat region at one end and 102 base pairs of repeat region at the other end. The nucleotide sequences of FIGS. 1A-1H begin with the internal repeat sequence and end within the terminal repeat sequence. The unique short region begins at base pair 274 of this Figure. Sequence ID NO:59 contains the nucleotide sequence of 18,912 base pairs of contiguous DNA from the unique short and repeat regions of the ILT virus. This sequence contains the entire 13,094 base pair unique short region as well as 2909 base pairs of internal repeat region and 2909 base pairs of short terminal repeat region. The nucleotide sequences begin with the internal repeat sequence and end within the terminal repeat sequence. The unique short region begins at base pair 2910.

Figure 2:
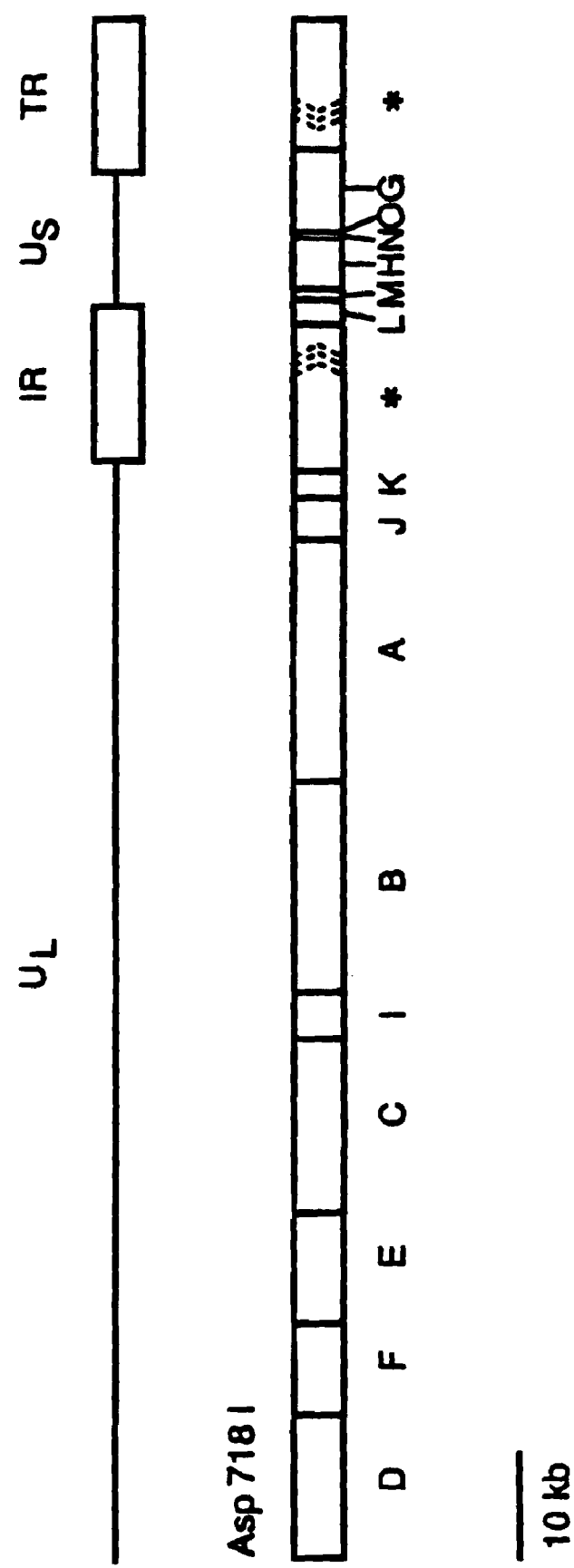
Figures 5A, 5B:
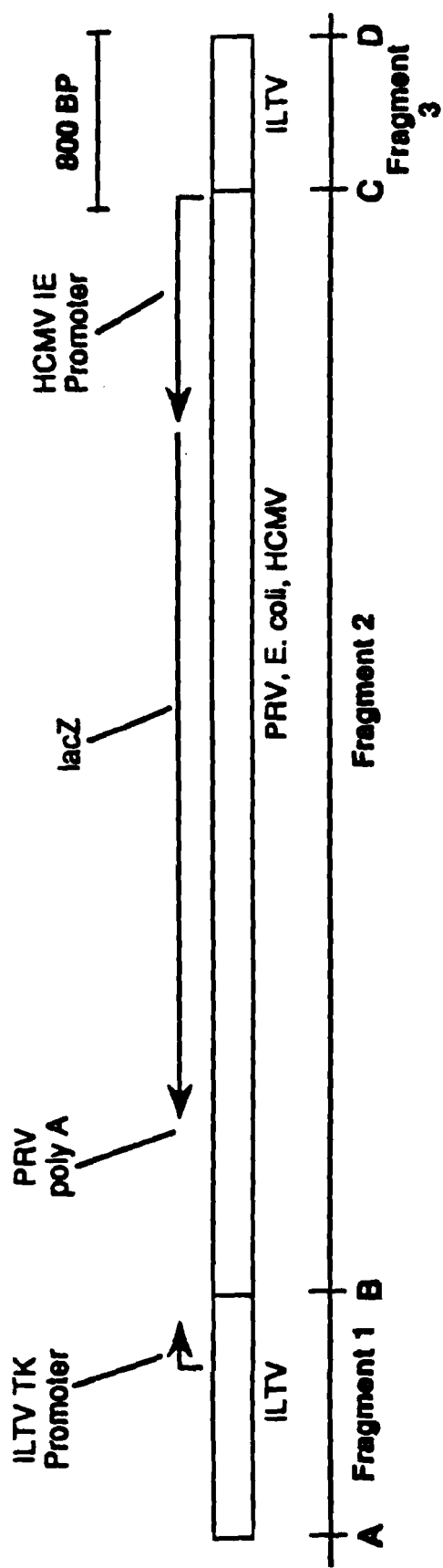
Figure 6A:
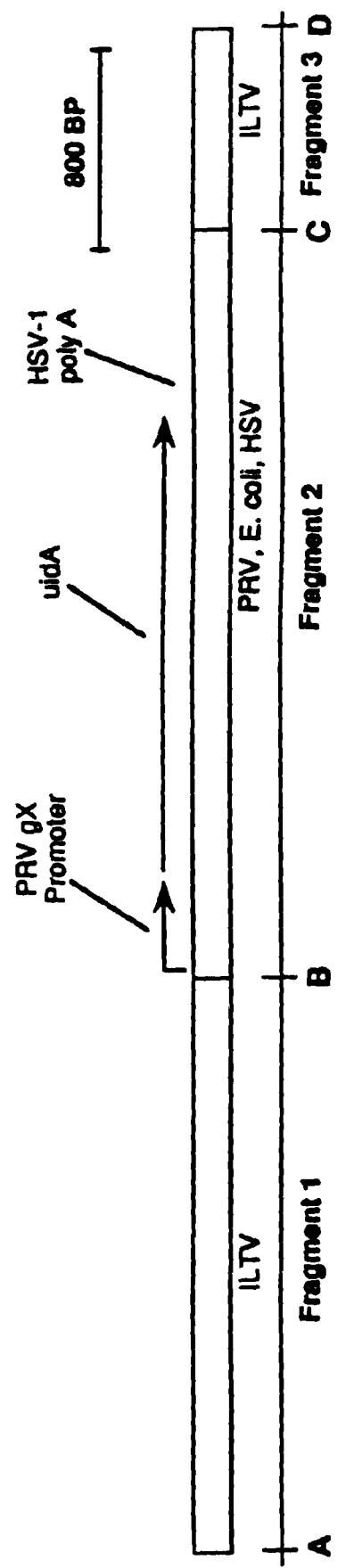
Figure 7A:
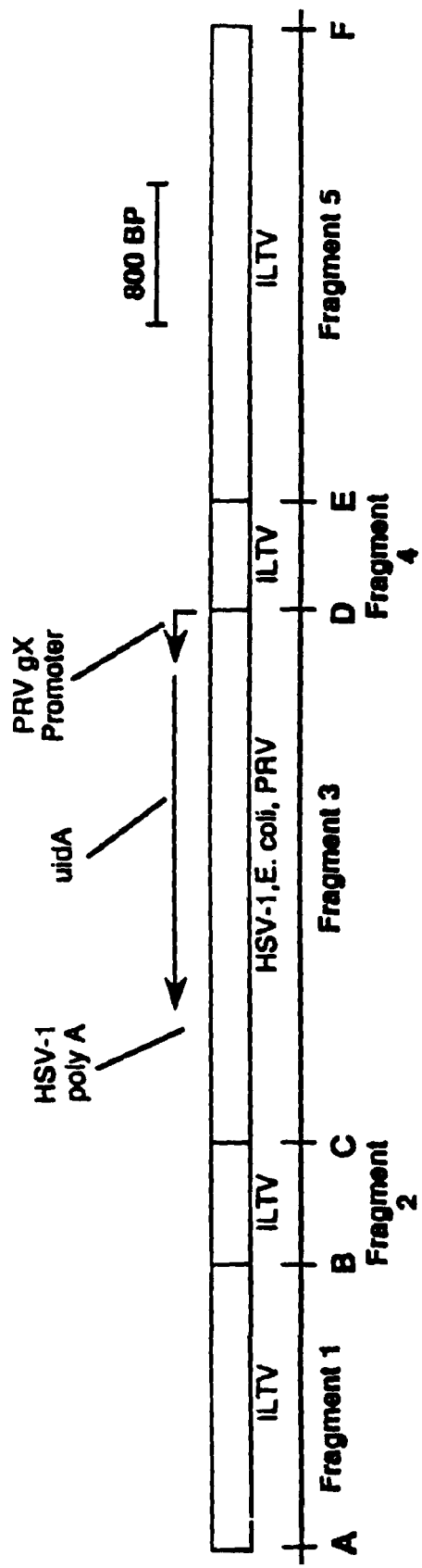
Figure 7B:
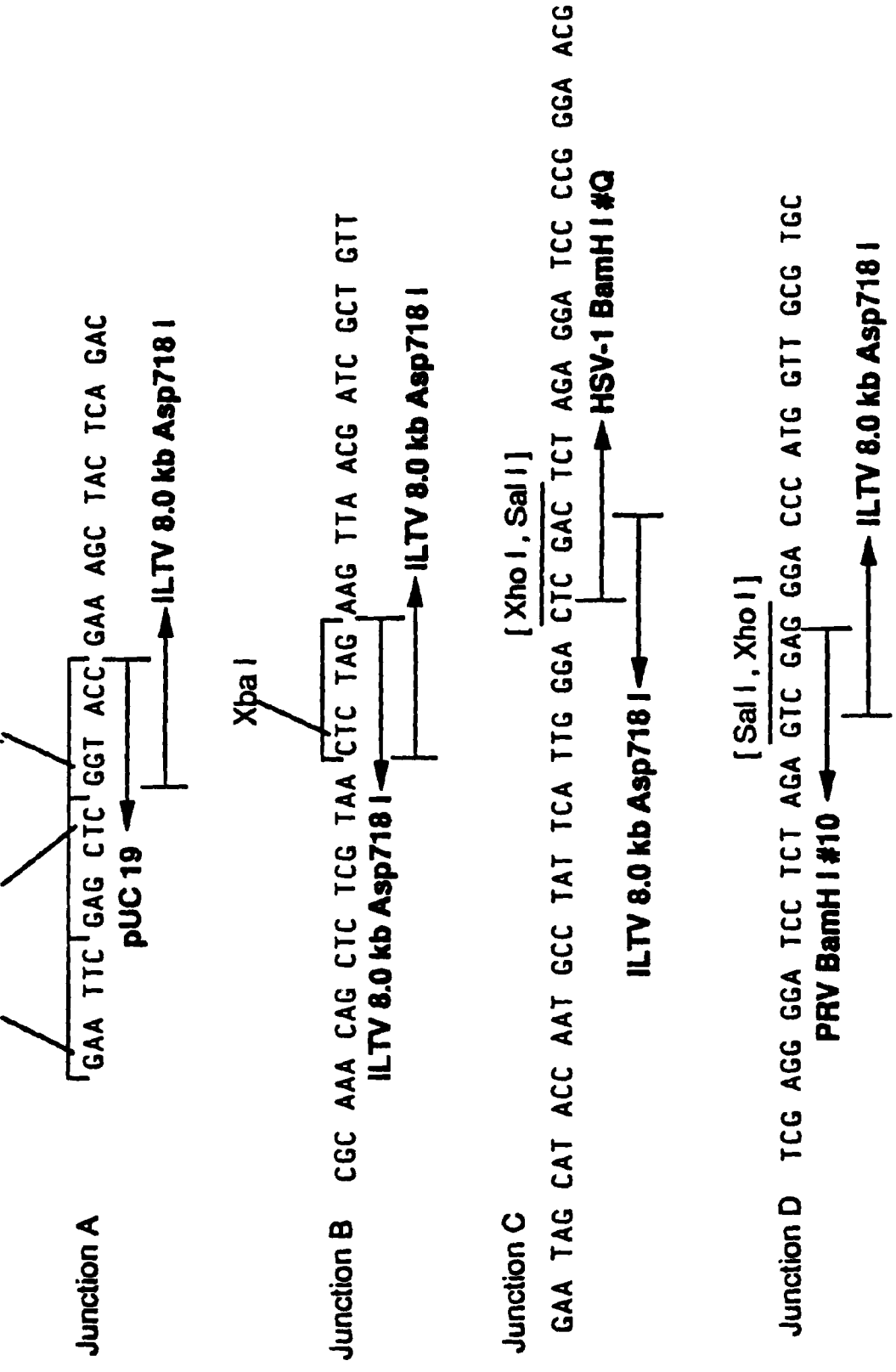
Figure 8C:
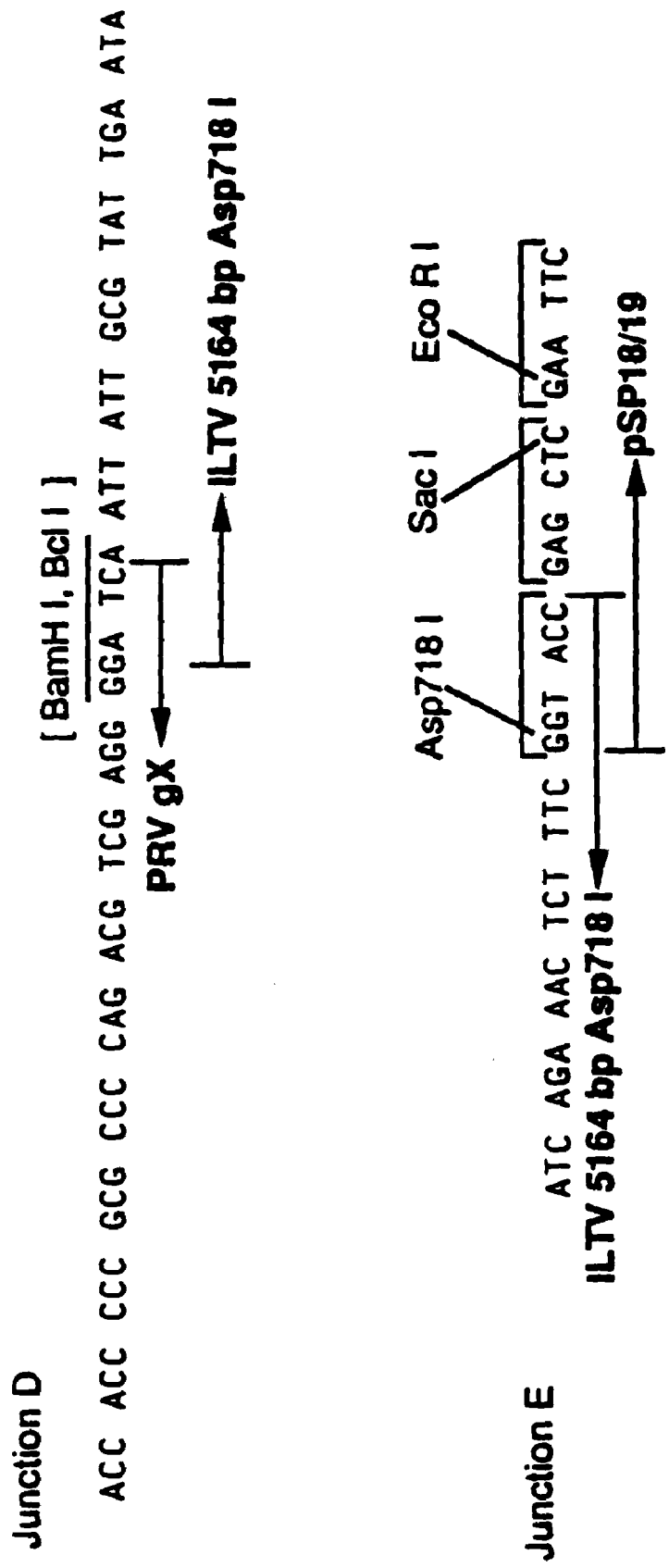
Figures 9A, 9B:
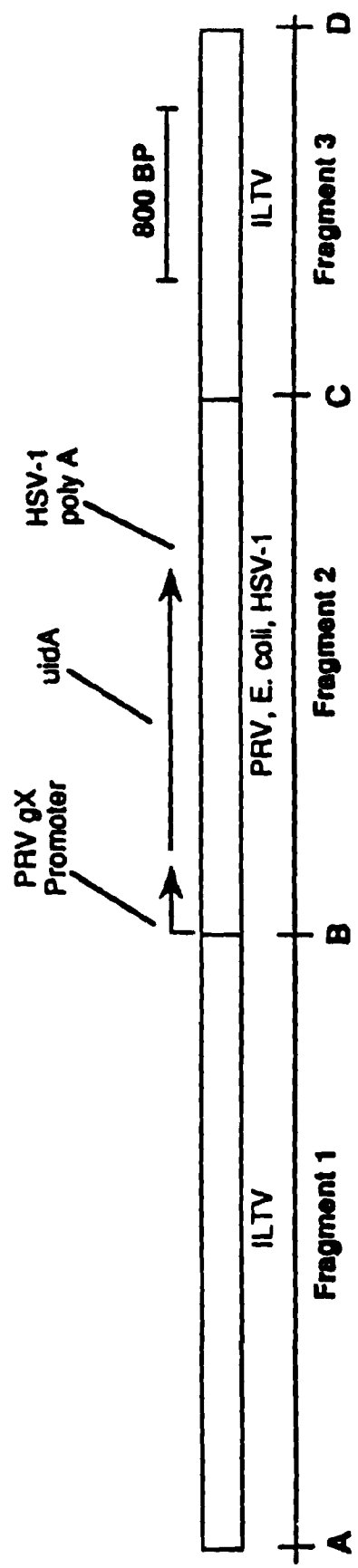
Figure 10A:
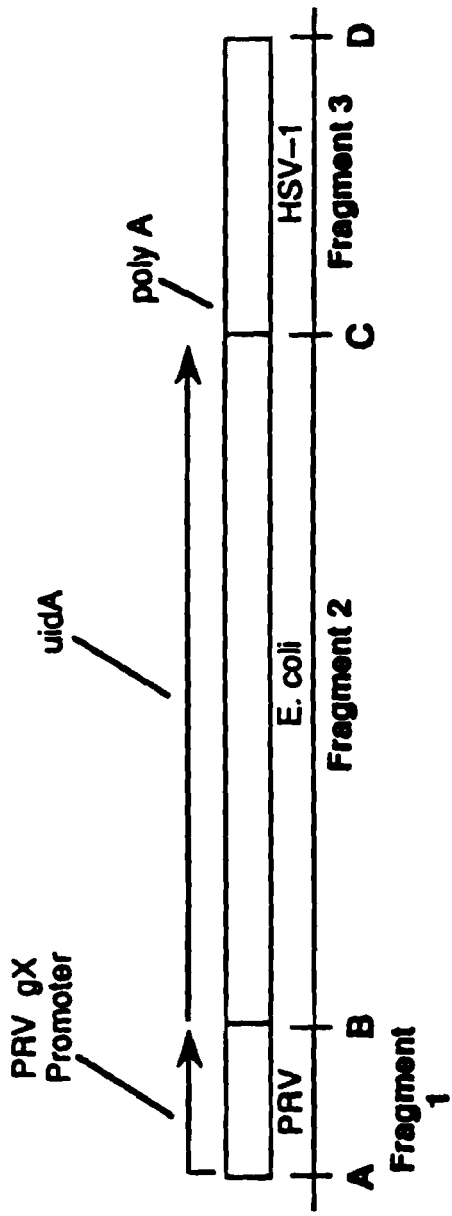
Figure 11B:
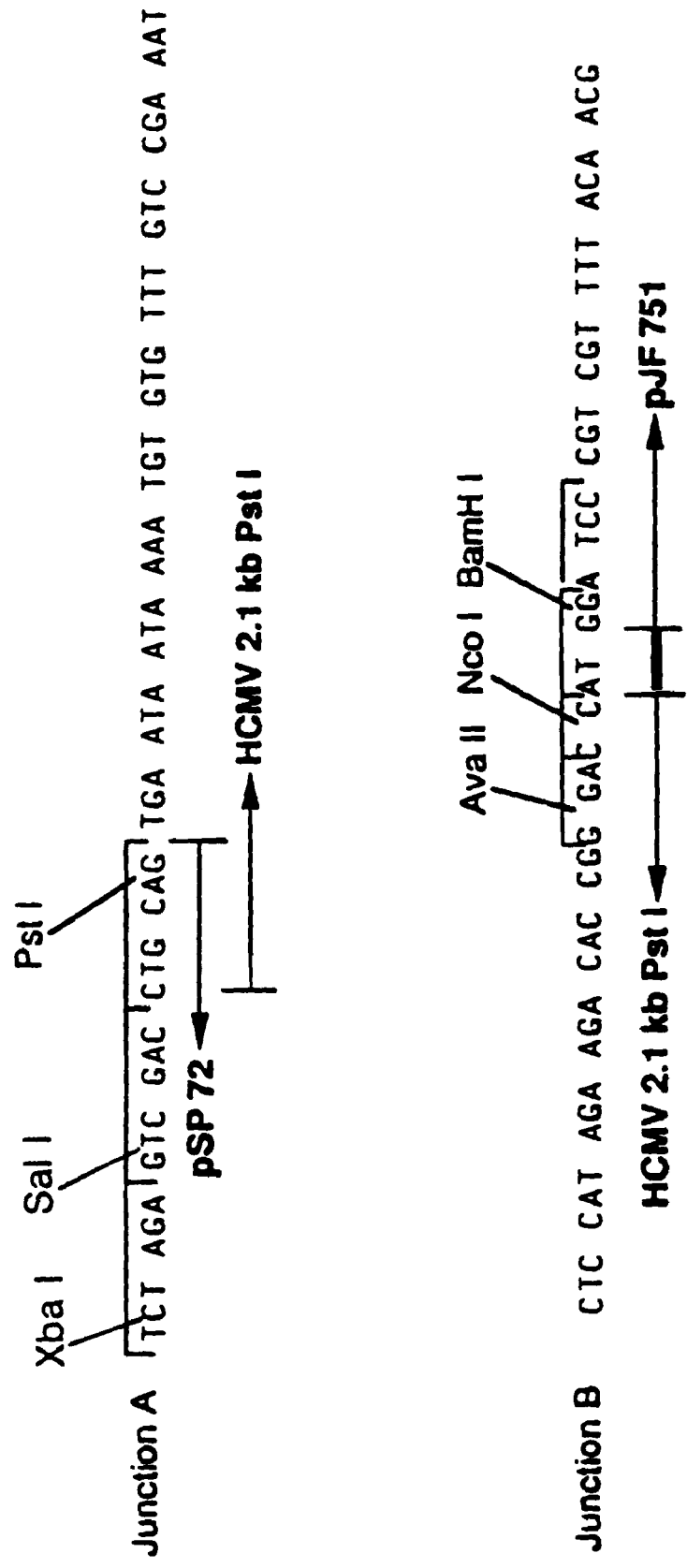
Figure 11C:
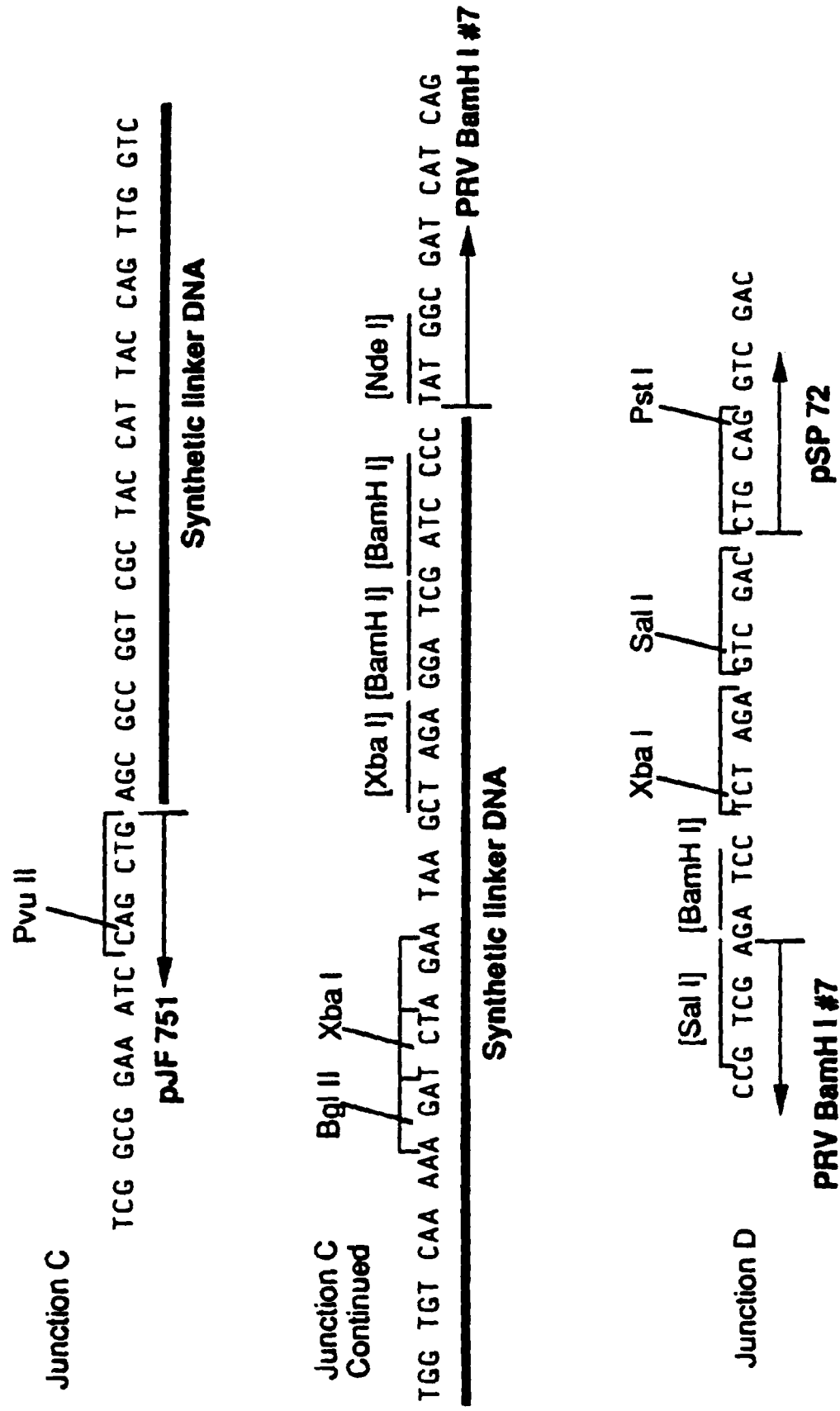

FIG. 2: Asp718 I restriction enzyme map of the infectious laryngotracheitis virus (ILTV) USDA 83-2 genome. The upper diagram identifies the unique long ($U_L$), internal repeat (IR), unique short ($U_S$), and terminal repeat (TR) sections found in the ILTV. A map of the Asp718 I restriction endonuclease sites in the ILTV genome is shown below. Letters A through O identify Asp718 I restriction endonuclease fragments with "A" representing the largest fragment. Fragment "L" is the 2.5 kb Asp718 I fragment, fragment "H" is the 5164 bp Asp718 I fragment, and fragment "G" is the 8.0 kb Asp718 I fragment. The fragments marked with asterisks contain a hypervariable region of approximately 900 bp that is repeated from one to 12 times. Since no one size predominates, these fragments appear in submolar amounts that are not well resolved on an ethidium bromide stained gel. The position of these repeats is indicated in the Figures by the crooked dashed lines.

FIG. 3: Open reading frames within the unique short region of infectious laryngotracheitis virus (ILTV) USDA 83-2. The 13.473 base pairs of the short region of ILTV contains the entire 13.098 base pair unique short region as well as 273 base pairs of repeat region at one end and 102 base pairs of repeat region at the other end. The unique short region contains 13 methionine initiated open reading frames (ORF) of greater than or equal to 110 amino acids (excluding smaller nested ORFs). All 13 ORFs were aligned to the Entrez release 6.0 virus division of the Genbank DNA database utilizing the IBI Mac Vector Protein to DNA alignment option (default settings). Eight of the ORFs exhibited significant homology to one or more other virus genes: unique short (US2), protein kinase (PK), unique long 47-like (UL47-like), and glycoproteins gG, g60, gD, gI, and gE.

FIGS. 4A-4B:

Detailed description of the DNA insertion in Homology Vector 472-73.27. Diagram showing the orientation of DNA fragments assembled in plasmid 472-73.27. The origin of each fragment is indicated in the table. The sequences located at each of the junctions between fragments are also shown (SEQ ID NO's: 20, 21, 22 and 23). The restriction sites used to generate each fragment as well as the synthetic linker sequences which were used to join the fragments are described for each junction. The location of several gene coding regions and regulatory elements is also given. Restriction sites in brackets [ ] indicate the remnants of sites which were destroyed during construction. The following abbreviations are used, infectious laryngotracheitis virus (ILTV), human cytomegalovirus immediate early (HCMV IE), pseudorabies virus (PRV), lactose operon Z gene (lacZ). *Escherichia coli* (*E. coli*), polyadenylation signal (poly A), and base pairs (BP).

FIGS. 5A-5B:

Detailed description of the DNA insertion in Homology Vector 501-94. Diagram showing the orientation of DNA fragments assembled in plasmid 501-94. The origin of each fragment is indicated in the table. The sequences located at each of the junctions between fragments are also shown (SEQ ID NO's: 24, 25, 26, and 27). The restriction sites used to generate each fragment as well as the synthetic linker sequences which were used to join the fragments are described for each junction. The location of several gene coding regions and regulatory elements is also given. Restriction sites in brackets [ ] indicate the remnants of sites which were destroyed during construction. The following abbreviations are used, infectious laryngotracheitis virus (ILTV), human cytomegalovirus immediate early (HCMV IE), pseudorabies virus (PRV), lactose operon Z gene (lacZ). *Escherichia coli* (*E. coli*), polyadenylation signal (poly A), thymidine kinase (TK), and base pairs (BP).

FIGS. 6A-6B:

Detailed description of the DNA insertion in Homology Vector 544-55.12. Diagram showing the orientation of DNA fragments assembled in plasmid 544-55.12. The origin of each fragment is indicated in the table. The sequences located at each of the junctions between fragments are also shown (SEQ ID NO's: 28, 29, 30, and 31). The restriction sites used to generate each fragment as well as the synthetic linker sequences which were used to join the fragments are described for each junction. The location of several gene coding regions and regulatory elements is also given. Restriction sites in brackets [ ] indicate the remnants of sites which were destroyed during construction. The following abbreviations are used, infectious laryngotracheitis virus (ILTV), herpes simplex virus type 1 (HSV-1), pseudorabies virus (PRV), β-glucuronidase gene (uidA). *Escherichia coli* (*E. coli*), polyadenylation signal (poly A), and base pairs (BP).

FIGS. 7A-7C:

Detailed description of the DNA insertion in Homology Vector 562-61.1F. Diagram showing the orientation of DNA fragments assembled in plasmid 562-61.1F. The origin of each fragment is indicated in the table. The sequences located at each of the junctions between fragments are also shown (SEQ ID NO's: 32, 33, 34 35, 36 and 37). The restriction sites used to generate each fragment as well as the synthetic linker sequences which were used to join the fragments are described for each junction. The location of several gene coding regions and regulatory elements is also given. Restriction sites in brackets [ ] indicate the remnants of sites which were destroyed during construction. The following abbreviations are used, infectious laryngotracheitis virus (ILTV), herpes simplex virus type 1 (HSV-1), pseudorabies virus (PRV), β-glucuronidase gene (uidA), *Escherichia coli* (*E. coli*), polyadenylation signal (poly A), and base pairs (BP).

FIGS. 8A-8C:

Detailed description of the DNA insertion in Homology Vector 560-52.F1. Diagram showing the orientation of DNA fragments assembled in plasmid 560-52.F1. The origin of each fragment is indicated in the table. The sequences located at each of the junctions between fragments are also shown (SEQ ID NO's: 38, 39, 40, 41, and 42). The restriction sites used to generate each fragment as well as the synthetic linker sequences which were used to join the fragments are described for each junction. The location of several gene coding regions and regulatory elements is also given. Restriction sites in brackets [ ] indicate the remnants of sites which were destroyed during construction. The following abbreviations are used, infectious laryngotracheitis virus (ILTV), herpes simplex virus type 1 (HSV-1), pseudorabies virus (PRV), β-glucuronidase gene (uidA), *Escherichia coli* (*E. coli*), polyadenylation signal (poly A), unique long 47 (UL47-like), open reading frame 4 (ORF4), glycoprotein G (gG), and base pairs (BP).

FIGS. 9A-9B:

Detailed description of the DNA insertion in Homology Vector 579-14.G2. Diagram showing the orientation of DNA fragments assembled in plasmid 579-14.G2. The origin of each fragment is indicated in the table. The sequences located at each of the junctions between fragments are also shown (SEQ ID NO's: 43, 44, 45, and 46). The restriction sites used to generate each fragment as well as the synthetic linker sequences which were used to join the fragments are described for each junction. The location of several gene coding regions and regulatory elements is also given. Restriction sites in brackets [ ] indicate the remnants of sites which were destroyed during construction. The following abbreviations are used, infectious laryngotracheitis virus (ILTV), herpes simplex virus type 1 (HSV-1), pseudorabies virus (PRV), β-glucuronidase gene (uidA), *Escherichia coli* (*E. coli*), polyadenylation signal (poly A), and base pairs (BP).

FIGS. 10A-10B:

Detailed description of the DNA insertion in Plasmid Vector 544-39.13. Diagram showing the orientation of DNA fragments assembled in plasmid 544-39.13. The origin of each fragment is indicated in the table. The sequences located at each of the junctions between fragments are also shown (SEQ ID NO's: 47, 48, 49, and 50). The restriction sites used to generate each fragment as well as the synthetic linker sequences which were used to join the fragments are described for each junction. The synthetic linker sequences are underlined by a heavy bar. The location of several gene coding regions and regulatory elements is also given. Restriction sites in brackets [ ] indicate the remnants of sites which were destroyed during construction. The following abbreviations are used, pseudorabies virus (PRV), β-glucuronidase gene (uidA), *Escherichia coli* (*E. coli*), herpes simplex virus type 1 (HSV-1), polyadenylation signal (poly A), and base pairs (BP).

FIGS. 11A-11C:

Detailed description of the DNA insertion in Plasmid Vector 388-65.2. Diagram showing the orientation of DNA fragments assembled in plasmid 388-65.2. The origin of each fragment is indicated in the table. The sequences located at each of the junctions between fragments are also shown (SEQ ID NO's: 51, 52, 53, and 54). The restriction sites used to generate each fragment as well as the synthetic linker sequences which were used to join the fragments are described for each junction. The synthetic linker sequences are underlined by a heavy bar. The location of several gene coding regions and regulatory elements is also given. Restriction sites in brackets [ ] indicate the remnants of sites which were destroyed during construction. The following abbreviations are used, human cytomegalovirus immediate early (HCMV IE), lactose operon Z gene (lacZ). *Escherichia coli* (*E. coli*), pseudorabies virus (PRV), polyadenylation signal (poly A), and base pairs (BP).

Figure 12:
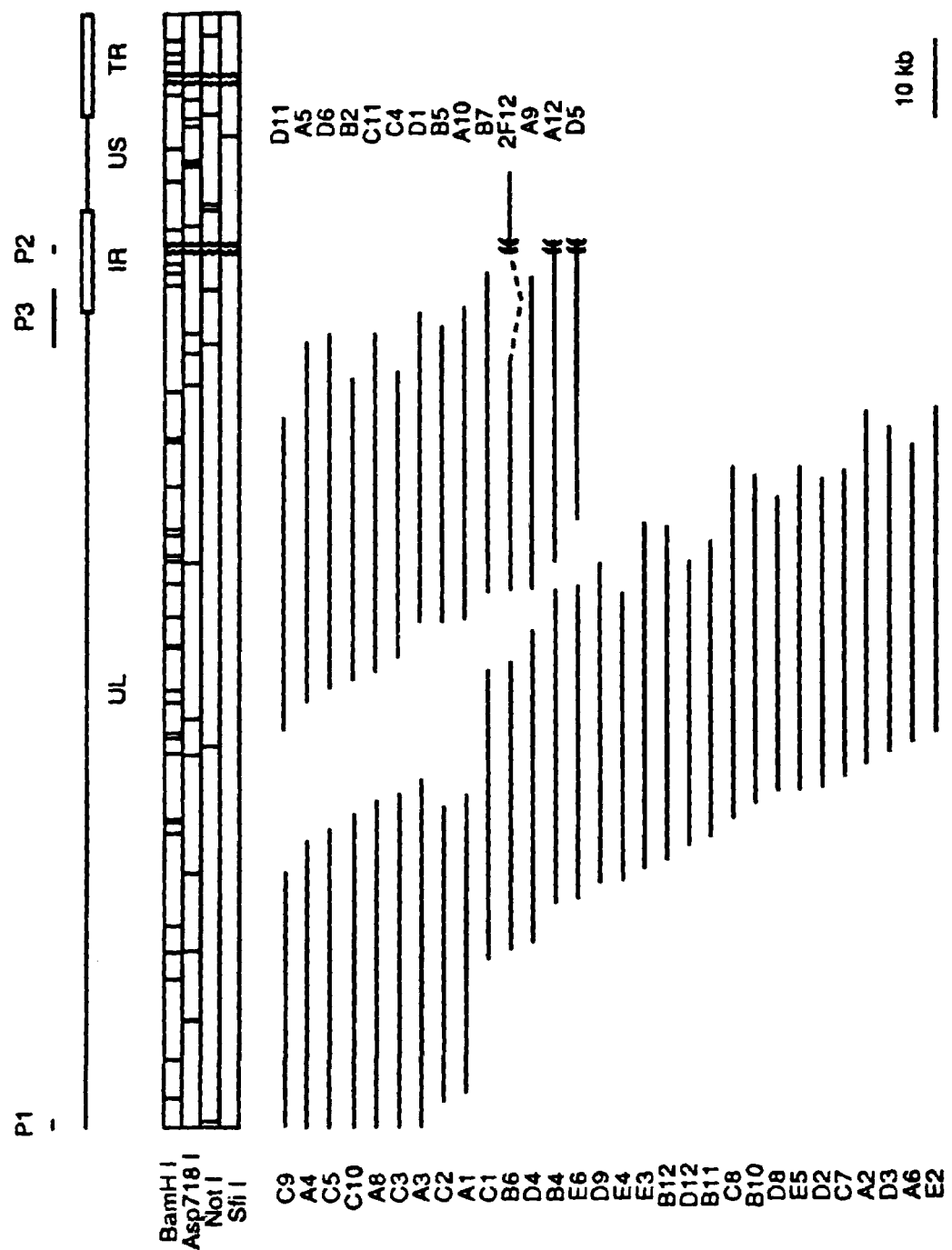

FIG. 12: The genome of the ILTV virus. Identifying the unique long (UL), unique short (US), internal repeat (IR), and terminal repeat (TR) Is shown. The BamHI, Asp718I, NotI, and SfiI restriction maps of the virus are drawn underneath, with the highly-repetitive region of the short repeats indicated by a set of wavy lines. The position of the cosmids used to determine the map of ILTV are drawn beneath the restriction map. Note that cosmid 2F12 contains two non-contiguous sections. Three probes used to characterize the ILTV genome are indicated as P1, P2, and P3. P1 is a 0.9 kb NotI fragment found at the terminus of the unique long region, P2 is the 856 bp HindIII fragment found in multiple copies within the short repeat, and P3 Is a 6.6 kb NotI fragment used to identify the fragments at the end of the terminal repeat.

Figure 13:
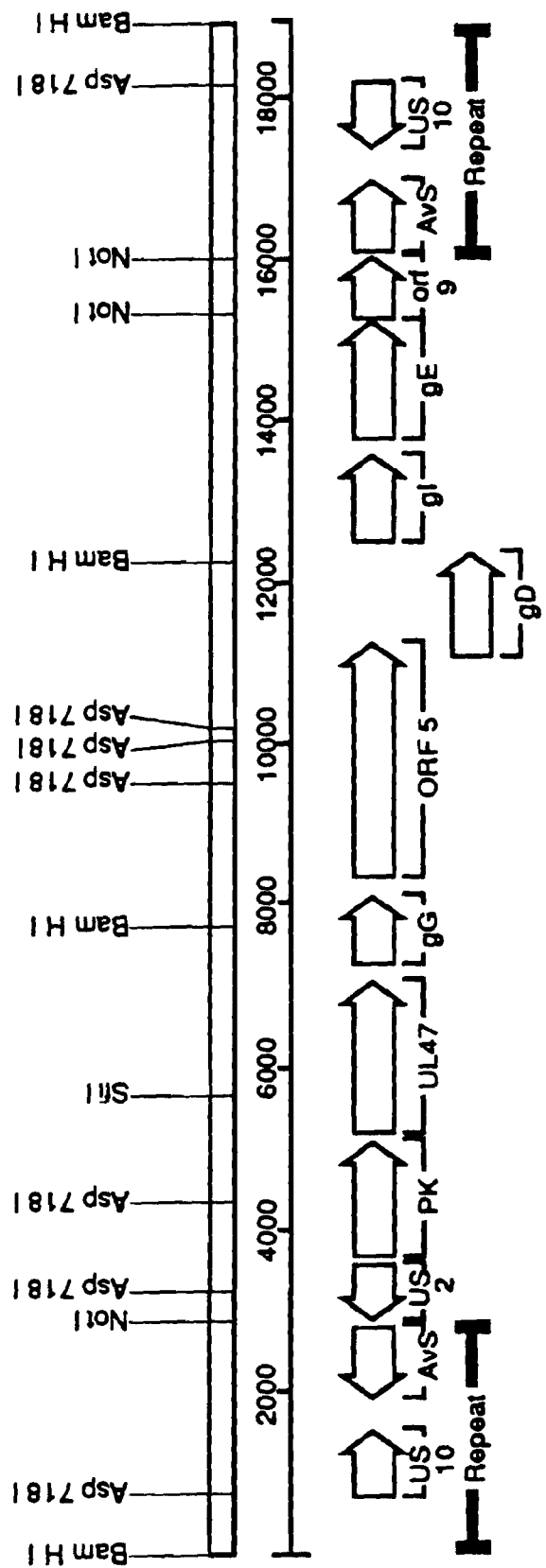

FIG. 13: The region sequenced, and the positions of the Asp718I, BamHI, NotI, and SfiI sites are shown. The and extent and orientation of the open reading frames found in the ILTV unique short and the flanking short repeat regions are indicated.

Figure 14:
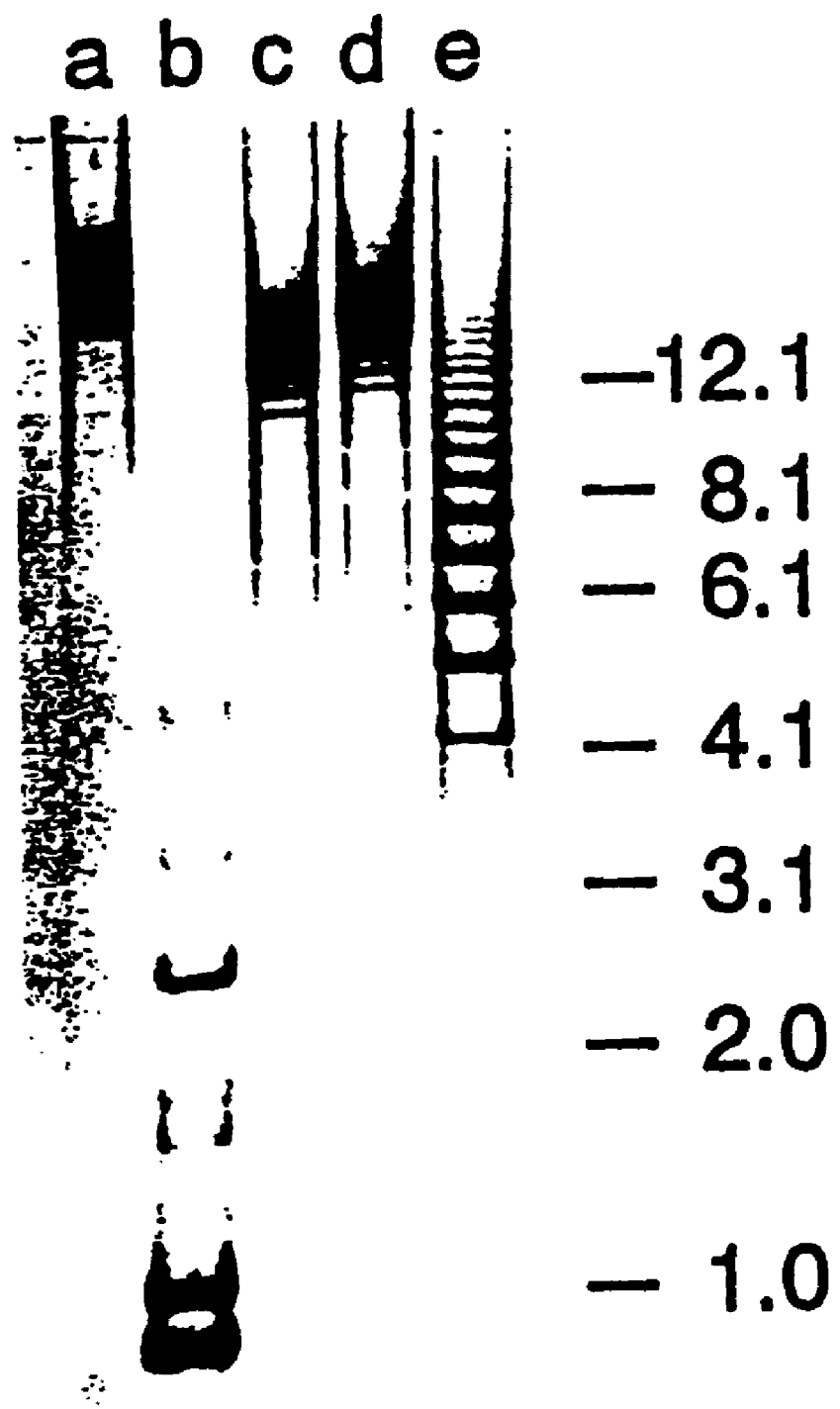

FIG. 14: Southern blot showing the repetition of an 856 bp element within the short repeat. Genomic ILTV DNA digested with SfiI (a), HindIII (b), NotI (c), Asp718I (d), or BamHI (e) was probed with an 856 bp HindIII fragment from the short repeat. Positions of molecular weight markers are indicated.

Figure 15:
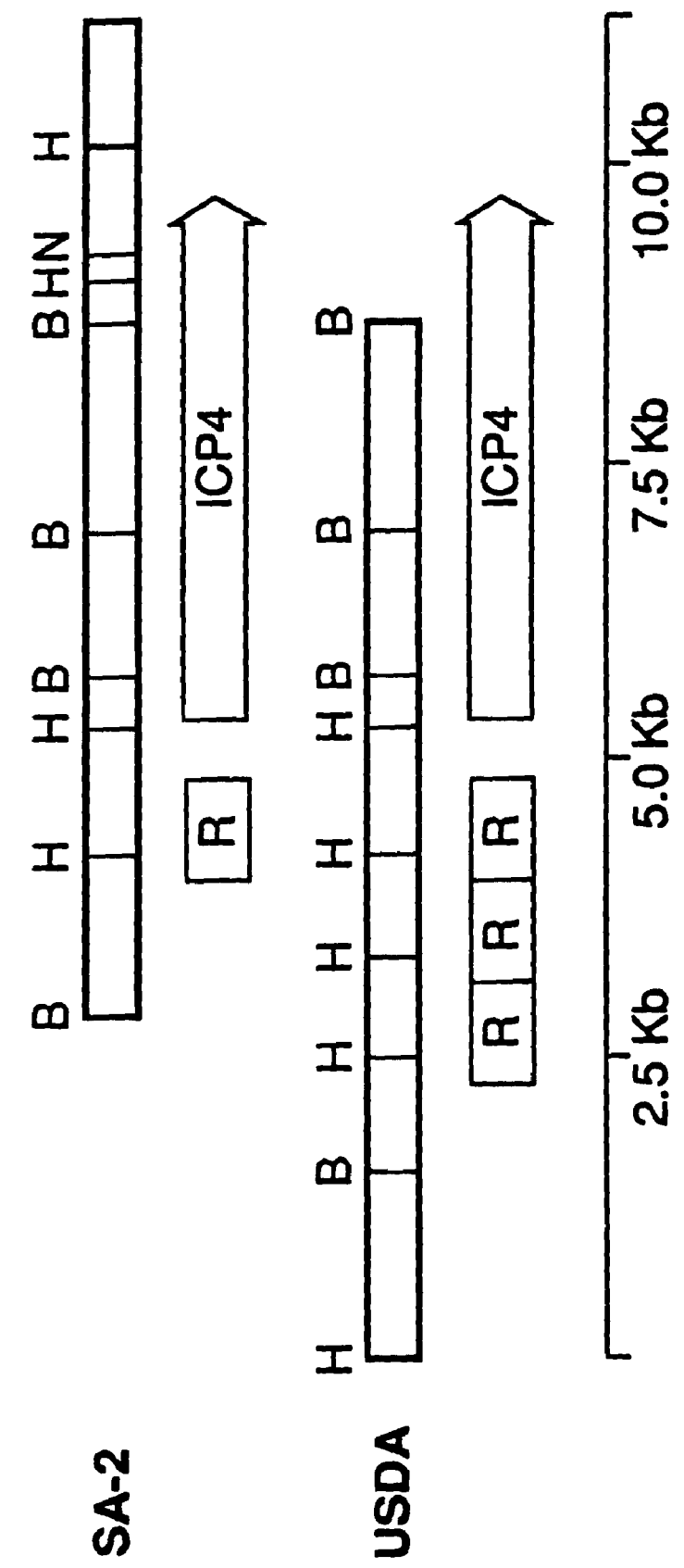

FIG. 15: Depiction of the position of the 856 bp repeat region in the USDA strain, compared to the same region from the SA-2 strain as described by Johnson et al. Three repeats are arbitrarily shown in the USDA strain, the region is not repeated in SA2, B=BamHI, H=HindIII, R-856 bp repeat.

Figure 16:

FIG. 16: Southern blot identifying fragments from the internal and terminal repeat that hybridized to a 6.6 kb NotI fragment containing the junction of the unique long and the internal repeat. Genomic ILTV DNA digested with NotI (a), Asp718I (b), and BamHI (c) was probed with the 6.6 kb NotI fragment. Positions of molecular weight markers are indicated.

FIG. 17: The relationship of herpesvirus UL47 proteins to each other and to the ILTV UL47 homolog in a conserved region. Amino acids shared between ILTV UL47 and the other UL47 proteins are in boldface type (SEQ ID NOs: 73-76). Pairwise comparisons have been made between the sequences as shown. A vertical bar indicates an identical amino acid, two dots indicate a positive probable acceptable mutation rate and one dot indicates a neutral probable acceptable mutation rate (60).

DETAILED DESCRIPTION OF THE INVENTION

The present invention provides a recombinant infectious laryngotracheitis virus comprising the infectious laryngotracheitis viral genome which contains a deletion in the unique short region of the viral genome, wherein the deletion is in the glycoprotein gG gene. Said deletion attenuates the virus, rendering it suitable for use as a vaccine against infectious laryngotracheitis virus. A preferred embodiment of this invention is a recombinant infectious laryngotracheitis designated S-ILT-014 (ATCC Accession No. 2427). The S-ILT-014 virus has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. on Sep. 22, 1993 under ATCC Accession No. 2427). Another preferred embodiment of this invention is a recombinant infectious laryngotracheitis virus designated S-ILT-002.

For purposes of this invention, "a recombinant infectious laryngotracheitis virus" is a live infectious laryngotracheitis virus which has been generated by the recombinant methods well known to those of skill in the art, e.g., the methods set forth in DNA TRANSFECTION FOR GENERATING RECOMBINANT ILT VIRUS in *Materials and Methods*, and the virus has not had genetic material essential for the replication of the infectious laryngotracheitis virus deleted.

The present invention further provides a recombinant infectious laryngotracheitis virus comprising the infectious laryngotracheitis viral genome which contains a deletion in the glycoprotein gG gene and a deletion in the US2 gene. One preferred embodiment of this invention is a recombinant infectious laryngotracheitis virus designated S-ILT-009.

The present invention further provides a recombinant infectious laryngotracheitis virus comprising the infectious laryngotracheitis viral genome which contains a deletion in the glycoprotein gG gene and a deletion in the ORF4 gene.

The present invention further provides a recombinant infectious laryngotracheitis virus which comprises the infectious laryngotracheitis viral genome which contains a deletion in the glycoprotein gG gene and a deletion in the UL47-like gene.

The present invention further provides a recombinant infectious laryngotracheitis virus which comprises the infectious laryngotracheitis viral genome which contains a deletion in the glycoprotein gG gene, a deletion in the ORF4 gene, and a deletion in the UL47-like gene. A preferred embodiment of this invention is a recombinant infectious laryngotracheitis virus designated S-ILT-015.

The present invention further provides a recombinant infectious laryngotracheitis virus which comprises the infectious laryngotracheitis viral genome which contains a deletion in the glycoprotein gG gene and a deletion in the glycoprotein g60 gene. A preferred embodiment of this invention is a recombinant infectious laryngotracheitis virus designated S-ILT-017.

The present invention further provides a recombinant infectious laryngotracheitis virus comprising the infectious laryngotracheitis viral genome which contains a deletion in the glycoprotein gG gene and a deletion in the glycoprotein gI gene.

The present invention further provides a recombinant infectious laryngotracheitis virus which comprises the infectious laryngotracheitis viral genome containing a deletion in the glycoprotein gG gene and a deletion in the thymidine kinase (TK) gene.

The present invention further provides a recombinant infectious laryngotracheitis virus comprising the infectious laryngotracheitis virus genome which contains a deletion in the unique short region of the viral genome, wherein the deletion in the glycoprotein gG gene, and which also contains an insertion of a foreign gene. The foreign gene is inserted into a non-essential site of the infectious laryngotracheitis viral genome in such a way that it is capable of being expressed in a recombinant infectious laryngotracheitis infected host cell.

For purposes of this invention, "a non-essential site" of the infectious laryngotracheitis viral genome is a region of the viral genome which is not necessary for viral infection and replication.

The following non-essential sites of the infectious laryngotracheitis viral genome are preferred sites for inserting a foreign gene into the virus: the thymidine kinase (TK) gene, the US2 gene, the UL47-like gene, the ORF4 gene, the glycoprotein gG gene, the glycoprotein g60 gene, and the glycoprotein gI gene.

The foreign gene, which is inserted into a non-essential site in the infectious laryngotracheitis viral genome, may encode a screenable marker, such as *E. coli* B-galactosidase or *E. coli* B-glucuronidase.

The foreign gene which is inserted into a non-essential site in the infectious laryngotracheitis viral genome, may encode an antigenic polypeptide which, when introduced into the host cell induces production of protective antibodies against an avian disease causing agent from which the antigen is derived or derivable. Antigenic polypeptide which includes, but is not limited to: marek's disease virus (MDV) gA, marek's disease virus gB, marek's disease virus gD, Newcastle disease virus (NDV) HN, Newcastle disease virus F, infectious laryngotracheitis virus (ILT) gB, infectious laryngotracheitis virus gI, infectious laryngotracheitis virus gD, infectious bursal disease virus (IBDV) VP2, infectious bursal disease virus VP3, infectious bursal disease virus VP4, infectious bursal disease virus polyprotein, infectious bronchitis virus (IBV) spike, infectious bronchitis virus matrix, avian encephalomyelitis virus, avian reovirus, avian paramyxovirus, avian influenza virus, avian adenovirus, fowl pox virus, avian coronavirus, avian rotavirus, chick anemia virus. *Salmonella* spp. *E. coli, Pasieurella* spp., *Bordelella* spp., *Eimeria* spp. *Hislomonas* spp. *Trichomonas* spp. Poultry nematodes, cestodes, trematodes, poultry mites/lice, and poultry protozoa.

In one embodiment of the recombinant infectious laryngotracheitis virus the foreign DNA sequence encodes a cytokine. In another embodiment the cytokine is chicken myelomonocytic growth factor (cMGF) or chicken interferon (cIFN). Cytokines include, but are not limited to: transforming growth factor beta, epidermal growth factor family, fibroblast growth factors, hepatocyte growth factor, insulin-like growth factors. B-nerve growth factor, platelet-derived growth factor, vascular endothelial growth factor, interleukin 1, IL-1 receptor antagonist, interleukin 2, interleukin 3, interleukin 4, interleukin 5, interleukin 6, IL-6 soluble receptor, interleukin 7, interleukin 8, interleukin 9, interleukin 10, interleukin 11, interleukin 12, interleukin 13, angiogenin, chemokines, colony stimulating factors, granulocyte-macrophage colony stimulating factors, erythropoietin, interferon, interferon gamma, leukemia inhibitory factor, oncostatin M, pleiotrophin, secretory leukocyte protease inhibitor, stem cell factor, tumor necrosis factors, and soluble TNF receptors. These cytokines are from humans, bovine, equine, feline, canine, porcine or avian. Recombinant ILT virus expressing cytokines is useful to enhance the immune response when combined with vaccines containing antigens of disease causing microorganisms.

Recombinant infectious laryngotracheitis virus expressing cytokines is used to enhance the immune response either alone or when combined with vaccines containing cytokines or antigen genes of disease causing microorganisms.

Antigenic polypeptide of a human pathogen which are derived from human herpesvirus include, but are not limited to: hepatitis B virus and hepatitis C virus hepatitis B virus surface and core antigens, hepatitis C virus, human immunodeficiency virus, herpes simplex virus-1, herpes simplex virus-2, human cytomegalovirus, Epstein-Barr virus, Varicella-Zoster virus, human herpesvirus-6, human herpesvirus-7, human influenza, measles virus, hantaan virus, pneumonia virus, rhinovirus, poliovirus, human respiratory syncytial virus, retrovirus, human T-cell leukemia virus, rabies virus, mumps virus, malaria (*Plasmodium falciparum*), Bordetella pertussis, Diptheria, *Rickettsia prowazekii*, *Borrelia berfdorferi*, Tetanus toxoid, malignant tumor antigens.

The antigenic polypeptide of an equine pathogen is derived from equine influenza virus, or equine herpesvirus. In one embodiment the antigenic polypeptide is equine influenza neuraminidase or hemagglutinin. Examples of such antigenic polypeptide are: equine influenza virus type A/Alaska 91 neuraminidase and hemagglutinin, equine influenza virus type A/Prague 56 neuraminidase and hemagglutinin, equine influenza virus type A/Miami 63 neuraminidase, equine influenza virus type A/Kentucky 81 neuraminidase and hemagglutinin, equine herpesvirus type 1 glycoprotein B, and equine herpesvirus type 1 glycoprotein D, *Streptococcus equi*, equine infectious anemia virus, equine encephalitis virus, equine rhinovirus and equine rotavirus.

The antigenic polypeptide of an equine pathogen is derived from bovine respiratory syncytial virus or bovine parainfluenza virus, and is capable of being expressed in a host infected by the recombinant infectious bovine rhinotracheitis virus. For example, the antigenic polypeptide is derived from bovine respiratory syncytial virus attachment protein (BRSV G), bovine respiratory syncytial virus fusion protein (BRSV F), bovine respiratory syncytial virus nucleocapsid protein (BRSV N), bovine parainfluenza virus type 3 fusion protein, and the bovine parainfluenza virus type 3 hemagglutinin neuraminidase.

The foreign gene may be put under control of an endogenous upstream infectious laryngotracheitis virus promoter, or it may be put under control of a heterologous upstream promoter. The heterologous upstream promoter may be derived from the HCMV IE promoter, the PRV gX promoter, and BHV-1.1 VP8 promoter.

The present invention further provides a recombinant infectious laryngotracheitis virus comprising the infectious laryngotracheitis viral genome which contains a deletion or other alteration in the unique short region of the viral genome, wherein the deletion or alteration is in the glycoprotein gG gene, so that upon replication, the recombinant virus produces no glycoprotein gG. The following recombinant viruses axe preferred embodiments of this invention: A recombinant infectious laryngotracheitis virus designated S-ILT-002, S-ILT-014, S-ILT-009, S-ILT-015, and S-ILT-017.

The present invention further provides a recombinant infectious laryngotracheitis virus comprising the infectious laryngotracheitis viral genome which contains a deletion or other alteration in the unique short region of the viral genome, wherein the deletion or alteration is in the glycoprotein gI gene, so that upon replication, the recombinant virus produces no glycoprotein gI.

The present invention further provides a recombinant infectious laryngotracheitis virus comprising the infectious laryngotracheitis viral genome which contains a deletion or other alteration in the unique short region of the viral genome, wherein the deletion or alteration is in the glycoprotein gG gene and in the glycoprotein gI gene, so that upon replication, the recombinant virus produces no glycoprotein gG and no glycoprotein gI.

The present invention further provides a recombinant infectious laryngotracheitis virus comprising the infectious laryngotracheitis viral genome which contains a deletion in the unique short region of the viral genome, wherein the deletion is in the US2 gene. UL47-like gene, glycoprotein g60 gene. It is contemplated that a deletion in any one of these genes will attenuate the virus, rendering it suitable to be used as a vaccine against infectious laryngotracheitis virus.

The present invention further provides a recombinant infectious laryngotracheitis virus which comprises a foreign gene inserted within the unique short region of the infectious laryngotracheitis viral genome, provided, however, that the insertion is not in the protein kinase gene, the glycoprotein gD gene, the glycoprotein gE gene and the ORF10 gene. The foreign gene is inserted in such a way that it is capable of being expressed in the recombinant infectious laryngotracheitis virus infected host cell. Preferred insertion sites are the US2 gene, the UL47-like gene, the ORF4 gene and the glycoprotein g60 gene.

A foreign gene may be inserted within any one of these sites in such a way that it may be expressed in a host cell which is infected which the recombinant infectious laryngotracheitis virus of the present invention.

The foreign gene thus inserted may encode a screenable marker, such as *E. coli* β-galactosidase or *E. coli* β-glucuronidase.

The foreign gene thus inserted may encode an antigenic polypeptide which, when introduced into the host cell, induces production of protective antibodies against an avian disease causing agent from which the antigen is derived or derivable. Such antigenic polypeptide may be derived or derivable from infectious bronchitis virus, Newcastle disease virus, infectious bursal disease virus, and Marek's disease virus. Such antigenic polypeptide may also be derived or derivable from avian encephalomyelitis virus, avian reovirus, avian paramyxovirus, avian influenza virus, avian adenovirus, fowl pox virus, avian coronavirus, avian rotavirus, chick anemia agent, *Salmonella* spp. *E. coli. Pasterurella* spp., *Bor-* *detella* spp. *Eimeria* spp. *Histomonas* spp., *Trichomonas* spp, Poultry nematodes, cestodes, trematodes, poultry mites/lice, poultry protozoa.

The foreign gene thus inserted may be put under control of an endogenous upstream infectious laryngotracheitis virus promoter, or it may be put under control of a heterologous upstream promoter. The heterologous upstream promoter may be the HCMV IE promoter, the PRV gX promoter or BHV-1.1 VP8 promoter.

The present invention further provides a vaccine for infectious laryngotracheitis virus which comprises a suitable carrier and an effective immunizing amount of any of the recombinant infectious laryngotracheitis virus of the present invention. This vaccine may contain either inactivated or live recombinant virus.

Suitable carriers for the recombinant virus are well known in the art and include proteins, sugars, etc. One example of such a suitable carrier is a physiologically balanced culture medium containing one or more stabilizing agents such as hydrolyzed proteins, lactose, etc. Preferably, the live vaccine is created by taking tissue culture fluids and adding stabilizing agents such as stabilizing, hydrolyzed proteins. Preferably, the inactivated vaccine uses tissue culture fluids directly after inactivation of the virus.

The present invention further provides a vaccine which comprises a suitable carrier and an effective immunizing amount of a recombinant infectious laryngotracheitis virus comprising the infectious laryngotracheitis viral genome which contains a deletion in the unique short region of the viral genome, wherein the deletion is in the glycoprotein gG gene. A preferred embodiment of this invention is a vaccine which comprises a suitable carrier and an effective immunizing amount of any one of the following viruses: recombinant infectious laryngotracheitis viruses designated S-ILT-014, S-ILT-002, S-ILT-009, S-ILT-015 and S-ILT-017.

The present invention further provides a multivalent vaccine for infectious laryngotracheitis virus and for one or more of other avian diseases which comprises an effective immunizing amount of a recombinant virus comprising the infectious laryngotracheitis viral genome which contains a deletion in the unique short region, wherein the deletion is in the glycoprotein gG gene, and an insertion of a foreign gene into a non-essential site of the viral genome.

The foreign gene encodes an antigenic polypeptide which induces host cell production of protective antibodies against an avian disease causing agent from which the antigen is derived or derivable.

The foreign gene may be derived or derivable from infectious bronchitis virus, Newcastle disease virus, infectious bursal disease virus, and Marek's disease virus, avian encephalomyelitis virus, avian reovirus, avian paramyxovirus, avian influenza virus, avian adenovirus, fowl pox virus, avian coronavirus, avian rotavirus, chick anemia agent, *Salmonella* spp., *E. coli, Pasteurella* spp., *Bordetella* spp., *Eimeria* spp., *Histomonas* spp., *Trichomonas* spp., poultry nematodes, cestodes, trematodes, poultry mites/lice, poultry protozoa.

The present invention further provides a vaccine which comprises a suitable carrier and an effective immunizing amount of a recombinant infectious laryngotracheitis virus comprising the infectious laryngotracheitis viral genome containing a deletion or other alteration in the unique short region of the viral genome, wherein the deletion or alteration is in the glycoprotein gG gene, so that upon replication, the recombinant virus produces no glycoprotein gG. A preferred embodiment of this invention is a vaccine which comprises a suitable carrier and an effective immunizing amount of any one of the following viruses: recombinant infectious laryngotracheitis viruses designated S-ILT-014. S-ILT-002, S-ILT-009, S-ILT-015 and S-ILT-017.

The present invention further provides a vaccine which comprises a suitable carrier and an effective immunizing amount of a recombinant infectious laryngotracheitis virus comprising the infectious laryngotracheitis viral genome which contains a deletion or other alteration in the unique short region of the viral genome, wherein the deletion or alteration is in the glycoprotein gI gene so that upon replication, the recombinant virus produces no glycoprotein gI.

The present invention further provides a vaccine which comprises a suitable carrier and an effective immunizing amount of a recombinant infectious laryngotracheitis virus comprising the infectious laryngotracheitis viral genome which contains a deletion or other alteration in the unique short region of the viral genome, wherein the deletion or alteration is in the glycoprotein gG gene and the glycoprotein gI gene so that upon replication, the recombinant virus produces no glycoprotein gG and glycoprotein gI.

The present invention further provides a vaccine which comprises a suitable carrier and an effective immunizing amount of a recombinant infectious laryngotracheitis virus comprising the infectious laryngotracheitis viral genome which contains a deletion in the unique short region of the viral genome, wherein the deletion is in the US2 gene, UL47-like gene, or glycoprotein g60 gene.

The present invention further provides a vaccine which comprises a suitable carrier and an effective immunizing amount of a recombinant infectious laryngotracheitis virus comprising the infectious laryngotracheitis viral genome which contains a deletion in the unique short region of the viral genome, wherein the deletion is in the US2 gene, ORF4 gene, UL47-like gene, or glycoprotein g60 gene, and insertion of a foreign gene into a non-essential site in the viral genome.

The foreign gene encodes an antigenic polypeptide which induces host cell production of protective antibodies against an avian disease causing agent from which the antigen is derived or derivable.

The foreign gene may be derived or derivable from infectious bronchitis virus. Newcastle disease virus, infectious bursal disease virus, and Marek's disease virus, avian encephalomyelitis virus, avian reovirus, avian paramyxovirus, avian influenza virus, avian adenovirus, fowl pox virus, avian coronavirus, avian rotavirus, chick anemia agent, *Salmonella* spp., *E. coli, Pasteurella* spp. *Bordetella* spp., *Eimeria* spp., *Histomonas* spp., *Trichomonas* spp. poultry nematodes, cestodes, trematodes, poultry mites/lice, poultry protozoa.

The present invention further provides a vaccine which comprises a suitable carrier and an effective immunizing amount of a recombinant infectious laryngotracheitis virus comprising the infectious laryngotracheitis viral genome which contains an insertion of a foreign gene into a non-essential site in the viral genome. The foreign gene encodes an antigenic polypeptide which induces host cell production of protective antibodies against an avian disease causing agent from which the antigen is derived or derivable.

The foreign gene may be derived or derivable from infectious bronchitis virus, Newcastle disease virus, infectious bursal disease virus, and Marek's disease virus, avian encephalomyelitis virus, avian reovirus, avian paramyxovirus, avian influenza virus, avian adenovirus, fowl pox virus, avian coronavirus, avian rotavirus, chick anemia agent, *Salmonella* spp. *E. coli, Pasterurella* spp., *Bordetella* spp. *Eimeria* spp. *Histomonas* spp., *Trichomonas* spp, Poultry nematodes, cestodes, trematodes, poultry mites/lice, poultry protozoa.

The present invention further provides a method of immunizing an animal against infectious laryngotracheitis virus which comprises administering to chickens or other poultry an effective immunizing dose of any of the vaccines of the present invention.

The present invention further provides a method for distinguishing chickens or other poultry which are vaccinated with an effective immunizing amount of a recombinant virus which produces no glycoprotein gG from those which are infected with a naturally-occurring infectious laryngotracheitis virus. This method comprises analyzing a sample of body fluid from the chickens or other poultry for the presence of glycoprotein gG of the infectious laryngotracheitis virus and at least one other antigen normally expressed in chickens or other poultry infected by a naturally-occurring infectious laryngotracheitis virus. The presence of antigen which is normally expressed in chickens or other poultry infected by a naturally-occurring infectious laryngotracheitis virus and the absence of glycoprotein gG in the body fluid is indicative of being vaccinated with the recombinant vaccine and not infected with a naturally-occurring infectious laryngotracheitis virus. The presence of glycoprotein gG and the antigen in the body fluid may be determined by detecting in the body fluid antibodies specific for the antigen and glycoprotein gG.

The present invention further provides a method for distinguishing chickens or other poultry which are vaccinated with an effective immunizing amount of a recombinant infectious laryngotracheitis virus which produces no glycoprotein gI from those which are infected with a naturally-occurring infectious laryngotracheitis virus. This method comprises analyzing a sample of body fluid from the chickens or other poultry for the presence of glycoprotein gI of the infectious laryngotracheitis virus and at least one other antigen normally expressed in chickens or other poultry infected by a naturally-occurring infectious laryngotracheitis virus. The presence of the antigen which is normally expressed in chickens or other poultry infected by a naturally-occurring infectious laryngotracheitis virus and the absence of glycoprotein gI in the body fluid is indicative of being vaccinated with the recombinant vaccine and not infected with a naturally-occurring infectious laryngotracheitis virus. The presence of the antigen and glycoprotein gI in the body fluid may be determined by detecting in the body fluid antibodies specific for the antigen and glycoprotein gI.

The present invention further provides a method for distinguishing chickens or other poultry which are vaccinated with an effective immunizing amount of a recombinant virus which produces no glycoprotein gG and no glycoprotein gI from those which are infected with a naturally-occurring infectious laryngotracheitis virus. This method comprises analyzing a sample of body-fluid from the chickens or other poultry for the presence of glycoprotein gG and gI of the infectious laryngotracheitis virus and at least one other antigen normally expressed in an animal infected by a naturally-occurring infectious laryngotracheitis virus. The presence of the antigen which is normally expressed in chickens or other poultry by a naturally-occurring infectious laryngotracheitis virus and the absence of glycoprotein gG and gI in the body fluid is indicative of being vaccinated with the vaccine and not infected with a naturally-occurring infectious laryngotracheitis virus. The presence of the antigen and glycoprotein gG and gI in the body fluid may be determined by detecting in the body fluid antibodies specific for the antigen and glycoprotein gG and gI.

The present invention further provides a homology vector for producing a recombinant infectious laryngotracheitis virus by inserting a foreign DNA into the unique short region of the infectious laryngotracheitis genomic DNA, which comprises a double-stranded DNA molecule consisting essentially of a double-stranded foreign gene, which is flanked on either side by the double-stranded DNA homologous to the DNA located in the unique short region of the genomic DNA, provided, however, that the flanking sequences are not homologous to the glycoprotein gD gene, the glycoprotein gE gene, the protein kinase gene, and the ORF10 gene. The foreign gene may encode a screenable marker, such as E. coli B-galactosidase or E. coli B-glucuronidase.

The present invention further provides a homology vector for producing a recombinant infectious laryngotracheitis virus by deleting DNA which encodes a screenable marker, which has been inserted into the infectious laryngotracheitis virus genomic DNA, which comprises a double stranded DNA molecule consisting essentially of a double-stranded DNA to be deleted, which is flanked on each side by a double stranded DNA homologous to the infectious laryngotracheitis virus glycoprotein gG gene, glycoprotein gI gene, US2 gene, or UL-47 like gene. Preferred embodiments of this invention are the homology vectors designated Homology Vector 544-55.12, Homology Vector 562-61.1F. Homology Vector 472-73.27, Homology Vector 560-52.F1 and Homology Vector 579-14.G2.

This invention provides an isolated nucleic acid molecule encoding a US10 gene (SEQ ID NOs:60 and 70), AvSp gene (SEQ ID NOs: 61 and 71), US2 gene (SEQ ID NO:62), PK gene (SEQ ID NO:63). UL47 gene (SEQ ID NO:64), gG gene (SEQ ID NO:65). ORF5 gene (SEQ ID NO: 66), gD gene (SEQ ID NO:67), gI gene (SEQ ID NO:68), g gene (SEQ ID NO:69), or ORF9 gene (SEQ ID NO:70).

This invention provides an isolated polypeptide encoded by the US10 gene (SEQ ID NOs:60 and 70), AvSp gene (SEQ ID NOs: 61 and 71), US2 gene (SEQ ID NO:62), PK gene (SEQ ID NO:63), UL47 gene (SEQ ID NO:64), gG gene (SEQ ID NO:65), ORF5 gene (SEQ ID NO: 66), gD gene (SEQ ID NO:67), gI gene (SEQ ID NO:68), gE gene (SEQ ID NO:69), or ORF9 gene (SEQ ID NO:70).

EXPERIMENTAL DETAILS

Materials and Methods

PREPARATION OF INFECTIOUS LARYNGOTRACHEITIS VIRUS STOCK SAMPLES. Infectious laryngotracheitis virus stock samples were prepared by infecting primary chicken embryo kidney cells (CEK: obtained from Spafas, Inc.) or primary chicken kidney cells (CK; obtained from chicks hatched from fertile eggs supplied by Hyvac) (50) in 225 cm$^2$ flasks with 0.5 ml of viral stock containing $10^5$-$10^6$ pfu in 1× Eagle's Basal Medium (modified) with Hank's salts (BME), 10% bromoethylamine (BEI)-treated fetal bovine serum (FBS), 1% glutamine stock, 2% penicillin/streptomycin (P/S) stock, and 1% sodium bicarbonate stock (these components are obtained from Irvine Scientific or an equivalent supplier, and hereafter the growth medium is referred to as complete BME medium). Viral stocks were then harvested 4-5 days later. Infected media and cells were resuspended in complete medium containing 20% sterile whole milk and stored frozen at −70° C.

PREPARATION OF INFECTIOUS LARYNGOTRACHEITIS VIRUS DNA. Four to five days after viral infection, cells and media were scraped from each flask into 15 ml conical centrifuge tubes and pelleted at 1700×g for 5 minutes at 4° C. Because as much as 50% of the virus may be in the media, the supernatants were saved and treated as will be described below. The cell pellets were resuspended in 1 ml PBS per tube, combined and centrifuged again at 1700×g for 5 minutes. The pellets were resuspended in 1 ml/flask of a buffer containing 10 mM Tris-HCl pH 7.5, 1 mM EDTA, and 1.5 mM MgCl$_2$ and were incubated for 15 minutes at 4° C. Twenty five µls of 20% NP40 per flask was added, and the mixture was then homogenized in a dounce homogenizer using an A pestle. The preparation was centrifuged at 1700×g for 10 minutes at 4° C. and the supernatant was retained. Ten µl of 0.5 M EDTA, 50 µl of 20% SDS, and 25 µl of 10 mg/ml proteinase K was added to the supernatant (per original flask). In some cases, this was then combined with virus obtained from the cell media supernatants (see above). The mixture was then treated at 65° C. for 1-16 hours, followed by two extractions with phenol saturated with 100 mM Tris-HCl, pH 8. DNA in the aqueous phase was then precipitated with added 3 M sodium acetate (1/10th volume) and 2.5 vols of 100% ethanol.

To obtain virus from the media, the cell media supernatants were centrifuged at 23,500×g for 30 minutes, and drained well. The pellet was resuspended in the above proteinase K-containing mixture as described. The DNA pellets were resuspended in 20 µl TE/flask and could be used at this point for further experiments or treated further to remove RNA with pancreatic RNase A, followed by phenol extraction and ethanol precipitation to obtain the DNA.

To prepare viral DNA minipreps, infected 10 cm dishes were scraped into conical centrifuge tubes and centrifuged 5 minutes at 1000×g. Cell media supernatants were kept and treated as above. The cell pellets were each resuspended in 0.5 ml of 10 mM Tris-HCl pH 7.5, 1 mM EDTA, 0.5% NP40, and incubated 10 minutes at room temperature. Ten µl of 10 mg/ml RNase A was added, and the preparation was centrifuged 5 minutes at 1000×g. Twenty-five µl of 20% SDS and 25 µl of 10 mg/ml proteinase K was added to the supernatant, and the entire preparation was added to the viral pellet from the cell media if it was used. The mixture was incubated at 55-65° C. for one hour, extracted with buffer-saturated phenol and precipitated by the addition of 1 ml of ethanol. The DNA pellet was resuspended in 20 µl of TE and stored at 4° C.

POLYMERASE FILL-IN REACTION. DNA was resuspended in buffer containing 50 mM Tris pH 7.4, 50 mM KCl, 5 mM MgCl$_2$, and 400 micromolar each of the four deoxyribonucleotides. Ten units of Klenow DNA polymerase (Gibco BRL) were added and the reaction was allowed to proceed for 15 minutes at room temperature. The DNA was phenol extracted and ethanol precipitated as above.

DNA SEQUENCING. Sequencing was performed using the Sequenase Kit (US Biochemicals) and $\alpha^{35}$S-dATP (New England Nuclear). Reactions using both the dGTP mixes and the dITP mixes were performed to clarify areas of compression. Alternatively, compressed areas were resolved on formamide gels. Templates were double-stranded plasmid subclones or single stranded M13 subclones, and primers were either made to the vector just outside the insert to be sequenced, or to previously obtained sequence. Sequence obtained was assembled and compared using Dnastar software. Manipulation and comparison of sequences obtained was performed with IBI MacVector. Superclone and Supersee Align programs from Coral Software.

MOLECULAR BIOLOGICAL TECHNIQUES. Techniques for the manipulation of bacteria and DNA, including such procedures as digestion with restriction endonucleases, gel electrophoresis, extraction of DNA from gels, ligation, phosphorylation with kinase, treatment with phosphatase, growth of bacterial cultures, transformation of bacteria with DNA, and other molecular biological methods are described (42, 43). The polymerase chain reaction (PCR) was used to introduce restriction sites convenient for the manipulation of various DNAs (44). In general amplified fragments were less than 500 base pairs in size and critical regions of amplified fragments were confirmed by DNA sequencing. Except as noted, these techniques were used with minor variation.

SOUTHERN BLOTTING OF DNA. The general procedure for Southern blotting was taken from Maniatis et al. (1982) and Sambrook, et. al. (1989) (42, 43). DNA was blotted to nylon membrane (Biorad Zetaprobe) in 0.4M NaOH and prehybridized for 5 minutes in a solution containing 0.25 M $Na_2HPO_4$, pH 7.2, 1 mM EDTA, 7% SDS at 65° C. Labeled probe was added that had been labeled by random priming using a Genius™ non-radioactive labeling kit from Boehringer-Mannheim. Hybridization was overnight at 65° C. Filters were washed twice with 40 mM $Na_2HPO_4$, pH 7.2, 1 mM EDTA, 5% SDS and then twice with 40 mM $Na_2HPO_4$, pH 7.2, 1 mM EDTA, 1% SDS for 30 minutes each at 65° C. Detection of bound probe was performed using the Boehringer Mannheim Genius™ non-radioactive detection kit.

DNA TRANSFECTION FOR GENERATING RECOMBINANT ILT VIRUS. The method is based upon the $CaCl_2$ procedure of Chen and Okayama (1987) (45) with the following modifications. Generation of recombinant ILT virus is dependent upon homologous recombination between ILT viral DNA and the plasmid homology vector containing the desired foreign DNA flanked by the appropriate herpesvirus cloned sequences. Plasmid DNA (10-40 mg) was added to 250 ml of a solution having a final concentration of 0.25 M $CaCl_2$. An equal volume of a buffer containing 50 mM MOPS (pH 6.95), 280 mM NaCl, and 1.5 mM $Na_2HPO_4$ was added to the DNA/$CaCl_2$ solution. After 10 minutes at room temperature, the mixture was added dropwise to a 6 cm dish of CEK cells on maintenance media, and placed at 39° C. for 4 to 5 hours. The cells were rinsed once with PBS, once with 20% glycerol in PBS for 2 minutes, rinsed again with PBS and fed with maintenance media. 1.5 ml of ILT viral stock was added to the media, and the cells were incubated overnight. The next day, fresh maintenance media was added, and the cells were incubated for two more days. The transfection stock was harvested, aliquoted, and frozen at −70° C.

PROCEDURE FOR GENERATING ILTV SUBGENOMIC DNA FRAGMENTS. The ability to generate herpesviruses by cotransfection of cloned overlapping subgenomic fragments has been demonstrated for pseudorabies virus (46). If deletions and/or insertions are engineered directly into the subgenomic fragments prior to the cotransfection, this procedure results in a high frequency of viruses containing the genomic alteration, greatly reducing the amount of screening required to purify the recombinant virus. The procedure of overlapping cosmids to map restriction enzyme sites was employed.

A library of subclones containing overlapping ILTV subgenomic fragments was generated as follows. USDA ILTV Strain 83-2 has been designated S-ILT-001. Approximately 20 μg of ILTV DNA (obtained from S-ILT-001) in 0.5 ml of 10 mM Tris-HCl pH 8.0, 1 mM EDTA (TE) was sheared by passing it twice through a 25 gauge needle as previously described (46). The DNA was centrifuged through a 15-40% glycerol gradient in 50 mM Tris-HCl pH 8.0, 1 mM EDTA, and 0.3 M NaCl for 5.5 hours at 274,000×g. Fractions were analyzed on a 0.3% agarose gel, and those containing DNA of 35-50 kb were pooled, diluted twofold with TE, and precipitated with one tenth volume of 3M sodium acetate and 2.5 volumes of ethanol. The tubes were centrifuged for one hour at 109,000×g at 10° C. Pellets were resuspended, transferred to microfuge tubes, and precipitated with one tenth volume of 3 M sodium acetate and 2.5 volumes of ethanol. The DNA was resuspended in TE. DNA ends were made blunt ended by the POLYMERASE FILL-IN REACTION. The DNA was purified by extraction with both buffer saturated phenol and ether, precipitated with sodium acetate and ethanol as above, and resuspended in TE, Half of this material was ligated with 3 mg of vector, pSY1626, by the DNA ligation reaction. The vector used was pSY1626, which was made as follows. Cosmid pHC79 (Gibco BRL) was cut with HindIII and AvaI to remove the tetracycline gene, and the ends were filled in with Klenow polymerase (FILL IN REACTION). The polylinker from pWE15 (Stratagene) was ligated into this vector. The polylinker was isolated by digestion with EcoRI, the ends were filled in with Klenow polymerase (FILL IN REACTION), and the fragment was purified on a LMP-agarose gel. DNA ligation was performed in the presence of melted agarose. The resulting cosmid, pSY1005, was modified at the EcoRI site to create pSY1626 by blunt-ended insertion of a 1.5 kb HindIII-BamHI fragment from pNEO (P-L Biochemicals) containing the neomycin resistance gene. pSY1626 was cut and made blunt at the BamHI site, and ligated with sheared ILTV fragments as described above. The ligation mixture was packaged using Gigapack XL (Stratagene) according to the manufacturers instructions. The packaging mixture was added to AG1 cells (Stratagene) grown in the presence of maltose, and colonies were selected on LB plates containing kanamycin. Cosmid subclones containing ILTV DNA were identified by comparing restriction enzyme maps of individual cosmid clones to each other and to ILVTV genomic DNA to obtain a contiguous sequence of ILTV genomic DNA.

SCREEN FOR RECOMBINANT ILTV EXPRESSING ENZYMATIC MARKER GENES. When the *E. coli* β-galactosidase or β-glucuronidase (uidA) marker gene was incorporated into a recombinant virus the plaques containing the recombinants were visualized by a simple assay. The enzymatic substrate was incorporated (300 μg/ml) into the agarose overlay during the plaque assay. For the lacZ marker gene the substrate Bluogal™ (halogenated indolyl-β-D-galactosidase, Gibco BRL) was used. For the uidA marker gene the substrate X-Glucuro Chx (5-bromo-4-chloro-3-indolyl-β-D-glucuronic acid Cyclohexylammonium salt, Biosynth AG) was used. Plaques that expressed active marker enzyme turned blue. The blue plaques were then picked onto fresh cells and purified by further blue plaque isolation. In recombinant virus strategies in which the enzymatic marker gene was removed, the assay involves plaque purifying white plaques from a background of parental blue plaques. Viruses were typically purified with five to ten rounds of plaque purification.

SCREEN FOR FOREIGN GENE EXPRESSION IN RECOMBINANT ILTV USING BLACK PLAQUE ASSAYS. To analyze expression of foreign antigens expressed by recombinant ILT viruses, monolayers of CEK cells were infected with recombinant ILT virus, overlaid with nutrient agarose media and incubated for 3-5 days at 39° C. Once plaques have developed, the agarose overlay was removed from the dish, the monolayer rinsed once with PBS, fixed with 100% methanol for 10 minutes at room temperature and the cells air dried. After re-hydrating the plate with PBS, the primary antibody was diluted to the appropriate dilution with PBS plus Blotto and incubated with the cell monolayer for 2 hours to overnight at room temperature. Unbound antibody was removed from the cells by washing four times with PBS at room temperature. The appropriate secondary antibody conjugate was diluted 1:500 with PBS and incubated with the cells for 2 hours at room temperature. Unbound secondary antibody was removed by washing the cells three times with PBS at room temperature The monolayer was rinsed in color development buffer (100 mM Tris pH 9.5/100 mM NaCl/5 mM MgCl2), and incubated 10 minutes to overnight at room temperature with freshly prepared substrate solution (0.3 mg/ml nitro blue tetrazolium+0.15 mg/ml 5-bromo-4-chloro-3-indolyl phosphatase in color development buffer). The reaction was stopped by replacing the substrate solution with TE (10 mM Tris, pH7.5/1 mM EDTA). Plaques expressing the correct antigen stain black.

PURIFICATION OF ILTV gG FROM ILT VIRUS OR RECOMBINANT VIRUSES EXPRESSING ILTV gG. ILTV gG was purified from the media of cells infected with either wild type ILTV or with FPV or SPV vectors expressing ILTV gG. Cells were allowed to go to complete cytopathic effect (CPE), the media was poured off, and cell debris was pelleted in a table-top centrifuge. The media was concentrated in an Amicon concentrator using a YM30 ultrafiltration membrane at 15 psi. The concentrate was dialyzed against 20 mM Tris-HCl, pH 7.0 and loaded onto a DEAE-Sephacel (Pharmacia) column equilibrated with the same buffer. The material was eluted using a salt gradient from 0 to 1.5 M NaCl in 20 mM Tris-HCl, pH 7.0. Three ml fractions were collected and assayed by Western blot. A peptide antibody against ILTV gG was used to identify fractions containing ILTV gG. Fractions were pooled and further concentrated in a Centricon-10 microconcentrator (Amicon).

GROWTH OF CHICKEN KIDNEY CELLS AND ILT VIRUS. An ILTV virus, designated fowl laryngotracheitis challenge virus, lot number 83-2, was obtained from the National Veterinary Services Laboratories, USDA/APHIS, Ames, Iowa. ILTV viruses were grown in primary chicken kidney cells (CK) obtained by dissection of kidneys from 6-9 day old SPF chicks, obtained from Hy-Vac Laboratory Eggs Co. Fresh kidney cells were minced and disassociated with 5 mg/ml trypsin and were then pelleted and resuspended at $1.3\times10^6$ cells/ml. Growth media (GM) was IX Eagle's Basal Medium (modified) with Hank's salts, with added 10% binary ethyleneimine-treated fetal bovine serum (FBS), 2 mM glutamine, 200 units/ml penicillin, 200 mg/ml streptomycin, and 8.9 mM sodium bicarbonate (85). After resuspension, cells were plated and incubated at 39° C. Cells were rinsed and fed after 24 hours with maintenance media (MM), which is GM with 1% FBS. CKs were inoculated with ILTV at 0.01 to 0.1 MOI and viral stocks were harvested 4-5 days later by scraping and sonicating. Titers were typically $10^5$-$10^6$ pfu/ml.

PREPARATION OF VIRAL DNA. Cells and media from infected flasks were pelleted at 1700 g for 5' at 4° C. Supernatant and cell pellet were initially treated separately. Virion particles were centrifuged out of the supernatant at 23,500 g for 30 minutes. The original cell pellet was rinsed with PBS and spun again. This pellet was resuspended in 1 ml/flask of a buffer containing 10 mM Tris-HCl pH 7.5, 1 mM EDTA, and 1.5 mM $MgCl_2$ and incubated 15'° C. To this was added 25 μl/flask of 20% NP40, and the mixture was dounce homogenized using an A pestle. The preparation was centrifuged at 1700 g, 10', 4° C., and the supernatant was retained and the pellet discarded. To the supernatant was added (per original flask) 10 μl of 0.5 M EDTA, 50 μl of 20% SDS, and 25 μl of 10 mg/ml proteinase K. This mixture was used to resuspend the pellet of viral particles obtained by high speed centrifugation of the first supernatant. The mixture was treated at 65° C. for 1-16 hours, extracted twice with buffer-saturated phenol, and precipitated with added salt and ethanol. The resulting DNA pellet was resuspended in 100 μl TE/flask. This was treated further to remove RNA with pancreatic RNase A, followed by phenol extraction and ethanol precipitation to obtain the DNA.

CREATION OF THE COSMID LIBRARY. The cosmid library of ILTV DNA was created following the protocol of van Zijl et al., (83). Approximately 20 μg of ILTV DNA in 0.5 ml of 10 mM Tris-HCl, pH 8.0, 1 mM EDTA (TE) was sheared by passing it twice through a 25 gauge needle. The DNA was centrifuged through a 15-40% glycerol gradient in 50 mM Tris-HCl, pH 8.0, 1 mM EDTA, 0.3 M NaCl for 5.5 h at 274,000 g. Fractions were analyzed on a 0.3% agarose gel, and those containing DNA of 35-50 kb were pooled, diluted twofold with TE, and precipitated with added salt and ethanol. The tubes were spun 1 h at 10° C. and 109,000 g. Pellets were resuspended and reprecipitated with added salt and ethanol. The DNA was resuspended in TE and the ends were made blunt by treatment with T4 DNA polymerase for 2 h at 15° C., in the presence of appropriate buffer and 25 μM dNTP, followed by treatment with Klenow polymerase for 16 h at 15° C. using 0.25 mM dNTP. The DNA was extracted with phenol and then ether, precipitated with added salt and ethanol, and resuspended in TE. This material was ligated overnight with 3 μg of cosmid vector pSY1626. Cosmid pSY1626 was made by digesting cosmid pHC79 (BRL) with HindIII and AvaI to remove the tetracycline gene. The remaining fragment and the EcoRI digested polylinker from pWE15 (Stratagene) were filled in with Klenow polymerase and ligated together. The resulting cosmid vector, pSY1005, was modified at the EcoRI site to create pSY1626 by blunt-ended insertion of a 1.5 kb HindIII-BamHI fragment from pNEO (P-L Biochemicals) containing the kanamycin resistance gene. PSY1626 was cut and made blunt at the BamHI site for use as the cosmid vector. The ligation mixture was packaged using Gigapack XL (Stratagene) according to the manufacturer's directions. Colonies were selected on LB plates containing kanamycin.

SEQUENCING. Manual sequencing was performed using $^{35}S$-dATP (NEN) with the BRL Sequenase Kit which uses the dideoxyribonucleotide chain termination method described by Sanger et al. (80). Reactions using both dGTP and dITP mixes were performed to clarify areas of compression. Alternatively, compressed areas were resolved on 8% acrylamide gels that were 40% in formamide. Automatic fluorescence sequencing was performed using an Applied Biosystems (ABI) 373A DNA Sequencer. Subclones were made to facilitate sequencing. Internal primers were synthesized on an ABI 392 DNA synthesizer. Sequence was obtained for both strands and was assembled using DNAstar software. Manipulation and comparison of sequences was performed with DNAstar programs, Superclone and Supersee programs from Coral Software. Comparisons with GenBank were performed at the NCBI using the BLAST network service (58).

HOMOLOGY VECTOR 501-94. The plasmid 501-94 was constructed for the purpose of deleting a portion of the thymidine kinase (TK) gene coding region from the ILT virus (28). It incorporates the HCMV IE promoter and a screenable marker, the *E. coli* lacZ gene, flanked by ILT virus DNA. The HCMV IE promoter-*E. coli* lacZ gene is inserted in the opposite transcriptional orientation to the ILTV TK gene. Upstream of the marker gene is an approximately 1087 base pair fragment of ILTV DNA which includes the first 77 amino acid codons of the ILTV TK gene. Downstream of the lacZ gene is an approximately 675 base pair fragment of ILTV DNA which includes 80 amino acid codons at the 3' end of the ILTV TK gene. When this plasmid is used according to the DNA TRANSFECTION FOR GENERATING RECOMBI- NANT ILT VIRUS, it will replace the DNA coding for amino acids 78 to 285 of the ILTV TK gene with DNA coding for the lacZ gene. The lacZ marker gene is under the control of the human cytomegalovirus (HCMV) immediate early (IE) gene promoter and also contains the pseudorabies virus (PRV) gX gene polyadenylation signal at the 3' end of the gene. A detailed description of the plasmid is given in FIGS. 5A-5D. It was constructed from the indicated DNA sources utilizing standard recombinant DNA techniques (42, 43). The plasmid vector is derived from an approximately 3002 base pair HindIII fragment of pSP64/65 (Promega). Fragment 1 is an approximately 1087 base pair HindIII to Bell subfragment of the ILTV 2.4 kb HindIII fragment. Fragment 2 is an approximately 5017 base pair SalI to SalI fragment containing the HCMV IE promoter, β-galactosidase (lacZ) marker gene, and PRV gX polyadenylation signal (see FIGS. 5A-5D). Fragment 3 is an approximately 675 base pair Bell to HindIII subfragment of the ILTV 2.4 kb HindIII fragment.

HOMOLOGY VECTOR 544-55.12. The plasmid 544-55.12 was constructed for the purpose of deleting a portion of the US2 gene coding region from the ILT virus and inserting a foreign DNA. It incorporates a screenable marker, the *E. coli* uidA gene flanked by ILT virus DNA. The PRV gX promoter-*E. coli* uidA gene is inserted in the opposite transcriptional orientation to the ILTV US2 gene. Upstream of the uidA gene is an approximately 2300 base pair fragment of ILTV DNA which includes 41 amino acid codons at the 3' end of the US2 gene (SEQ ID NO 2: aa. 188-229). Downstream of the uidA gene is an approximately 809 base pair fragment of ILTV DNA which includes 22 amino acid codons at the 5' end of the US2 gene (SEQ ID NO 2: aa. 1-22). When this plasmid is used according to the DNA TRANSFECTION FOR GENERATING RECOMBINANT ILT VIRUS, it will replace the ILTV US2 DNA coding for amino acids 23 to 187 with DNA coding for the *E. coli* uidA gene. The uidA marker gene is under the control of the pseudorabies virus (PRV) gX promoter and also contains the herpes simplex virus type 1 thymidine kinase (HSV-1 TK) gene polyadenylation signal at the 3' end of the gene. A detailed description of the plasmid is given in FIGS. 6A-6D. It was constructed from the indicated DNA sources utilizing standard recombinant DNA techniques (42, 43). The plasmid vector is derived from an approximately 2958 base pair Asp718I restriction fragment of a pSP18/pSP19 fusion such that the multiple cloning site is EcoRI/SacI/Asp718I/SacI/EcoRI. Fragment 1 is an approximately 2300 base pair Asp718I to DraI subfragment (SEQ ID NO 1: Nucl. 1-405) of the ILTV 2.5 kb Asp718I fragment. Fragment 2 is an approximately 3039 base pair XbaI fragment containing the PRV gX promoter, the *E. coli* uidA gene, and the HSV-1 TK polyadenylation site (See FIGS. 6A-6D). Fragment 3 is an approximately 809 base pair XbaI to Asp718I subfragment of the ILTV 1097 bp Asp718I fragment (SEQ ID NO 1: Nucl. 905-1714).

HOMOLOGY VECTOR 562-61.1F. The plasmid 562-61.1F was constructed for the purpose of deleting part of the gI gene from the ILT virus and inserting a foreign DNA. It incorporates a screenable marker, the *E. coli* uidA gene, flanked by ILT virus DNA. The PRV gX promoter-*E. coli* uidA gene is transcribed in the opposite direction to the ILTV gI gene promoter. The 983 base pair deletion begins 12 base pairs upstream of the translation initiation codon and deletes 324 of 363 amino acid codons at the 5' end of the ILTV gI gene (SEQ ID NO 11: aa. 325-363). When this plasmid is used according to the DNA TRANSFECTION FOR GENERATING RECOMBINANT ILT VIRUS, it will replace the DNA coding for the ILTV gI gene with DNA coding for the *E. coli* uidA gene. A detailed description of the plasmid is given in FIGS. 7A-7D. It was constructed from the indicated DNA sources utilizing standard recombinant DNA techniques (42, 43). The plasmid vector is derived from an approximately 2647 base pair Asp718I to HindIII fragment of pUC19. Fragment 1 is an approximately 1619 base pair Asp718I to XbaI subfragment of the ILTV 8.0 kb Asp718I fragment (SEQ ID NO 1: Nucl. 7556-9175). Fragment 2 is an approximately 691 base pair XbaI to XhoI fragment (SEQ ID NO 1: Nucl. 9175-9861) generated by the polymerase chain reaction (PCR). The template was the ILTV 8.0 kb Asp718I fragment. The upstream primer 92.09 (5'-CCTAGCACCCTTGTATCGCG-3'; SEQ ID NO. 55) sits down at a site 821 base pairs upstream of the ILTV gI gene and synthesizes DNA toward the 3' end of the gene. The downstream primer 92.11 (5'-CGC <u>CTCGAG</u>TCCCAATGAATAGGCATTGG-3': SEQ ID NO. 56) sits down at a site 12 base pairs upstream of the translation start site of the ILTV gI gene and synthesizes DNA toward the 5' end of the gD gene. The product of the PCR reaction is 818 base pairs. This DNA fragment is digested with XbaI at the 5' end (a restriction enzyme site present in the ILTV DNA) and XhoI at the 3' end (a restriction enzyme site created in the PCR primer-see underlined sequence) to create an approximately 691 base pair XbaI to XhoI fragment. Fragment 3 is an approximately 3051 base pair SalI fragment containing the PRV gX promoter, the uidA gene, and the HSV-1 TK polyadenylation site (See FIGS. 6A-6D), Fragment 4 is an approximately 624 base pair XhoI to HindIII fragment generated by PCR (SEQ ID NO 1: Nucl. 10,847-11,461). The template was the ILTV 8.0 kb Asp718I fragment. The upstream primer 92.10 (5'-CGC <u>CTCGAG</u>GACCCATGGTTGCGTGCG-3'; SEQ ID NO. 57) sits down at a site 117 base pairs upstream from the translation termination codon within the ILTV gI gene. The downstream primer 92.08 (5'-CTCGTCCGAACGAGTTA-CAG-3'; SEQ ID NO. 58) sits down at a site 604 base pairs downstream of the translation termination site of the ILTV gI gene and within the ILTV gE gene. The PCR product (729 base pairs) is digested with XhoI which is a unique site generated by the upstream PCR primer (underlined) and with HindIII at a site within the ILTV gE gene. Restriction endonuclease digestion with XhoI and HindIII creates an approximately 624 base pair Fragment 4. Fragment 5 is an approximately 2700 base pair HindIII subfragment of the ILTV 8.0 kb Asp718I fragment (SEQ ID NO 1: Nucl. 11,461-13,473 plus unsequenced DNA).

HOMOLOGY VECTOR 472-73.27. The plasmid 472-73.27 was constructed for the purpose of deleting a portion of the glycoprotein G (gG) gene coding region from the ILT virus and inserting a foreign DNA. It incorporates a screenable marker, the *E. coli* lacZ gene, flanked by ILT virus DNA. The HCMV IE promoter-*E. coli* lacZ gene is transcribed in the same direction to the ILTV gG gene promoter. The 874 base pair deletion of the ILTV gG gene extends from 60 nucleotides upstream of the translation initiation site to 814 nucleotides into the amino acid coding sequence, removing the coding capacity of 271 of 292 amino acids of the gG protein (SEQ ID NO 7). When this plasmid is used according to the DNA TRANSFECTION FOR GENERATING RECOMBINANT ILT VIRUS, it will replace the DNA coding for amino acids 1 to 271 of the ILTV gG gene with DNA coding for the *E. coli* lacZ gene. A detailed description of the plasmid is given in FIGS. 4A-4D. It was constructed from the indicated DNA sources utilizing standard recombinant DNA techniques (42, 43). The plasmid vector is derived from an approximately 2686 base pair Asp718I restriction fragment of pUC19 (Gibco, BRL). Fragment 1 is an approximately 2830 base pair Asp718I to NheI subfragment of the ILTV 5164 bp Asp718I fragment (SEQ ID NO 1: Nucl. 1714-4544). Fragment 2 is an approximately 5017 base pair SalI to SalI fragment containing the HCMV IE promoter, E. coli β-galactosidase (lacZ) marker gene, and PRV gX polyadenylation signal (see FIGS. 4A-4D). Fragment 3 is an approximately 1709 base pair SalI to Asp1181 subfragment of the ILTV 5164 bp Asp718I fragment (SEQ ID NO 1: Nucl. 5419-6878).

HOMOLOGY VECTOR 560-52.F1. The plasmid 560-52.F1 was constructed for the purpose of deleting part of the UL47-like gene, all of ORF4, and part of the ILTV gG gene from the ILT virus and inserting a foreign DNA. It incorporates a screenable marker, the E. coli uidA gene, flanked by ILT virus DNA. The PRV gX promoter-E. coli uidA gene is transcribed in the opposite direction to the ILTV UL47-like, ORF4, and gG gene promoters. The 2640 base pair deletion removes 442 of 511 amino acid codons at the 3' end of the UL47-like gene (SEQ ID NO 4), the entire coding sequence of the ORF4 gene (SEQ ID NO 5) and 271 of 293 amino acid codons at the 5' end of the ILTV gG gene (SEQ ID NO 7). When this plasmid is used according to the DNA TRANSFECTION FOR GENERATING RECOMBINANT ILT VIRUS, it will replace the DNA coding for the ILTV UL47-like, ORF4 and gG genes with DNA coding for the PRV gX promoter-E. coli uidA gene. A detailed description of the plasmid is given in FIGS. 8A-8D. It was constructed from the indicated DNA sources utilizing standard recombinant DNA techniques (42, 43). The plasmid vector is derived from an approximately 2958 base pair Asp718I restriction fragment of pSP18/pSP19 such that the multiple cloning site is EcoRI/SacI/Asp718I/SacI/EcoRI. Fragment 1 is an approximately 1066 base pair Asp718I to BssHII subfragment of the ILTV 5164 bp Asp718I fragment (SEQ ID NO 1: Nucl. 1714-2777). Fragment 2 is an approximately 123 base pair SalI to BclI subfragment of the ILTV 5164 bp Asp1181 fragment. Fragment 3 is an approximately 3027 base pair BamHI fragment containing the PRV gX promoter, the uidA gene, and the HSV-1 TK polyadenylation site (See FIGS. 8A-8D). Fragment 4 is an approximately 1334 base pair BclI to Asp718I subfragment, of the ILTV 5164 bp Asp718I fragment (SEQ ID NO 1: Nucl. 5544-6878).

HOMOLOGY VECTOR 579-14.G2. The plasmid 579-14.G2 was constructed for the purpose of deleting the entire gG gene and a portion of the g60 gene from the ILT virus and inserting a foreign DNA. It incorporates a PRV gX promoter and a screenable marker, the E. coli uidA gene, flanked by ILT virus DNA. The PRV gX promoter-E. coli uidA gene is transcribed in the same direction to the ILTV gG and g60 gene promoters. The 3351 base pair deletion includes the entire coding sequence of the ILTV gG gene (SEQ ID NO 7) and 733 of 986 amino acid codons from the 5' end of the g60 gene (SEQ ID NO 8). When this plasmid is used according to the DNA TRANSFECTION FOR GENERATING RECOMBINANT ILT VIRUS, it will replace the DNA coding for the ILTV gG gene and amino acids 1 to 733 of the ILTV g60 gene with DNA coding for the coli uidA gene. A detailed description of the plasmid is given in FIGS. 9A-9D. It was constructed from the indicated DNA sources utilizing standard recombinant DNA techniques (42, 43). The plasmid vector pUC19 (Gibco, BRL) is derived from an approximately 2677 base pair Asp718I to BamHI fragment. Fragment 1 is an approximately 2830 base pair Asp718I to NheI subfragment of the ILTV 5164 bp Asp718I fragment (SEQ ID NO 1: Nucl. 1714-4544). Fragment 2 is an approximately 3051 base pair SalI fragment containing the PRV gX promoter, E. coli β-glucuronidase (uidA) marker gene, and an HSV-1 TK polyadenylation site (See FIGS. 9A-9D). Fragment 3 is an approximately 1709 base pair SalI to BamHI subfragment of the ILTV 4545 base pair BamHI fragment (SEQ ID NO 1: Nucl. 7895-9604).

PLASMID 544-39.13. Plasmid 544-39.13 contains the β-glucuronidase expression cassette consisting of the PRV gX promoter, E. coli β-glucuronidase (uidA) marker gene, and an HSV-1 TK polyadenylation site. A detailed description of the marker gene is given in FIGS. 10A-10D. It was constructed utilizing standard recombinant DNA techniques (42, 43) by joining restriction fragments from the following sources with the synthetic DNA sequences indicated in FIGS. 10A-10D. The plasmid vector pSP71 (Promega) is derived from an approximately 3066 base pair XmaI to SmaI fragment. Fragment 1 is an approximately 422 base pair SalI to EcoRI restriction subfragment of the PRV BamHI restriction fragment #10 (47). Note that the EcoRI site was introduced at the location indicated in FIGS. 12A-12D by PCR cloning. Fragment 2 is an approximately 1826 base pair EcoRI to SmaI fragment of the plasmid pRAJ260 (Clonetech). Note that the EcoRI and XmaI sites were introduced at the locations indicated in FIGS. 10A-10D by PCR cloning. Fragment 3 is an approximately 784 base pair XmaI subfragment of the HSV-1 BamHI restriction fragment Q (48). Note that this fragment is oriented such that the polyadenylation sequence (AATAAA) is located closest to the junction with the E. coli uidA gene.

PLASMID 388-65.2. Plasmid 388-65.2 contains the β-galactosidase expression cassette consisting of the HCMV immediate early (IE) promoter, the E. coli lacZ marker gene, and the PRV gX gene polyadenylation site. A detailed description of the β-galactosidase expression cassette is given in FIGS. 11A-11D. It was constructed utilizing standard recombinant DNA techniques (42, 43) by joining restriction fragments from the following sources with the synthetic DNA sequences indicated in FIGS. 11A-11D. The plasmid vector pSP72 (Promega) is derived from an approximately 3076 base pair PstI to PstI fragment. Fragment 1 is a 1154 base pair PstI to AvaII fragment derived from a HCMV 2.1 kb PstI fragment containing the HCMV IE promoter. Fragment 2 is a 3010 base pair BamHI to PvuII fragment derived from plasmid pJF751 (49) containing the E. coli lacZ gene. Fragment 3 is an approximately 750 base pair NdeI to SalI fragment derived from PRV BamHI #7 which contains the carboxy-terminal 19 amino acids and the polyadenylation signal of the PRV gX gene.

EXAMPLES

Example 1

Complete sequence of the unique short region of Infectious Laryngotracheitis Virus (ILTV): The sequence of 13.473 base pairs of contiguous DNA from the short region of the ILT virus (SEQ. ID. NO. 1) was determined. This sequence contains the entire 13.098 base pair unique short region as well as 273 base pairs of repeat region at one end and 102 base pairs of repeat region at the other end. The unique short region contains 13 methionine initiated open reading frames (ORF) of greater than or equal to 110 amino acids (excluding smaller nested ORFs). All 13 ORFs were aligned to the Entrez release 6.0 virus division of the Genbank DNA database utilizing the IBI MacVector Protein to DNA alignment option (default settings). Eight of the ORFs exhibited significant homology to one or more other virus genes (see Table I). The nucleotide sequence numbers referred to below begin within the internal repeat sequence and end within the terminal repeat sequence. The unique short region begins at base pair 274 of SEQUENCE ID NO. 1.

TABLE I

Sequence Homology between Infectious Laryngotracheitis Virus (ILTV) Open Reading Frames in the Unique Short Region and other Viral Proteins

| Open Reading Frame(ORF) | Start(BP) | End(BP) | Length(aa) | Genbank Allignment[a] |
|---|---|---|---|---|
| 1 (Rc)[b] | 970 | 281 | 229 | EHV-1 US2 |
| 2 | 1059 | 2489 | 476 | MDV PK |
| 3 | 2575 | 4107 | 510 | HSV-1 UL47 |
| 4 | 4113 | 4445 | 110 | NS[c] |
| 4 (RC) | 4519 | 4139 | 126 | NS |
| 5 | 4609 | 5487 | 292 | PRV gX |
| 6 | 5697 | 8654 | 985 | ILTV g60 |
| 6 (RC) | 7826 | 6948 | 292 | HSV-2 UL39 |
| 7 | 8462 | 9766 | 434 | PRV g50 |
| 8 | 9874 | 10962 | 362 | VZV gI |
| 8 (RC) | 11150 | 10617 | 177 | NS |
| 9 | 11159 | 12658 | 499 | VZV gE |
| 10 | 12665 | 13447 | 260 | NS |

[a]Sequence allignment scored to the Entrez Release 6.0 of Genbank Virus Database.
[b]RC = Reverse Complement.
[c]NS = No score above 120 was found.
Other Abbreviations: EHV = Equine herpesvirus; MDV = Mareks disease virus; HSV-1 = Herpes Simplex virus 1; PRV = Pseudorabies virus; ILTV = Infectious laryngotracheitis virus; HSV-2 = Herpes Simplex virus 2; VZV = Varicella-Zoster virus; BP = base pairs; aa = amino acids.

US2 Gene

The US2 gene consists of 690 base pairs and codes for a protein 229 amino acids in length and molecular weight approximately 25.272 daltons (SEQ. ID. NO. 12, 13). The ILTV US2 is homologous to the Equine herpesvirus (EHV)-1 and EHV-4 US2 proteins. The US2 gene is transcribed from nucleotide 970 to 281 on the reverse complement strand of the ILTV unique short region (SEQ. ID. NO. 1). The function of the US2 gene product is unknown.

Protein Kinase Gene

The protein kinase gene consists of 1431 base pairs from nucleotide 1059 to 2489 and codes for a protein 476 amino acids in length and molecular weight approximately 54.316 daltons (SEQ. ID. NO. 2), The ILTV protein kinase is homologous to the protein kinases from Mareks disease virus (MDV), Equine herpesvirus (EHV)-1 and -4, Pseudorabies virus (PRV). Varicella-Zoster virus (VZV), Simian varicella virus (SVV), and Herpes Simplex virus (HSV)-1 and -2.

UL47-like Gene

The UL47-like gene is unique in its location within the unique short region of ILT virus. The UL47-like gene in all other known herpesviruses is located within the unique long sequence. The UL47-like gene consists of 1533 base pairs from nucleotide 2575 to 4107 and codes for a protein 510 amino acids in length and molecular weight approximately 57.615 daltons (SEQ. ID. NO. 3).

ORF4

ORF4 codes for a protein of unknown function. ORF4 consists of 333 base pairs from nucleotide 4113 to 4445 and codes for an open reading frame 110 amino acids in length and molecular weight approximately 12,015 daltons (SEQ. ID. NO. 4), ORF4 Reverse Complement ORF4 Reverse Complement (RC) codes for a protein of unknown function. ORF4 RC consists of 380 base pairs from nucleotide 4519 to 4139 and codes for an open reading, frame 126 amino acids in length and molecular weight approximately 13.860 daltons (SEQ. ID. NOS. 14, 15).

gG Gene

The gG gene consists of 879 base pairs from nucleotide 4609 to 5487 and codes for a glycoprotein 292 amino acids in length and molecular weight approximately 31.699 daltons (SEQ. ID. NO. 5). ILTV gG glycoprotein is homologous to PRV gX, Bovine herpesvirus (BHV)-1.3 gG. EHV-1 gG and EHV-4 gG. Recombinant ILTV gG protein produced in a Swinepox virus vector or a Fowlpox virus vector can be purified (see Materials and Methods) and reacts to peptide antisera to ILTV gG. The peptide antisera reacts to ILTV gG from wild type virus, but not to viruses deleted for the ILTV gG gene. Deletion of the gG gene results in an attenuated ILT virus that is useful as a vaccine against ILT disease in chickens (see table in Example 6) and also serves as a negative marker to distinguish vaccinated from infected animals.

g60 Gene

The g60 gene has been identified as glycoprotein 60 (33, 53). The g60 gene consists of 2958 base pairs from nucleotide 5697 to 8654 and codes for a glycoprotein 985 amino acids in length and molecular weight approximately 106,505 daltons (SEQ. ID. NO. 6).

ORF6 Reverse Complement

ORF6 RC consists of 878 base pairs from nucleotide 7826 to 6948 and codes for an open reading frame 292 amino acids in length and molecular weight approximately 32,120 daltons (SEQ. ID. NO. 16, 17). The ILTV ORF6 RC shares limited homology to portions of the HSV-1 and HSV-2 ribonucleotide reductase large subunit (UL39).

gD Gene

The expression of the gD glycoprotein in vectored fowlpox virus or herpesvirus of turkeys (33) is sufficient to raise a protective immune response in the chicken. The gD gene consists of 1305 base pairs from nucleotide 8462 to 9766 and codes for a glycoprotein 434 amino acids in length and molecular weight approximately 48,477 daltons (SEQ. ID. NO. 10, 11). The ILTV gD glycoprotein is homologous to the PRV g50, and the gD from HSV-1. MDV. IPV, and BHV-1.1. Monoclonal antibodies raised to ILT virus react specifically with gD protein from ILTV and also react to ILTV gD protein expressed in a Herpesvirus of Turkeys (HVT) virus vector. ILTV gD expressed in the HVT vector is useful as a subunit vaccine.

gI Gene

The gI gene consists of 1089 base pairs from nucleotide 9874 to 10.962 and codes for a glycoprotein 362 amino acids in length and molecular weight approximately 39,753 daltons (SEQ. ID. NO. 7). The ILTV gI glycoprotein is homologous to the VZV gI. Recombinant ILTV gI protein expressed in a swinepox virus vector reacts to convalescent sera from ILTV-infected chickens. Deletion of the gI gene results in an attenuated ILT virus that is useful as a vaccine against ILT disease in chickens. Recombinant viruses deleted for gI are safe in animal trials when vaccinated by a natural route directly into the respiratory tract, whereas parental virus causes lesions in 90% of the birds inoculated via the same route. Deletion of the gI gene serves as a negative marker to distinguish vaccinated from infected animals.

ORF8 Reverse Complement

ORF8 Reverse Complement codes for a protein of unknown function. ORF8 RC consists of 533 base pairs from nucleotide 11,150 to 10,617 and codes for an open reading frame 177 amino acids in length and molecular weight approximately 19,470 daltons (SEQ. ID. NO. 18, 19).

gE Gene

The gE gene consists of 1500 base pairs from nucleotide 11,159 to 12,658 and codes for a glycoprotein 499 amino acids in length and molecular weight approximately 55,397 daltons (SEQ. ID. NO. 8). The ILTV gE glycoprotein is homologous to the gE glycoproteins from VZV. Simian herpesvirus (SHV). EHV-1, HSV-1, and PRV. The ILTV gE is a neutralizing antigen useful as a subunit vaccine.

ORF10

ORF10 consists of 783 base pairs from nucleotide 12,665 to 13,447 and codes for a protein 261 amino acids in length and molecular weight approximately 27,898 daltons (SEQ. ID. NO. 9).

Example 2

S-ILT-004

S-ILT-004 is an infectious laryngotracheitis virus (ILTV) that has an approximately 620 base pair deletion of the thymidine kinase (TK) gene (28). The gene for E. coli β-galactosidase (lacZ) was inserted in the place of the TK gene and is under the control of the HCMV immediate early (IE) promoter. Transcription of the HCMV IE promoter-lac Z gene is in the opposite orientation to the TK promoter.

S-ILT-004 was constructed using homology vector 501-94 (see Materials and Methods) and S-ILT-001 (USDA ILTV Strain 83-2) in the DNA TRANSFECTION FOR GENERATING RECOMBINANT ILT VIRUS. The transfection stock was screened by the Bluogal™ SCREEN FOR RECOMBINANT HERPESVIRUS EXPRESSING ENZYMATIC MARKER GENES. The result of blue plaque purification was recombinant virus S-ILT-004. This virus was characterized by restriction mapping and the SOUTHERN BLOTTING OF DNA procedure. This analysis confirmed the presence of the β-galactosidase (lacZ) marker gene and the deletion of approximately 619 base pairs of the TK gene. The remaining TK gene sequence codes for protein including amino acids 1 to 77, and amino acids 286 to 363. The HCMV IE promoter-lacZ gene is in the opposite orientation to the TK gene transcription.

S-ILT-004 is attenuated by deletion of the ILTV TK gene, but retains other genes known to be involved in the immune response in chickens to ILT virus. Therefore, S-ILT-004 may be useful as a killed vaccine to protect chickens from ILT disease.

Example 3

S-ILT-009

S-ILT-009 is an infectious laryngotracheitis virus (ILTV) that has an approximately 498 base pair deletion of the ILTV US2 gene and an approximately 874 base pair deletion of the ILTV gG gene. The gene for E. coli β-glucuronidase (uidA) was inserted in the place of the US2 gene and is under the control of the pseudorabies virus (PRV) gX promoter.

S-ILT-009 was constructed using homology vector 544-55.12 (see Materials and Methods) and S-ILT-002 in the DNA TRANSFECTION FOR GENERATING RECOMBINANT ILT VIRUS. S-ILT-002 was constructed as described in Example 5 (S-ILT-014). The transfection stock was screened by the X-Gluc SCREEN FOR RECOMBINANT HERPESVIRUS EXPRESSING ENZYMATIC MARKER GENES. The resulting purification of a blue plaque was recombinant virus S-ILT-009. This virus was characterized by restriction mapping and the SOUTHERN BLOTTING OF DNA procedure. This analysis confirmed the presence of the PRV gX promoter-β-glucuronidase (uidA) marker gene and the deletion of approximately 498 base pairs of the ILTV US2 gene and an approximately 874 base pair deletion of the ILTV gG gene. However, during the Bluogal™ SCREEN FOR RECOMBINANT HERPESVIRUS EXPRESSING ENZYMATIC MARKER GENES, a deletion of the HCMV IE promoter-lacZ gene was detected within the existing ILTV gG deletion. The remaining insert into the ILTV gG deletion contains approximately 2000 base pairs of DNA of which all of the lacZ gene and part of the PRV gX polyadenylation site are missing. The deletion was characterized by detailed restriction mapping and determined to be slightly different from the S-ILT-014 deletion (See Example 5).

S-ILT-009 is attenuated by deletion of the ILTV US2 and gG genes, but retains other genes known to be involved in the immune response in chickens to ILT virus. Therefore, S-ILT-009 is useful as an attenuated live vaccine or as a killed vaccine to protect chickens from ILT disease as shown in the table. Since S-ILT-009 does not express the ILTV gG genes, it is utilized as a negative marker to distinguish vaccinated animals from infected animals as described previously.

TABLE II

EFFICACY OF RECOMBINANT LIVE ILT VIRUS S-ILT-009 AGAINST VIRULENT INFECTIOUS LARYNGOTRACHEITIS VIRUS CHALLENGE

| Vaccine | Gene(s) Deleted | Dose | Route | Challenge[a] | Protection[b] |
|---|---|---|---|---|---|
| S-ILT-009 | gG-, US2- | $7.8 \times 10^3$ | IO[c] | OS[d] | 70% |
| S-ILT-009 | gG-, US2- | $1.56 \times 10^3$ | IO | OS | 77% |
| Controls | | | | OS | 0% |
| ASL embryo | | | IO | OS | 90% |

14 day old chicks
[a]USDA Challenge virus = $1.0 \times 10^{4.5}$ pfu
[b]Protection = # healthy birds/total (%).
[c]Intraocular
[d]Orbital Sinus Example 4

S-ILT-011

S-ILT-011 is an infectious laryngotracheitis virus (ILTV) that has an approximately 983 base pair deletion of the ILTV gI gene. The gene for E. coli β-glucuronidase (uidA) was inserted in the place of the gI gene and is under the control of the pseudorabies virus (PRV) gX promoter. The PRV gX promoter-uidA gene is in the opposite orientation to the direction of transcription of the ILTV gI promoter.

S-ILT-011 was constructed using homology vector 562-61.1F (see Materials and Methods) and S-ILT-001 in the DNA TRANSFECTION FOR GENERATING RECOMBINANT ILT VIRUS. The transfection stock was screened by the X-Gluc SCREEN FOR RECOMBINANT HERPESVIRUS EXPRESSING ENZYMATIC MARKER GENES. The result of blue plaque purification was recombinant virus S-ILT-011. This virus was characterized by restriction mapping and the SOUTHERN BLOTTING OF DNA procedure. This analysis confirmed the presence of the β-glucuronidase (uidA) marker gene and the deletion of approximately 983 base pairs of the ILTV gI gene which deletes 325 of 363 amino acid codons from the 5' end of the gI gene.

S-ILT-011 is attenuated and is useful as a killed vaccine to protect chickens from ILT disease. S-ILT-011 shows a small plaque phenotype in tissue culture which is indicative of slow viral growth and attenuation. Since S-ILT-011 does not express the ILTV gI gene, it may be utilized as a negative marker to distinguish vaccinated animals from infected animals. As indicated in Example 1, ILTV-infected chickens make antibodies against ILTV gI protein.

Example 5

S-ILT-013

S-ILT-013 is an infectious laryngotracheitis virus (ILTV) that has an approximately 983 base pair deletion of the ILTV gI gene and an approximately 874 base pair deletion of the ILTV gG gene (and a deletion of the HCMV IE promoter lacZ marker gene making the lacZ gene nonfunctional). The gene for *E. coli* β-glucuronidase (uidA) was inserted in the place of the gI gene and is under the control of the pseudorabies virus (PRV) gX promoter.

S-ILT-013 was constructed using homology vector 562-61.1F (see Materials and Methods) and S-ILT-014 in the DNA TRANSFECTION FOR GENERATING RECOMBINANT ILT VIRUS. The transfection stock was screened by the X-Gluc SCREEN FOR RECOMBINANT HERPESVIRUS EXPRESSING ENZYMATIC MARKER GENES. The result of blue plaque purification was recombinant virus S-ILT-013. This virus was characterized by restriction mapping and the SOUTHERN BLOTTING OF DNA procedure. This analysis confirmed the presence of the β-glucuronidase (uidA) marker gene and the deletion of approximately 983 base pairs of the ILTV gI gene which removes 325 of 363 amino acid codons from the 5' end of the gI gene. This analysis also confirmed an approximately 874 base pair deletion of the ILTV gG gene and an approximately 1906 base pair insertion of a partial HCMV IE promoter-lacZ marker gene DNA, of which a portion of the HCMV IE promoter and almost none of the lacZ gene remains (see Example 6).

S-ILT-013 is attenuated and is useful as a killed vaccine to protect chickens from ILT disease. S-ILT-013 shows a small plaque phenotype in tissue culture which is indicative of slow viral growth and attenuation. Since S-ILT-013 does not express the ILTV gI or gG genes, ILTV gI and gG may be utilized as negative markers to distinguish vaccinated animals from infected animals.

Example 6

S-ILT-014

S-ILT-014 is an infectious laryngotracheitis virus (ILTV) that has an approximately 874 base pair deletion of the ILTV gG gene and a deletion of the inserted HCMV IE promoter lacZ marker gene making the lacZ gene nonfunctional. S-ILT-014 was derived from a purified S-ILT-002 virus stock in which a deletion of the HCMV IE promoter lacZ marker gene occurred.

S-ILT-002 was constructed using homology vector 472-73.27 (See Materials and Methods) and S-ILT-001 in the DNA TRANSFECTION FOR GENERATING RECOMBINANT ILT VIRUS. The virus S-ILT-002 has a 874 base pair deletion within the ILTV gG gene and an insertion of the *E. coli* β-galactosidase (lacZ) gene in place of the ILTV gG gene. However, during the Bluogal™ SCREEN FOR RECOMBINANT HERPESVIRUS EXPRESSING ENZYMATIC MARKER GENES, a white plaque was picked which contained a deletion of the lacZ gene within the ILTV gG deletion.

This virus, S-ILT-014, was characterized by restriction mapping, DNA SEQUENCING and the SOUTHERN BLOTTING OF DNA procedure. This analysis confirmed the presence of an approximately 874 base pair deletion of the ILTV gG gene and approximately 1956 base pair insertion of a partial HCMV IE promoter lacZ marker gene DNA (2958 base pairs deleted). The remaining HCMV IE promoter lacZ marker gene DNA consists of an approximately 686 base pair DNA fragment of the approximately 1154 base pair HCMV IE promoter and an approximately 1270 base pair DNA fragment containing approximately 520 base pairs of the 3010 base pair β-galactosidase (lacZ) marker gene and all of the approximately 750 base pair PRV gX polyadenylation signal.

S-ILT-014 is useful as an attenuated live vaccine or as a killed vaccine to protect chickens from ILT disease as indicated in the table below. Since S-ILT-014 does not express the ILTV gG gene and ILTV-infected chickens make antibodies to gG as indicated in Example 1. ILTV gG is utilized as a negative marker to distinguish vaccinated animals from infected animals.

TABLE III

EFFICACY OF RECOMBINANT LIVE ILT VIRUS S-ILT-014 AGAINST VIRULENT INFECTIOUS LARYNGOTRACHEITIS VIRUS CHALLENGE

| Vaccine | Gene(s) Deleted | Dose | Route | Challenge[a] | Protection[b] |
|---|---|---|---|---|---|
| S-ILT-014 | gG- | $1.08 \times 10^4$ | IO[c] | OS[d] | 97% |
| S-ILT-014 | gG- | $2.16 \times 10^3$ | IO | OS | 97% |
| Controls | | | | OS | 0% |
| ASL embryo | | | IO | OS | 90% |

14 day old chicks
[a]USDA Challenge virus = $1.0 \times 10^{4.5}$ pfu
[b]Protection = # healthy birds/total (%).
[c]Intraocular
[d]Orbitual Sinus Example 7

S-ILT-015

S-ILT-015 is an infectious laryngotracheitis virus (ILTV) that has an approximately 2640 base pair deletion of the UL47-like gene, the ORF4 gene, and ILTV gG gene. The gene for *E. coli* β-glucuronidase (uidA) was inserted in the place of the UL47-like, ORF4, and gG genes and is under the control of the pseudorabies virus (PRV) gX promoter. The PRV gX promoter-uidA gene is in the opposite orientation to the direction of transcription of the ILTV UL47-like. ORF4, and gG promoters.

S-ILT-015 was constructed using homology vector 560-52.F1 (see Materials and Methods) and S-ILT-001 in the DNA TRANSFECTION FOR GENERATING RECOMBINANT ILT VIRUS. The transfection stock was screened by the X-Gluc SCREEN FOR RECOMBINANT HERPESVIRUS EXPRESSING ENZYMATIC MARKER GENES. The result of blue plaque purification was recombinant virus S-ILT-015. This virus was characterized by restriction mapping and the SOUTHERN BLOTTING OF DNA procedure. These results confirmed the presence of a 2640 base pair deletion which includes 442 of a total 511 amino acid codons at the 3' end of the UL47-like gene, all of the ORF4 gene and 271 of 293 amino acid codons of the 5' end of the gG gene.

S-ILT-015 is useful as an attenuated live vaccine or as a killed vaccine to protect chickens from ILT disease as indicated in the table below. Since S-ILT-015 does not express the ILTV gG gene. ILTV gG is utilized as a negative marker to distinguish vaccinated animals from infected animals.

TABLE IV

EFFICACY OF RECOMBINANT LIVE ILT VIRUS
S-ILT-015 AGAINST VIRULENT INFECTIOUS
LARYNGOTRACHEITIS VIRUS CHALLENGE

| Vaccine | Gene(s) Deleted | Dose | Route | Challenge[a] | Protection[b] |
|---|---|---|---|---|---|
| S-ILT-015 | gG-, UL47-like | $1.0 \times 10^5$ | IO[c] | OS[d] | 70% |
| Controls | | | | OS | 0% |
| ASL embryo | | | IO | OS | 90% |

14 day old chicks
[a]USDA Challenge virus = $1.0 \times 10^{4.5}$ pfu
[b]Protection = # healthy birds/total (%).
[c]Intraocular
[d]Orbital Sinus

Example 8

S-ILT-017

S-ILT-017 is an infectious laryngotracheitis virus (ILTV) that has an approximately 3351 base pair deletion of the ILTV gG gene, ORF4 gene and the g60 gene. The gene for E. coli β-glucuronidase (uidA) was inserted in the place of the ILTV gG and g60 genes and is under the control of the pseudorabies virus (PRV) gX promoter.

S-ILT-017 was constructed using homology vector 579-14.G2 (see Materials and Methods) and S-ILT-001 in the DNA TRANSFECTION FOR GENERATING RECOMBINANT ILT VIRUS. The transfection stock was screened by the X-Gluc SCREEN FOR RECOMBINANT HERPESVIRUS EXPRESSING ENZYMATIC MARKER GENES. The result of blue plaque purification was recombinant virus S-ILT-017.

S-ILT-017 is attenuated by deletion of the ILTV g60 and gG genes, but retains other genes known to be involved in the immune response in chickens to ILT virus. Therefore, S-ILT-017 may be used as a killed vaccine to protect chickens from ILT disease. Since S-ILT-017 does not express the ILTV gG or g60 genes, it is used as a negative marker to distinguish vaccinated animals from infected animals.

Example 9

Recombinant Infectious Laryngotracheitis Viruses that Express Infectious Bronchitis Virus (IBV) Spike and Matrix Protein Genes:

A homology vector is used to generate ILT viruses containing the IBV Arkansas spike protein gene. The recombinant ILT virus contains a deletion of one or more ILTV genes, including gG, US2, UL47-like, and ORF4, and the insertion of two foreign genes: the E. coli β-glucuronidase gene (uidA) and the IBV Arkansas spike protein gene. The uidA gene is under the control of the PRV gX promoter and the IBV Arkansas spike protein gene is under the control of the HCMV IE promoter.

To construct a homology vector containing the foreign genes inserted into the ILT virus, a DNA fragment containing the HCMV-IE promoter, the IBV Arkansas spike protein and the HSV-1 TK polyadenylation signal is inserted into a restriction enzyme site at the position of the deletion of the ILTV gG gene in the ILTV homology vector. A DNA fragment containing the PRV gX promoter and the E. coli β-glucuronidase (uidA) gene is inserted into a unique restriction enzyme site within the ILTV homology vector. A recombinant virus is constructed by combining the final homology vector containing the IBV Arkansas spike gene and the E. coli β-glucuronidase (uidA) gene and S-ILT-001 in the DNA TRANSFECTION FOR GENERATING RECOMBINANT ILT VIRUS. The transfection stock is screened by the X-Gluc SCREEN FOR RECOMBINANT HERPESVIRUS EXPRESSING ENZYMATIC MARKER GENES to detect the presence of the uidA gene and by the BLACK PLAQUE ASSAY FOR FOREIGN GENE EXPRESSION to detect the presence of the IBV Arkansas spike protein.

A similar strategy is used to construct recombinant ILT viruses carrying the IBV S1 protein from Arkansas, Massachusetts, or Connecticut serotypes, IBV matrix protein from Arkansas, Massachusetts, or Connecticut serotypes, and IBV nucleocapsid from Arkansas, Massachusetts, or Connecticut serotypes. The strategy is also used to construct recombinant ILT viruses carrying the Newcastle Disease virus (NDV) HN and F genes and the Infectious Bursal Disease virus (IBDV) polyprotein or portions thereof. The strategy is also used to construct recombinant ILT viruses carrying the Mareks Disease virus (MDV) gA, gD, and gB genes.

Recombinant ILT virus carrying these antigens are valuable as a multivalent vaccine to protect chickens from diseases caused by ILTV and one or more of the viruses IBV, NDV, IBDV, or MDV. Since the ILTV vaccines described here do not express ILTV gG, it is useful as a negative marker to distinguish vaccinated animals from infected animals.

Example 10

Vaccines Utilizing ILTV to Express Antigens from Various Disease Causing Microorganisms:

Antigens from the following microorganisms are utilized to develop poultry vaccines: Chick anemia agent, Avian encephalomyelitis virus, Avian reovirus, Avian paramyxoviruses, Avian influenza virus, Avian adenovirus, Fowl pox virus, Avian coronavirus, Avian rotavirus, *Salmonella* spp., *E. coli*, *Pasteurella* spp., *Haemophilus* spp. *Chlamydia* spp., *Mycoplasma* spp., *Campylobacter* spp. *Bordetella* spp., Poultry nematodes, cestodes, trematodes, Poultry mites/lice. Poultry protozoa (*Eimeria* spp., *Histomonas* spp. *Trichomonas* spp.).

Example 11

A Genomic Map of Infectious Laryngotracheitis Virus and the Sequence and Organization of Genes Present in the Unique Short Region A cosmid library of the ILTV genome was created to facilitate restriction endonuclease mapping. Forty-three overlapping cosmids were analyzed by digestion with Asp718I and NotI. Asp718I was known to cut the genome relatively infrequently (63), and it was found that NotI cut the genome less than ten times, which enabled cutting the vector away from the ILTV DNA insert. Comparison of these cosmid digests allowed the order of the Asp718I fragments covering 85% of the ILTV genome to be determined (FIG. 12). On the long end of the genome, seven cosmids were identified which all contained a NotI site 0.9 kb from the end of the cloned insert; all other cosmid inserts had heterogeneous ends from shearing. This 0.9 kb fragment was used as a probe (P1 in FIG. 12) to genomic ILTV digested with Asp718I, NotI, or BamHI: the sizes of the genomic fragments that hybridized were identical to the size of the fragments excised from the cloned cosmid insert, indicating that the cloned insert extended all the way or very close to the end of the unique long. The 0.9 kb fragment did not hybridize to other bands in the ILTV digest, consistent with previous reports that this virus resembles PRV, and contains no long repeat (66). Once the cosmid clones were ordered, the restriction sites for a more frequent cutting enzyme, BamHI, were mapped.

The resulting map indicated that the cosmid library did not include clones from the unique short portion of the genome. Cosmids spanning the unique short region of HVT (76) and PRV (83) have been found to be underrepresented in cosmid libraries. The Asp718I fragments found in the cosmid clones with an Asp718I digest of wild type ILTV and identified fragments of 8.0, 5.1, and 2.5 kb which were not represented in the cosmid library (FIG. 13) were compared. These fragments were cloned into plasmids and hybridized to each other and to ILTV digested with BamHI. The Asp718I 2.5 and 8.0 kb fragments cross-hybridized, Indicating that they contained sequence repeated in both clones. Fine mapping of the Asp718I 2.5 and 8.0 kb fragments showed them to contain 2.1 kb of identical sequence. Hybridization to ILTV digested with BamHI identified BamHI bands of 7.5, 6.5, and 4.5 kb which overlapped the Asp718I fragments. These BamHI fragments were cloned and analyzed by restriction digestion and hybridization. This allowed the map of the entire unique short region and some of the flanking short repeat to be elucidated (FIG. 13). Subclones of this region were made, and the entire unique short region was sequenced.

To complete the genomic map, the map searched for an Asp1181 or BamHI fragment that spanned the region between the short repeat sequences of the 8.0or 2.5 kb Asp718I fragments mentioned above and the unique long region identified in the cosmid map. A 10 kb NotI fragment from the rightmost end of cosmid D5 (FIG. 12) was hybridized to genomic ILTV digests on Southern blots. Interestingly, ladders of hybridizing bands were seen when the enzymes BamHI, NotI, and Asp718I were used. The bands corresponding to these ladders were not generally visible in ethidium bromide stained gels. Subsequent subcloning and mapping of the 10 kb D5 fragment indicated that it contained up to 5 repeats of an 856 bp segment, and that the cosmid insert ended within a repeat motif. HindIII, which cuts once within the repeat, was used to clone the 856 bp fragment. When this fragment (FIG. 12, P2) was used to probe ILTV digested with SfiI, NotI, Asp718I, and BamHI, ladders of hybridization were again seen (FIG. 14). These ladders arise from varying numbers of the 856 bp repeat in different viral molecules. SfiI cuts only once in this ILTV strain, and a ladder at very high molecular weight can be seen. Because the unique short is expected to invert, two overlapping SfiI ladders containing the unique short and terminal repeat ($TR_s$) should be present; however, the bands are too large in this region to make this distinction. NotI and Asp718I cut further away from the repeat, generating ladders beginning at 10.5 or 12 kb. The Asp718I digest should generate two overlapping ladders, because one fragment is bounded by an Asp718I site in the unique long, while the other is bounded by the end of the $TR_s$. In contrast, only one ladder should be generated by the NotI digest. Comparison of FIG. 14 lane c (NotI) with lane d (Asp718I) does suggest that in lane d a second ladder is superimposed on the first, starting somewhat higher. BamHI cuts close to the repeated region, and a ladder beginning at 3.4 kb is found, HindIII cuts within the repeat and generates a strongly hybridizing 856 bp band, as well as the two flanking HindIII fragments of about 1.1 and 2.5 kb, which each contain a portion of the repeated sequence. The presence of this 856 bp repeat accounted for the occasional observation of very fine submolar bands in ethidium bromide-stained Asp718I digests. It also accounted for the lack, in ethidium bromide-stained gels, of a molar or half-molar quantity Asp718I or BamHI band greater than 10 kb, which was expected to span this region based on analysis of the cosmid clones. Instead, because of the presence of the 856 bp repeat, this band exists as many submolar bands comprising the ladder. As can be seen in the BamHI digest, there can be thirteen or more repeats of the region. Comparison of the repeat sequence to the sequence submitted to GenBank by Johnson et al. (67) indicated that it corresponded (99% identity) to nucleotides 1140 to 1996 of their sequence, which is a region just upstream of the ILTV ICP4 gene. The relationship of the repeat to the surrounding sequence is depicted in FIG. 15. Restriction digests indicate that the region to the right of the repeat as shown is similar in the two strains; however, the position of the BamHI site indicated to the left of the repeat differs between them.

To identify the remainder of the short repeat from the 856 bp repetitive region to the BamHI fragments used for sequencing the unique short, the 8.0 kb Asp718I fragment containing part of the short repeat was used as a probe to a second cosmid library of ILTV. One cosmid, clone 2F12, hybridized to the probe. Restriction endonuclease analysis of 2F12 and comparison to the cosmid map indicated that it was not a single contiguous cosmid, but was composed of two large non-contiguous fragments (see FIG. 12). The break in the rightmost fragment was within a repeat of the 856 bp region. This fragment included at least two 856 bp repeats, and extended 4.6 kb through the remainder of the short repeat into the unique short.

To identify the end of the $TR_s$, the 6.6 kb NotI fragment spanning the unique long and the short internal repeat ($IR_s$) (P3 in FIG. 2) was used as a probe. It was noted that a 2.9 kb NotI fragment seen in gels stained with ethidium bromide was not represented in the restriction endonuclease map, and considered that it might represent the end of the $TR_s$. Hybridization of a NotI digest of ILTV with P3 indicated that this was indeed the case (FIG. 16). The 2.9 kb NotI band hybridizes, as does the 6.6 kb band corresponding to the probe. In the BamHI digest, the predicted 13 kb fragment containing a portion of the $IR_s$ and a 3.5 kb fragment corresponding to the end of the $TR_s$ are evident. In the Asp718I digest, an overlapping 2.7 kb fragment from the unique long hybridizes, and the high molecular weight ladder described previously was seen.

Sequencing of the ILTV unique short and flanking region identified nine open reading frames in the unique region and two (duplicated) in the repeat region as diagrammed in FIG. 13 (SEQ ID NO:59). Comparison of the proteins encoded by these ORFs to the GenBank database (BLAST homology search, National Center for Biological Information. NCBI) demonstrated identity for most of the potential proteins with other known herpesvirus gene products. Table V summarizes the closest homologies found for each gene and gives the probability scores for those homologies as generated by the search program. ORF2 (SEQ ID NO:63), the protein kinase (PK) gene (SEQ ID NO:63), is the most highly conserved of the ILTV ORFs to its herpes homologues. In contrast, the glycoprotein genes are less conserved. It should be noted that portions of the sequences of the ILTV protein kinase, gG, and ORF 5 genes have been published (69, 70 and 81); however, these genes were mapped to the unique long region. A description of each of the nine unique short genes and the two genes in the flanking short repeat follows.

The first open reading frame in the unique short encodes a 229 aa protein showing identity to other herpesvirus US2 proteins (SEQ ID NO:62). Like other US2 genes, it is in the opposite orientation to the remaining ORFs in the unique short. The coding sequence of the gene ends just within the unique short region, and a potential poly-A addition site is found 115 bases downstream in the short repeat. Two possible TATA promoters are found 37 and 70 bases upstream from the initiation codon.

ORF2 encodes a protein kinase with strong identity to many other herpesvirus protein kinases and to cellular protein kinases. The organization of the US2 and PK genes, with their 5' ends close together and their promoters possibly overlapping, is similar to that found in other herpesviruses. Two TATA sequences are present 14 and 49 bases upstream of the PK start codon, and two polyadenylation signals are found, one immediately after the stop codon, and one 50 bases downstream.

ORF3 encodes a 623 aa protein with similarity to the herpes simplex virus UL47 gene (SEQ ID NO:64). The program comparing this protein with other UL47 proteins projects a poor probability score for this homology. However, at least one of the regions of identity between ILTV and HSV UL47 corresponds to a region that is conserved among other herpesvirus UL47 homologues, suggesting that this identity is significant (FIG. 17). Additionally, it should be noted that equally poor probability scores for homology generated by comparisons of the gG or gI genes are also seen for certain homologue pairings, suggesting that these scores are not sufficient for determining homology. It is interesting that the ILTV UL47 gene, normally found in the unique long region of other herpesviruses, appears to have been transposed into the unique short in ILTV.

The fourth open reading frame encodes a 292 aa glycoprotein homologous to PRV gG (SEQ ID NO:65). Four N-linked glycosylation sites with the consensus sequence NXT or NXS are present. The protein has a signal sequence of 26 aa, which could be cleaved at G/AP, but lacks a transmembrane anchor. It is therefore likely that this protein is secreted, similar to other herpesvirus gG homologues. This gene has a consensus TATA sequence 83 bases upstream from the ATG start, and has two potential polyadenylation sites 73 and 166 bases downstream from the stop codon.

ORF5 could encode a protein of 985 amino acids (SEQ ID NO:66). A hydrophobic signal sequence is found at the amino terminus, and a hydrophobic sequence is present at the carboxy terminus. Nine glycosylation sites are found, suggesting that this is a glycoprotein. ORF 5 contains an imperfect repeat, consisting of 30 to 36 bp repeated approximately 23 times from amino acid 431 to amino acid 677. The hydrophilic amino acid consensus sequence created by this repeat is FTQTPSTEPET/A. Comparison of ORE 5 with other herpesvirus sequences (Table V) shows similarity- to the glycoprotein product from the equine herpesvirus 1 US5 gene (EUS5, 82). The low probability score for this identity arises primarily from the fact that both genes contain threonine-rich repeats. It is not clear whether this reflects homology in form, function, or both. Both the EUS5 and the ILTV ORE 5 genes are large, have similar positions among flanking genes in the unique short, have signal sequences, and encode glycoproteins, but other sequence similarities are not seen. It is interesting that the ORE 5 repeat region shows similarity to mucin genes, which also contain threonine rich repeats. The human mucin gene, for example, has the repeat GTOTPTTTPI TTTTTVTPTPTPT, where 7 of the first 11 amino acids are identical to the ORE 5 repeat sequence. Again, whether this reflects a similarity in function of the encoded proteins is unclear. A TATA sequence is found 560 bases upstream of the start codon; the nearest consensus polyadenylation signal is at the end of the gI gene. This suggests that the ORE 5 transcript may be coterminal with the gD transcript.

The open reading frame for the gD homologue (ORF 6) (SEQ ID NO:67) overlaps the end of ORF 5. Four in-frame methionines are found within the first 58 amino acids of the open reading frame, and it is not clear which is the actual translational start codon. Because a potential TATA promoter sequence is located only 6-9 bases upstream from the first possible ATG codon, this codon would probably not be within RNA transcribed from this promoter; however, there are several TATA sequences further upstream that may also be used to initiate transcription. The other three potential initiation codons are found at aa 23, 47, and 58 within this ORF. Comparison of the sequences surrounding the four ATGs with the eukaryotic translational initiation consensus sequence A/GCCATGG (71) suggests that the latter two ATG codons may be preferred translational start sites. The protein sequences derived from each of these starts were examined for the presence of eukaryotic signal sequences and signal cleavage sites. A start at aa 58 within the ORF would result in a signal peptide of 26 amino acids with a predicted cleavage site between two alanine residues. This same signal sequence would be positioned much further from the amino terminus and embedded in a more hydrophilic sequence if the other start sites were used. The start of ILTV gD was tentatively assigned to position 58, which would result in a protein 377 amino acids long. Of course, it is possible that more than one initiation codon is used in vivo. Experiments of Zeinik et al. (88) suggest that alternate in-frame ATG codons are used to initiate MDV and HVT gD transcription in vitro, though the in vivo situation was not addressed. Additional experiments on gD transcription and translation in ILTV are necessary to identify its translational start codon.

The ILTV gD homologue has a secretory signal sequence and a transmembrane helix (aa 352-372) at the carboxy terminus. Only one potential glycosylation site is found at position 250-252; this is of the form NPS, and may not be glycosylated due to the proline residue. There is some question, therefore, as to whether processed ILTV gD contains N-linked oligosaccharides. This would be similar to the gD homologue in pseudorabies virus, gp50, which also lacks N-linked glycosylation sites (75). As in other herpesviruses, the gD coding sequence lacks a poly-A addition signal immediately following the gene, and the closest signal is at the end of the gI gene.

The seventh open reading frame encodes a protein of 362 aa and is most homologous to *varicella zoster* virus glycoprotein I (SEQ ID NO:68). The encoded protein shows all the characteristics of related gI glycoproteins, including a signal sequence with a potential cleavage site at positions 22 and 23 between a glycine and an isoleucine, a transmembrane helix at the carboxy terminus from 272-292, and four possible N-linked glycosylation sites. A TATA sequence is present 51 bases upstream from the methionine start codon. Two possible poly-A addition signals are found within the coding sequence for ILTV gI, and may be the signals used by the gD and ORF 5 transcription units upstream.

The gE gene (ORF 8) follows the gI. This gene is 499 aa long, and contains four N-linked glycosylation sites (SEQ ID NO:69). A signal sequence of 18 amino acids is present, and there are two and possibly three membrane-associated helices in the carboxy terminal portion of the protein. The gE gene has a TATA box 86 bases upstream of the start codon, and a potential poly-A addition signal just prior to the 3' end of the coding region. This may serve as the polyadenylation site for the gI gene.

The ninth open reading frame extends across the junction of the unique short and the short repeat, and could encode a protein of 260 amino acids (SEQ ID NO:70). This protein has no signal sequence or membrane anchor, but has one possible N-linked glycosylation site. In a search of GenBank, some similarity is found between this protein and BLRF2 of EBV, but the significance of this similarity is unknown. The poly-A addition signal in the short repeat may be utilized by this gene. A potential TATA sequence is found 178 bases upstream of the first ATG of this ORF.

The first open reading frame in the short repeat (SRORF1) (SEQ ID NOs: 61 and 71) encodes a 294 aa protein which displays homology to the gene product of MDV SORF3 (79 and 84) and HVT ORF3 (87). In MDV and HVT, the corresponding gene is found as one copy in the unique short, and its function is unknown. No homology has been identified with mammalian herpesviruses; this gene appears to be specific to avian herpesviruses. MDV SORF3 has been deleted by Parcells et al. (74), and does not appear to be absolutely required for infection in chickens.

SRORF2 encodes a protein of 278 amino acids with homology to other herpesvirus US10 genes (SEQ ID NOs:60 and 72). A zinc finger motif, found in the EHV-4 US10, is highly conserved in the ILTV US10 (ammo acids 201-218); this suggests that the ILTV US10 gene is a DNA binding protein. Regulatory sequences include a poly-A addition signal 163 bp after the stop codon; it is unclear where the promoter for this gene resides.

Discussion:

The organization of the genes in the unique short region of ILTV is similar to that seen in other herpesviruses. Several genes encoding glycoproteins are present, and the order of these genes is similar to that seen in equine herpesvirus 1, particularly with respect to ORF 5. Similarities to avian herpesviruses are also evident in the presence of the avian-specific gene, SRORF1, and its position relative to US2 and PK, though it differs from HVT and MDV in that it is in the short repeat and is duplicated, also appearing downstream from the ORF 9 gene. The PK gene itself has the most identify to MDV and HVT PK genes; however, other genes are found to be more like their homologues in diverse herpesviruses such as EHV, PRV, and SHV SA8. Unusual characteristics of the ILTV unique short are the inclusion of a gene normally found in the unique long, the UL47 homologue, and the presence of the unique gene, ORF 5, which contains a set of degenerate repeats.

This analysis of the structure of ILTV disagrees with previous reports. Comparison of the sequences described here with those of the Australian ILTV isolate SA-2 indicates that a 32 kd protein described by Kongsuwan et al. (70) is almost identical to the gG in this application, and the sequenced fragment of the g60 protein presented by Kongsuwan et al. (69) is part of the ORF 5 gene in this application. However, they Identified the 5 kb Asp718I fragment containing both of these genes as coming from the unique long region of SA-2 (66). Recently, Guo et al, (62) reported the sequence of a region from the USDA challenge strain which they ascribed to the unique short on the basis of comparison to the map presented by Johnson et al. (66). No identity was found between this sequence and the unique short sequence described here. Instead, the sequence described by Guo ex al. (62) shows 98% identity to a sequence recently submitted to GenBank by Johnson ex al. (67 and 68), which is reported to encode the ICP4 gene of ILTV. The BamHI sites within the ICP4 coding region generate two contiguous fragments of 1.2 and 1.7 kb (see FIG. 15). In the map described here, two contiguous BamHI fragments of this size are found within the short repeats (FIG. 12). In addition, the 856 bp repeat element, which is found just upstream of the ICP4 gene (FIG. 15), was mapped in this application within the short repeats. This indicates that the ICP4 gene in the strain used in these studies is present in the $IR_s$ and the $TR_s$. It is possible, but unlikely, that the Australian SA-2 vaccine strain underwent an unusual rearrangement which altered the relationship of the unique long, unique short, and short repeat. However, Guo et al. (62) used the same challenge strain as the one described in this application, and the sequence they reported is not in the unique short, but in the short repeats, similar to the ICP4 genes of other herpesviruses.

The gene encoded by ORF 5 contains threonine rich, degenerate repeats. These are similar in composition and in their repetitive nature to repeats found in mucin genes. This repeated region in mucin is modified by O-linked oligosaccharides and is highly hydrophilic. It is interesting to speculate on what the function of this somewhat similar region might be in infection, if it is expressed in toto in ILTV. At least a portion of this gene is known to be expressed, as Kongsuwan et al. (69) cloned and sequenced a fragment from it by probing a lambda gt11 library with a monoclonal antibody that was known, to bind to a 60 kd ILTV protein (g60) on Western blots (86). The relationship of such a 60 kd protein to the predicted 985 aa product from ORF 5 is unknown. Comparison of the application sequence with the complete sequence of the g60 coding region (81) shows a 98.5% homology between the SA-2 strain and the USDA strain. Interestingly, there is an Insertion of a block of 10 amino acids in g60 relative to the ORF 5 protein; this difference reflects one additional degenerate repeat sequence in the SA-2 strain.

As mentioned above, Kongsuwan et al. (70) described an ILTV gene that encoded a 32 kd protein with similarity to PRV gG. A comparison of the ILTV gG protein sequence described in this application with their 32 kd protein found 10 amino acid differences in the first 273 residues of the protein. At amino acid 274, a deletion of one base pair in SA-2 relative to the USDA strain created a frame shift, such that 19 additional residues were found in the challenge strain as opposed to 26 in SA-2. A peptide was made from the carboxy terminal sequence elicited antisera in mice which reacted with ILTV gG; this indicates that the sequence described in this application reflects the actual carboxy terminus in the USDA strain. A similar situation was found when the ILTV gD protein described in this application was compared with the ILTV gD sequence submitted to GenBank by Johnson et al. (68). Ten differences were found in the first 419 amino acids, after which a deletion of a base in the SA-2 strain relative to the sequence described in this application caused the predicted carboxy termini to differ, with 15 more amino acids in the USDA strain and 9 in SA-2. These differences could arise from errors introduced during cloning and sequencing of these genes. It is also possible that the carboxy termini of the ILTV gG and gD genes are variable between these strains.

The 856 bp repeat unit identified within the short repeat is just upstream of the ICP4 gene, described by Johnson et al. (67), but, from the sequence alone, it does not appear to be repetitive in the SA-2 strain. The BamHI fragment containing this repetitive region is 2848 bp long in SA-2. The smallest repeat, seen faintly in the BamHI ladder of FIG. 14, is 3.4 kb long. This is not quite large enough to include two repeats, and suggests that other alterations between the two strains may exist in this region. A repeat of this sort has not been previously described for this or other ILTV strains, though the submolar nature of the bands may have obscured its presence. The appearance of the ladder is reminiscent of defective interfering particles, but it is not believed that this represents a case of defective interfering particles in the viral stock used here Several reasons for this follow. 1) Defective interfering particles are generally found when viruses are passaged at high multiplicity, and the ILTV viral stocks of this application were passaged at low multiplicity. In fact, viral stocks originating from a single picked plaque exhibited similar ladders when their DNA was subjected to Southern blot analysis, suggesting that a single viral particle containing a set number of repeats could regenerate the full range of the ladder after being grown for a short period of time. 2) If populations of defective interfering particles were present, one might expect to encounter digest fragments that would not be accommodated in the linear viral map (see, for example, 77), yet all but one of the cosmids analyzed make a contiguous map, with Asp718I bands identical to those present in genomic ILTV digests. The exception, 2F12, was unusual in being the only one of several hundred cosmid clones screened which contained part of the unique short. This probably represented an aberrant cloning event, and not a widespread phenomenon related to defective viral particles. 3) Defective interfering particles often are present in larger molar amounts than standard viral particles, such that restriction fragments originating from the defective particles are overrepresented. In contrast, the bands of the 856 bp ladder are submolar, and are only rarely visible in ethidium bromide stained gels, 4) Defective interfering particles contain origins of replication. The 856 bp repeat itself does not contain a herpesvirus origin of replication as defined by the consensus sequence of Baumann et ah (59). From these considerations it was concluded that varying numbers of 856 bp units are present in the short repeats of standard viral DNA from the USDA challenge strain of ILTV. Since fragments exist that contain thirteen or more repeats of the region, genomic DNA from ILTV could vary by over 11 kb in the short repeat regions. Repetitive regions have been identified in other herpesviruses: for example, Marek's disease virus contains a 132 bp repetitive sequence in the long repeat regions (61 and 73) and expansion of this repeat is associated with reduction of viral oncogenicity. The presence of the 856 bp tandem repeats in ILTV, in contrast, does not appear to affect viral pathogenicity, since this strain does cause severe clinical disease in chickens. It would be interesting to examine other ILTV strains for the presence of this repeat.

Table V indicates the ORFs of the ILTV unique shorn and the HSV nomenclature for these genes, in those cases where homology is found. The third column shows the best matches from the Blast homology search (NCBI), and the probability scores assigned by the program for the matches indicated. Smaller numbers indicate less likelihood that the match could occur randomly.

A genomic map of infectious laryngotracheitis virus (ILTV) and a 18,912 bp sequence containing the entire unique short region and a portion of the flanking short repeats is presented. In determining the genomic map, an 856 bp region repeated as many as 13 times was identified within the short repeats. The unique short sequence contains 9 potential open reading frames (ORFs). Six of these ORFs show homology to other known herpesvirus unique short genes. Using the herpes simplex virus nomenclature, these genes are the US2, protein kinase, and glycoproteins G, D, I, and E (SORFs 1, 2, 4. 6, 7, and 8, respectively). Interestingly, an open reading frame with homology to HSV-1 UL47 (SORE 3) is found in the unique short. One very large open reading frame (ORF 5) is present and contains a threonine rich, degenerate repeat sequence. This gene appears to be unique to ILTV among sequenced herpesviruses. Two ORFs were identified within the short repeat region. SRORF1 is homologous to a gene (SORF3) found in the unique short region in both MDV and HVT, and appears to be specific to avian herpesviruses. SRORF2 has homology to HSV US10.

TABLE V

| ORF | HSV Homolog | Best Matches | Blast Score |
|---|---|---|---|
| 1 | US2 | EHV1 EUS1 | $3.1 \times 10^{-13}$ |
|   |   | EHV4 EUS1 | $5.3 \times 10^{-12}$ |
|   |   | HSV2 US2 | $6.7 \times 10^{-7}$ |
| 2 | PK | MDV PK | $8.2 \times 10^{-36}$ |
|   |   | HVT PK | $5.4 \times 10^{-35}$ |
|   |   | HSV1 PK | $4.1 \times 10^{-30}$ |
| 3 | UL47 | HSV1 UL47 | $6.0 \times 10^{-1}$ |
|   |   | EHV1 UL47 | $9.9 \times 10^{-1}$ |
|   |   | MDV UL47 | $9.9 \times 10^{-1}$ |
| 4 | gG | PRV gG | $5.3 \times 10^{-5}$ |
|   |   | BHV1 gG | $1.7 \times 10^{-2}$ |
|   |   | EHV1 gG | $6.8 \times 10^{-1}$ |
| 5 | ORF 5 | EHV1 EUS5 | $1.9 \times 10^{-45}$ |
|   |   | Human mucin | $1.1 \times 10^{-25}$ |
| 6 | gD | MDV gD | $6.8 \times 10^{-4}$ |
|   |   | PRV g50 | $2.0 \times 10^{-3}$ |
|   |   | HVT gD | $3.5 \times 10^{-3}$ |
| 7 | gI | VZV gI | $4.2 \times 10^{-2}$ |
|   |   | HVT gI | $7.9 \times 10^{-2}$ |
|   |   | SVV gI | $4.3 \times 10^{-1}$ |
| 8 | gE | SHV SA8 gE | $1.7 \times 10^{-6}$ |
|   |   | HSV1 gE | $1.1 \times 10^{-3}$ |
|   |   | BHV1 gE | $1.5 \times 10^{-2}$ |
| 9 | ORF 9 | EBV BLRF2 | $5.7 \times 10^{-1}$ |
| SR1 | no HSV homologue | MDV "ORF3" | $4.8 \times 10^{-4}$ |
|   |   | HVT "ORF3" | $2.6 \times 10^{-1}$ |
| SR2 | US 10 | EHV-4 US10 | $1.2 \times 10^{-1}$ |
|   |   | HSV-1 US10 | $8.7 \times 10^{-1}$ |
|   |   | EHV-1 US10 | $8.7 \times 10^{-1}$ |

REFERENCES

1. L. Nicolson, et. al., Virology 179, 378-387 (1990).
2. R. W. Price and A. Kahn, Infection and Immunity, 34, 571-580 (1981).
3. M. P. Riggio, et. al. Journal of Virology 63, 1123-1133 (1989).
4. G. R. Robertson and J. M. Whalley, Nucleic Acids Research 16, 11303-11317 (1988).
5. B. Roizman, et. al. Cold Spring Harbor Conference on New Approaches to Viral Vaccines (September 1983).
6. B. Roizman, et. al., Archives of Virology 123, 425-449 (1992).
7. F. A. Ferrari, et. al., Journal of Bacteriology 161, 556-562 (1985).
8. R. A. Bhat, et. al., Nucleic Acids Research 17, 1159-1176 (1989)
9. The Herpesviruses, Volume 1, B. Roizman, ed. Plenum Press, New York, (1982).
10. Diseases of Poultry, Eighth Edition, M. S. Hofstad, Ed., pp 444-451, Iowa State University Press, 1984.
11. M. C. Wark, et. al., Journal of Biological Standardization 7: 73-80 (1979).
12. S. Davison, et. al., Avian Diseases 33: 18-23 (1989).
13. S. Davison, et. al., Avian Diseases 33: 24-29 (1989).
14. J. R. Andreasen Jr. et. al., Avian Diseases 33: 516-523 (1989).
15. J. R. Andreasen Jr., et. al., Avian Diseases 33: 524-530 (1989).
16. J. S. Guy, et. al. Avian Diseases 34: 106-113 (1990).
17. J. R. Andreasen Jr., et. al., Avian Diseases 34: 185-192 (1990).
18. J. J. York, and K. J. Fahey, Archives of Virology 115: 289-297 (1990).

19. C. S. Hughes, et. al., Archives of Virology 121: 213-218 (1991).
20. T. J. Bagust. et. al. Patent Application WO 91/02053
21. J. S. Guy, et. al., Avian Diseases 35: 348-355 (1991).
22. M. A. Johnson, et. al., Archives of Virology 119: 181-198 (1991).
23. D. A. Leib. et. al. Archives of Virology 93: 287-294 (1987).
24. M. Kotiw, et. al., Veterinary Microbiology 11: 319-330 (1986).
25. J. S. Guy, et. al. Avian Diseases 33: 316-323 (1989).
26. J. R. Andreasen Jr., et. al. Avian Diseases 34: 646-656 (1990).
27. M. M. Binns, et. al., PCT Patent Application WO 90/02802.
28. A. M. Griffin and M. E. G. Boursnell, Journal of General Viroloev 71 841-850 (1990).
29. D. J. Poulsen, et. al., Virus Genes 5: 335-347 (1991).
30. A. M. Griffin, Journal of General Virology 72: 393-398 (1991)
31. A. M. Griffin, Journal of General Virology 70: 3085-3089 (1989).
32. A. M. Griffin, Nucleic Acids Research 18: 3664 (1990).
33. Y. M. Saif, et. al., AVMA 130th Annual Meeting, Jul. 17-21, 1993, Minneapolis, Minn.
34. J. J. York, et. al., Virology 161: 340-347 (1987).
35. J. J. York, et. al. Archives of Virology 115: 147-162 (1990).
36. C. T. Prideaux, et al., Archives of Virology 123: 181-192 (1992).
37. R. W. Honess, Journal of General Virology 65, 2077-2107 (1984).
38. M. L. Cook & J. G. Stevens, Journal of General Virology 31, 75-80 (1976).
39. S. Joshi, et. al. Journal of Virology 65, 5524-5530 (1991).
40. M. Wachsman, et. al., Journal of General Virology 70, 2513-2520 (1989).
41. R. A. Bhat, et. al., Nucleic Acids Research 17, 1159-1176 (1989)
42. T. Maniatis. et. al. Molecular Cloning: A Laboratory Manual, Cold Spring Harbor Press, Cold Spring Harbor, N.Y. (1982)
43. J. Sambrook, et al. Molecular Cloning; A Laboratory Manual, Second Edition, Cold Spring Harbor Press. Cold Spring Harbor, N.Y. (1989).
44. M. A. Innis. et. al. PCR Protocols: A Guide to Methods and Applications, Academic Press, San Diego (1990).
45. C. Chen and Okayama, H., Moi. Cell Biol. 7, 2745-2752 (1987).
46. M. van Zip. et. al. Journal of Virology 62, 2191-2195 (1988).
47. B. Lomniczi, et. al. Journal of Virology 49 970-979 (1984).
48. D. J. McGeoch, et. al., Journal of Molecular Biology 181, 1-13 (1985).
49. F. A. Ferrari, et. al. Journal of Bacteriology 161, 556-562 (1985).
50. J. M. Sharma and L. G. Raggi, Avian Disease 13, 268-279 (1969).
51. D. H. Kingsley, J. W. Hazel, and C. L. Keeler, Jr., Abstract from the 65th Northeastern Conference on Avian Diseases, Jun. 9-11, 1993. University of Delaware, Newark, Del.
52. D. W. Key and E. Nagy, Abstract from the 65th Northeastern Conference on Avian Diseases, Jun. 9-11, 1993. University of Delaware. Newark, Del.
53. M. G. Sheppard, et. al., PCT Patent Application WO 92/03554.
54. T. Honda, et. al., U.S. Pat. No. 4,980,162.
55. Federal Register, Vol. 55, No. 90, pp. 19245-19253
56. T. Ben-Porat, et. al., Virology 154 325-334 (1986).
57. F. Zuckerman. et. al. in Vaccination and Control of Aujeszky's Disease, Ed. J. van Oirschot, Kluwer, London (1989), pp. 107-117.
58. Altschul, S.F. Gish, W., Miller, W., Myers, E. W., and Lipman, D. J. (1990). Basic local alignment search tool. J. Mol. Biol. 215, 403-410.
59. Baumann. R. P., Yalamanchili. V. R. R., and O'Caliaghan. D. J. (1989) Functional mapping and DNA sequence of an equine herpesvirus 1 origin of replication. J. Virol. 63, 1275-1283.
60. Dayhoff, M. O., Barker, W. C., and Hunt, L. T. (1983) Establishing homologies in protein sequences. Methods Enzymol 91, 524-545.
61. Fukuchi. K., Tanaka, A. Schierman. L. W., Witter, R. L., and Nonoyama, M. (1985). The structure of Marek disease virus DNA: the presence of unique expansion in nonpathogenic viral DNA. Proc. Natl. Acad. Sci. USA 82, 75 S-754.
62. Guo, P., Scholz, E., Maloney, B., and Welniak, E. (1994). Construction of recombinant avian infectious laryngotracheitis vims expressing the β-galactosidase gene and DNA sequencing of the insert region. Virology 202, 771-781.
63. Guy, J. S., Barnes, H. J., Munger, L. I. and Rose, L. (3989). Restriction endonuclease analysis of infectious laryngotracheitis viruses: Comparison of modified-live vaccine viruses and North Carolina field isolates. Avian Diseases 33, 316-323.
64. Holland, T. C., Sandri-Goldin, R. M., Holland, L. E. Madia S. D. Levine. M., and Glorioso, J. C. (1983). Physical mapping of the mutation in an antigenic variant of herpes simplex virus type 1 by use of an immunoreactive plaque assay. J. Virol. 46, 649-652.
65. Hughes, C. S., Williams, R. A., Gaskell, R. M., Jordan, F. T. W., Bradbury, J. M., Bennett, M., and Jones, R. C. (1991). Latency and reactivation of infectious larynogotracheitis vaccine virus. Arch. Virol. 121, 213-218.
66. Johnson, M. A., Prideaux, C. T., Kongsuwan, K., Sheppard, M., and Fahey, K. J. (1991). Gallid herpesvirus 1 (infectious laryngotracheitis virus): cloning and physical maps of the SA-2 strain. Arch. Virol. 119, 181-198.
67. Johnson, M. A., Tyack, S. G., Prideaux, C. T., Kongsuwan, K. and Sheppard, M. (1994). Gallid herpesvirus 1 major immediate early protein (ICP4) gene. GenBank L32139.
68. Johnson, M. A., Tyack, S. G. Prideaux, C. T., Kongsuwan. K. and Sheppard. M. (1994). Gallid herpesvirus 1 glycoprotein D (gD) gene, complete cds. GenBank L31965.
69. Kongsuwan, K., Johnson, M. A., Prideaux, C. T., and Sheppard, M. (1993). Use of Igt11 and monoclonal antibodies to map the gene for the 60,000 dalton glycoprotein of infectious laryngotracheitis virus. Virus Genes 7, 297-303.
70. Kongsuwan, K. Johnson. M. A., Prideaux. C. T., and Sheppard, M. (1993). Identification of an infectious laryngotracheitis vims gene encoding an immunogenic protein with a predicted M, of 32 kilodaltons. Virus Research 29, 125-140.
71. Kozak, M. (1987). An analysis of 5'-noncoding sequences from 699 vertebrate messenger RNAs. Nucleic Acids Res. 15, 8125-8148.
72. Leib, D. A., Bradbury, J. M., Gaskell, R. M., Hughes, C. S., and iones. R. C. (1986). Restriction endonuclease patterns of some European, and American isolates of avian infectious larynogotracheitis virus. Avian Dis. 30, 835-837.

73. Maotani, K. Kanamori. A., Ikuta. K., Ueda. S. Kate. S., and Hirai. S. (1986). Amplification of atandem direct repeat within inverted repeats of Marek's disease virus DNA during serial in vitro passage. J. Virol. 58, 657-660.

74. Parcells, M. S. Anderson, A. S., Cantello, J. L., and Morgan. R. W. (1994) Characterization of Marek's disease virus insertion and deletion mutants that lack US1 (ICP22 homolog), US10, and/or US2 and neighboring short-component open reading frames. J. Virol. 68, 8239-8253.

75. Petrovskis, E. A., Timmins, J. G., Armentrout, M. A., Marchioli, C. C., Yancey, R. J., Jr., and Post, L. (1986) DNA sequence of the gene for pseudorabies virus gp50, a glycoprotein without N-linked glvcosvlation. J. Virol. 59, 216-223.

76. Reilly, J. D., and Silva, R. F. (1993). Cosmid library of the turkey herpesvirus genome constructed from nanogram quantities of viral DNA associated with an excess of cellular DNA. J. Virol. Methods 41, 323-331.

77. Rixon, F. J., and Ben-Porat, T. (1979). Structuraly evolution of the DNA of pseudorabies-defective viral particles. Virology 97, 151-163.

78. Roizmann, B., Desrosiers, R. C., Fleckenstein, B., Lopez, C, Minson, A. C., and Studdert, M. J. (1992). The family Herpesviridae: an update. Arch. Virol. 123, 425-449.

79. Sakaguchi, M., Urakawa, T., Hirayama, Y., Miki, N., Yamamoto, M., and Hirai, K. (1992) Sequence determination and genetic content of an 8.9 kb restriction fragment in the short unique region and the internal inverted repeat of Marek's disease virus type 1 DNA. Virus Genes 6, 365-378.

80. Sanger, F., Nicklen. S., and Coulson, A. R. (1977). DNA sequencing with chain-terminating inhibitors. Proc. Natl. Acad. Sci., USA 74, 5463-5467.

81. Sheppard. M.G. Prideaux, C. Johnson, M. Fahey. K. J., York, J. J., and Kongsuwan, K. (1992). Infectious laryngotracheitis vaccine. International Patent Publication no. WO92/03554.

82. Telford, E. A. R., Watson, M. S., McBride, K., and Davison, A. J. (3992). The DNA sequence of equine herpesvirus-1. Virology 189, 304-316.

83. van Ziji, M., Quint, W., Briaire, J., de Rover, T., Gielkens, A., and Berns. A. (1988). Regeneration of herpesviruses from molecularly cloned subgenomic fragments. J. Virol. 62, 2191-2195.

84. Velicer. L.F., Brunovskis. P., and Coussens. P. M. (1992) Marek's disease herpesvirus DNA segment encoding glycoproteins gD, gI and gE. International Patent Publication no. WO92/03547.

85. Wark. M. C. Tarmock, G. A., and Pye, D. (1979). The development and evaluation of a cell culture vaccine against infectious laryngotracheitis virus. J. Biological Standardization 7, 73-80.

86. York, J. J., Sonza, S., Brandon, M. R., and Fahey, K. J. (1990). Antigens of infectious laryngotracheitis herpevirus defined by monoclonal antibodies. Arch. Virol. 115, 147-162.

87. Zelnik, V., Darteil, R., Audonnet J. D., Smith, G. D., Riviere, M. Pastorek, J., and Ross, L. J. N. (1993) The complete sequence and gene organization of the short unique region of herpesvirus of turkevs. J. Gen. Virol. 74, 2151-2162.

88. Zelnik, V., Ross, N. L. J., and Pastorek, J. (1994). Characterization of proteins encoded by the short unique region of herpesvirus of turkeys by in vitro expression. J. Gen. Virol. 75, 2747-2753.

---

What is claimed is:

1. A recombinant infectious laryngotracheitis virus comprising the infectious laryngotracheitis viral genome which contains a deletion in the unique short region of the viral genome, wherein the deletion is in the glycoprotein g60 gene.

2. The recombinant infectious laryngotracheitis virus of claim 1, wherein a foreign gene is inserted in the glycoprotein g60 gene.

3. A recombinant infectious laryngotracheitis virus comprising the infectious laryngotracheitis viral genome which contains a deletion in the unique short region of the viral genome, wherein the deletion is in a gene selected from a group consisting of the US2 gene, the UL47-like gene, and the glycoprotein g60 gene.

4. A recombinant infectious laryngotracheitis virus of claim 3, wherein the foreign gene is inserted in the gene selected from a group consisting of the US2 gene, UL-47 like gene, ORF4 gene and glycoprotein g60 gene.

5. The recombinant infectious laryngotracheitis virus of claim 4, wherein the foreign gene encodes an antigenic polypeptide.

6. The recombinant infectious laryngotracheitis virus of claim 5, wherein the antigenic polypeptide, when introduced into the host cell, induces production of protective antibodies against an avian disease causing agent from which the antigen is derived or derivable.

7. The recombinant infectious laryngotracheitis virus of claim 6, wherein the antigenic polypeptide is derived from or derivable from a group consisting of infectious bronchitis virus, Newcastle disease virus, infectious bursal disease virus, and Marek's disease virus.

8. The recombinant infectious laryngotracheitis virus of claim 4, wherein the foreign gene is under control of a heterologous upstream promoter.

9. The recombinant infectious laryngotracheitis virus of claim 8, wherein the promoter is selected from a group consisting of HCMV IE promoter, PRV gX promoter, and BHV-1.1 VP8 promoter.

* * * * *

SEQUENCE LISTING

```
<160> NUMBER OF SEQ ID NOS: 76

<210> SEQ ID NO 1
<211> LENGTH: 13473
<212> TYPE: DNA
<213> ORGANISM: Infectious Laryngotracheitis Virus
<220> FEATURE:
<221> NAME/KEY: CDS
<222> LOCATION: (1059)..(2489)
<220> FEATURE:
<221> NAME/KEY: CDS
<222> LOCATION: (2575)..(4107)
<220> FEATURE:
<221> NAME/KEY: CDS
<222> LOCATION: (4113)..(4445)
<220> FEATURE:
<221> NAME/KEY: CDS
<222> LOCATION: (4609)..(5487)
<220> FEATURE:
<221> NAME/KEY: CDS
<222> LOCATION: (5697)..(8654)
<220> FEATURE:
<221> NAME/KEY: CDS
<222> LOCATION: (9874)..(10962)
<220> FEATURE:
<221> NAME/KEY: CDS
<222> LOCATION: (11159)..(12658)
<220> FEATURE:
<221> NAME/KEY: CDS
<222> LOCATION: (12665)..(13447)

<400> SEQUENCE: 1 cccgtgc

-continued

```
atggtcgcca accctccaaa tgctacccgc cggcccacgc aacgcgggct tttataaaga      120
tggcgcgcga gacaataaca cttactcatc cgcgtacgcg tttattattg tcaatatttg      180
tgtggttatt attactgcta ccgcccttgt ttctgcaagg ccctcgccgc ggcccaggcc      240
actattccgg cagcggccgc cgacgcggcg agcgtcgccg ctaacgtcgg cgccgcgggg      300
agcgggtttt cttcgactta aatagactcc cgagaaaaaa ttttggctgc cgttcgccat      360
catccgagtc ggaaacacag tatgcggccg agttaggttt tacttttaaa aactttaccg      420
tgctgtacgg ccagggcgtt ctcaggctcg aaggggcaag agttgtccag actgatgggt      480
gactcagaga cagcgttgtc ttgtctccgt ttaccaaaaa tatttccact cctctctcaa      540
aatttttacc tccggtttcg gtaattagga aagttttttgg cgcagggagg tttaaagctg     600
ccatgcatat gtcagcggta cccagcaccc acaaatggaa ctcttttgcg gcatacgcgc      660
cagatgacaa atggtaaaac cctgcgtcca agccgctcca ctcgggactt actccaggcg      720
ggtcgccccc ctcaccgaac cgaatcacgg gtctgcacat cctgggaagg gaaaacagct      780
ccccggaaac ttcgtacaga gatgccgggc gcacgattac cgataatgta ctcggacgat      840
cgtaactcgc catagttttc actgcgtgaa ccaattcttt ccatccagaa tccgagagct      900
caaatctaga attaggtagt ttgtagtgcg aatcgaccgc agaaactata gtcacttttta      960 caggcgccat cgccgctcag actccacccc gctatgatgt cagaaatata acgctcttat     1020
tctagcagag tcaggccaat atatacagct tagagaag atg cgg ttt cgg cgc atc     1076
                                         Met Arg Phe Arg Arg Ile
                                           1               5 tgt tca cgc tct agg gca gaa aaa cga aga aga aca acc gag aat ccg        1124
Cys Ser Arg Ser Arg Ala Glu Lys Arg Arg Arg Thr Thr Glu Asn Pro
         10                  15                  20 ctt acc tca aaa cgc gtt tgc gta ttg gat agt ttc tca cgg aca atg        1172
Leu Thr Ser Lys Arg Val Cys Val Leu Asp Ser Phe Ser Arg Thr Met
     25                  30                  35 tca ttg cgc ccc tat gca gaa att ttg ccg acc gcg gaa ggc gtc gag        1220
Ser Leu Arg Pro Tyr Ala Glu Ile Leu Pro Thr Ala Glu Gly Val Glu
 40                  45                  50 cgc ctc gcc gaa ctt gtt agt gtg aca atg aca gaa cgc gcg gaa cct        1268
Arg Leu Ala Glu Leu Val Ser Val Thr Met Thr Glu Arg Ala Glu Pro
55                  60                  65                  70 gtg aca gag aat aca gct gta aac agt atc ccc ccg gct aac gag aac        1316
Val Thr Glu Asn Thr Ala Val Asn Ser Ile Pro Pro Ala Asn Glu Asn
                 75                  80                  85 ggg cag aac ttc gca tat gca ggc gat ggg ccc tcg act act gaa aaa        1364
Gly Gln Asn Phe Ala Tyr Ala Gly Asp Gly Pro Ser Thr Thr Glu Lys
             90                  95                 100 gtt gac ggc tcg cat aca gac ttc gat gaa gca tcg agc gac tac gcc        1412
Val Asp Gly Ser His Thr Asp Phe Asp Glu Ala Ser Ser Asp Tyr Ala
        105                 110                 115 ggc cct gtc ccg ctc gcg caa act aga ttg aag cat tcg gat gaa ttt        1460
Gly Pro Val Pro Leu Ala Gln Thr Arg Leu Lys His Ser Asp Glu Phe
    120                 125                 130 ctt cag cac ttc cga gtt tta gac gat ttg gtg gag ggg gct tac ggg        1508
Leu Gln His Phe Arg Val Leu Asp Asp Leu Val Glu Gly Ala Tyr Gly
135                 140                 145                 150 ttt atc tgc ggc gtc cgt cgc tac acc gag gaa gag caa cgt cga aga        1556
Phe Ile Cys Gly Val Arg Arg Tyr Thr Glu Glu Glu Gln Arg Arg Arg
                155                 160                 165 ggg gtt aac agt act aac cag ggg aaa tca aaa tgt aag cgc ctg ata        1604
Gly Val Asn Ser Thr Asn Gln Gly Lys Ser Lys Cys Lys Arg Leu Ile
```

-continued

```
                        170                     175                     180
gct aaa tat gtg aaa aat gga aca agg gcg gcc tct cag ctg gaa aat            1652
Ala Lys Tyr Val Lys Asn Gly Thr Arg Ala Ala Ser Gln Leu Glu Asn
            185                     190                     195 gaa att ttg gtt ctc ggg cgc cta aat cac gag aat gtt ctc aag atc            1700
Glu Ile Leu Val Leu Gly Arg Leu Asn His Glu Asn Val Leu Lys Ile
    200                     205                     210 cag gaa atc ctt cgg tac ccg gat aat acg tac atg tta acg cag agg            1748
Gln Glu Ile Leu Arg Tyr Pro Asp Asn Thr Tyr Met Leu Thr Gln Arg
215                     220                     225                     230 tat cag ttc gac ttg tac agc tac atg tac gat gaa gcg ttc gac tgg            1796
Tyr Gln Phe Asp Leu Tyr Ser Tyr Met Tyr Asp Glu Ala Phe Asp Trp
                235                     240                     245 aaa gac agt cca atg ctt aaa cag act aga cgc atc atg aag cag ctc            1844
Lys Asp Ser Pro Met Leu Lys Gln Thr Arg Arg Ile Met Lys Gln Leu
            250                     255                     260 atg tca gcg gtc tcg tat atc cat tca aag aaa ctg att cac agg gac            1892
Met Ser Ala Val Ser Tyr Ile His Ser Lys Lys Leu Ile His Arg Asp
            265                     270                     275 atc aaa ctc gaa aat att ttc tta aac tgc gac ggc aag aca gtg ctg            1940
Ile Lys Leu Glu Asn Ile Phe Leu Asn Cys Asp Gly Lys Thr Val Leu
    280                     285                     290 ggc gac ttt gga act gtc acg cct ttt gaa aat gag cgg gag ccc ttc            1988
Gly Asp Phe Gly Thr Val Thr Pro Phe Glu Asn Glu Arg Glu Pro Phe
295                     300                     305                     310 gaa tat gga tgg gtg ggg acc gtg gct act aac tct ccc gag ata ctc            2036
Glu Tyr Gly Trp Val Gly Thr Val Ala Thr Asn Ser Pro Glu Ile Leu
                315                     320                     325 gcc agg gat tcg tac tgt gaa att aca gac att tgg agc tgc gga gta            2084
Ala Arg Asp Ser Tyr Cys Glu Ile Thr Asp Ile Trp Ser Cys Gly Val
            330                     335                     340 gta ttg ctg gaa atg gta agc cat gaa ttt tgc ccg atc ggc gat ggc            2132
Val Leu Leu Glu Met Val Ser His Glu Phe Cys Pro Ile Gly Asp Gly
            345                     350                     355 ggg gga aat ccg cac cag caa ttg ctg aaa gtt atc gac tct ctc tca            2180
Gly Gly Asn Pro His Gln Gln Leu Leu Lys Val Ile Asp Ser Leu Ser
360                     365                     370 gtt tgt gat gaa gag ttc cca gac ccc ccg tgt aat ctg tac aat tat            2228
Val Cys Asp Glu Glu Phe Pro Asp Pro Pro Cys Asn Leu Tyr Asn Tyr
375                     380                     385                     390 ttg cat tat gcg agc atc gat cgc gcc gga cat acg gtc ccg tcg ctc            2276
Leu His Tyr Ala Ser Ile Asp Arg Ala Gly His Thr Val Pro Ser Leu
                395                     400                     405 ata cgg aac ctc cac ctt ccg gcg gat gtg gaa tac cct cta gtt aaa            2324
Ile Arg Asn Leu His Leu Pro Ala Asp Val Glu Tyr Pro Leu Val Lys
            410                     415                     420 atg ctt act ttt gac tgg cgt ttg aga ccc agc gcg gcc gaa gta ttg            2372
Met Leu Thr Phe Asp Trp Arg Leu Arg Pro Ser Ala Ala Glu Val Leu
            425                     430                     435 gca atg cca ctg ttt tcg gct gaa gag gaa cgg acc ata aca att att            2420
Ala Met Pro Leu Phe Ser Ala Glu Glu Glu Arg Thr Ile Thr Ile Ile
            440                     445                     450 cat gga aaa cat aaa ccc atc cga ccc gaa atc cgt gcg cgg gtg cca            2468
His Gly Lys His Lys Pro Ile Arg Pro Glu Ile Arg Ala Arg Val Pro
455                     460                     465                     470 cgg tcc atg agt gaa ggt taa taataaagga cggagataga gaactgaagc               2519
Arg Ser Met Ser Glu Gly
                475 gtcagatttt tttaaaaaaa taaatgatcg agaacttatg atttgtcttt cttga atg           2577
```

-continued

|  |  |  |  |  |  |  |  | Met |  |  |  |  |  |  |  |
|---|---|---|---|---|---|---|---|---|---|---|---|---|---|---|---|

```
acc ttg ccc cat cga tta acg aaa aga cct ttc gcg cgt cga ttc tgc    2625
Thr Leu Pro His Arg Leu Thr Lys Arg Pro Phe Ala Arg Arg Phe Cys
        480                 485                 490 tcg gtc ttt gtg ata cat tat agt gag act aaa ctc gac cga tat aac    2673
Ser Val Phe Val Ile His Tyr Ser Glu Thr Lys Leu Asp Arg Tyr Asn
495                 500                 505 aag aca atg tta ctc tat aga ccg gac tca acc atg cgg cat agc gga    2721
Lys Thr Met Leu Leu Tyr Arg Pro Asp Ser Thr Met Arg His Ser Gly
510                 515                 520                 525 ggc gac gca aat cac aga ggg ata agg ccg agg cgg aaa tct att gga    2769
Gly Asp Ala Asn His Arg Gly Ile Arg Pro Arg Arg Lys Ser Ile Gly
                530                 535                 540 gcg ttt agc gcg cgc gaa aag act gga aaa cga aat gcg ctg acg gaa    2817
Ala Phe Ser Ala Arg Glu Lys Thr Gly Lys Arg Asn Ala Leu Thr Glu
            545                 550                 555 agc agc tcc tcc tcc gac atg cta gat ccg ttt tcc acg gat aag gaa    2865
Ser Ser Ser Ser Ser Asp Met Leu Asp Pro Phe Ser Thr Asp Lys Glu
        560                 565                 570 ttt ggc ggt aag tgg acg gta gac gga cct gcc gac att act gcc gag    2913
Phe Gly Gly Lys Trp Thr Val Asp Gly Pro Ala Asp Ile Thr Ala Glu
575                 580                 585 gtc ctt tct cag gca tgg gac gtt ctc caa tta gtg aag cat gaa gat    2961
Val Leu Ser Gln Ala Trp Asp Val Leu Gln Leu Val Lys His Glu Asp
590                 595                 600                 605 gcg gag gag gag aga gtg act tat gag tcc aaa ccg acc ccg ata cag    3009
Ala Glu Glu Glu Arg Val Thr Tyr Glu Ser Lys Pro Thr Pro Ile Gln
                610                 615                 620 ccg ttc aat gcc tgg ccg gac ggg ccg agt tgg aac gcg cag gat ttt    3057
Pro Phe Asn Ala Trp Pro Asp Gly Pro Ser Trp Asn Ala Gln Asp Phe
            625                 630                 635 act cga gcg cca ata gtt tat ccc tct gcg gag gta ttg gac gca gag    3105
Thr Arg Ala Pro Ile Val Tyr Pro Ser Ala Glu Val Leu Asp Ala Glu
        640                 645                 650 gcg ttg aaa gta ggg gca ttc gtt agc cga gtt tta caa tgt gta ccg    3153
Ala Leu Lys Val Gly Ala Phe Val Ser Arg Val Leu Gln Cys Val Pro
655                 660                 665 ttc acg cga tca aag aaa agc gtt acg gtg cgg gat gcg cag tcg ttt    3201
Phe Thr Arg Ser Lys Lys Ser Val Thr Val Arg Asp Ala Gln Ser Phe
670                 675                 680                 685 ttg ggg gac tcg ttc tgg aga ata atg cag aac gtt tac acg gtt tgc    3249
Leu Gly Asp Ser Phe Trp Arg Ile Met Gln Asn Val Tyr Thr Val Cys
                690                 695                 700 tta cga cag cac ata act cga ctc agg cac cct tcc agc aaa agc att    3297
Leu Arg Gln His Ile Thr Arg Leu Arg His Pro Ser Ser Lys Ser Ile
            705                 710                 715 gtt aac tgc aac gac cct cta tgg tac gcc tac gcg aat caa ttt cac    3345
Val Asn Cys Asn Asp Pro Leu Trp Tyr Ala Tyr Ala Asn Gln Phe His
        720                 725                 730 tgg aga gga atg cgc gtg ccg tcg ctt aaa tta gcc tct ccc ccg gag    3393
Trp Arg Gly Met Arg Val Pro Ser Leu Lys Leu Ala Ser Pro Pro Glu
735                 740                 745 gag aat att caa cac ggc cca atg gcc gcc gtt ttt aga aac gcg ggg    3441
Glu Asn Ile Gln His Gly Pro Met Ala Ala Val Phe Arg Asn Ala Gly
750                 755                 760                 765 gct ggt ctg ttc ctg tgg cct gcc atg cgc gca gcc ttt gaa gag cgc    3489
Ala Gly Leu Phe Leu Trp Pro Ala Met Arg Ala Ala Phe Glu Glu Arg
                770                 775                 780 gac aag cga ctg tta aga gca tgc ctg tct tca ctc gat atc atg gac    3537
```

```
                Asp Lys Arg Leu Leu Arg Ala Cys Leu Ser Ser Leu Asp Ile Met Asp
                            785                 790                 795 gca gcc gtc ctc gcg tcg ttt cca ttt tac tgg cgc ggc gtc caa gac          3585
Ala Ala Val Leu Ala Ser Phe Pro Phe Tyr Trp Arg Gly Val Gln Asp
            800                 805                 810 acc tcg cgc ttc gag cct gcg ctg ggc tgt ttg tca gag tac ttt gca          3633
Thr Ser Arg Phe Glu Pro Ala Leu Gly Cys Leu Ser Glu Tyr Phe Ala
            815                 820                 825 cta gtg gtg tta ctg gcc gag acg gtc tta gcg acc atg ttc gac cac          3681
Leu Val Val Leu Leu Ala Glu Thr Val Leu Ala Thr Met Phe Asp His
830                 835                 840                 845 gca ctg gta ttc atg agg gcg ctg gca gac ggc aat ttc gat gac tat          3729
Ala Leu Val Phe Met Arg Ala Leu Ala Asp Gly Asn Phe Asp Asp Tyr
            850                 855                 860 gac gaa act aga tat ata gac ccc gtt aaa aac gag tac ctg aac gga          3777
Asp Glu Thr Arg Tyr Ile Asp Pro Val Lys Asn Glu Tyr Leu Asn Gly
            865                 870                 875 gcc gag ggt act ctg tta cgg ggc ata gtg gcc tcc aac acc gct ctg          3825
Ala Glu Gly Thr Leu Leu Arg Gly Ile Val Ala Ser Asn Thr Ala Leu
            880                 885                 890 gcg gtg gtt tgc gca aac acc tat tcg acg ata aga aaa ctc ccg tcc          3873
Ala Val Val Cys Ala Asn Thr Tyr Ser Thr Ile Arg Lys Leu Pro Ser
895                 900                 905 gtg gca act agc gcg tgc aat gtt gcc tac agg acc gaa acg ctg aaa          3921
Val Ala Thr Ser Ala Cys Asn Val Ala Tyr Arg Thr Glu Thr Leu Lys
910                 915                 920                 925 gcg agg cgc cct ggc atg agc gac ata tac cgg ata tta caa aaa gag          3969
Ala Arg Arg Pro Gly Met Ser Asp Ile Tyr Arg Ile Leu Gln Lys Glu
                930                 935                 940 ttt ttc ttt tac att gcg tgg ctc cag agg gtt gca aca cac gca aat          4017
Phe Phe Phe Tyr Ile Ala Trp Leu Gln Arg Val Ala Thr His Ala Asn
            945                 950                 955 ttc tgt tta aac att ctg aag aga agc gtg gat acg ggc ccc cgc cat          4065
Phe Cys Leu Asn Ile Leu Lys Arg Ser Val Asp Thr Gly Pro Arg His
            960                 965                 970 ttt tgt tca ggg cca gct cgg aga agc ggc tgc agc agt taa ataaa atg       4115
Phe Cys Ser Gly Pro Ala Arg Arg Ser Gly Cys Ser Ser                Met
975                 980                 985 ctc tgc ccc ctt ctc gtg ccg att caa tat gaa gac ttt  tcg aag gcc         4163
Leu Cys Pro Leu Leu Val Pro Ile Gln Tyr Glu Asp Phe  Ser Lys Ala
            990                 995                 1000 atg ggg  tct gag ctc aag agg  gaa aag tta gag aca  ttc gtt aaa           4208
Met Gly  Ser Glu Leu Lys Arg  Glu Lys Leu Glu Thr  Phe Val Lys
            1005                1010                1015 gct att  tcc agc gac agg gac  ccg agg ggg tcc tta  aga ttt ctc           4253
Ala Ile  Ser Ser Asp Arg Asp  Pro Arg Gly Ser Leu  Arg Phe Leu
            1020                1025                1030 att tcg gac cat gca agg gaa  att att gca gac gga  gta cgg ttt            4298
Ile Ser Asp His Ala Arg Glu  Ile Ile Ala Asp Gly  Val Arg Phe
            1035                1040                1045 aag ccg gta ata gac gag ccg  gtt cgg gct tca gtt  gcg ctg agt            4343
Lys Pro Val Ile Asp Glu Pro  Val Arg Ala Ser Val  Ala Leu Ser
            1050                1055                1060 acc gct gcc gct ggg aaa gtg  aaa gcg cga cgc tta  acc tca gtt            4388
Thr Ala Ala Ala Gly Lys Val  Lys Ala Arg Arg Leu  Thr Ser Val
            1065                1070                1075 cgc gcg ccc gta ccg ccc gca  ggc gcc gtt tcc gcg  cgc cgg aaa            4433
Arg Ala Pro Val Pro Pro Ala  Gly Ala Val Ser Ala  Arg Arg Lys
            1080                1085                1090
```

```
tcg gaa  ata tga taaaaatgct tggcatttgc gggcgaagag gcgtgatctg        4485
Ser Glu  Ile
    1095 aagggctcca caatgacgta actgagctac gcatccctat aaagtgtacs cgctgaccgc   4545 tagcccatac agtgttacag gaggggagag agacaacttc agctcgaagt ctgaagagac   4605 atc atg agc ggc ttc agt aac ata gga tcg att gcc acc gtt tcc        4650
Met Ser Gly Phe Ser Asn Ile Gly Ser Ile Ala Thr Val Ser
    1100                1105                1110 cta gta tgc tcg ctt ttg tgc gca tct gta tta ggg gcg ccg gta        4695
Leu Val Cys Ser Leu Leu Cys Ala Ser Val Leu Gly Ala Pro Val
             1115                1120                1125 ctg gac ggg ctc gag tcg agc cct ttc ccg ttc ggg ggc aaa att        4740
Leu Asp Gly Leu Glu Ser Ser Pro Phe Pro Phe Gly Gly Lys Ile
             1130                1135                1140 ata gcc cag gcg tgc aac cgc acc acg att gag gtg acg gtc ccg        4785
Ile Ala Gln Ala Cys Asn Arg Thr Thr Ile Glu Val Thr Val Pro
             1145                1150                1155 tgg agc gac tac tct ggt cgc acc gaa gga gtg tca gtc gag gtg        4830
Trp Ser Asp Tyr Ser Gly Arg Thr Glu Gly Val Ser Val Glu Val
             1160                1165                1170 aaa tgg ttc tac ggg aat agt aat ccc gaa agc ttc gtg ttc ggg        4875
Lys Trp Phe Tyr Gly Asn Ser Asn Pro Glu Ser Phe Val Phe Gly
             1175                1180                1185 gtg gat agc gaa acg ggc agt gga cac gag gac ctg tct acg tgc        4920
Val Asp Ser Glu Thr Gly Ser Gly His Glu Asp Leu Ser Thr Cys
             1190                1195                1200 tgg gct cta atc cat aat ctg aac gcg tct gtg tgc agg gcg tct        4965
Trp Ala Leu Ile His Asn Leu Asn Ala Ser Val Cys Arg Ala Ser
             1205                1210                1215 gac gcc ggg ata cct gat ttc gac aag cag tgc gaa aaa gtg cag        5010
Asp Ala Gly Ile Pro Asp Phe Asp Lys Gln Cys Glu Lys Val Gln
             1220                1225                1230 aga aga ctg cgc tcc ggg gtg gaa ctt ggt agt tac gtg tct ggc        5055
Arg Arg Leu Arg Ser Gly Val Glu Leu Gly Ser Tyr Val Ser Gly
             1235                1240                1245 aat gga tcc ctg gtg ctg tac cca ggg atg tac gat gcc ggc atc        5100
Asn Gly Ser Leu Val Leu Tyr Pro Gly Met Tyr Asp Ala Gly Ile
             1250                1255                1260 tac gcc tac cag ctc tca gtg ggt ggg aag gga tat acc ggg tct        5145
Tyr Ala Tyr Gln Leu Ser Val Gly Gly Lys Gly Tyr Thr Gly Ser
             1265                1270                1275 gtt tat cta gac gtc gga cca aac ccc gga tgc cac gac cag tat        5190
Val Tyr Leu Asp Val Gly Pro Asn Pro Gly Cys His Asp Gln Tyr
             1280                1285                1290 ggg tac acc tat tac agc ctg gcc gac gag gcg tca gac tta tca        5235
Gly Tyr Thr Tyr Tyr Ser Leu Ala Asp Glu Ala Ser Asp Leu Ser
             1295                1300                1305 tct tat gac gta gcc tcg ccc gaa ctc gac ggt cct atg gag gaa        5280
Ser Tyr Asp Val Ala Ser Pro Glu Leu Asp Gly Pro Met Glu Glu
             1310                1315                1320 gat tat tcc aat tgt cta gac atg ccc ccg cta cgc cca tgg aca        5325
Asp Tyr Ser Asn Cys Leu Asp Met Pro Pro Leu Arg Pro Trp Thr
             1325                1330                1335 acc gtt tgt tcg cat gac gtc gag gag cag gaa aac gcc acg gac        5370
Thr Val Cys Ser His Asp Val Glu Glu Gln Glu Asn Ala Thr Asp
             1340                1345                1350 gag ctt tac cta tgg gac gag gaa tgc gcc ggt ccg ctg gac gag        5415
Glu Leu Tyr Leu Trp Asp Glu Glu Cys Ala Gly Pro Leu Asp Glu
             1355                1360                1365
```

```
                                                          -continued tac gtc gac gaa agg  tca gag acg atg  ccc agg atg gtt  gtc ttt            5460
Tyr Val Asp Glu Arg  Ser Glu Thr Met  Pro Arg Met Val  Val Phe
            1370              1375                 1380 tca ccg ccc tct acg  ctc cag cag tag ccacccgaga gtgtttttg                 5507
Ser Pro Pro Ser Thr  Leu Gln Gln
            1385 tgagcgccca cgcaacatac ctaactgctt catttctgat caattattgc gtattgaata         5567 aataaacagt acaaaagcat caggtgtggt ttgcgtgtct gtgctaaacc atggcgtgtg         5627 cgggtgaaac cgtaaattac gtgataataa atagcatagg agttggcgtg cagcgtattt         5687 cgccgagag atg ggg aca atg tta gtg ttg  cgc ctt ttc cta ctt  gca           5735
           Met Gly Thr Met Leu Val Leu  Arg Leu Phe Leu Leu  Ala
               1390             1395                  1400 gta gcg gac gcg  gcg ttg ccg acc  ggc aga ttc tgc  cga gtt tgg            5780
Val Ala Asp Ala  Ala Leu Pro Thr  Gly Arg Phe Cys  Arg Val Trp
            1405              1410                 1415 aag gtg cct ccg  gga gga acc atc  caa gag aac ctg  gcg gtg ctc            5825
Lys Val Pro Pro  Gly Gly Thr Ile  Gln Glu Asn Leu  Ala Val Leu
            1420              1425                 1430 gcg gaa tcg ccg  gtc acg gga cac  gcg aca tat ccg  ccg cct gaa            5870
Ala Glu Ser Pro  Val Thr Gly His  Ala Thr Tyr Pro  Pro Pro Glu
            1435              1440                 1445 ggc gcc gtc agc  ttt cag att ttt  gcg gac acc cct  act ttg cgc            5915
Gly Ala Val Ser  Phe Gln Ile Phe  Ala Asp Thr Pro  Thr Leu Arg
            1450              1455                 1460 att cgc tac ggg  cct acg gag gac  gaa ctt gca ctg  gag cgc ggg            5960
Ile Arg Tyr Gly  Pro Thr Glu Asp  Glu Leu Ala Leu  Glu Arg Gly
            1465              1470                 1475 acg tcc gcc tca  gac gcg gac aac  gtg aca ttt tcg  ctg tca tat            6005
Thr Ser Ala Ser  Asp Ala Asp Asn  Val Thr Phe Ser  Leu Ser Tyr
            1480              1485                 1490 cgc ccg cgc cca  gaa att cac gga  gca tac ttc acc  ata ggg gta            6050
Arg Pro Arg Pro  Glu Ile His Gly  Ala Tyr Phe Thr  Ile Gly Val
            1495              1500                 1505 ttc gct act ggc  cag agc acg gaa  agc agc tat tcg  gtc atc agt            6095
Phe Ala Thr Gly  Gln Ser Thr Glu  Ser Ser Tyr Ser  Val Ile Ser
            1510              1515                 1520 cgg gtc tta gtt  aac gcc tct ctg  gaa cgg tcc gtg  cgc ctg gaa            6140
Arg Val Leu Val  Asn Ala Ser Leu  Glu Arg Ser Val  Arg Leu Glu
            1525              1530                 1535 acg ccg tgc gat  gaa aat ttt ttg  cag aac gag cct  aca tgg ggc            6185
Thr Pro Cys Asp  Glu Asn Phe Leu  Gln Asn Glu Pro  Thr Trp Gly
            1540              1545                 1550 tcg aag cgt tgg  tta ggc ccc ccg  tcg cct tat gtg  cga gat aac            6230
Ser Lys Arg Trp  Leu Gly Pro Pro  Ser Pro Tyr Val  Arg Asp Asn
            1555              1560                 1565 gat gtc gcc gtg  ttg aca aaa gcg  cag tac att ggg  gag tgc tac            6275
Asp Val Ala Val  Leu Thr Lys Ala  Gln Tyr Ile Gly  Glu Cys Tyr
            1570              1575                 1580 tcc aac tcg gcg  gcc cag acg ggc  ctc acg tct ctc  aac atg acc            6320
Ser Asn Ser Ala  Ala Gln Thr Gly  Leu Thr Ser Leu  Asn Met Thr
            1585              1590                 1595 ttt ttc tat tcg  cct aaa aga ata  gta aac gtc acg  tgg aca acc            6365
Phe Phe Tyr Ser  Pro Lys Arg Ile  Val Asn Val Thr  Trp Thr Thr
            1600              1605                 1610 ggc ggc ccc tcc  ccc tcg cgc ata  acg gta tac tcg  tcg cgg gag            6410
Gly Gly Pro Ser  Pro Ser Arg Ile  Thr Val Tyr Ser  Ser Arg Glu
            1615              1620                 1625
```

```
aac ggg cag ccc gtg ttg agg aac gtt tct gac ggg ttc ttg gtt       6455
Asn Gly Gln Pro Val Leu Arg Asn Val Ser Asp Gly Phe Leu Val
            1630                1635                1640 aag tac act ccc gac att gac ggc cgg gcc atg ata aac gtt att       6500
Lys Tyr Thr Pro Asp Ile Asp Gly Arg Ala Met Ile Asn Val Ile
            1645                1650                1655 gcc aat tat tcg ccg gcg gac tcc ggc agc gtc ctc gcg ttt acg       6545
Ala Asn Tyr Ser Pro Ala Asp Ser Gly Ser Val Leu Ala Phe Thr
            1660                1665                1670 gcc ttt agg gaa gga aaa ctc cca tcc gcg att caa ctg cac cgg       6590
Ala Phe Arg Glu Gly Lys Leu Pro Ser Ala Ile Gln Leu His Arg
            1675                1680                1685 ata gat atg tcc ggg act gag ccg ccg ggg act gaa acg acc ttc       6635
Ile Asp Met Ser Gly Thr Glu Pro Pro Gly Thr Glu Thr Thr Phe
            1690                1695                1700 gac tgt caa aaa atg ata gaa acc ccg tac cga gcg ctc ggg agc       6680
Asp Cys Gln Lys Met Ile Glu Thr Pro Tyr Arg Ala Leu Gly Ser
            1705                1710                1715 aat gtt ccc agg gac gac tct atc cgt ccg ggg gcc act ctg cct       6725
Asn Val Pro Arg Asp Asp Ser Ile Arg Pro Gly Ala Thr Leu Pro
            1720                1725                1730 ccg ttc gat acc gca gca cct gat ttc gat aca ggt act tcc ccg       6770
Pro Phe Asp Thr Ala Ala Pro Asp Phe Asp Thr Gly Thr Ser Pro
            1735                1740                1745 acc ccc act acc gtg cca gag cca gcc att act aca ctc ata ccg       6815
Thr Pro Thr Thr Val Pro Glu Pro Ala Ile Thr Thr Leu Ile Pro
            1750                1755                1760 cgc agc act agc gat atg gga ttc ttc tcc acg gca cgt gct acc       6860
Arg Ser Thr Ser Asp Met Gly Phe Phe Ser Thr Ala Arg Ala Thr
            1765                1770                1775 gga tca gaa act ctt tcg gta ccc gtc cag gaa acg gat aga act       6905
Gly Ser Glu Thr Leu Ser Val Pro Val Gln Glu Thr Asp Arg Thr
            1780                1785                1790 ctt tcg aca act cct ctt acc ctt cca ctg act ccc ggt gag tca       6950
Leu Ser Thr Thr Pro Leu Thr Leu Pro Leu Thr Pro Gly Glu Ser
            1795                1800                1805 gaa aat aca ctg ttt cct acg acc gcg ccg ggg att tct acc gag       6995
Glu Asn Thr Leu Phe Pro Thr Thr Ala Pro Gly Ile Ser Thr Glu
            1810                1815                1820 acc ccg agc gcg gca cat gaa act aca cag acc cag agt gca gaa       7040
Thr Pro Ser Ala Ala His Glu Thr Thr Gln Thr Gln Ser Ala Glu
            1825                1830                1835 acg gtg gtc ttt act cag agt ccg agt acc gag tcg gaa acc gcg       7085
Thr Val Val Phe Thr Gln Ser Pro Ser Thr Glu Ser Glu Thr Ala
            1840                1845                1850 cgg tcc cag agt cag gaa ccg tgg tat ttt act cag act ccg agt       7130
Arg Ser Gln Ser Gln Glu Pro Trp Tyr Phe Thr Gln Thr Pro Ser
            1855                1860                1865 act gaa cag gcg gct ctt act cag acg cag atc gca gaa acg gag       7175
Thr Glu Gln Ala Ala Leu Thr Gln Thr Gln Ile Ala Glu Thr Glu
            1870                1875                1880 gcg ttg ttt act cag act ccg agt gct gaa cag atg act ttt act       7220
Ala Leu Phe Thr Gln Thr Pro Ser Ala Glu Gln Met Thr Phe Thr
            1885                1890                1895 cag act ccg ggt gca gaa acc gag gca cct gcc cag acc ccg agc       7265
Gln Thr Pro Gly Ala Glu Thr Glu Ala Pro Ala Gln Thr Pro Ser
            1900                1905                1910 acg ata ccc gag ata ttt act cag tct cgt agc acg ccc ccc gaa       7310
Thr Ile Pro Glu Ile Phe Thr Gln Ser Arg Ser Thr Pro Pro Glu
            1915                1920                1925
```

-continued

| | | | | | | | | | | | | | |
|---|---|---|---|---|---|---|---|---|---|---|---|---|---|
| acc | gct | cgc | gct | ccg | agc | gcg | gcg | ccg | gag | gtt | ttt | aca | cag | agt | 7355 |
| Thr | Ala | Arg | Ala | Pro | Ser | Ala | Ala | Pro | Glu | Val | Phe | Thr | Gln | Ser | |
| | | | 1930 | | | | 1935 | | | | | 1940 | | | |

| tcg | agt | acg | gta | acg | gag | gtg | ttt | act | cag | acc | ccg | agc | acg | gta | 7400 |
| Ser | Ser | Thr | Val | Thr | Glu | Val | Phe | Thr | Gln | Thr | Pro | Ser | Thr | Val | |
| | | | 1945 | | | | 1950 | | | | | 1955 | | | |

| ccg | aaa | act | act | ctg | agt | tcg | agt | act | gaa | ccg | gcg | att | ttt | act | 7445 |
| Pro | Lys | Thr | Thr | Leu | Ser | Ser | Ser | Thr | Glu | Pro | Ala | Ile | Phe | Thr | |
| | | | 1960 | | | | 1965 | | | | | 1970 | | | |

| cgg | act | cag | agc | gcg | gga | act | gag | gcc | ttt | act | cag | act | tcg | agt | 7490 |
| Arg | Thr | Gln | Ser | Ala | Gly | Thr | Glu | Ala | Phe | Thr | Gln | Thr | Ser | Ser | |
| | | | 1975 | | | | 1980 | | | | | 1985 | | | |

| gcc | gag | ccg | gac | act | atg | cga | act | cag | agt | act | gaa | aca | cac | ttt | 7535 |
| Ala | Glu | Pro | Asp | Thr | Met | Arg | Thr | Gln | Ser | Thr | Glu | Thr | His | Phe | |
| | | | 1990 | | | | 1995 | | | | | 2000 | | | |

| ttc | act | cag | gcc | ccg | agt | acg | gta | ccg | aaa | gct | act | cag | act | ccg | 7580 |
| Phe | Thr | Gln | Ala | Pro | Ser | Thr | Val | Pro | Lys | Ala | Thr | Gln | Thr | Pro | |
| | | | 2005 | | | | 2010 | | | | | 2015 | | | |

| agt | aca | gag | ccg | gag | gtg | ttg | act | cag | agt | ccg | agt | acc | gaa | cct | 7625 |
| Ser | Thr | Glu | Pro | Glu | Val | Leu | Thr | Gln | Ser | Pro | Ser | Thr | Glu | Pro | |
| | | | 2020 | | | | 2025 | | | | | 2030 | | | |

| gtg | cct | ttc | acc | cgg | act | ctg | ggc | gca | gag | ccg | gaa | att | act | cag | 7670 |
| Val | Pro | Phe | Thr | Arg | Thr | Leu | Gly | Ala | Glu | Pro | Glu | Ile | Thr | Gln | |
| | | | 2035 | | | | 2040 | | | | | 2045 | | | |

| acc | ccg | agc | gcg | gca | ccg | gag | gtt | tat | act | cgg | agt | tcg | agt | acg | 7715 |
| Thr | Pro | Ser | Ala | Ala | Pro | Glu | Val | Tyr | Thr | Arg | Ser | Ser | Ser | Thr | |
| | | | 2050 | | | | 2055 | | | | | 2060 | | | |

| atg | cca | gaa | act | gca | cag | agc | aca | ccc | ctg | gcc | tcg | caa | aac | cct | 7760 |
| Met | Pro | Glu | Thr | Ala | Gln | Ser | Thr | Pro | Leu | Ala | Ser | Gln | Asn | Pro | |
| | | | 2065 | | | | 2070 | | | | | 2075 | | | |

| acc | agt | tcg | gga | acc | ggg | acg | cat | aat | act | gaa | ccg | agg | act | tat | 7805 |
| Thr | Ser | Ser | Gly | Thr | Gly | Thr | His | Asn | Thr | Glu | Pro | Arg | Thr | Tyr | |
| | | | 2080 | | | | 2085 | | | | | 2090 | | | |

| cca | gtg | caa | acg | aca | cca | cat | acc | cag | aaa | ctc | tac | aca | gaa | aat | 7850 |
| Pro | Val | Gln | Thr | Thr | Pro | His | Thr | Gln | Lys | Leu | Tyr | Thr | Glu | Asn | |
| | | | 2095 | | | | 2100 | | | | | 2105 | | | |

| aag | act | tta | tcg | ttt | cct | act | gtt | gtt | tca | gaa | ttc | cat | gag | atg | 7895 |
| Lys | Thr | Leu | Ser | Phe | Pro | Thr | Val | Val | Ser | Glu | Phe | His | Glu | Met | |
| | | | 2110 | | | | 2115 | | | | | 2120 | | | |

| tcg | acg | gca | gag | tcg | cag | acg | ccc | cta | ttg | gac | gtc | aaa | att | gta | 7940 |
| Ser | Thr | Ala | Glu | Ser | Gln | Thr | Pro | Leu | Leu | Asp | Val | Lys | Ile | Val | |
| | | | 2125 | | | | 2130 | | | | | 2135 | | | |

| gag | gtg | aag | ttt | tca | aac | gat | ggc | gaa | gta | acg | gcg | act | tgc | gtt | 7985 |
| Glu | Val | Lys | Phe | Ser | Asn | Asp | Gly | Glu | Val | Thr | Ala | Thr | Cys | Val | |
| | | | 2140 | | | | 2145 | | | | | 2150 | | | |

| tcc | acc | gtc | aaa | tct | ccc | tat | agg | gta | gaa | act | aat | tgg | aaa | gta | 8030 |
| Ser | Thr | Val | Lys | Ser | Pro | Tyr | Arg | Val | Glu | Thr | Asn | Trp | Lys | Val | |
| | | | 2155 | | | | 2160 | | | | | 2165 | | | |

| gac | ctc | gta | gat | gta | atg | gat | gaa | att | tct | ggg | aac | agt | ccc | gcc | 8075 |
| Asp | Leu | Val | Asp | Val | Met | Asp | Glu | Ile | Ser | Gly | Asn | Ser | Pro | Ala | |
| | | | 2170 | | | | 2175 | | | | | 2180 | | | |

| ggg | gtt | ttt | aac | agt | aat | gag | aaa | tgg | cag | aaa | cag | ctg | tac | tac | 8120 |
| Gly | Val | Phe | Asn | Ser | Asn | Glu | Lys | Trp | Gln | Lys | Gln | Leu | Tyr | Tyr | |
| | | | 2185 | | | | 2190 | | | | | 2195 | | | |

| aga | gta | acc | gat | gga | aga | aca | tcg | gtc | cag | cta | atg | tgc | ctg | tcg | 8165 |
| Arg | Val | Thr | Asp | Gly | Arg | Thr | Ser | Val | Gln | Leu | Met | Cys | Leu | Ser | |
| | | | 2200 | | | | 2205 | | | | | 2210 | | | |

| tgc | acg | agc | cat | tct | ccg | gaa | cct | tac | tgt | ctt | ttc | gac | acg | tct | 8210 |
| Cys | Thr | Ser | His | Ser | Pro | Glu | Pro | Tyr | Cys | Leu | Phe | Asp | Thr | Ser | |

-continued

```
         2215                  2220                  2225
ctt ata gcg agg  gaa aaa gat atc  gcg cca gag tta  tac ttt acc           8255
Leu Ile Ala Arg  Glu Lys Asp Ile  Ala Pro Glu Leu  Tyr Phe Thr
         2230                  2235                  2240 tct gat ccg caa  acg gca tac tgc  aca ata act ctg  ccg tcc ggc           8300
Ser Asp Pro Gln  Thr Ala Tyr Cys  Thr Ile Thr Leu  Pro Ser Gly
         2245                  2250                  2255 gtt gtt ccg aga  ttc gaa tgg agc  ctt aat aat gtt  tca ctg ccg           8345
Val Val Pro Arg  Phe Glu Trp Ser  Leu Asn Asn Val  Ser Leu Pro
         2260                  2265                  2270 gaa tat ttg acg  gcc acg acc gtt  gtt tcg cat acc  gct ggc caa           8390
Glu Tyr Leu Thr  Ala Thr Thr Val  Val Ser His Thr  Ala Gly Gln
         2275                  2280                  2285 agt aca gtg tgg  aag agc agc gcg  aga gca ggc gag  gcg tgg att           8435
Ser Thr Val Trp  Lys Ser Ser Ala  Arg Ala Gly Glu  Ala Trp Ile
         2290                  2295                  2300 tct ggc cgg gga  ggc aat ata tac  gaa tgc acc gtc  ctc atc tca           8480
Ser Gly Arg Gly  Gly Asn Ile Tyr  Glu Cys Thr Val  Leu Ile Ser
         2305                  2310                  2315 gac ggc act cgc  gtt act acg cga  aag gag agg tgc  tta aca aac           8525
Asp Gly Thr Arg  Val Thr Thr Arg  Lys Glu Arg Cys  Leu Thr Asn
         2320                  2325                  2330 aca tgg att gcg  gtg gaa aac ggt  gct gct cag gcg  cag ctg tat           8570
Thr Trp Ile Ala  Val Glu Asn Gly  Ala Ala Gln Ala  Gln Leu Tyr
         2335                  2340                  2345 tca ctc ttt tct  gga ctt gtg tca  gga tta tgc ggg  agc ata tct           8615
Ser Leu Phe Ser  Gly Leu Val Ser  Gly Leu Cys Gly  Ser Ile Ser
         2350                  2355                  2360 gct ttg tac gca  acg cta tgg acc  gcc att tat ttt tga ggaatgcttt        8664
Ala Leu Tyr Ala  Thr Leu Trp Thr  Ala Ile Tyr Phe
         2365                  2370 ttggactatc gtactgcttt cttccttcgc tagccagagc accgccgccg tcacgtacga       8724
ctacatttta ggccgtcgcg cgctcgacgc gctaaccata ccggcggttg cccgtataa        8784 cagatacctc actagggtat caagaggctg cgacgttgtc gagctcaacc cgatttctaa       8844
cgtggacgac atgatatcgg cggccaaaga aaaagagaag gggggcccctt cgaggcctc      8904 cgtcgtctgg ttctacgtga ttaagggcga cgacggcgag acaagtact gtccaatcta       8964 tagaaaagag tacagggaat gtggcgacgt acaactgcta tctgaatgcg ccgttcaatc      9024
tgcacagatg tgggcagtgg actatgttcc tagcacccct tgtatcgcgaa atggcgcggg    9084 actgactata ttctccccca ctgctgcgct ctctggccaa tacttgctga ccctgaaaat      9144
cgggagattt gcgcaaacag ctctcgtaac tctagaagtt aacgatcgct gtttaaagat      9204
cgggtcgcag cttaactttt taccgtcgaa atgctggaca acagaacagt atcagactgg      9264
atttcaaggc gaacacctttt atccgatcgc agacaccaat acacgacacg cggacgacgt     9324
atatcgggga tacgaagata ttctgcagcg ctggaataat ttgctgagga aaagaatcc      9384 tagcgcgcca gaccctcgtc cagatagcgt cccgcaagaa attccgctg taaccaagaa       9444 agcggaaggg cgcaccccgg acgcagaaag cagcgaaaag aaggcccctc cagaagactc      9504
ggaggacgac atgcaggcag aggcttctgg agaaaatcct gccgccctcc ccgaagacga      9564
cgaagtcccc gaggacaccg agcacgatga tccaaactcg gatcctgact attacaatga     9624
catgcccgcc gtgatcccgg tggaggagac tactaaaagt tctaatgccg tctccatgcc    9684
catattcgcg gcgttcgtag cctgcgcggt cgcgctcgtg gggctactgg tttggagcat     9744
cgtaaaatgc gcgcgtagct aatcgagcct agaataggtg gtttcttcct acatgccacg     9804
```

-continued

```
cctcacgctc ataatataaa tcacatggaa tagcatacca atgcctattc attgggacgt      9864 tcgaaaagc atg gca tcg cta ctt gga act ctg gct ctc ctt gcc gcg         9912
           Met Ala Ser Leu Leu Gly Thr Leu Ala Leu Leu Ala Ala
               2375            2380            2385 acg ctc gca ccc ttc ggc gcg atg gga atc gtg atc act gga aat           9957
Thr Leu Ala Pro Phe Gly Ala Met Gly Ile Val Ile Thr Gly Asn
        2390            2395            2400 cac gtc tcc gcc agg att gac gac gat cac atc gtg atc gtc gcg           10002
His Val Ser Ala Arg Ile Asp Asp Asp His Ile Val Ile Val Ala
        2405            2410            2415 cct cgc ccc gaa gct aca att caa ctg cag cta ttt ttc atg cct           10047
Pro Arg Pro Glu Ala Thr Ile Gln Leu Gln Leu Phe Phe Met Pro
        2420            2425            2430 ggc cag aga ccc cac aaa ccc tac tca gga acc gtc cgc gtc gcg           10092
Gly Gln Arg Pro His Lys Pro Tyr Ser Gly Thr Val Arg Val Ala
        2435            2440            2445 ttt cgg tct gat ata aca aac cag tgc tac cag gaa ctt agc gag           10137
Phe Arg Ser Asp Ile Thr Asn Gln Cys Tyr Gln Glu Leu Ser Glu
        2450            2455            2460 gag cgc ttt gaa aat tgc act cat cga tcg tct tct gtt ttt gtc           10182
Glu Arg Phe Glu Asn Cys Thr His Arg Ser Ser Ser Val Phe Val
        2465            2470            2475 ggc tgt aaa gtg acc gag tac acg ttc tcc gcc tcg aac aga cta           10227
Gly Cys Lys Val Thr Glu Tyr Thr Phe Ser Ala Ser Asn Arg Leu
        2480            2485            2490 acc gga cct cca cac ccg ttt aag ctc act ata cga aat cct cgt           10272
Thr Gly Pro Pro His Pro Phe Lys Leu Thr Ile Arg Asn Pro Arg
        2495            2500            2505 ccg aac gac agc ggg atg ttc tac gta att gtt cgg cta gac gac           10317
Pro Asn Asp Ser Gly Met Phe Tyr Val Ile Val Arg Leu Asp Asp
        2510            2515            2520 acc aaa gaa ccc att gac gtc ttc gcg atc caa cta tcg gtg tat           10362
Thr Lys Glu Pro Ile Asp Val Phe Ala Ile Gln Leu Ser Val Tyr
        2525            2530            2535 caa ttc gcg aac acc gcc gcg act cgc gga ctc tat tcc aag gct           10407
Gln Phe Ala Asn Thr Ala Ala Thr Arg Gly Leu Tyr Ser Lys Ala
        2540            2545            2550 tcg tgt cgc acc ttc gga tta cct acc gtc caa ctt gag gcc tat           10452
Ser Cys Arg Thr Phe Gly Leu Pro Thr Val Gln Leu Glu Ala Tyr
        2555            2560            2565 ctc agg acc gag gaa agt tgg cgc aac tgg caa gcg tac gtt gcc           10497
Leu Arg Thr Glu Glu Ser Trp Arg Asn Trp Gln Ala Tyr Val Ala
        2570            2575            2580 acg gag gcc acg acg acc agc gcc gag gcg aca acc ccg acg ccc           10542
Thr Glu Ala Thr Thr Thr Ser Ala Glu Ala Thr Thr Pro Thr Pro
        2585            2590            2595 gtc act gca acc agc gcc tcc gaa ctt gaa gcg gaa cac ttt acc           10587
Val Thr Ala Thr Ser Ala Ser Glu Leu Glu Ala Glu His Phe Thr
        2600            2605            2610 ttt ccc tgg cta gaa aat ggc gtg gat cat tac gaa ccg aca ccc           10632
Phe Pro Trp Leu Glu Asn Gly Val Asp His Tyr Glu Pro Thr Pro
        2615            2620            2625 gca aac gaa aat tca aac gtt act gtc cgt ctc ggg aca atg agc           10677
Ala Asn Glu Asn Ser Asn Val Thr Val Arg Leu Gly Thr Met Ser
        2630            2635            2640 cct acg cta att ggg gta acc gtg gct gcc gtc gtg agc gca acg           10722
Pro Thr Leu Ile Gly Val Thr Val Ala Ala Val Val Ser Ala Thr
        2645            2650            2655
```

```
atc ggc ctc gtc att gta att tcc atc gtc acc aga aac atg tgc       10767
Ile Gly Leu Val Ile Val Ile Ser Ile Val Thr Arg Asn Met Cys
        2660                2665                2670 acc ccg cac cga aaa tta gac acg gtc tcg caa gac gac gaa gaa       10812
Thr Pro His Arg Lys Leu Asp Thr Val Ser Gln Asp Asp Glu Glu
        2675                2680                2685 cgt tcc caa act aga agg gaa tcg cga aaa ttt gga ccc atg gtt       10857
Arg Ser Gln Thr Arg Arg Glu Ser Arg Lys Phe Gly Pro Met Val
        2690                2695                2700 gcg tgc gaa ata aac aag ggc gct gac cag gat agt gaa ctt gtg       10902
Ala Cys Glu Ile Asn Lys Gly Ala Asp Gln Asp Ser Glu Leu Val
        2705                2710                2715 gaa ctg gtt gcg att gtt aac ccg tct gcg cta agc tcg ccc gac       10947
Glu Leu Val Ala Ile Val Asn Pro Ser Ala Leu Ser Ser Pro Asp
        2720                2725                2730 tca ata aaa atg tga ttaagtctga atgtggctct ccaatcattt cgattctcta   11002
Ser Ile Lys Met
        2735 atctcccaat cctctcaaaa ggggcagtat cggacacgga ctgggagggg cgtactacac 11062 gatagttata tggtacagca gaggcctctg aacacttagg aggagaattc agccggggag 11122 agcccctgtt gagtaggctt gggagcatat tgcagg atg aac atg tta gtg  ata  11176
                                        Met Asn Met Leu Val Ile
                                                            2740 gtt ctc gcc tct tgt ctt gcg cgc cta act ttt gcg acg cga cac       11221
Val Leu Ala Ser Cys Leu Ala Arg Leu Thr Phe Ala Thr Arg His
        2745                2750                2755 gtc ctc ttt ttg gaa ggc act cag gct gtc ctc ggg gaa gat gat       11266
Val Leu Phe Leu Glu Gly Thr Gln Ala Val Leu Gly Glu Asp Asp
        2760                2765                2770 ccc aga aac gtt ccg gaa ggg act gta atc aaa tgg aca aaa gtc       11311
Pro Arg Asn Val Pro Glu Gly Thr Val Ile Lys Trp Thr Lys Val
        2775                2780                2785 ctg cgg aac gcg tgc aag atg aag gcg gcc gat gtc tgc tct tcg       11356
Leu Arg Asn Ala Cys Lys Met Lys Ala Ala Asp Val Cys Ser Ser
        2790                2795                2800 cct aac tat tgc ttt cat gat tta att tac gac gga gga aag aaa       11401
Pro Asn Tyr Cys Phe His Asp Leu Ile Tyr Asp Gly Gly Lys Lys
        2805                2810                2815 gac tgc ccg ccc gcg gga ccc ctg tct gca aac ctg gta att tta       11446
Asp Cys Pro Pro Ala Gly Pro Leu Ser Ala Asn Leu Val Ile Leu
        2820                2825                2830 cta aag cgc ggc gaa agc ttc gtc gtg ctg ggt tct ggg cta cac       11491
Leu Lys Arg Gly Glu Ser Phe Val Val Leu Gly Ser Gly Leu His
        2835                2840                2845 aac agc aat ata act aat atc atg tgg aca gag tac gga ggc ctg       11536
Asn Ser Asn Ile Thr Asn Ile Met Trp Thr Glu Tyr Gly Gly Leu
        2850                2855                2860 ctc ttt gat cct gta act cgt tcg gac gag gga atc tat ttt cga       11581
Leu Phe Asp Pro Val Thr Arg Ser Asp Glu Gly Ile Tyr Phe Arg
        2865                2870                2875 cgg atc tct cag cca gat ctg gcc atg gaa act aca tcg tac aac       11626
Arg Ile Ser Gln Pro Asp Leu Ala Met Glu Thr Thr Ser Tyr Asn
        2880                2885                2890 gtc agc gtt ctt tcg cac gta gac gag aag gct cca gca ccg cac       11671
Val Ser Val Leu Ser His Val Asp Glu Lys Ala Pro Ala Pro His
        2895                2900                2905 gag gtg gag ata gac acc atc aag ccg tca gag gcc cac gcg cac       11716
Glu Val Glu Ile Asp Thr Ile Lys Pro Ser Glu Ala His Ala His
        2910                2915                2920
```

-continued

| | | |
|---|---|---|
| gtg gaa tta caa atg ctg ccg ttt cat gaa ctc aac gac aac agc<br>Val Glu Leu Gln Met Leu Pro Phe His Glu Leu Asn Asp Asn Ser<br>2925                              2930                         2935 | | 11761 |
| ccc acc tat gtg acc cct gtt ctt aga gtc ttc cca ccg acc gag<br>Pro Thr Tyr Val Thr Pro Val Leu Arg Val Phe Pro Pro Thr Glu<br>2940                              2945                         2950 | | 11806 |
| cac gta aaa ttt aac gtt acg tat tcg tgg tat ggg ttt gat gtc<br>His Val Lys Phe Asn Val Thr Tyr Ser Trp Tyr Gly Phe Asp Val<br>2955                              2960                         2965 | | 11851 |
| aaa gag gag tgc gaa gaa gtg aaa ctg ttc gag ccg tgc gta tac<br>Lys Glu Glu Cys Glu Glu Val Lys Leu Phe Glu Pro Cys Val Tyr<br>2970                              2975                         2980 | | 11896 |
| cat cct aca gac ggc aaa tgt cag ttt ccc gca acc aac cag aga<br>His Pro Thr Asp Gly Lys Cys Gln Phe Pro Ala Thr Asn Gln Arg<br>2985                              2990                         2995 | | 11941 |
| tgc ctc ata gga tct gtc ttg atg gcg gaa ttc ttg ggc gcg gcc<br>Cys Leu Ile Gly Ser Val Leu Met Ala Glu Phe Leu Gly Ala Ala<br>3000                              3005                         3010 | | 11986 |
| tct ttg ctg gat tgt tcc cgc gat act cta gaa gac tgc cac gaa<br>Ser Leu Leu Asp Cys Ser Arg Asp Thr Leu Glu Asp Cys His Glu<br>3015                              3020                         3025 | | 12031 |
| aat cgc gtg ccg aac cta cgg ttc gat tcg cga ctc tcc gag tca<br>Asn Arg Val Pro Asn Leu Arg Phe Asp Ser Arg Leu Ser Glu Ser<br>3030                              3035                         3040 | | 12076 |
| cgc gca ggc ctg gtg atc agt cct ctt ata gcc atc ccc aaa gtt<br>Arg Ala Gly Leu Val Ile Ser Pro Leu Ile Ala Ile Pro Lys Val<br>3045                              3050                         3055 | | 12121 |
| ttg att ata gtc gtt tcc gac gga gac att ttg gga tgg agc tac<br>Leu Ile Ile Val Val Ser Asp Gly Asp Ile Leu Gly Trp Ser Tyr<br>3060                              3065                         3070 | | 12166 |
| acg gtg ctc ggg aaa cgt aac agt ccg cgc gta gta gtc gaa acg<br>Thr Val Leu Gly Lys Arg Asn Ser Pro Arg Val Val Val Glu Thr<br>3075                              3080                         3085 | | 12211 |
| cac atg ccc tcg aag gtc ccg atg aac aaa gta gta att ggc agt<br>His Met Pro Ser Lys Val Pro Met Asn Lys Val Val Ile Gly Ser<br>3090                              3095                         3100 | | 12256 |
| ccc gga cca atg gac gaa acg ggt aac tat aaa atg tac ttc gtc<br>Pro Gly Pro Met Asp Glu Thr Gly Asn Tyr Lys Met Tyr Phe Val<br>3105                              3110                         3115 | | 12301 |
| gtc gcg ggg gtg gcc gcg acg tgc gta att ctt aca tgc gct ctg<br>Val Ala Gly Val Ala Ala Thr Cys Val Ile Leu Thr Cys Ala Leu<br>3120                              3125                         3130 | | 12346 |
| ctt gtg ggg aaa aag aag tgc ccc gcg cac caa atg ggt act ttt<br>Leu Val Gly Lys Lys Lys Cys Pro Ala His Gln Met Gly Thr Phe<br>3135                              3140                         3145 | | 12391 |
| tcc aag acc gaa cca ttg tac gcg ccg ctc ccc aaa aac gag ttt<br>Ser Lys Thr Glu Pro Leu Tyr Ala Pro Leu Pro Lys Asn Glu Phe<br>3150                              3155                         3160 | | 12436 |
| gag gcc ggc ggg ctt acg gac gat gag gaa gtg att tat gac gaa<br>Glu Ala Gly Gly Leu Thr Asp Asp Glu Glu Val Ile Tyr Asp Glu<br>3165                              3170                         3175 | | 12481 |
| gta tac gaa ccc cta ttt cgc ggc tac tgt aag cag gaa ttc cgc<br>Val Tyr Glu Pro Leu Phe Arg Gly Tyr Cys Lys Gln Glu Phe Arg<br>3180                              3185                         3190 | | 12526 |
| gaa gat gtg aat acc ttt ttc ggt gcg gtc gtg gag gga gaa agg<br>Glu Asp Val Asn Thr Phe Phe Gly Ala Val Val Glu Gly Glu Arg<br>3195                              3200                         3205 | | 12571 |
| gcc tta aac ttt aaa tcc gcc atc gca tca atg gca gat cgc atc<br>Ala Leu Asn Phe Lys Ser Ala Ile Ala Ser Met Ala Asp Arg Ile | | 12616 |

-continued

```
              3210                3215                3220
ctg gca aat aaa agc ggc aga agg aat atg gat agc tat tag ttggtc        12664
Leu Ala Asn Lys Ser Gly Arg Arg Asn Met Asp Ser Tyr
            3225                3230 atg cct ttt aag acc aga ggg gcc gaa gac gcg gcc gcg ggc aag           12709
Met Pro Phe Lys Thr Arg Gly Ala Glu Asp Ala Ala Ala Gly Lys
3235                3240                3245 aac agg ttt aag aaa tcg aga aat cgg gaa atc tta ccg acc aga           12754
Asn Arg Phe Lys Lys Ser Arg Asn Arg Glu Ile Leu Pro Thr Arg
3250                3255                3260 ctg cgt ggc acc ggt aag aaa act gcc gga ttg tcc aat tat acc           12799
Leu Arg Gly Thr Gly Lys Lys Thr Ala Gly Leu Ser Asn Tyr Thr
3265                3270                3275 cag cct att ccc tgg aac cct aaa ttc tgc agc gcg cgc ggg gaa           12844
Gln Pro Ile Pro Trp Asn Pro Lys Phe Cys Ser Ala Arg Gly Glu
3280                3285                3290 tct gac aac cac gcg tgt aaa gac act ttt tat cgc agg acg tgc           12889
Ser Asp Asn His Ala Cys Lys Asp Thr Phe Tyr Arg Arg Thr Cys
3295                3300                3305 tgc gca tcg cgc tct acc gtt tcc agt caa ccc gat tcc ccc cac           12934
Cys Ala Ser Arg Ser Thr Val Ser Ser Gln Pro Asp Ser Pro His
3310                3315                3320 aca ccc atg cct act gag tat ggg cgc gtg ccc tcc gca aag cgc           12979
Thr Pro Met Pro Thr Glu Tyr Gly Arg Val Pro Ser Ala Lys Arg
3325                3330                3335 aaa aaa cta tca tct tca gac tss gag ggc gcg cac caa ccc cta           13024
Lys Lys Leu Ser Ser Ser Asp Xaa Glu Gly Ala His Gln Pro Leu
3340                3345                3350 gta tcc tgt aaa ctt ccg gat tct caa gca gca ccg gcg cga acc           13069
Val Ser Cys Lys Leu Pro Asp Ser Gln Ala Ala Pro Ala Arg Thr
3355                3360                3365 tat agt tct gcg caa aga tat act gtt gac gag gtt tcg tcg cca           13114
Tyr Ser Ser Ala Gln Arg Tyr Thr Val Asp Glu Val Ser Ser Pro
3370                3375                3380 act ccg cca ggc gtc gac gct gtt gcg gac tta gaa acg cgc gcg           13159
Thr Pro Pro Gly Val Asp Ala Val Ala Asp Leu Glu Thr Arg Ala
3385                3390                3395 gaa ctt cct ggc gct acg acg gaa caa acg gaa agt aaa aat aag           13204
Glu Leu Pro Gly Ala Thr Thr Glu Gln Thr Glu Ser Lys Asn Lys
3400                3405                3410 ctc ccc aac caa caa tcg cgc ctg aag ccg aaa ccc aca aac gag           13249
Leu Pro Asn Gln Gln Ser Arg Leu Lys Pro Lys Pro Thr Asn Glu
3415                3420                3425 cac gtc gga ggg gag cgg tgc ccc tcc gaa ggc acg gtc gag gcg           13294
His Val Gly Gly Glu Arg Cys Pro Ser Glu Gly Thr Val Glu Ala
3430                3435                3440 cca tcg ctc ggc atc ctc tcg cgc gtc ggg gca gcg ata gca aac           13339
Pro Ser Leu Gly Ile Leu Ser Arg Val Gly Ala Ala Ile Ala Asn
3445                3450                3455 gag ctg gct cgt atg cgg agg gcg tgt ctt ccg ctc gcc gcg tcg           13384
Glu Leu Ala Arg Met Arg Arg Ala Cys Leu Pro Leu Ala Ala Ser
3460                3465                3470 gcg gcc gct gcc gga ata gtg gcc tgg gcc gcg gcg agg gcc ttg           13429
Ala Ala Ala Ala Gly Ile Val Ala Trp Ala Ala Ala Arg Ala Leu
3475                3480                3485 cag aaa caa ggg cgg tag cagtaataat aaccacacaa atattg                  13473
Gln Lys Gln Gly Arg
3490
```

<210> SEQ ID NO 2
<211> LENGTH: 476
<212> TYPE: PRT
<213> ORGANISM: Infectious Laryngotracheitis Virus

<400> SEQUENCE: 2

```
Met Arg Phe Arg Arg Ile Cys Ser Arg Ser Arg Ala Glu Lys Arg Arg
1               5                   10                  15
Arg Thr Thr Glu Asn Pro Leu Thr Ser Lys Arg Val Cys Val Leu Asp
                20                  25                  30
Ser Phe Ser Arg Thr Met Ser Leu Arg Pro Tyr Ala Glu Ile Leu Pro
            35                  40                  45
Thr Ala Glu Gly Val Glu Arg Leu Ala Glu Leu Val Ser Val Thr Met
    50                  55                  60
Thr Glu Arg Ala Glu Pro Val Thr Glu Asn Thr Ala Val Asn Ser Ile
65                  70                  75                  80
Pro Pro Ala Asn Glu Asn Gly Gln Asn Phe Ala Tyr Ala Gly Asp Gly
                85                  90                  95
Pro Ser Thr Thr Glu Lys Val Asp Gly Ser His Thr Asp Phe Asp Glu
            100                 105                 110
Ala Ser Ser Asp Tyr Ala Gly Pro Val Pro Leu Ala Gln Thr Arg Leu
        115                 120                 125
Lys His Ser Asp Glu Phe Leu Gln His Phe Arg Val Leu Asp Asp Leu
    130                 135                 140
Val Glu Gly Ala Tyr Gly Phe Ile Cys Gly Val Arg Arg Tyr Thr Glu
145                 150                 155                 160
Glu Glu Gln Arg Arg Gly Val Asn Ser Thr Asn Gln Gly Lys Ser
                165                 170                 175
Lys Cys Lys Arg Leu Ile Ala Lys Tyr Val Lys Asn Gly Thr Arg Ala
            180                 185                 190
Ala Ser Gln Leu Glu Asn Glu Ile Leu Val Leu Gly Arg Leu Asn His
        195                 200                 205
Glu Asn Val Leu Lys Ile Gln Glu Ile Leu Arg Tyr Pro Asp Asn Thr
    210                 215                 220
Tyr Met Leu Thr Gln Arg Tyr Gln Phe Asp Leu Tyr Ser Tyr Met Tyr
225                 230                 235                 240
Asp Glu Ala Phe Asp Trp Lys Asp Ser Pro Met Leu Lys Gln Thr Arg
                245                 250                 255
Arg Ile Met Lys Gln Leu Met Ser Ala Val Ser Tyr Ile His Ser Lys
            260                 265                 270
Lys Leu Ile His Arg Asp Ile Lys Leu Glu Asn Ile Phe Leu Asn Cys
        275                 280                 285
Asp Gly Lys Thr Val Leu Gly Asp Phe Gly Thr Val Thr Pro Phe Glu
    290                 295                 300
Asn Glu Arg Glu Pro Phe Glu Tyr Gly Trp Val Gly Thr Val Ala Thr
305                 310                 315                 320
Asn Ser Pro Glu Ile Leu Ala Arg Asp Ser Tyr Cys Glu Ile Thr Asp
                325                 330                 335
Ile Trp Ser Cys Gly Val Val Leu Leu Glu Met Val Ser His Glu Phe
            340                 345                 350
Cys Pro Ile Gly Asp Gly Gly Asn Pro His Gln Gln Leu Leu Lys
        355                 360                 365
Val Ile Asp Ser Leu Ser Val Cys Asp Glu Glu Phe Pro Asp Pro Pro
    370                 375                 380
```

```
Cys Asn Leu Tyr Asn Tyr Leu His Tyr Ala Ser Ile Asp Arg Ala Gly
385                 390                 395                 400

His Thr Val Pro Ser Leu Ile Arg Asn Leu His Leu Pro Ala Asp Val
            405                 410                 415

Glu Tyr Pro Leu Val Lys Met Leu Thr Phe Asp Trp Arg Leu Arg Pro
                420                 425                 430

Ser Ala Ala Glu Val Leu Ala Met Pro Leu Phe Ser Ala Glu Glu Glu
            435                 440                 445

Arg Thr Ile Thr Ile Ile His Gly Lys His Lys Pro Ile Arg Pro Glu
450                 455                 460

Ile Arg Ala Arg Val Pro Arg Ser Met Ser Glu Gly
465                 470                 475

<210> SEQ ID NO 3
<211> LENGTH: 510
<212> TYPE: PRT
<213> ORGANISM: Infectious Laryngotracheitis Virus

<400> SEQUENCE: 3

Met Thr Leu Pro His Arg Leu Thr Lys Arg Pro Phe Ala Arg Arg Phe
1               5                   10                  15

Cys Ser Val Phe Val Ile His Tyr Ser Glu Thr Lys Leu Asp Arg Tyr
            20                  25                  30

Asn Lys Thr Met Leu Leu Tyr Arg Pro Asp Ser Thr Met Arg His Ser
        35                  40                  45

Gly Gly Asp Ala Asn His Arg Gly Ile Arg Pro Arg Arg Lys Ser Ile
    50                  55                  60

Gly Ala Phe Ser Ala Arg Glu Lys Thr Gly Lys Arg Asn Ala Leu Thr
65                  70                  75                  80

Glu Ser Ser Ser Ser Asp Met Leu Asp Pro Phe Ser Thr Asp Lys
                85                  90                  95

Glu Phe Gly Gly Lys Trp Thr Val Asp Gly Pro Ala Asp Ile Thr Ala
            100                 105                 110

Glu Val Leu Ser Gln Ala Trp Asp Val Leu Gln Leu Val Lys His Glu
        115                 120                 125

Asp Ala Glu Glu Glu Arg Val Thr Tyr Glu Ser Lys Pro Thr Pro Ile
    130                 135                 140

Gln Pro Phe Asn Ala Trp Pro Asp Gly Pro Ser Trp Asn Ala Gln Asp
145                 150                 155                 160

Phe Thr Arg Ala Pro Ile Val Tyr Pro Ser Ala Glu Val Leu Asp Ala
                165                 170                 175

Glu Ala Leu Lys Val Gly Ala Phe Val Ser Arg Val Leu Gln Cys Val
            180                 185                 190

Pro Phe Thr Arg Ser Lys Lys Ser Val Thr Val Arg Asp Ala Gln Ser
        195                 200                 205

Phe Leu Gly Asp Ser Phe Trp Arg Ile Met Gln Asn Val Tyr Thr Val
    210                 215                 220

Cys Leu Arg Gln His Ile Thr Arg Leu Arg His Pro Ser Ser Lys Ser
225                 230                 235                 240

Ile Val Asn Cys Asn Asp Pro Leu Trp Tyr Ala Tyr Ala Asn Gln Phe
                245                 250                 255

His Trp Arg Gly Met Arg Val Pro Ser Leu Lys Leu Ala Ser Pro Pro
            260                 265                 270

Glu Glu Asn Ile Gln His Gly Pro Met Ala Ala Val Phe Arg Asn Ala
        275                 280                 285
```

```
Gly Ala Gly Leu Phe Leu Trp Pro Ala Met Arg Ala Ala Phe Glu Glu
    290                 295                 300

Arg Asp Lys Arg Leu Leu Arg Ala Cys Leu Ser Ser Leu Asp Ile Met
305                 310                 315                 320

Asp Ala Ala Val Leu Ala Ser Phe Pro Phe Tyr Trp Arg Gly Val Gln
                325                 330                 335

Asp Thr Ser Arg Phe Glu Pro Ala Leu Gly Cys Leu Ser Glu Tyr Phe
                340                 345                 350

Ala Leu Val Val Leu Leu Ala Glu Thr Val Leu Ala Thr Met Phe Asp
            355                 360                 365

His Ala Leu Val Phe Met Arg Ala Leu Ala Asp Gly Asn Phe Asp Asp
        370                 375                 380

Tyr Asp Glu Thr Arg Tyr Ile Asp Pro Val Lys Asn Glu Tyr Leu Asn
385                 390                 395                 400

Gly Ala Glu Gly Thr Leu Leu Arg Gly Ile Val Ala Ser Asn Thr Ala
                405                 410                 415

Leu Ala Val Val Cys Ala Asn Thr Tyr Ser Thr Ile Arg Lys Leu Pro
                420                 425                 430

Ser Val Ala Thr Ser Ala Cys Asn Val Ala Tyr Arg Thr Glu Thr Leu
            435                 440                 445

Lys Ala Arg Arg Pro Gly Met Ser Asp Ile Tyr Arg Ile Leu Gln Lys
        450                 455                 460

Glu Phe Phe Tyr Ile Ala Trp Leu Gln Arg Val Ala Thr His Ala
465                 470                 475                 480

Asn Phe Cys Leu Asn Ile Leu Lys Arg Ser Val Asp Thr Gly Pro Arg
                485                 490                 495

His Phe Cys Ser Gly Pro Ala Arg Arg Ser Gly Cys Ser Ser
                500                 505                 510

<210> SEQ ID NO 4
<211> LENGTH: 110
<212> TYPE: PRT
<213> ORGANISM: Infectious Laryngotracheitis Virus

<400> SEQUENCE: 4

Met Leu Cys Pro Leu Leu Val Pro Ile Gln Tyr Glu Asp Phe Ser Lys
1               5                   10                  15

Ala Met Gly Ser Glu Leu Lys Arg Glu Lys Leu Glu Thr Phe Val Lys
            20                  25                  30

Ala Ile Ser Ser Asp Arg Asp Pro Arg Gly Ser Leu Arg Phe Leu Ile
        35                  40                  45

Ser Asp His Ala Arg Glu Ile Ile Ala Asp Gly Val Arg Phe Lys Pro
    50                  55                  60

Val Ile Asp Glu Pro Val Arg Ala Ser Val Ala Leu Ser Thr Ala Ala
65                  70                  75                  80

Ala Gly Lys Val Lys Ala Arg Arg Leu Thr Ser Val Arg Ala Pro Val
                85                  90                  95

Pro Pro Ala Gly Ala Val Ser Ala Arg Arg Lys Ser Glu Ile
                100                 105                 110

<210> SEQ ID NO 5
<211> LENGTH: 292
<212> TYPE: PRT
<213> ORGANISM: Infectious Laryngotracheitis Virus

<400> SEQUENCE: 5
```

```
Met Ser Gly Phe Ser Asn Ile Gly Ser Ile Ala Thr Val Ser Leu Val
1               5                   10                  15

Cys Ser Leu Leu Cys Ala Ser Val Leu Gly Ala Pro Val Leu Asp Gly
            20                  25                  30

Leu Glu Ser Ser Pro Phe Pro Phe Gly Gly Lys Ile Ile Ala Gln Ala
        35                  40                  45

Cys Asn Arg Thr Thr Ile Glu Val Thr Val Pro Trp Ser Asp Tyr Ser
50                  55                  60

Gly Arg Thr Glu Gly Val Ser Val Glu Val Lys Trp Phe Tyr Gly Asn
65                  70                  75                  80

Ser Asn Pro Glu Ser Phe Val Phe Gly Val Asp Ser Glu Thr Gly Ser
                85                  90                  95

Gly His Glu Asp Leu Ser Thr Cys Trp Ala Leu Ile His Asn Leu Asn
            100                 105                 110

Ala Ser Val Cys Arg Ala Ser Asp Ala Gly Ile Pro Asp Phe Asp Lys
        115                 120                 125

Gln Cys Glu Lys Val Gln Arg Arg Leu Arg Ser Gly Val Glu Leu Gly
130                 135                 140

Ser Tyr Val Ser Gly Asn Gly Ser Leu Val Leu Tyr Pro Gly Met Tyr
145                 150                 155                 160

Asp Ala Gly Ile Tyr Ala Tyr Gln Leu Ser Val Gly Gly Lys Gly Tyr
                165                 170                 175

Thr Gly Ser Val Tyr Leu Asp Val Gly Pro Asn Pro Gly Cys His Asp
            180                 185                 190

Gln Tyr Gly Tyr Thr Tyr Tyr Ser Leu Ala Asp Glu Ala Ser Asp Leu
        195                 200                 205

Ser Ser Tyr Asp Val Ala Ser Pro Glu Leu Asp Gly Pro Met Glu Glu
210                 215                 220

Asp Tyr Ser Asn Cys Leu Asp Met Pro Pro Leu Arg Pro Trp Thr Thr
225                 230                 235                 240

Val Cys Ser His Asp Val Glu Glu Gln Glu Asn Ala Thr Asp Glu Leu
                245                 250                 255

Tyr Leu Trp Asp Glu Glu Cys Ala Gly Pro Leu Asp Glu Tyr Val Asp
            260                 265                 270

Glu Arg Ser Glu Thr Met Pro Arg Met Val Val Phe Ser Pro Pro Ser
        275                 280                 285

Thr Leu Gln Gln
    290

<210> SEQ ID NO 6
<211> LENGTH: 985
<212> TYPE: PRT
<213> ORGANISM: Infectious Laryngotracheitis Virus

<400> SEQUENCE: 6

Met Gly Thr Met Leu Val Leu Arg Leu Phe Leu Leu Ala Val Ala Asp
1               5                   10                  15

Ala Ala Leu Pro Thr Gly Arg Phe Cys Arg Val Trp Lys Val Pro Pro
            20                  25                  30

Gly Gly Thr Ile Gln Glu Asn Leu Ala Val Leu Ala Glu Ser Pro Val
        35                  40                  45

Thr Gly His Ala Thr Tyr Pro Pro Glu Gly Ala Val Ser Phe Gln
50                  55                  60

Ile Phe Ala Asp Thr Pro Thr Leu Arg Ile Arg Tyr Gly Pro Thr Glu
```

```
                65                  70                  75                  80
Asp Glu Leu Ala Leu Glu Arg Gly Thr Ser Ala Ser Asp Ala Asp Asn
                    85                  90                  95
Val Thr Phe Ser Leu Ser Tyr Arg Pro Arg Pro Glu Ile His Gly Ala
                100                 105                 110
Tyr Phe Thr Ile Gly Val Phe Ala Thr Gly Gln Ser Thr Glu Ser Ser
                115                 120                 125
Tyr Ser Val Ile Ser Arg Val Leu Val Asn Ala Ser Leu Glu Arg Ser
            130                 135                 140
Val Arg Leu Glu Thr Pro Cys Asp Glu Asn Phe Leu Gln Asn Glu Pro
145                 150                 155                 160
Thr Trp Gly Ser Lys Arg Trp Leu Gly Pro Ser Pro Tyr Val Arg
                    165                 170                 175
Asp Asn Asp Val Ala Val Leu Thr Lys Ala Gln Tyr Ile Gly Glu Cys
                180                 185                 190
Tyr Ser Asn Ser Ala Ala Gln Thr Gly Leu Thr Ser Leu Asn Met Thr
            195                 200                 205
Phe Phe Tyr Ser Pro Lys Arg Ile Val Asn Val Thr Trp Thr Thr Gly
        210                 215                 220
Gly Pro Ser Pro Ser Arg Ile Thr Val Tyr Ser Ser Arg Glu Asn Gly
225                 230                 235                 240
Gln Pro Val Leu Arg Asn Val Ser Asp Gly Phe Leu Val Lys Tyr Thr
                    245                 250                 255
Pro Asp Ile Asp Gly Arg Ala Met Ile Asn Val Ile Ala Asn Tyr Ser
                260                 265                 270
Pro Ala Asp Ser Gly Ser Val Leu Ala Phe Thr Ala Phe Arg Glu Gly
            275                 280                 285
Lys Leu Pro Ser Ala Ile Gln Leu His Arg Ile Asp Met Ser Gly Thr
        290                 295                 300
Glu Pro Pro Gly Thr Glu Thr Thr Phe Asp Cys Gln Lys Met Ile Glu
305                 310                 315                 320
Thr Pro Tyr Arg Ala Leu Gly Ser Asn Val Pro Arg Asp Asp Ser Ile
                    325                 330                 335
Arg Pro Gly Ala Thr Leu Pro Pro Phe Asp Thr Ala Ala Pro Asp Phe
                340                 345                 350
Asp Thr Gly Thr Ser Pro Thr Pro Thr Thr Val Pro Glu Pro Ala Ile
            355                 360                 365
Thr Thr Leu Ile Pro Arg Ser Thr Ser Asp Met Gly Phe Phe Ser Thr
        370                 375                 380
Ala Arg Ala Thr Gly Ser Glu Thr Leu Ser Val Pro Val Gln Glu Thr
385                 390                 395                 400
Asp Arg Thr Leu Ser Thr Thr Pro Leu Thr Leu Pro Leu Thr Pro Gly
                    405                 410                 415
Glu Ser Glu Asn Thr Leu Phe Pro Thr Thr Ala Pro Gly Ile Ser Thr
                420                 425                 430
Glu Thr Pro Ser Ala Ala His Glu Thr Thr Gln Thr Gln Ser Ala Glu
            435                 440                 445
Thr Val Val Phe Thr Gln Ser Pro Ser Thr Glu Ser Glu Thr Ala Arg
        450                 455                 460
Ser Gln Ser Gln Glu Pro Trp Tyr Phe Thr Gln Thr Pro Ser Thr Glu
465                 470                 475                 480
Gln Ala Ala Leu Thr Gln Thr Gln Ile Ala Glu Thr Glu Ala Leu Phe
                    485                 490                 495
```

```
Thr Gln Thr Pro Ser Ala Glu Gln Met Thr Phe Thr Gln Thr Pro Gly
        500                 505                 510

Ala Glu Thr Glu Ala Pro Ala Gln Thr Pro Ser Thr Ile Pro Glu Ile
        515                 520                 525

Phe Thr Gln Ser Arg Ser Thr Pro Pro Glu Thr Ala Arg Ala Pro Ser
        530                 535                 540

Ala Ala Pro Glu Val Phe Thr Gln Ser Ser Thr Val Thr Glu Val
545                 550                 555                 560

Phe Thr Gln Thr Pro Ser Thr Val Pro Lys Thr Thr Leu Ser Ser Ser
                565                 570                 575

Thr Glu Pro Ala Ile Phe Thr Arg Thr Gln Ser Ala Gly Thr Glu Ala
            580                 585                 590

Phe Thr Gln Thr Ser Ser Ala Glu Pro Asp Thr Met Arg Thr Gln Ser
        595                 600                 605

Thr Glu Thr His Phe Phe Thr Gln Ala Pro Ser Thr Val Pro Lys Ala
        610                 615                 620

Thr Gln Thr Pro Ser Thr Glu Pro Glu Val Leu Thr Gln Ser Pro Ser
625                 630                 635                 640

Thr Glu Pro Val Pro Phe Thr Arg Thr Leu Gly Ala Glu Pro Glu Ile
                645                 650                 655

Thr Gln Thr Pro Ser Ala Ala Pro Glu Val Tyr Thr Arg Ser Ser Ser
            660                 665                 670

Thr Met Pro Glu Thr Ala Gln Ser Thr Pro Leu Ala Ser Gln Asn Pro
        675                 680                 685

Thr Ser Ser Gly Thr Gly Thr His Asn Thr Glu Pro Arg Thr Tyr Pro
        690                 695                 700

Val Gln Thr Thr Pro His Thr Gln Lys Leu Tyr Thr Glu Asn Lys Thr
705                 710                 715                 720

Leu Ser Phe Pro Thr Val Val Ser Glu Phe His Glu Met Ser Thr Ala
                725                 730                 735

Glu Ser Gln Thr Pro Leu Leu Asp Val Lys Ile Val Glu Val Lys Phe
            740                 745                 750

Ser Asn Asp Gly Glu Val Thr Ala Thr Cys Val Ser Thr Val Lys Ser
        755                 760                 765

Pro Tyr Arg Val Glu Thr Asn Trp Lys Val Asp Leu Val Asp Val Met
        770                 775                 780

Asp Glu Ile Ser Gly Asn Ser Pro Ala Gly Val Phe Asn Ser Asn Glu
785                 790                 795                 800

Lys Trp Gln Lys Gln Leu Tyr Tyr Arg Val Thr Asp Gly Arg Thr Ser
                805                 810                 815

Val Gln Leu Met Cys Leu Ser Cys Thr Ser His Ser Pro Glu Pro Tyr
            820                 825                 830

Cys Leu Phe Asp Thr Ser Leu Ile Ala Arg Glu Lys Asp Ile Ala Pro
        835                 840                 845

Glu Leu Tyr Phe Thr Ser Asp Pro Gln Thr Ala Tyr Cys Thr Ile Thr
        850                 855                 860

Leu Pro Ser Gly Val Val Pro Arg Phe Glu Trp Ser Leu Asn Asn Val
865                 870                 875                 880

Ser Leu Pro Glu Tyr Leu Thr Ala Thr Val Val Ser His Thr Ala
                885                 890                 895

Gly Gln Ser Thr Val Trp Lys Ser Ser Ala Arg Ala Gly Glu Ala Trp
        900                 905                 910
```

-continued

Ile Ser Gly Arg Gly Gly Asn Ile Tyr Glu Cys Thr Val Leu Ile Ser
915 920 925

Asp Gly Thr Arg Val Thr Thr Arg Lys Glu Arg Cys Leu Thr Asn Thr
930 935 940

Trp Ile Ala Val Glu Asn Gly Ala Ala Gln Ala Gln Leu Tyr Ser Leu
945 950 955 960

Phe Ser Gly Leu Val Ser Gly Leu Cys Gly Ser Ile Ser Ala Leu Tyr
965 970 975

Ala Thr Leu Trp Thr Ala Ile Tyr Phe
980 985

<210> SEQ ID NO 7
<211> LENGTH: 362
<212> TYPE: PRT
<213> ORGANISM: Infectious Laryngotracheitis Virus

<400> SEQUENCE: 7

Met Ala Ser Leu Leu Gly Thr Leu Ala Leu Leu Ala Ala Thr Leu Ala
1 5 10 15

Pro Phe Gly Ala Met Gly Ile Val Ile Thr Gly Asn His Val Ser Ala
20 25 30

Arg Ile Asp Asp Asp His Ile Val Ile Val Ala Pro Arg Pro Glu Ala
35 40 45

Thr Ile Gln Leu Gln Leu Phe Phe Met Pro Gly Gln Arg Pro His Lys
50 55 60

Pro Tyr Ser Gly Thr Val Arg Val Ala Phe Arg Ser Asp Ile Thr Asn
65 70 75 80

Gln Cys Tyr Gln Glu Leu Ser Glu Glu Arg Phe Glu Asn Cys Thr His
85 90 95

Arg Ser Ser Ser Val Phe Val Gly Cys Lys Val Thr Glu Tyr Thr Phe
100 105 110

Ser Ala Ser Asn Arg Leu Thr Gly Pro Pro His Pro Phe Lys Leu Thr
115 120 125

Ile Arg Asn Pro Arg Pro Asn Asp Ser Gly Met Phe Tyr Val Ile Val
130 135 140

Arg Leu Asp Asp Thr Lys Glu Pro Ile Asp Val Phe Ala Ile Gln Leu
145 150 155 160

Ser Val Tyr Gln Phe Ala Asn Thr Ala Ala Thr Arg Gly Leu Tyr Ser
165 170 175

Lys Ala Ser Cys Arg Thr Phe Gly Leu Pro Thr Val Gln Leu Glu Ala
180 185 190

Tyr Leu Arg Thr Glu Glu Ser Trp Arg Asn Trp Gln Ala Tyr Val Ala
195 200 205

Thr Glu Ala Thr Thr Thr Ser Ala Glu Ala Thr Thr Pro Thr Pro Val
210 215 220

Thr Ala Thr Ser Ala Ser Glu Leu Glu Ala Glu His Phe Thr Phe Pro
225 230 235 240

Trp Leu Glu Asn Gly Val Asp His Tyr Glu Pro Thr Pro Ala Asn Glu
245 250 255

Asn Ser Asn Val Thr Val Arg Leu Gly Thr Met Ser Pro Thr Leu Ile
260 265 270

Gly Val Thr Val Ala Ala Val Val Ser Ala Thr Ile Gly Leu Val Ile
275 280 285

Val Ile Ser Ile Val Thr Arg Asn Met Cys Thr Pro His Arg Lys Leu
290 295 300

-continued

```
Asp Thr Val Ser Gln Asp Asp Glu Glu Arg Ser Gln Thr Arg Arg Glu
305                 310                 315                 320

Ser Arg Lys Phe Gly Pro Met Val Ala Cys Glu Ile Asn Lys Gly Ala
                325                 330                 335

Asp Gln Asp Ser Glu Leu Val Glu Leu Val Ala Ile Val Asn Pro Ser
            340                 345                 350

Ala Leu Ser Ser Pro Asp Ser Ile Lys Met
        355                 360

<210> SEQ ID NO 8
<211> LENGTH: 499
<212> TYPE: PRT
<213> ORGANISM: Infectious Laryngotracheitis Virus
<400> SEQUENCE: 8

Met Asn Met Leu Val Ile Val Leu Ala Ser Cys Leu Ala Arg Leu Thr
1               5                   10                  15

Phe Ala Thr Arg His Val Leu Phe Leu Glu Gly Thr Gln Ala Val Leu
            20                  25                  30

Gly Glu Asp Asp Pro Arg Asn Val Pro Glu Gly Thr Val Ile Lys Trp
        35                  40                  45

Thr Lys Val Leu Arg Asn Ala Cys Lys Met Lys Ala Ala Asp Val Cys
    50                  55                  60

Ser Ser Pro Asn Tyr Cys Phe His Asp Leu Ile Tyr Asp Gly Gly Lys
65                  70                  75                  80

Lys Asp Cys Pro Pro Ala Gly Pro Leu Ser Ala Asn Leu Val Ile Leu
                85                  90                  95

Leu Lys Arg Gly Glu Ser Phe Val Val Leu Gly Ser Gly Leu His Asn
            100                 105                 110

Ser Asn Ile Thr Asn Ile Met Trp Thr Glu Tyr Gly Gly Leu Leu Phe
        115                 120                 125

Asp Pro Val Thr Arg Ser Asp Glu Gly Ile Tyr Phe Arg Arg Ile Ser
    130                 135                 140

Gln Pro Asp Leu Ala Met Glu Thr Thr Ser Tyr Asn Val Ser Val Leu
145                 150                 155                 160

Ser His Val Asp Glu Lys Ala Pro Ala Pro His Glu Val Glu Ile Asp
                165                 170                 175

Thr Ile Lys Pro Ser Glu Ala His Ala His Val Glu Leu Gln Met Leu
            180                 185                 190

Pro Phe His Glu Leu Asn Asp Asn Ser Pro Thr Tyr Val Thr Pro Val
        195                 200                 205

Leu Arg Val Phe Pro Pro Thr Glu His Val Lys Phe Asn Val Thr Tyr
    210                 215                 220

Ser Trp Tyr Gly Phe Asp Val Lys Glu Glu Cys Glu Glu Val Lys Leu
225                 230                 235                 240

Phe Glu Pro Cys Val Tyr His Pro Thr Asp Gly Lys Cys Gln Phe Pro
                245                 250                 255

Ala Thr Asn Gln Arg Cys Leu Ile Gly Ser Val Leu Met Ala Glu Phe
            260                 265                 270

Leu Gly Ala Ala Ser Leu Leu Asp Cys Ser Arg Asp Thr Leu Glu Asp
        275                 280                 285

Cys His Glu Asn Arg Val Pro Asn Leu Arg Phe Asp Ser Arg Leu Ser
    290                 295                 300

Glu Ser Arg Ala Gly Leu Val Ile Ser Pro Leu Ile Ala Ile Pro Lys
```

```
                305                 310                 315                 320
Val Leu Ile Ile Val Ser Asp Gly Asp Ile Leu Gly Trp Ser Tyr
                    325                 330                 335

Thr Val Leu Gly Lys Arg Asn Ser Pro Arg Val Val Glu Thr His
                340                 345                 350

Met Pro Ser Lys Val Pro Met Asn Lys Val Val Ile Gly Ser Pro Gly
                    355                 360                 365

Pro Met Asp Glu Thr Gly Asn Tyr Lys Met Tyr Phe Val Val Ala Gly
        370                 375                 380

Val Ala Ala Thr Cys Val Ile Leu Thr Cys Ala Leu Leu Val Gly Lys
385                 390                 395                 400

Lys Lys Cys Pro Ala His Gln Met Gly Thr Phe Ser Lys Thr Glu Pro
                405                 410                 415

Leu Tyr Ala Pro Leu Pro Lys Asn Glu Phe Glu Ala Gly Gly Leu Thr
                420                 425                 430

Asp Asp Glu Glu Val Ile Tyr Asp Glu Val Tyr Glu Pro Leu Phe Arg
            435                 440                 445

Gly Tyr Cys Lys Gln Glu Phe Arg Glu Asp Val Asn Thr Phe Phe Gly
    450                 455                 460

Ala Val Val Glu Gly Glu Arg Ala Leu Asn Phe Lys Ser Ala Ile Ala
465                 470                 475                 480

Ser Met Ala Asp Arg Ile Leu Ala Asn Lys Ser Gly Arg Arg Asn Met
                485                 490                 495

Asp Ser Tyr

<210> SEQ ID NO 9
<211> LENGTH: 260
<212> TYPE: PRT
<213> ORGANISM: Infectious Laryngotracheitis Virus
<220> FEATURE:
<221> NAME/KEY: misc_feature
<222> LOCATION: (113)..(113)
<223> OTHER INFORMATION: The 'Xaa' at location 113 stands for Trp,
      Cys, or Ser.

<400> SEQUENCE: 9

Met Pro Phe Lys Thr Arg Gly Ala Glu Asp Ala Ala Gly Lys Asn
1               5                   10                  15

Arg Phe Lys Lys Ser Arg Asn Arg Glu Ile Leu Pro Thr Arg Leu Arg
                20                  25                  30

Gly Thr Gly Lys Lys Thr Ala Gly Leu Ser Asn Tyr Thr Gln Pro Ile
            35                  40                  45

Pro Trp Asn Pro Lys Phe Cys Ser Ala Arg Gly Glu Ser Asp Asn His
    50                  55                  60

Ala Cys Lys Asp Thr Phe Tyr Arg Arg Thr Cys Cys Ala Ser Arg Ser
65                  70                  75                  80

Thr Val Ser Ser Gln Pro Asp Ser Pro His Thr Pro Met Pro Thr Glu
                85                  90                  95

Tyr Gly Arg Val Pro Ser Ala Lys Arg Lys Lys Leu Ser Ser Ser Asp
            100                 105                 110

Xaa Glu Gly Ala His Gln Pro Leu Val Ser Cys Lys Leu Pro Asp Ser
        115                 120                 125

Gln Ala Ala Pro Ala Arg Thr Tyr Ser Ser Ala Gln Arg Tyr Thr Val
    130                 135                 140

Asp Glu Val Ser Ser Pro Thr Pro Pro Gly Val Asp Ala Val Ala Asp
145                 150                 155                 160
```

```
Leu Glu Thr Arg Ala Glu Leu Pro Gly Ala Thr Thr Glu Gln Thr Glu
            165                 170                 175

Ser Lys Asn Lys Leu Pro Asn Gln Gln Ser Arg Leu Lys Pro Lys Pro
            180                 185                 190

Thr Asn Glu His Val Gly Gly Glu Arg Cys Pro Ser Glu Gly Thr Val
            195                 200                 205

Glu Ala Pro Ser Leu Gly Ile Leu Ser Arg Val Gly Ala Ala Ile Ala
            210                 215                 220

Asn Glu Leu Ala Arg Met Arg Arg Ala Cys Leu Pro Leu Ala Ala Ser
225                 230                 235                 240

Ala Ala Ala Ala Gly Ile Val Ala Trp Ala Ala Arg Ala Leu Gln
            245                 250                 255

Lys Gln Gly Arg
            260

<210> SEQ ID NO 10
<211> LENGTH: 1305
<212> TYPE: DNA
<213> ORGANISM: Infectious Laryngotracheitis Virus

<400> SEQUENCE: 10
atgcaccgtc ctcatctcag acggcactcg cgttactacg cgaaaggaga ggtgcttaac      60
aaacacatgg attgcggtgg aaaacggtgc tgctcaggcg cagctgtatt cactcttttc     120
tggacttgtg tcaggattat gcgggagcat atctgctttg tacgcaacgc tatggaccgc     180
catttatttt tgaggaatgc ttttggact atcgtactgc tttcttcctt cgctagccag     240
agcaccgccg ccgtcacgta cgactacatt ttaggccgtc gcgcgctcga cgcgctaacc     300
ataccggcgg ttggcccgta taacagatac ctcactaggg tatcaagagg ctgcgacgtt     360
gtcgagctca acccgatttc taacgtggac gacatgatat cggcggccaa agaaaaagag     420
aagggggggcc ctttcgaggc ctccgtcgtc tggttctacg tgattaaggg cgacgacggc     480
gaggacaagt actgtccaat ctatagaaaa gagtacaggg aatgtggcga cgtacaactg     540
ctatctgaat gcgccgttca atctgcacag atgtgggcag tggactatgt tcctagcacc     600
cttgtatcgc gaaatggcgc gggactgact atattctccc ccactgctgc gctctctggc     660
caatacttgc tgaccctgaa atcggggaga tttgcgcaaa cagctctcgt aactctagaa     720
gttaacgatc gctgtttaaa gatcgggtcg cagcttaact ttttaccgtc gaaatgctgg     780
acaacagaac agtatcagac tggatttcaa ggcgaacacc tttatccgat cgcagacacc     840
aatacacgac acgcggacga cgtatatcgg ggatacgaag atattctgca gcgctggaat     900
aatttgctga ggaaaaagaa tcctagcgcg ccagaccctc gtccagatag cgtcccgcaa     960
gaaattcccg ctgtaaccaa gaaagcggaa gggcgcaccc cggacgcaga aagcagcgaa    1020
aagaaggccc ctccagaaga ctcggaggac gacatgcagg cagaggcttc tggagaaaat    1080
cctgccgccc tccccgaaga cgacgaagtc cccgaggaca ccgagcacga tgatccaaac    1140
tcggatcctg actattacaa tgacatgccc gccgtgatcc cggtggagga gactactaaa    1200
agttctaatg ccgtctccat gcccatattc gcggcgttcg tagcctgcgc ggtcgcgctc    1260
gtggggctac tggtttggag catcgtaaaa tgcgcgcgta gctaa                    1305

<210> SEQ ID NO 11
<211> LENGTH: 434
<212> TYPE: PRT
<213> ORGANISM: Infectious Laryngotracheitis Virus
```

```
<400> SEQUENCE: 11

Met His Arg Pro His Leu Arg Arg His Ser Arg Tyr Tyr Ala Lys Gly
1               5                   10                  15

Glu Val Leu Asn Lys His Met Asp Cys Gly Lys Arg Cys Cys Ser
            20                  25                  30

Gly Ala Ala Val Phe Thr Leu Phe Trp Thr Cys Val Arg Ile Met Arg
        35                  40                  45

Glu His Ile Cys Phe Val Arg Asn Ala Met Asp Arg His Leu Phe Leu
        50                  55                  60

Arg Asn Ala Phe Trp Thr Ile Val Leu Leu Ser Ser Phe Ala Ser Gln
65                  70                  75                  80

Ser Thr Ala Ala Val Thr Tyr Asp Tyr Ile Leu Gly Arg Arg Ala Leu
                85                  90                  95

Asp Ala Leu Thr Ile Pro Ala Val Gly Pro Tyr Asn Arg Tyr Leu Thr
                100                 105                 110

Arg Val Ser Arg Gly Cys Asp Val Val Glu Leu Asn Pro Ile Ser Asn
            115                 120                 125

Val Asp Asp Met Ile Ser Ala Ala Lys Glu Lys Glu Lys Gly Gly Pro
130                 135                 140

Phe Glu Ala Ser Val Val Trp Phe Tyr Val Ile Lys Gly Asp Asp Gly
145                 150                 155                 160

Glu Asp Lys Tyr Cys Pro Ile Tyr Arg Lys Glu Tyr Arg Glu Cys Gly
                165                 170                 175

Asp Val Gln Leu Leu Ser Glu Cys Ala Val Gln Ser Ala Gln Met Trp
            180                 185                 190

Ala Val Asp Tyr Val Pro Ser Thr Leu Val Ser Arg Asn Gly Ala Gly
        195                 200                 205

Leu Thr Ile Phe Ser Pro Thr Ala Ala Leu Ser Gly Gln Tyr Leu Leu
210                 215                 220

Thr Leu Lys Ile Gly Arg Phe Ala Gln Thr Ala Leu Val Thr Leu Glu
225                 230                 235                 240

Val Asn Asp Arg Cys Leu Lys Ile Gly Ser Gln Leu Asn Phe Leu Pro
                245                 250                 255

Ser Lys Cys Trp Thr Thr Glu Gln Tyr Gln Thr Gly Phe Gln Gly Glu
            260                 265                 270

His Leu Tyr Pro Ile Ala Asp Thr Asn Thr Arg His Ala Asp Asp Val
        275                 280                 285

Tyr Arg Gly Tyr Glu Asp Ile Leu Gln Arg Trp Asn Asn Leu Leu Arg
290                 295                 300

Lys Lys Asn Pro Ser Ala Pro Asp Pro Arg Pro Asp Ser Val Pro Gln
305                 310                 315                 320

Glu Ile Pro Ala Val Thr Lys Lys Ala Glu Gly Arg Thr Pro Asp Ala
                325                 330                 335

Glu Ser Ser Glu Lys Lys Ala Pro Pro Glu Asp Ser Glu Asp Asp Met
            340                 345                 350

Gln Ala Glu Ala Ser Gly Glu Asn Pro Ala Ala Leu Pro Glu Asp Asp
        355                 360                 365

Glu Val Pro Glu Asp Thr Glu His Asp Pro Asn Ser Asp Pro Asp
        370                 375                 380

Tyr Tyr Asn Asp Met Pro Ala Val Ile Pro Val Glu Glu Thr Thr Lys
385                 390                 395                 400

Ser Ser Asn Ala Val Ser Met Pro Ile Phe Ala Ala Phe Val Ala Cys
```

-continued

```
                        405                 410                 415
Ala Val Ala Leu Val Gly Leu Leu Val Trp Ser Ile Val Lys Cys Ala
                420                 425                 430

Arg Ser

<210> SEQ ID NO 12
<211> LENGTH: 690
<212> TYPE: DNA
<213> ORGANISM: Infectious Laryngotracheitis Virus

<400> SEQUENCE: 12
atggcgcctg taaaagtgac tatagtttct gcggtcgatt cgcactacaa actacctaat      60
tctagatttg agctctcgga ttctggatgg aaagaattgg ttcacgcagt gaaaactatg     120
gcgagttacg atcgtccgag tacattatcg gtaatcgtgc gcccggcatc tctgtacgaa     180
gtttccgggg agctgttttc ccttcccagg atgtgcagac ccgtgattcg gttcggtgag     240
gggggcgacc cgcctggagt aagtcccgag tggagcggct ggacgcagg gttttaccat      300 ttgtcatctg gcgcgtatgc cgcaaaagag ttccatttgt gggtgctggg taccgctgac     360
atatgcatgg cagcttttaaa cctccctgcg ccaaaaactt tcctaattac cgaaaccgga    420
ggtaaaaatt ttgagagagg agtggaaata ttttggtaa acggagacaa gacaacgctg      480
tctctgagtc acccatcagt ctggacaact cttgcccctt cgagcctgag aacgccctgg     540
ccgtacagca cggtaaagtt tttaaaagta aaacctaact cggccgcata ctgtgtttcc     600
gactcggatg atggcgaacg gcagccaaaa ttttttctcg ggagtctatt taagtcgaag     660
aaaccccgct ccccgcggcg ccgacgttag                                      690

<210> SEQ ID NO 13
<211> LENGTH: 229
<212> TYPE: PRT
<213> ORGANISM: Infectious Laryngotracheitis Virus

<400> SEQUENCE: 13

Met Ala Pro Val Lys Val Thr Ile Val Ser Ala Val Asp Ser His Tyr
1               5                   10                  15

Lys Leu Pro Asn Ser Arg Phe Glu Leu Ser Asp Ser Gly Trp Lys Glu
            20                  25                  30

Leu Val His Ala Val Lys Thr Met Ala Ser Tyr Asp Arg Pro Ser Thr
        35                  40                  45

Leu Ser Val Ile Val Arg Pro Ala Ser Leu Tyr Glu Val Ser Gly Glu
    50                  55                  60

Leu Phe Ser Leu Pro Arg Met Cys Arg Pro Val Ile Arg Phe Gly Glu
65                  70                  75                  80

Gly Gly Asp Pro Pro Gly Val Ser Pro Glu Trp Ser Gly Leu Asp Ala
                85                  90                  95

Gly Phe Tyr His Leu Ser Ser Gly Ala Tyr Ala Ala Lys Glu Phe His
            100                 105                 110

Leu Trp Val Leu Gly Thr Ala Asp Ile Cys Met Ala Ala Leu Asn Leu
        115                 120                 125

Pro Ala Pro Lys Thr Phe Leu Ile Thr Glu Thr Gly Gly Lys Asn Phe
    130                 135                 140

Glu Arg Gly Val Glu Ile Phe Leu Val Asn Gly Asp Lys Thr Thr Leu
145                 150                 155                 160

Ser Leu Ser His Pro Ser Val Trp Thr Thr Leu Ala Pro Ser Ser Leu
                165                 170                 175
```

Arg Thr Pro Trp Pro Tyr Ser Thr Val Lys Phe Leu Lys Val Lys Pro
            180                 185                 190

Asn Ser Ala Ala Tyr Cys Val Ser Asp Ser Asp Gly Glu Arg Gln
        195                 200                 205

Pro Lys Phe Phe Leu Gly Ser Leu Phe Lys Ser Lys Lys Pro Arg Ser
    210                 215                 220

Pro Arg Arg Arg Arg
225

<210> SEQ ID NO 14
<211> LENGTH: 381
<212> TYPE: DNA
<213> ORGANISM: Infectious Laryngotracheitis Virus

<400> SEQUENCE: 14
atgcgtagct cagttacgtc attgtggagc ccttcagatc acgcctcttc gcccgcaaat    60
gccaagcatt tttatcatat ttccgatttc cggcgcgcgg aaacggcgcc tgcgggcggt   120
acgggcgcgc gaactgaggt taagcgtcgc gctttcactt tcccagcggc agcggtactc   180
agcgcaactg aagcccgaac cggctcgtct atcaccggct aaaccgtac tccgtctgca    240 ataatttccc ttgcatggtc cgaaatgaga atcttaagg accccctcgg gtccctgtcg    300
ctggaaatag ctttaacgaa tgtctctaac ttttccctct tgagctcaga ccccatggcc   360
ttcgaaaagt cttcatattg a                                             381

<210> SEQ ID NO 15
<211> LENGTH: 126
<212> TYPE: PRT
<213> ORGANISM: Infectious Laryngotracheitis Virus

<400> SEQUENCE: 15

Met Arg Ser Ser Val Thr Ser Leu Trp Ser Pro Ser Asp His Ala Ser
1               5                   10                  15

Ser Pro Ala Asn Ala Lys His Phe Tyr His Ile Ser Asp Phe Arg Arg
            20                  25                  30

Ala Glu Thr Ala Pro Ala Gly Gly Thr Gly Ala Arg Thr Glu Val Lys
        35                  40                  45

Arg Arg Ala Phe Thr Phe Pro Ala Ala Val Leu Ser Ala Thr Glu
    50                  55                  60

Ala Arg Thr Gly Ser Ser Ile Thr Gly Leu Asn Arg Thr Pro Ser Ala
65                  70                  75                  80

Ile Ile Ser Leu Ala Trp Ser Glu Met Arg Asn Leu Lys Asp Pro Leu
                85                  90                  95

Gly Ser Leu Ser Leu Glu Ile Ala Leu Thr Asn Val Ser Asn Phe Ser
            100                 105                 110

Leu Leu Ser Ser Asp Pro Met Ala Phe Glu Lys Ser Ser Tyr
        115                 120                 125

<210> SEQ ID NO 16
<211> LENGTH: 879
<212> TYPE: DNA
<213> ORGANISM: Infectious Laryngotracheitis Virus

<400> SEQUENCE: 16
atgtggtgtc gtttgcactg gataagtcct cggttcagta ttatgcgtcc cggttcccga    60
actggtaggg ttttgcgagg ccaggggtgt gctctgtgca gttctggca tcgtactcga    120

```
actccgagta taaacctccg gtgccgcgct cggggtctga gtaatttccg gctctgcgcc      180
cagagtccgg gtgaaaggca caggttcggt actcggactc tgagtcaaca cctccggctc      240
tgtactcgga gtctgagtag ctttcggtac cgtactcggg gcctgagtga aaaagtgtgt      300
ttcagtactc tgagttcgca tagtgtccgg ctcggcactc gaagtctgag taaaggcctc      360
agttcccgcg ctctgagtcc gagtaaaaat cgccggttca gtactcgaac tcagagtagt      420
tttcggtacc gtgctcgggg tctgagtaaa cacctccgtt accgtactcg aactctgtgt      480
aaaaacctcc ggcgccgcgc tcggagcgcg agcggtttcg ggggcgtgc tacgagactg      540 agtaaatatc tcgggtatcg tgctcggggt ctgggcaggt gcctcggttt ctgcacccgg      600
agtctgagta aaagtcatct gttcagcact cggagtctga gtaaacaacg cctccgtttc      660
tgcgatctgc gtctgagtaa agccgcctg ttcagtactc ggagtctgag taaaatacca      720
cggttcctga ctctgggacc gcgcggtttc cgactcggta ctcggactct gagtaaagac      780
caccgtttct gcactctggg tctgtgtagt ttcatgtgcc gcgctcgggg tctcggtaga      840
aatccccggc gcggtcgtag gaaacagtgt attttctga                            879
```

<210> SEQ ID NO 17
<211> LENGTH: 292
<212> TYPE: PRT
<213> ORGANISM: Infectious Laryngotracheitis Virus

<400> SEQUENCE: 17

```
Met Trp Cys Arg Leu His Trp Ile Ser Pro Arg Phe Ser Ile Met Arg
1               5                   10                  15

Pro Gly Ser Arg Thr Gly Arg Val Leu Arg Gly Gln Gly Cys Ala Leu
            20                  25                  30

Cys Ser Phe Trp His Arg Thr Thr Pro Ser Ile Asn Leu Arg Cys
        35                  40                  45

Arg Ala Arg Gly Leu Ser Asn Phe Arg Leu Cys Ala Gln Ser Pro Gly
    50                  55                  60

Glu Arg His Arg Phe Gly Thr Arg Thr Leu Ser Gln His Leu Arg Leu
65                  70                  75                  80

Cys Thr Arg Ser Leu Ser Ser Phe Arg Tyr Arg Thr Arg Gly Leu Ser
                85                  90                  95

Glu Lys Val Cys Phe Ser Thr Leu Ser Ser His Ser Val Arg Leu Gly
            100                 105                 110

Thr Arg Ser Leu Ser Lys Gly Leu Ser Ser Arg Ala Leu Ser Pro Ser
        115                 120                 125

Lys Asn Arg Arg Phe Ser Thr Arg Thr Gln Ser Ser Phe Arg Tyr Arg
    130                 135                 140

Ala Arg Gly Leu Ser Lys His Leu Arg Tyr Arg Thr Arg Thr Leu Cys
145                 150                 155                 160

Lys Asn Leu Arg Arg Arg Ala Arg Ser Ala Ser Gly Phe Gly Gly Arg
                165                 170                 175

Ala Thr Arg Leu Ser Lys Tyr Leu Gly Tyr Arg Ala Arg Gly Leu Gly
            180                 185                 190

Arg Cys Leu Gly Phe Cys Thr Arg Ser Leu Lys Ser His Leu Phe
        195                 200                 205

Ser Thr Arg Ser Leu Ser Lys Gln Arg Leu Arg Phe Cys Asp Leu Arg
    210                 215                 220

Leu Ser Lys Ser Arg Leu Phe Ser Thr Arg Ser Leu Ser Lys Ile Pro
225                 230                 235                 240
```

```
Arg Phe Leu Thr Leu Gly Pro Arg Gly Phe Arg Leu Gly Thr Arg Thr
                245                 250                 255

Leu Ser Lys Asp His Arg Phe Cys Thr Leu Gly Leu Cys Ser Phe Met
            260                 265                 270

Cys Arg Ala Arg Gly Leu Gly Arg Asn Pro Arg Gly Arg Arg Lys
        275                 280                 285

Gln Cys Ile Phe
    290

<210> SEQ ID NO 18
<211> LENGTH: 534
<212> TYPE: DNA
<213> ORGANISM: Infectious Laryngotracheitis Virus

<400> SEQUENCE: 18
atgctcccaa gcctactcaa caggggctct ccccggctga attctcctcc taagtgttca     60
gaggcctctg ctgtaccata taactatcgt gtagtacgcc cctcccagtc cgtgtccgat    120
actgcccctt ttgagaggat tgggagatta gagaatcgaa atgattggag agccacattc    180
agacttaatc acattttat tgagtcgggc gagcttagcg cagacgggtt aacaatcgca    240
accagttcca caagttcact atcctggtca gcgcccttgt ttatttcgca cgcaaccatg    300
ggtccaaatt ttcgcgattc ccttctagtt tgggaacgtt cttcgtcgtc ttgcgagacc    360
gtgtctaatt ttcggtgcgg ggtgcacatg tttctggtga cgatggaaat tacaatgacg    420
aggccgatcg ttgcgctcac gacggcagcc acggttaccc caattagcgt agggctcatt    480
gtcccgagac ggacagtaac gtttgaattt tcgtttgcgg gtgtcggttc gtaa          534

<210> SEQ ID NO 19
<211> LENGTH: 177
<212> TYPE: PRT
<213> ORGANISM: Infectious Laryngotracheitis Virus

<400> SEQUENCE: 19

Met Leu Pro Ser Leu Leu Asn Arg Gly Ser Pro Arg Leu Asn Ser Pro
1               5                   10                  15

Pro Lys Cys Ser Glu Ala Ser Ala Val Pro Tyr Asn Tyr Arg Val Val
            20                  25                  30

Arg Pro Gln Ser Val Ser Asp Thr Ala Pro Phe Glu Arg Ile Gly
        35                  40                  45

Arg Leu Glu Asn Arg Asn Asp Trp Arg Ala Thr Phe Arg Leu Asn His
    50                  55                  60

Ile Phe Ile Glu Ser Gly Glu Leu Ser Ala Asp Gly Leu Thr Ile Ala
65                  70                  75                  80

Thr Ser Ser Thr Ser Ser Leu Ser Trp Ser Ala Pro Leu Phe Ile Ser
                85                  90                  95

His Ala Thr Met Gly Pro Asn Phe Arg Asp Ser Leu Leu Val Trp Glu
            100                 105                 110

Arg Ser Ser Ser Ser Cys Glu Thr Val Ser Asn Phe Arg Cys Gly Val
        115                 120                 125

His Met Phe Leu Val Thr Met Glu Ile Thr Met Thr Arg Pro Ile Val
    130                 135                 140

Ala Leu Thr Thr Ala Ala Thr Val Thr Pro Ile Ser Val Gly Leu Ile
145                 150                 155                 160

Val Pro Arg Arg Thr Val Thr Phe Glu Phe Ser Phe Ala Gly Val Gly
                165                 170                 175
```

Ser

```
<210> SEQ ID NO 20
<211> LENGTH: 48
<212> TYPE: DNA
<213> ORGANISM: Artificial Sequence
<220> FEATURE:
<223> OTHER INFORMATION: linker

<400> SEQUENCE: 20
gaattcgagc tcggtacccg gataatacgt acatgttaac gcagaggt                48

<210> SEQ ID NO 21
<211> LENGTH: 36
<212> TYPE: DNA
<213> ORGANISM: Artificial Sequence
<220> FEATURE:
<223> OTHER INFORMATION: linker

<400> SEQUENCE: 21
gctgaccgct agtcgacctg cagtgaataa taaaat                             36

<210> SEQ ID NO 22
<211> LENGTH: 48
<212> TYPE: DNA
<213> ORGANISM: Artificial Sequence
<220> FEATURE:
<223> OTHER INFORMATION: linker

<400> SEQUENCE: 22
tgtccgtcga gatcctctag agtcgacgaa aggtcagaga cgatgccc                48

<210> SEQ ID NO 23
<211> LENGTH: 38
<212> TYPE: DNA
<213> ORGANISM: Artificial Sequence
<220> FEATURE:
<223> OTHER INFORMATION: linker

<400> SEQUENCE: 23
cggatcagaa actctttcgg tacccgggat cctctaga                           38

<210> SEQ ID NO 24
<211> LENGTH: 33
<212> TYPE: DNA
<213> ORGANISM: Artificial Sequence
<220> FEATURE:
<223> OTHER INFORMATION: linker

<400> SEQUENCE: 24
gaatacaagc ttagatgcat atttactcga gcc                                33

<210> SEQ ID NO 25
<211> LENGTH: 51
<212> TYPE: DNA
<213> ORGANISM: Artificial Sequence
<220> FEATURE:
<223> OTHER INFORMATION: linker

<400> SEQUENCE: 25
ggtttggcgg agcggatatg atctcgacct gcagtgaata taaaatgtg t             51

<210> SEQ ID NO 26
<211> LENGTH: 48
<212> TYPE: DNA
<213> ORGANISM: Artificial Sequence
```

```
<220> FEATURE:
<223> OTHER INFORMATION: linker

<400> SEQUENCE: 26
tgtccgtcga gatcctctag agtcgagatc agcaaaatgt tcacgggg         48

<210> SEQ ID NO 27
<211> LENGTH: 18
<212> TYPE: DNA
<213> ORGANISM: Artificial Sequence
<220> FEATURE:
<223> OTHER INFORMATION: linker

<400> SEQUENCE: 27
aagcttggcg taatcatg                                          18

<210> SEQ ID NO 28
<211> LENGTH: 39
<212> TYPE: DNA
<213> ORGANISM: Artificial Sequence
<220> FEATURE:
<223> OTHER INFORMATION: linker

<400> SEQUENCE: 28
ggaattcgag ctcggtacct cgtggcgagc gcaggcggc                   39

<210> SEQ ID NO 29
<211> LENGTH: 51
<212> TYPE: DNA
<213> ORGANISM: Artificial Sequence
<220> FEATURE:
<223> OTHER INFORMATION: linker

<400> SEQUENCE: 29
ggccgagtta ggttttactt ttctagagga tccctcgac gtctggggcg c       51

<210> SEQ ID NO 30
<211> LENGTH: 48
<212> TYPE: DNA
<213> ORGANISM: Artificial Sequence
<220> FEATURE:
<223> OTHER INFORMATION: linker

<400> SEQUENCE: 30
ttgctgcgtt cccggggatc ctctagaatt aggtagtttg tagtgcga         48

<210> SEQ ID NO 31
<211> LENGTH: 42
<212> TYPE: DNA
<213> ORGANISM: Artificial Sequence
<220> FEATURE:
<223> OTHER INFORMATION: linker

<400> SEQUENCE: 31
tcaagatcca ggaaatcctt cggtaccgag ctcgaattcg ta               42

<210> SEQ ID NO 32
<211> LENGTH: 33
<212> TYPE: DNA
<213> ORGANISM: Artificial Sequence
<220> FEATURE:
<223> OTHER INFORMATION: linker

<400> SEQUENCE: 32
gaattcgagc tcggtaccga aagctactca gac                         33
```

<210> SEQ ID NO 33
<211> LENGTH: 42
<212> TYPE: DNA
<213> ORGANISM: Artificial Sequence
<220> FEATURE:
<223> OTHER INFORMATION: linker

<400> SEQUENCE: 33
cgcaaacagc tctcgtaact ctagaagtta acgatcgctg tt        42

<210> SEQ ID NO 34
<211> LENGTH: 57
<212> TYPE: DNA
<213> ORGANISM: Artificial Sequence
<220> FEATURE:
<223> OTHER INFORMATION: linker

<400> SEQUENCE: 34
gaatagcata ccaatgccta ttcattggga ctcgactcta gaggatcccc gggaacg      57

<210> SEQ ID NO 35
<211> LENGTH: 42
<212> TYPE: DNA
<213> ORGANISM: Artificial Sequence
<220> FEATURE:
<223> OTHER INFORMATION: linker

<400> SEQUENCE: 35
tcgaggggat cctctagagt cgagggaccc atggttgcgt gc        42

<210> SEQ ID NO 36
<211> LENGTH: 42
<212> TYPE: DNA
<213> ORGANISM: Artificial Sequence
<220> FEATURE:
<223> OTHER INFORMATION: linker

<400> SEQUENCE: 36
tttactaaag cgcggcgaaa gcttcgtcgt gctgggttct gg        42

<210> SEQ ID NO 37
<211> LENGTH: 21
<212> TYPE: DNA
<213> ORGANISM: Artificial Sequence
<220> FEATURE:
<223> OTHER INFORMATION: linker

<400> SEQUENCE: 37
aagcttggcg taatcatggt c        21

<210> SEQ ID NO 38
<211> LENGTH: 48
<212> TYPE: DNA
<213> ORGANISM: Artificial Sequence
<220> FEATURE:
<223> OTHER INFORMATION: linker

<400> SEQUENCE: 38
ggaattcgag ctcggtaccc ggataatacg tacatgttaa cgcagagg        48

<210> SEQ ID NO 39
<211> LENGTH: 45
<212> TYPE: DNA
<213> ORGANISM: Artificial Sequence
<220> FEATURE:
<223> OTHER INFORMATION: linker

<400> SEQUENCE: 39
atctattgga gcgtttagcg cgcgtcgacg aaaggtcaga gacga					45

<210> SEQ ID NO 40
<211> LENGTH: 27
<212> TYPE: DNA
<213> ORGANISM: Artificial Sequence
<220> FEATURE:
<223> OTHER INFORMATION: linker

<400> SEQUENCE: 40
ctgcttcatt tctgatcccc gggaacg					27

<210> SEQ ID NO 41
<211> LENGTH: 51
<212> TYPE: DNA
<213> ORGANISM: Artificial Sequence
<220> FEATURE:
<223> OTHER INFORMATION: linker

<400> SEQUENCE: 41
accacccccg cgccccagac gtcgagggga tcaattattg cgtattgaat a					51

<210> SEQ ID NO 42
<211> LENGTH: 33
<212> TYPE: DNA
<213> ORGANISM: Artificial Sequence
<220> FEATURE:
<223> OTHER INFORMATION: linker

<400> SEQUENCE: 42
atcagaaact ctttcggtac cgagctcgaa ttc					33

<210> SEQ ID NO 43
<211> LENGTH: 48
<212> TYPE: DNA
<213> ORGANISM: Artificial Sequence
<220> FEATURE:
<223> OTHER INFORMATION: linker

<400> SEQUENCE: 43
gaattcgagc tcggtacccg gataatacgt acatgttaac gcagaggt					48

<210> SEQ ID NO 44
<211> LENGTH: 33
<212> TYPE: DNA
<213> ORGANISM: Artificial Sequence
<220> FEATURE:
<223> OTHER INFORMATION: linker

<400> SEQUENCE: 44
gctgaccgct agtcgactct agaggatccc ctc					33

<210> SEQ ID NO 45
<211> LENGTH: 42
<212> TYPE: DNA
<213> ORGANISM: Artificial Sequence
<220> FEATURE:
<223> OTHER INFORMATION: linker

<400> SEQUENCE: 45
cgttcccggg gatcctctag agtcgacggc agagtcgcag ac					42

<210> SEQ ID NO 46

```
<211> LENGTH: 30
<212> TYPE: DNA
<213> ORGANISM: Artificial Sequence
<220> FEATURE:
<223> OTHER INFORMATION: linker

<400> SEQUENCE: 46
tgatccaaac tcggatcctc tagagtcgac                                         30

<210> SEQ ID NO 47
<211> LENGTH: 48
<212> TYPE: DNA
<213> ORGANISM: Artificial Sequence
<220> FEATURE:
<223> OTHER INFORMATION: linker

<400> SEQUENCE: 47
aagcttgggc tgcaggtcga ctctagagga tcccctcgac gtctgggg                     48

<210> SEQ ID NO 48
<211> LENGTH: 60
<212> TYPE: DNA
<213> ORGANISM: Artificial Sequence
<220> FEATURE:
<223> OTHER INFORMATION: linker

<400> SEQUENCE: 48
cacacctttg cgcatctcca cagctcaaca atgaattcca tgttacgtcc tgtagaaacc        60

<210> SEQ ID NO 49
<211> LENGTH: 60
<212> TYPE: DNA
<213> ORGANISM: Artificial Sequence
<220> FEATURE:
<223> OTHER INFORMATION: linker

<400> SEQUENCE: 49
cagggaggca aacaatgaat caacaactct cccgggagat ggggaggct aactgaaaca         60

<210> SEQ ID NO 50
<211> LENGTH: 45
<212> TYPE: DNA
<213> ORGANISM: Artificial Sequence
<220> FEATURE:
<223> OTHER INFORMATION: linker

<400> SEQUENCE: 50
tgctgcgttc ccggggatcc tctagagtcg acctgcagcc caagc                        45

<210> SEQ ID NO 51
<211> LENGTH: 48
<212> TYPE: DNA
<213> ORGANISM: Artificial Sequence
<220> FEATURE:
<223> OTHER INFORMATION: linker

<400> SEQUENCE: 51
tctagagtcg acctgcagtg aataataaaa tgtgtgtttg tccgaaat                     48

<210> SEQ ID NO 52
<211> LENGTH: 45
<212> TYPE: DNA
<213> ORGANISM: Artificial Sequence
<220> FEATURE:
<223> OTHER INFORMATION: linker

<400> SEQUENCE: 52
```

```
ctccatagaa gacaccggga ccatggatcc cgtcgtttta caacg          45

<210> SEQ ID NO 53
<211> LENGTH: 105
<212> TYPE: DNA
<213> ORGANISM: Artificial Sequence
<220> FEATURE:
<223> OTHER INFORMATION: linker

<400> SEQUENCE: 53
tcggcggaaa tccagctgag cgccggtcgc taccattacc agttggtctg gtgtcaaaaa    60
gatctagaat aagctagagg atcgatcccc tatggcgatc atcag                    105

<210> SEQ ID NO 54
<211> LENGTH: 36
<212> TYPE: DNA
<213> ORGANISM: Artificial Sequence
<220> FEATURE:
<223> OTHER INFORMATION: linker

<400> SEQUENCE: 54
ccgtcgagat cctctagagt cgacctgcag gtcgac                    36

<210> SEQ ID NO 55
<211> LENGTH: 20
<212> TYPE: DNA
<213> ORGANISM: Artificial Sequence
<220> FEATURE:
<223> OTHER INFORMATION: primer

<400> SEQUENCE: 55
cctagcaccc ttgtatcgcg                                      20

<210> SEQ ID NO 56
<211> LENGTH: 29
<212> TYPE: DNA
<213> ORGANISM: Artificial Sequence
<220> FEATURE:
<223> OTHER INFORMATION: primer

<400> SEQUENCE: 56
cgcctcgagt cccaatgaat aggcattgg                            29

<210> SEQ ID NO 57
<211> LENGTH: 27
<212> TYPE: DNA
<213> ORGANISM: Artificial Sequence
<220> FEATURE:
<223> OTHER INFORMATION: primer

<400> SEQUENCE: 57
cgcctcgagg acccatggtt gcgtgcg                              27

<210> SEQ ID NO 58
<211> LENGTH: 20
<212> TYPE: DNA
<213> ORGANISM: Artificial Sequence
<220> FEATURE:
<223> OTHER INFORMATION: primer

<400> SEQUENCE: 58
ctcgtccgaa cgagttacag                                      20

<210> SEQ ID NO 59
```

<211> LENGTH: 18913
<212> TYPE: DNA
<213> ORGANISM: Infectious Laryngotracheitis Virus

<400> SEQUENCE: 59

```
ggatcccgaa gagctctccc agaagttttt cttttcggac gtatcggagg acgaagaacc      60
ggcacgcggg aggagctgga gcgacccgga gtcggaggaa gagcagcctg ggtgccgggg     120
agtggacttg ggcgaggagg acacgggaca cagctccacc gagtcagagc ccacgcaatc     180
tgacttagac tttattgacg acagctctcc ggcgccgccg ccatttgcta tccccgcgt      240
ccgtgcgtta ttgcggtgcg cggcacccgc aaagacccac ggaaggcttc ggccgccagg     300
gcgggtaggc gcactcttaa aagacggagg ttgtcatttt cttcttcctc tgacgaggaa     360
tccgaggaga gaagtaaaaa agaagaagcg gcctcgaccc ctgcacggcg acgcaaggcc     420
gaggcctcga cgagcagata gaggagacgc ggggcagaac ctccccctcc ctcccacccc     480
cctactctgg acatttattg cccgctcgat ccattctcat ccagaacttc tttcccgctc     540
agccttcacg cagaagcgga cgcgcgcccc tttgcgaccg ccggacatcc cgccgccccc     600
cccccttcac gcccggcgca atccgtagcc gtccaactcg gcccagcaca accgcagtag     660
accgcccgga ccgctctcct ctagacacat ccctaaatgg aaaacatgct cgacgggtgc     720
tacccgctgg cgctgatgga cagcgatcac attactgcgc acgcgtacc tcgtggcgag      780
cgcaggcggc aaggtgccgc tgtcgcctcg tcggagtcgg ccgactcggt agaccccgtgc     840
attcggatcg cctcgcggct ctggcgcgag ttagtcgaga tcgtccga actcaaggac        900
ggttacggag agttcacgtc agcgagagac cgccgcaacg cgctgattgc tgccaacgaa     960
cggctacgtt cggcttttct gggggccagc cgggcgacgc gcggcctagg tttgaggccg    1020
cggtgggcgt cgacggagag cgtcgccaac tcccccactg acccgaataa cggcaacggg    1080
ttgggagaat tagaggaggc aatgaagggg atcgagggcg atttctggct cgactctctg    1140
gacggtgacc gcttcgagga cgagagccgt accatgcaga gcgagaatat gcgtttcgtg    1200
atcgagaaag aactgttatc ctggctgtcc cgacacctgc cggccgacct cgcgtccgcc    1260
gagcgagaga cctcccggtc tctcctggcg gccgggcact ggtgctgctt gtggcaccct    1320
cggccgtgcc gcgaagcgtg tttgtacgac tcgatttacg tgcagagtct tttctgcgtc    1380
gggacgggga gagtcccgca atcggagatg cgccgtcgcg aatacctggc cgccttgcgc    1440
gccggcgcgg ctgccgccaa ctctcccgaa gtgagcgcct cgatctttgc gagggacgct    1500
ggaatcgcgc tggcgctggc gcggcgccgt tgacgggaga atgacgccct ctagcggctt    1560
ccttacctcc gcgtccctga caacctcgcg ggttttaca ctgtcctccg tccactctcc      1620
cccctcaccc actccgcggc agcgaaacac aaccccccc cccccccaga aacgagcgac      1680
acgcgagcgc tgcgaaataa ataaagtaat attattgtgt gtttttcacg ttgttgcaat    1740
cgagaggccg tttgtctgtc tgtgtctgtg cggagctagg cttttccggg cggccccgtt    1800
ccaccgttcg gttaggccgg tggcgacggg acatagagaa agatagagcg cgcgccctgg    1860
cggcgagagg gtgttgcggg ggtaaatggg accctgagct caccattttg gcgggggatt    1920
gcacgggtaa caaaaagctc tctcgcacat aatgatttcc cttaaacagt ggctgtaaaa    1980
gctttcttcg actgggacgc gcacgtccgg agacatgatc ttatcggtag ctacacagtt    2040
catgaggtgg gccacgaacg cgcggatcga gttttgggaa ccttcgggga ggtcttccgg    2100
gagggtgaag tttgacagag gcagcgctat caccaggagg ctccgcacca tctccatgcc    2160
tatccttatc gccgcgagtc cggcggccgg cgcgctgctc tggttattcc agtgcgcgga    2220
```

```
ccgcgagtgc gccctcccc gggctctgat atagagcacc ggcagctcga cggcggcgga    2280
gaaaaaagaa agaatgtccg gcccaatgac tggaactttg ggcacgtctc ttatttccca    2340
cgcggcggcc cggggaatct gcttgcccca gaccttgctt tccaactccc cgttcggccc    2400
cccaactaac tccgacagcg cggtccacag tcctaccgcc gctgcgacgg cgcgcttagc    2460
cgcgggcgct attcgcgggt cgtgcgccgt gatatcttcg gcgacctgca gactgcccag    2520
cctttccttc ccttcaaaat acgcgcgggc ggcctgtacg atcaccgcgg ccagatcggg    2580
ccaaaagaaa atatcgcaac tctgcgacgc ccgccagaat ctccctccgg gcaggtccgt    2640
gcccctaaag gccgccgaga aagctaagtc caaatgtgac gtcggaggtc tcgacatggt    2700
cgccaaccct ccaaatgcta cccgccggcc cacgcaacgc gggcttttat aaagatggcg    2760
cgcgagacaa taacacttac tcatccgcgt acgcgtttat tattgtcaat atttgtgtgg    2820
ttattattac tgctaccgcc cttgtttctg caaggccctc gccgcggccc aggccactat    2880
tccggcagcg gccgccgacg cggcgagcgt cgccgctaac gtcggcgccg cggggagcgg    2940
ggtttcttcg acttaaatag actcccgaga aaaaattttg gctgccgttc gccatcatcc    3000
gagtcggaaa cacagtatgc ggccgagtta ggttttactt ttaaaaactt taccgtgctg    3060
tacggccagg gcgttctcag gctcgaaggg gcaagagttg tccagactga tgggtgactc    3120
agagacagcg ttgtcttgtc tccgtttacc aaaaatattt ccactcctct ctcaaaattt    3180
ttacctccgg tttcggtaat taggaaagtt tttggcgcag ggaggtttaa agctgccatg    3240
catatgtcag cggtacccag cacccacaaa tggaactctt tgcggcata cgcgccagat    3300 gacaaatggt aaaaccctgc gtccaagccg ctccactcgg gacttactcc aggcgggtcg    3360 ccccctcac cgaaccgaat cacgggtctg cacatcctgg gaagggaaaa cagctccccg    3420
gaaacttcgt acagagatgc cgggcgcacg attaccgata atgtactcgg acgatcgtaa    3480
ctcgccatag ttttcactgc gtgaaccaat tctttccatc cagaatccga gagctcaaat    3540
ctagaattag gtagtttgta gtgcgaatcg accgcagaaa ctatagtcac ttttacaggc    3600
gccatcgccg ctcagactcc accccgctat gatgtcagaa atataacgct cttattctag    3660
cagagtcagg ccaatatata cagcttagag aagatgcggt ttcggcgcat ctgttcacgc    3720
tctagggcag aaaaacgaag aagaacaacc gagaatccgc ttacctcaaa acgcgtttgc    3780
gtattggata gtttctcacg gacaatgtca ttgcgcccct atgcagaaat tttgccgacc    3840
gcggaaggcg tcgagcgcct cgccgaactt gttagtgtga caatgacaga acgcgcggaa    3900
cctgtgacag agaatacagc tgtaaacagt atcccccccgg ctaacgagaa cgggcagaac    3960
ttcgcatatg caggcgatgg gccctcgact actgaaaaag ttgacggctc gcatacagac    4020
ttcgatgaag catcgagcga ctacgccggc cctgtcccgc tcgcgcaaac tagattgaag    4080
cattcggatg aatttcttca gcacttccga gttttagacg atttggtgga ggggcttac    4140 gggtttatct gcgacgtccg tcgctacacc gaggaagagc aacgtcgaag agggggttaac    4200 agtactaacc aggggaaatc aaaatgtaag cgcctgatag ctaaatatgt gaaaaatgga    4260
acaagggcgg cctctcagct ggaaaatgaa attttggttc tcgggcgcct aaatcacgag    4320
aatgttctca agatccagga aatccttcgg taccccggata atacgtacat gttaacgcag    4380
aggtatcagt tcgacttgta cagctacatg tacgatgaag cgttcgactg gaaagacagt    4440
ccaatgctta aacagactag acgcatcatg aagcagctca tgtcagcggt ctcgtatatc    4500
cattcaaaga aactgattca cagggacatc aaactcgaaa atattttctt aaactgcgac    4560
```

```
ggcaagacag tgctgggcga ctttggaact gtcacgcctt ttgaaaatga gcgggagccc    4620
ttcgaatatg gatgggtggg gaccgtggct actaactctc ccgagatact cgccagggat    4680
tcgtactgtg aaattacaga catttggagc tgcggagtag tattgctgga aatggtaagc    4740
catgaatttt gcccgatcgg cgatggcggg ggaaatccgc accagcaatt gctgaaagtt    4800
atcgactctc tctcagtttg tgatgaagag ttcccagacc ccccgtgtaa tctgtacaat    4860
tatttgcatt atgcgagcat cgatcgcgcc ggacatacgg tcccgtcgct catacggaac    4920
ctccaccttc cggcggatgt ggaatacccct ctagttaaaa tgcttacttt tgactggcgt    4980
ttgagaccca cgcggccga agtattggca atgccactgt tttcggctga agaggaacgg    5040
accataacaa ttattcatgg aaaacataaa cccatccgac ccgaaatccg tgcgcgggtg    5100
ccacggtcca tgagtgaagg ttaataataa aggacggaga tagagaactg aagcgtcaga    5160 ttttttttaaa aaaataaatg atcgagaact tatgatttgt ctttcttgaa tgaccttgcc    5220
ccatcgatta acgaaaagac ctttcgcgcg tcgattctgc tcggtctttg tgatacatta    5280
tagtgagact aaactcgacc gatataacaa gacaatgtta ctctatagac cggactcaac    5340
catgcggcat agcggaggcg acgcaaatca cagagggata aggccgaggc ggaaatctat    5400
tggagcgttt agcgcgcgcg aaaagactgg aaaacgaaat gcgctgacgg aaagcagctc    5460
ctcctccgac atgctagatc cgttttccac ggataaggaa tttggcggta agtggacggt    5520
agacggacct gccgacatta ctgccgaggt cctttctcag gcatgggacg ttctccaatt    5580
agtgaagcat gaagatgcgg aggaggagag agtgacttat gagtccaaac cgaccccgat    5640
acagccgttc aatgcctggc cggacgggcc gagttggaac gcgcaggatt ttactcgagc    5700
gccaatagtt tatccctctg cggaggtatt ggacgcagag gcgttgaaag taggggcatt    5760
cgttagccga gttttacaat gtgtaccgtt cacgcgatca agaaaagcg ttacggtgcg    5820 ggatgcgcag tcgttttttgg gggactcgtt ctggagaata atgcagaacg tttacacggt    5880
tgtcttacga cagcacataa ctcgactcag gcacccttcc agcaaaagca ttgttaactg    5940 caacgacccct ctatggtacg cctacgcgaa tcaatttcac tggagaggaa tgcgcgtgcc    6000
gtcgcttaaa ttagcctctc ccccggagga gaatattcaa cacggcccaa tggccgccgt    6060
ttttagaaac gcggggggctg gtctgttcct gtggcctgcc atgcgcgcag cctttgaaga    6120
gcgcgacaag cgactgttaa gagcatgcct gtcttcactc gatatcatgg acgcagccgt    6180
cctcgcgtcg tttccatttt actgcgcgcg cgtccaagac acctcgcgct tcgagcctgc    6240
gctgggctgt ttgtcagagt actttgcact agtggtgtta ctggccgaga cggtcttagc    6300
gaccatgttc gaccacgcac tggtattcat gagggcgctg gcagacggca atttcgatga    6360
ctatgacgaa actagatata tagaccccgt taaaaacgag tacctgaacg gagccgaggg    6420
tactctgtta cggggcatag tggcctccaa caccgctctg gcggtggttt gcgcaaacac    6480
ctattcgacg ataagaaaac tcccgtccgt ggcaactagc gcgtgcaatg ttgcctacag    6540
gaccgaaacg ctgaaagcga ggcgccctgg catgagcgac atataccgga tattacaaaa    6600
agagtttttc ttttacattg cgtggctcca gagggttgca acacacgcaa atttctgttt    6660
aaacattctg aagagaagcg tggatacggg ggccccgcca ttttttgttca gggccagctc    6720 ggagaagcgg ctgcagcagt taaataaaat gctctgcccc cttctcgtgc cgattcaata    6780
tgaagacttt tcgaaggcca tggggtctga gctcaagagg gaaaagttag agacattcgt    6840
taaagctatt tccagcgaca gggacccgag ggggtcctta agatttctca tttcggacca    6900
tgcaagggaa attattgcag acggagtacg gtttaagccg gtgatagacg agccggttcg    6960
```

```
ggcttcagtt cgctgagta ccgctgccgc tgggaaagtg aaagcgcgac gcttaacctc   7020
agttcgcgcg cccgtaccgg gcgcaggcgc cgtttccgcg cgccggaaat cggaaatatg   7080
ataaaaatgc ttggcatttg cgggcgaaga ggcgtgatct gaagggctcc acaatgacgt   7140
aactgagcta cgcatcccta taaagtgtac ccgctgaccg ctagcccata cagtgttaca   7200
ggagggagag agacaacttc agctcgaagt ctgaagagac atcatgagcg gcttcagta   7260 acataggatc gattgccacc gtttccctag tatgctcgct tttgtgcgca tctgtattag   7320
gggcgccggt actggacggg ctcgagtcga gccctttccc gttcggggc aaaattatag   7380 cccaggcgtg caaccgcacc acgattgagg tgacggtccc gtggagcgac tactctggtc   7440
gcaccgaagg agtgtcagtc gaggtgaaat ggttctacgg aatagtaat cccgaaagct   7500 tcgtgttcgg ggtggatagc gaaacgggca gtggacacga ggacctgtct acgtgctggg   7560
ctctaatcca taatctgaac gcgtctgtgt gcagggcgtc tgacgccggg atacctgatt   7620
tcgacaagca gtgcgaaaaa gtgcagagaa gactgcgctc cggggtggaa cttggtagtt   7680
acgtgtctgg caatggatcc ctggtgctgt acccagggat gtacgatgcc ggcatctacg   7740
cctaccagct ctcagtgggt gggaagggat ataccgggtc tgtttatcta gacgtcggac   7800
caaaccccgg atgccacgac cagtatgggt acacctatta cagcctggcc gacgaggcgt   7860
cagacttatc atcttatgac gtagcctcgc ccgaactcga cggtcctatg gaggaagatt   7920
attccaattg tctagacatg cccccgctac gcccatggac aaccgtttgt tcgcatgacg   7980
tcgaggagca ggaaaacgcc acggacgagc tttacctatg ggacgaggaa tgcgccggtc   8040
cgctggacga gtacgtcgac gaaaggtcag agacgatgcc caggatggtt gtcttttcac   8100
cgccctctac gctccagcag tagccacccg agagtgtttt tgtgagcgc ccacgcaaca   8160 tacctaactg cttcatttct gatcaattat tgcgtattga ataaataaac agtacaaaag   8220
catcaggtgt ggtttgcgtg tctgtgctaa accatggcgt gtgcgggtga aaccgtaaat   8280
tacgtgataa taaatagcat aggagttggc gtgcagcgta tttcgccgag agatggggac   8340
aatgttagtg ttgcgccttt tcctacttgc agtagcggac gcggcgttgc cgaccggcag   8400
attctgccga gtttggaagg tgcctccggg aggaaccatc caagagaacc tggcggtgct   8460
cgcggaatcg ccgtcacgg acacgcgac atatccgccg cctgaaggcg ccgtcagctt   8520
tcagattttt gcggacaccc ctactttgcg cattcgctac ggcgctacgg aggacgaact   8580
tgcactggag cgcgggacgt ccgcctcaga cgcggacaac gtgacatttt cgctgtcata   8640
tcgcccgcgc ccagaaattc acggagcata cttcaccata ggggtattcg ctactggcca   8700
gagcacggaa agcagctatt cggtcatcag tcgggtctta gttaacgcct ctctggaacg   8760
gtccgtgcgc ctggaaacgc cgtgcgatga aattttttg cagaacgagc ctacatgggg   8820
ctcgaagcgt tggttaggcc ccccgtcgcc ttatgtgcga gataacgatg tcgccgtgtt   8880
gacaaaagcg cagtacattg gggagtgcta ctccaactcg gcggcccaga cggggctcac   8940
gtctctcaac atgaccttt tctattcgcc taaaagaata gtaaacgtca cgtggacaac   9000
cggcggcccc tcccctcgc gcataacggt atactcgtcg cgggagaacg ggcagcccgt   9060
gttgaggaac gttctgacg ggttcttggt taagtacact cccgacattg acggccgggc   9120
catgataaac gttattgcca attattcgcc ggcggactcc ggcagcgtcc tcgcgtttac   9180
ggcctttagg gaaggaaaac tcccatccgc gattcaactg caccggatag atatgtccgg   9240
gactgagccg ccggggactg aaacgacctt cgactgtcaa aaaatgatag aaaccccgta   9300
```

```
ccgagcgctc gggagcaatg ttcccaggga cgactctatc cgtccggggg ccactctgcc   9360
tccgttcgat accgcagcac ctgatttcga tacaggtact tccccgaccc ccactaccgt   9420
gccagagcca gccattacta cactcatacc gcgcagcact agcgatatgg gattcttctc   9480
cacggcacgt gctaccggat cagaaactct ttcggtaccc gtccaggaaa cggatagaac   9540
tctttcgaca actcctctta cccttccact gactcccggt gagtcagaaa atacactgtt   9600
tcctacgacc gcgccgggga tttctaccga gaccccgagc gcggcacatg aaactacaca   9660
gacccagagt gcagaaacgg tggtctttac tcagagtccg agtaccgagt cggaaaccgc   9720
gcggtcccag agtcaggaac cgtggtattt tactcagact ccgagtactg aacaggcggc   9780
tcttactcag acgcagatcg cagaaacgga ggcgttgttt actcagactc cgagtgctga   9840
acagatgact tttactcaga ctccgggtgc agaaaccgag gcacctgccc agaccccgag   9900
cacgataccc gagatattta ctcagtctcg tagcacgccc cccgaaaccg ctcgcgctcc   9960
gagcgcggcg ccggaggttt ttacacagag ttcgagtacg gtaacggagg tgtttactca  10020
gaccccgagc acggtaccga aaactactct gagttcgagt actgaaccgg cgattttttac 10080
tcggactcag agcgcgggaa ctgaggcctt tactcagact tcgagtgccg agccggacac  10140
tatgcgaact cagagtactg aaacacactt tttcactcag gccccgagta cggtaccgaa  10200
agctactcag actccgagta cagagccgga ggtgttgact cagagtccga gtaccgaacc  10260
tgtgcctttc acccggactc tgggcgcaga gccggaaatt actcagaccc cgagcgcggc  10320
accggaggtt tatactcgga gttcgagtac gatgccagaa actgcacaga gcacacccct  10380
ggcctcgcaa acccctacca gttcgggaac cgggacgcat aatactgaac cgaggactta  10440
tccagtgcaa acgacaccac atacccagaa actctacaca gaaaataaga ctttatcgtt  10500
tcctactgtt gtttcagaat tccatgagat gtcgacggca gagtcgcaga cgcccctatt  10560
ggacgtcaaa attgtagagg tgaagttttc aaacgatggc gaagtaacgg cgacttgcgt  10620
ttccaccgtc aaatctccct atagggtaga aactaattgg aaagtagacc tcgtagatgt  10680
aatggatgaa atttctggga acagtcccgc cgggggtttt aacagtaatg agaaatggca  10740
gaaacagctg tactacagag taaccgatgg aagaacatcg gtccagctaa tgtgcctgtc  10800
gtgcacgagc cattctccgg aaccttactg tcttttcgac acgtctctta tagcgaggga  10860
aaaagatatc gcgccagagt tatactttac ctctgatccg caaacggcat actgcacaat  10920
aactctgccg tccggcgttg ttccgagatt cgaatggagc cttaataatg tttcactgcc  10980
ggaatatttg acgccacga ccgttgtttc gcataccgct ggccaaagta cagtgtggaa  11040
gagcagcgcg agagcaggcg aggcgtggat ttctggccgg ggaggcaata tatacgaatg  11100
caccgtcctc atctcagacg gcactcgcgt tactacgcga aaggagaggt gcttaacaaa  11160
cacatggatt gcggtggaaa acggtgctgc tcaggcgcag ctgtattcac tcttttctgg  11220
acttgtgtca ggattatgcg ggagcatatc tgctttgtac gcaacgctat ggaccgccat  11280
ttatttttga ggaatgcttt ttggactatc gtactgcttt cttccttcgc tagccagagc  11340
accgccgccg tcacgtacga ctacattta ggccgtcgcg cgctcgacgc gctaaccata  11400
ccggcggttg gcccgtataa cagatacctc actagggtat caagaggctg cgacgttgtc  11460
gagctcaacc cgatttctaa cgtggacgac atgatatcgg cggccaaaga aaagagaag   11520
ggggccctt tcgaggcctc cgtcgtctgg ttctacgtga ttaagggcga cgacgcgag   11580
gacaagtact gtccaatcta tagaaaagag tacagggaat gtggcgacgt acaactgcta  11640
tctgaatgcg ccgttcaatc tgcacagatg tgggcagtgg actatgttcc tagcaccctt  11700
```

```
gtatcgcgaa atggcgcggg actgactata ttctccccca ctgctgcgct ctctggccaa    11760
tacttgctga ccctgaaaat cgggagattt gcgcaaacag ctctcgtaac tctagaagtt    11820
aacgatcgct gtttaaagat cgggtcgcag cttaactttt taccgtcgaa atgctggaca    11880
acagaacagt atcagactgg atttcaaggc gaacaccttt atccgatcgc agacaccaat    11940
acacgacacg cggacgacgt atatcgggga tacgaagata ttctgcagcg ctggaataat    12000
ttgctgagga aaagaatcc tagcgcgcca gaccctcgtc cagatagcgt cccgcaagaa    12060
attcccgctg taaccaagaa agcggaaggg cgcaccccgg acgcagaaag cagcgaaaag    12120
aaggcccctc cagaagactc ggaggacgac atgcaggcag aggcttctgg agaaaatcct    12180
gccgccctcc ccgaagacga cgaagtcccc gaggacaccg agcacgatga tccaaactcg    12240
gatcctgact attacaatga catgcccgcc gtgatcccgg tggaggagac tactaaaagt    12300
tctaatgccg tctccatgcc catattcgcg gcgttcgtag cctgcgcggt cgcgctcgtg    12360
gggctactgg tttggagcat cgtaaaatgc gcgcgtagct aatcgagcct agaataggtg    12420
gtttcttcct acatgccacg cctcacgctc ataaatataa atcacatgga atagcatacc    12480 aatgccatt cattgggacg ttcgaaaagc atggcatcgc tacttggaac tctggctctc    12540
cttgccgcga cgctcgcacc cttcggcgcg atgggaatcg tgatcactgg aaatcacgtc    12600
tccgccagga ttgacgacga tcacatcgtg atcgtcgcgc ctcgccccga agctacaatt    12660
caactgcagc tatttttcat gcctggccag agaccccaca aaccctactc aggaaccgtc    12720
cgcgtcgcgt ttcggtctga tataacaaac cagtgctacc aggaacttag cgaggagcgc    12780
tttgaaaatt gcactcatcg atcgtcttct gtttttgtcg gctgtaaagt gaccgagtac    12840
acgttctccg cctcgaacag actaaccgga cctccacacc cgtttaagct cactatacga    12900
aatcctcgtc cgaacgacag cgggatgttc tacgtaattg ttcggctaga cgacaccaaa    12960
gaacccattg acgtcttcgc gatccaacta tcggtgtatc aattcgcgaa caccgccgcg    13020
actcgcggac tctattccaa ggcttcgtgt cgcaccttcg gattacctac cgtccaactt    13080
gaggcctatc tcaggaccga ggaaagttgg cgcaactggc aagcgtacgt tgccacggag    13140
gccacgacga ccagcgccga ggcgacaacc ccgacgcccg tcactgcaac cagcgcctcc    13200
gaacttgaag cggaacactt tacctttccc tggctagaaa atggcgtgga tcattacgaa    13260
ccgacacccg caaacgaaaa ttcaaacgtt actgtccgtc tcgggacaat gagccctacg    13320
ctaattgggg taaccgtggc tgccgtcgtg agccgaacga tcggcctcgt cattgtaatt    13380
tccatcgtca ccagaaacat gtgcaccccg caccgaaaat tagacacggt ctcgcaagac    13440
gacgaagaac gttcccaaac tagaagggaa tcgcgaaaat ttggacccat ggttgcgtgc    13500
gaaataaaca agggggctga ccaggatagt gaacttgtgg aactggttgc gattgttaac    13560
ccgtctcgcg taagctcgcc cgactcaata aaaatgtgat taagtctgaa tgtggctctc    13620
caatcatttc gattctctaa tctcccaatc ctctcaaaag gggcagtatc ggacacggac    13680
tgggaggggc gtacacgata gttatatggt acagcagagg cctctgaaca cttaggagga    13740
gaattcagcc ggggagagcc cctgttgagt aggcttggga gcatattgca ggatgaacat    13800
gttagtgata gttctcgcct cttgtcttgc gcgcctaact tttgcgacgc gacacgtcct    13860
ctttttggaa ggcactcagg ctgtcctcgg ggaagatgat cccagaaacg ttccggaagg    13920
gactgtaatc aaatggacaa aagtcctgcg gaacgcgtgc aagatgaagg cggccgatgt    13980
ctgctcttcg cctaactatt gctttcatga tttaatttac gacggaggaa agaaagactg    14040
```

```
cccgcccgcg ggacccctgt ctgcaaacct ggtaatttta ctaaagcgcg gcgaaagctt    14100
cgtcgtgctg ggttctgggc tacacaacag caatataact aatatcatgt ggacagagta    14160
cggaggcctg ctctttgatc ctgtaactcg ttcggacgag ggaatctatt ttcgacggat    14220
ctctcagcca gatctggcca tggaaactac atcgtacaac gtcagcgttc tttcgcacgt    14280
agacgagaag gctccagcac cgcacgaggt ggagatagac accatcaagc cgtcagaggc    14340
ccacgcgcac gtggaattac aaatgctgcc gtttcatgaa ctcaacgaca acagccccac    14400
ctatgtgacc cctgttctta gagtcttccc accgaccgag cacgtaaaat ttaacgttac    14460
gtattcgtgg tatgggtttg atgtcaaaga ggagtgcgaa gaagtgaaac tgttcgagcc    14520
gtgcgtatac catcctacag acggcaaatg tcagtttccc gcaaccaacc agagatgcct    14580
cataggatct gtcttgatgg cggaattctt gggcgcggcc tctttgctgg attgttcccg    14640
cgatactcta gaagactgcc acgaaaatcg cgtgccgaac ctacggttcg attcgcgact    14700
ctccgagtca cgcgcaggcc tggtgatcag tcctcttata gccatcccca aagttttgat    14760
tatagtcgtt tccgacggag acatttuggg atggagctac acggtgctcg ggaaacgtaa    14820
cagtccgcgc gtagtagtcg aaacgcacat gccctcgaag gtcccgatga acaaagtagt    14880
aattggcagt cccggaccaa tggacgaaac gggtaactat aaaatgtact tcgtcgtcgc    14940
gggggtggcc gcgacgtgcg taattcttac atgcgctctg cttgtgggga aaagaagtg    15000 ccccgcgcac caaatgggta cttttttccaa gaccgaacca ttgtacgcgc cgctccccaa    15060
aaacgagttt gaggccggcg ggcttacgga cgatgaggaa gtgatttatg acgaagtata    15120 cgaacccta tttcgcggct actgtaagca ggaattccgc gaagatgtga ataccttttt    15180
cggtgcggtc gtggagggag aaagggcctt aaactttaaa tccgccatcg catcaatggc    15240
agatcgcatc ctggcaaata aaagcggcag aaggaatatg gatagctatt agttggtcat    15300 gcctttaag accagagggg ccgaagacgc ggccgcgggc aagaacaggt ttaagaaatc    15360
gagaaatcgg gaaatcttac cgaccagact gcgtggcacc ggtaagaaaa ctgccggatt    15420
gtccaattat acccagccta ttccctggaa ccctaaattc tgcagcgcgc gcggggaatc    15480
tgacaaccac gcgtgtaaag acacttttta tcgcaggacg tgctgcgcat cgcgctctac    15540
cgtttccagt caacccgatt ccccccacac acccatgcct actgagtatg ggcgcgtgcc    15600
ctccgcaaag cgcaaaaaac tatcatcttc agactgcgag ggcgcgcacc aaccccctagt    15660 atcctgtaaa cttccggatt ctcaagcagc accggcgcga acctatagtt ctgcgcaaag    15720
atatactgtt gacgaggttt cgtcgccaac tccgccaggc gtcgacgctg ttgcggactt    15780
agaaacgcgc gcggaacttc ctggcgctac gacggaacaa acggaaagta aaaataagct    15840
ccccaaccaa caatcgcgcc tgaagccgaa acccacaaac gagcacgtcg gagggagcg    15900 gtgcccctcc gaaggcacgg tcgaggcgcc atcgctcggc atcctctcgc gcgtcggggc    15960
agcgatagca aacgagctgg ctcgtatgcg gagggcgtgt cttccgctcg ccgcgtcggc    16020
ggccgctgcc ggaatagtgg cctgggccgc ggcgagggcc ttgcagaaac aagggcggta    16080
gcagtaataa taaccacaca aatattgaca ataataaacg cgtacgcgga tgagtaagtg    16140
ttattgtctc gcgcgccatc tttataaaag cccgcgttgc gtgggccggc gggtagcatt    16200
tggagggttg gcgaccatgt cgagacctcc gacgtcacat ttggacttag ctttctcggc    16260
ggcctttagg ggcacggacc tgcccggagg gagattctgg cgggcgtcgc agagttgcga    16320
tatttctttt tggcccgatc tggccgcggt gatcgtacag gccgcccgcg cgtatttga    16380 agggaaggaa aggctgggca gtctgcaggt cgccgaagat atcacggcgc acgacccgcg    16440
```

```
aatagcgccc gcggctaagc gcgccgtcgc agcggcggta ggactgtgga ccgcgctgtc    16500
ggagttagtt gggggggccga acggggagtt ggaaagcaag gtctggggca agcagattcc    16560
ccgggccgcc gcgtgggaaa taagagacgt gcccaaagtt ccagtcattg ggccggacat    16620
tctttctttt ttctccgccg ccgtcgagct gccggtgctc tatatcagag cccggggagg    16680
ggcgcactcg cggtccgcgc actggaataa ccagagcagc gcgccggccg ccggactcgc    16740
ggcgataagg ataggcatgg agatggtgcg gagcctcctg gtgatagcgc tgcctctgtc    16800
aaacttcacc ctcccggaag acctccccga aggttcccaa aactcgatcc gcgcgttcgt    16860
ggcccacctc atgaactgtg tagctaccga taagatcatg tctccggacg tgcgcgtccc    16920
agtcgaagaa agcttttaca gccactgttt aagggaaatc attatgtgcg agagagcttt    16980
ttgttacccg tgcaatcccc cgccaaaatg gtgagctcag ggtcccattt accccgcaa     17040 caccctctcg ccgccagggc gcgcgctcta tctttctcta tgtcccgtcg ccaccggcct    17100
aaccgaacgg tggaacgggg ccgccgggga agcctagct ccgcacagac acagacagac     17160
aaacggcctc tcgattgcaa caacgtgaaa aacacacaat aatattactt tatttatttc    17220
gcagcgctcg cgtgtcgctc gtttctgggg ggggggggg gttgtgtttc gctgccgcgg     17280
agtgggtgag gggggagagt ggacggagga cagtgtaaaa acccgcgagg ttgtcaggga    17340
cgcggaggta aggaagccgc tagagggcgt cattctcccg tcaacggcgc cgcgccagcg    17400
ccagcgcgat tccagcgtcc ctcgcaaaga tcgaggcgct cacttcggga gagttggcgg    17460
cagccgcgcc ggcgcgcaag gcggccaggt attcgcgacg gcgcatctcc gattgcggga    17520
ctctccccgt cccgacgcag aaaagactct gcacgtaaat cgagtcgtac aaacacgctt    17580
cgcggcacgg ccgagggtgc cacaagcagc accagtgccc ggccgccagg agagaccggg    17640
aggtctctcg ctcggcggac gcgaggtcgg ccggcaggtg tcgggacagc caggataaca    17700
gttctttctc gatcacgaaa cgcatattct cgctctgcat ggtacggctc tcgtcctcga    17760
agcggtcacc gtccagagag tcgagccaga aatcgccctc gatcccttcc attgcctcct    17820
ctaattctcc caaccgttg ccgttattcg ggtcagtggg ggagttggcg acgctctccg     17880
tcgacgccca ccgcggcctc aaacctaggc gcgcgtcgc ccggctggcc cccagaaaag     17940
ccgaacgtag ccgttcgttg gcagcaatca gcgcgttgcg gcggtctctc gctgacgtga    18000
actctccgta accgtccttg agttcggacg atatctcgac taactcgcgc cagagccgcg    18060
aggcgatccg aatgcacggg tctaccgagt cggccgactc cgacgaggcg acagcggcac    18120
cttgccgcct gcgctcgcca cgaggtaccg cgtgcgcagt aatgtgatcg ctgtccatca    18180
gcgccagcgg gtagcacccg tcgagcatgt tttccattta gggatgtgtc tagaggagag    18240
cggtccgggc ggtctactgc ggttgtgctg ggccgagttg gacggctacg gattgcgccg    18300
ggcgtgaagg ggggggggcg gcgggatgtc cggcggtcgc aaaggggcgc gcgtccgctt    18360
ctgcgtgaag gctgagcggg aaagaagttc tggatgagaa tggatcgagc gggcaataaa    18420
tgtccagagt agggggtgg gagggagggg gaggttctgc cccgcgtctc ctctatctgc     18480
tcgtcgaggc ctcggccttg cgtcgccgtg cagggtcga ggccgcttct tcttttttac     18540
ttctctcctc ggattcctcg tcagaggaag aagaaaatga caacctccgt cttttaagag    18600
tgcgcctacc cgccctggcg gccgaagcct tccgtgggtc tttgcgggtg ccgcgcaccg    18660
caataacgca cggacgcggg ggatagcaaa tggcggcggc gccggagagc tgtcgtcaat    18720
aaagtctaag tcagattgcg tgggctctga ctcggtggag ctgtgtcccg tgtcctcctc    18780
```

```
gcccaagtcc actccccggc acccaggctg ctcttcctcc gactccgggt cgctccagct    18840
cctcccgcgt gccggttctt cgtcctccga tacgtccgaa aagaaaaact tctgggagag    18900
ctcttcggga tcc                                                       18913
```

<210> SEQ ID NO 60
<211> LENGTH: 278
<212> TYPE: PRT
<213> ORGANISM: Infectious Laryngotracheitis Virus

<400> SEQUENCE: 60

```
Met Glu Asn Met Leu Asp Gly Cys Tyr Pro Leu Ala Leu Met Asp Ser
  1               5                  10                  15

Asp His Ile Thr Ala His Ala Val Pro Arg Gly Glu Arg Arg Arg Gln
             20                  25                  30

Gly Ala Val Ala Ser Ser Glu Ser Ala Asp Ser Val Asp Pro Cys
         35                  40                  45

Ile Arg Ile Ala Ser Arg Leu Trp Arg Glu Leu Val Glu Ile Ser Ser
     50                  55                  60

Glu Leu Lys Asp Gly Tyr Gly Glu Phe Thr Ser Ala Arg Asp Arg Arg
 65                  70                  75                  80

Asn Ala Leu Ile Ala Ala Asn Glu Arg Leu Arg Ser Ala Phe Leu Gly
                 85                  90                  95

Ala Ser Arg Ala Thr Arg Gly Leu Gly Leu Arg Pro Arg Trp Ala Ser
            100                 105                 110

Thr Glu Ser Val Ala Asn Ser Pro Thr Asp Pro Asn Asn Gly Asn Gly
        115                 120                 125

Leu Gly Glu Leu Glu Glu Ala Met Glu Gly Ile Glu Gly Asp Phe Trp
    130                 135                 140

Leu Asp Ser Leu Asp Gly Asp Arg Phe Glu Asp Glu Ser Arg Thr Met
145                 150                 155                 160

Gln Ser Glu Asn Met Arg Phe Val Ile Glu Lys Glu Leu Leu Ser Trp
                165                 170                 175

Leu Ser Arg His Leu Pro Ala Asp Leu Ala Ser Ala Glu Arg Glu Thr
            180                 185                 190

Ser Arg Ser Leu Leu Ala Ala Gly His Trp Cys Cys Leu Trp His Pro
        195                 200                 205

Arg Pro Cys Arg Glu Ala Cys Leu Tyr Asp Ser Ile Tyr Val Gln Ser
    210                 215                 220

Leu Phe Cys Val Gly Thr Gly Arg Val Pro Gln Ser Glu Met Arg Arg
225                 230                 235                 240

Arg Glu Tyr Leu Ala Ala Leu Arg Ala Gly Ala Ala Ala Asn Ser
                245                 250                 255

Pro Glu Val Ser Ala Ser Ile Phe Ala Arg Asp Ala Gly Ile Ala Leu
            260                 265                 270

Ala Leu Ala Arg Arg Arg
        275
```

<210> SEQ ID NO 61
<211> LENGTH: 294
<212> TYPE: PRT
<213> ORGANISM: Infectious Laryngotracheitis Virus

<400> SEQUENCE: 61

```
Met Ser Lys Cys Tyr Cys Leu Ala Arg His Leu Tyr Lys Ser Pro Arg
  1               5                  10                  15
```

-continued

```
Cys Val Gly Arg Arg Val Ala Phe Gly Gly Leu Ala Thr Met Ser Arg
            20                  25                  30

Pro Pro Thr Ser His Leu Asp Leu Ala Phe Ser Ala Ala Phe Arg Gly
        35                  40                  45

Thr Asp Leu Pro Gly Gly Arg Phe Trp Arg Ala Ser Gln Ser Cys Asp
    50                  55                  60

Ile Phe Phe Trp Pro Asp Leu Ala Ala Val Ile Val Gln Ala Ala Arg
65                  70                  75                  80

Ala Tyr Phe Glu Gly Lys Glu Arg Leu Gly Ser Leu Gln Val Ala Glu
                85                  90                  95

Asp Ile Thr Ala His Asp Pro Arg Ile Ala Pro Ala Ala Lys Arg Ala
            100                 105                 110

Val Ala Ala Ala Val Gly Leu Trp Thr Ala Leu Ser Glu Leu Val Gly
        115                 120                 125

Gly Pro Asn Gly Glu Leu Glu Ser Lys Val Trp Gly Lys Gln Ile Pro
    130                 135                 140

Arg Ala Ala Ala Trp Glu Ile Arg Asp Val Pro Lys Val Pro Val Ile
145                 150                 155                 160

Gly Pro Asp Ile Leu Ser Phe Phe Ser Ala Ala Val Glu Leu Pro Val
                165                 170                 175

Leu Tyr Ile Arg Ala Arg Gly Gly Ala His Ser Arg Ser Ala His Trp
            180                 185                 190

Asn Asn Gln Ser Ser Ala Pro Ala Ala Gly Leu Ala Ala Ile Arg Ile
        195                 200                 205

Gly Met Glu Met Val Arg Ser Leu Leu Val Ile Ala Leu Pro Leu Ser
    210                 215                 220

Asn Phe Thr Leu Pro Glu Asp Leu Pro Glu Gly Ser Gln Asn Ser Ile
225                 230                 235                 240

Arg Ala Phe Val Ala His Leu Met Asn Cys Val Ala Thr Asp Lys Ile
                245                 250                 255

Met Ser Pro Asp Val Arg Val Pro Val Glu Glu Ser Phe Tyr Ser His
            260                 265                 270

Cys Leu Arg Glu Ile Ile Met Cys Glu Arg Ala Phe Cys Tyr Pro Cys
        275                 280                 285

Asn Pro Pro Pro Lys Trp
    290
```

<210> SEQ ID NO 62
<211> LENGTH: 229
<212> TYPE: PRT
<213> ORGANISM: Infectious Laryngotracheitis Virus

<400> SEQUENCE: 62

```
Met Ala Pro Val Lys Val Thr Ile Val Ser Ala Val Asp Ser His Tyr
1               5                   10                  15

Lys Leu Pro Asn Ser Arg Phe Glu Leu Ser Asp Ser Gly Trp Lys Glu
            20                  25                  30

Leu Val His Ala Val Lys Thr Met Ala Ser Tyr Asp Arg Pro Ser Thr
        35                  40                  45

Leu Ser Val Ile Val Arg Pro Ala Ser Leu Tyr Glu Val Ser Gly Glu
    50                  55                  60

Leu Phe Ser Leu Pro Arg Met Cys Arg Pro Val Ile Arg Phe Gly Glu
65                  70                  75                  80

Gly Gly Asp Pro Pro Gly Val Ser Pro Glu Trp Ser Gly Leu Asp Ala
                85                  90                  95
```

```
Gly Phe Tyr His Leu Ser Ser Gly Ala Tyr Ala Ala Lys Glu Phe His
                100                 105                 110

Leu Trp Val Leu Gly Thr Ala Asp Ile Cys Met Ala Ala Leu Asn Leu
            115                 120                 125

Pro Ala Pro Lys Thr Phe Leu Ile Thr Glu Thr Gly Gly Lys Asn Phe
        130                 135                 140

Glu Arg Gly Val Glu Ile Phe Leu Val Asn Gly Asp Lys Thr Thr Leu
145                 150                 155                 160

Ser Leu Ser His Pro Ser Val Trp Thr Thr Leu Ala Pro Ser Ser Leu
                165                 170                 175

Arg Thr Pro Trp Pro Tyr Ser Thr Val Lys Phe Leu Lys Val Lys Pro
            180                 185                 190

Asn Ser Ala Ala Tyr Cys Val Ser Asp Ser Asp Gly Glu Arg Gln
        195                 200                 205

Pro Lys Phe Phe Leu Gly Ser Leu Phe Lys Ser Lys Lys Pro Arg Ser
210                 215                 220

Pro Arg Arg Arg Arg
225

<210> SEQ ID NO 63
<211> LENGTH: 476
<212> TYPE: PRT
<213> ORGANISM: Infectious Laryngotracheitis Virus

<400> SEQUENCE: 63

Met Arg Phe Arg Arg Ile Cys Ser Arg Ser Arg Ala Glu Lys Arg Arg
1               5                   10                  15

Arg Thr Thr Glu Asn Pro Leu Thr Ser Lys Arg Val Cys Val Leu Asp
            20                  25                  30

Ser Phe Ser Arg Thr Met Ser Leu Arg Pro Tyr Ala Glu Ile Leu Pro
        35                  40                  45

Thr Ala Glu Gly Val Glu Arg Leu Ala Glu Leu Val Ser Val Thr Met
    50                  55                  60

Thr Glu Arg Ala Glu Pro Val Thr Glu Asn Thr Ala Val Asn Ser Ile
65                  70                  75                  80

Pro Pro Ala Asn Glu Asn Gly Gln Asn Phe Ala Tyr Ala Gly Asp Gly
                85                  90                  95

Pro Ser Thr Thr Glu Lys Val Asp Gly Ser His Thr Asp Phe Asp Glu
            100                 105                 110

Ala Ser Ser Asp Tyr Ala Gly Pro Val Pro Leu Ala Gln Thr Arg Leu
        115                 120                 125

Lys His Ser Asp Glu Phe Leu Gln His Phe Arg Val Leu Asp Asp Leu
    130                 135                 140

Val Glu Gly Ala Tyr Gly Phe Ile Cys Asp Val Arg Arg Tyr Thr Glu
145                 150                 155                 160

Glu Glu Gln Arg Arg Gly Val Asn Ser Thr Asn Gln Gly Lys Ser
                165                 170                 175

Lys Cys Lys Arg Leu Ile Ala Lys Tyr Val Lys Asn Gly Thr Arg Ala
            180                 185                 190

Ala Ser Gln Leu Glu Asn Glu Ile Leu Val Leu Gly Arg Leu Asn His
        195                 200                 205

Glu Asn Val Leu Lys Ile Gln Glu Ile Leu Arg Tyr Pro Asp Asn Thr
    210                 215                 220

Tyr Met Leu Thr Gln Arg Tyr Gln Phe Asp Leu Tyr Ser Tyr Met Tyr
```

-continued

```
225                 230                 235                 240

Asp Glu Ala Phe Asp Trp Lys Asp Ser Pro Met Leu Lys Gln Thr Arg
                245                 250                 255

Arg Ile Met Lys Gln Leu Met Ser Ala Val Ser Tyr Ile His Ser Lys
            260                 265                 270

Lys Leu Ile His Arg Asp Ile Lys Leu Glu Asn Ile Phe Leu Asn Cys
        275                 280                 285

Asp Gly Lys Thr Val Leu Gly Asp Phe Gly Thr Val Thr Pro Phe Glu
    290                 295                 300

Asn Glu Arg Glu Pro Phe Glu Tyr Gly Trp Val Gly Thr Val Ala Thr
305                 310                 315                 320

Asn Ser Pro Glu Ile Leu Ala Arg Asp Ser Tyr Cys Glu Ile Thr Asp
                325                 330                 335

Ile Trp Ser Cys Gly Val Val Leu Leu Glu Met Val Ser His Glu Phe
            340                 345                 350

Cys Pro Ile Gly Asp Gly Gly Gly Asn Pro His Gln Gln Leu Leu Lys
        355                 360                 365

Val Ile Asp Ser Leu Ser Val Cys Asp Glu Glu Phe Pro Asp Pro Pro
    370                 375                 380

Cys Asn Leu Tyr Asn Tyr Leu His Tyr Ala Ser Ile Asp Arg Ala Gly
385                 390                 395                 400

His Thr Val Pro Ser Leu Ile Arg Asn Leu His Leu Pro Ala Asp Val
                405                 410                 415

Glu Tyr Pro Leu Val Lys Met Leu Thr Phe Asp Trp Arg Leu Arg Pro
            420                 425                 430

Ser Ala Ala Glu Val Leu Ala Met Pro Leu Phe Ser Ala Glu Glu Glu
        435                 440                 445

Arg Thr Ile Thr Ile Ile His Gly Lys His Lys Pro Ile Arg Pro Glu
    450                 455                 460

Ile Arg Ala Arg Val Pro Arg Ser Met Ser Glu Gly
465                 470                 475

<210> SEQ ID NO 64
<211> LENGTH: 623
<212> TYPE: PRT
<213> ORGANISM: Infectious Laryngotracheitis Virus
<400> SEQUENCE: 64

Met Thr Leu Pro His Arg Leu Thr Lys Arg Pro Phe Ala Arg Arg Phe
1               5                   10                  15

Cys Ser Val Phe Val Ile His Tyr Ser Glu Thr Lys Leu Asp Arg Tyr
            20                  25                  30

Asn Lys Thr Met Leu Leu Tyr Arg Pro Asp Ser Thr Met Arg His Ser
        35                  40                  45

Gly Gly Asp Ala Asn His Arg Gly Ile Arg Pro Arg Arg Lys Ser Ile
    50                  55                  60

Gly Ala Phe Ser Ala Arg Glu Lys Thr Gly Lys Arg Asn Ala Leu Thr
65                  70                  75                  80

Glu Ser Ser Ser Ser Ser Asp Met Leu Asp Pro Phe Ser Thr Asp Lys
                85                  90                  95

Glu Phe Gly Gly Lys Trp Thr Val Asp Gly Pro Ala Asp Ile Thr Ala
            100                 105                 110

Glu Val Leu Ser Gln Ala Trp Asp Val Leu Gln Leu Val Lys His Glu
        115                 120                 125
```

```
Asp Ala Glu Glu Glu Arg Val Thr Tyr Glu Ser Lys Pro Thr Pro Ile
    130                 135                 140

Gln Pro Phe Asn Ala Trp Pro Asp Gly Pro Ser Trp Asn Ala Gln Asp
145                 150                 155                 160

Phe Thr Arg Ala Pro Ile Val Tyr Pro Ser Ala Glu Val Leu Asp Ala
                165                 170                 175

Glu Ala Leu Lys Val Gly Ala Phe Val Ser Arg Val Leu Gln Cys Val
            180                 185                 190

Pro Phe Thr Arg Ser Lys Lys Ser Val Thr Val Arg Asp Ala Gln Ser
        195                 200                 205

Phe Leu Gly Asp Ser Phe Trp Arg Ile Met Gln Asn Val Tyr Thr Val
210                 215                 220

Val Leu Arg Gln His Ile Thr Arg Leu Arg His Pro Ser Ser Lys Ser
225                 230                 235                 240

Ile Val Asn Cys Asn Asp Pro Leu Trp Tyr Ala Tyr Ala Asn Gln Phe
                245                 250                 255

His Trp Arg Gly Met Arg Val Pro Ser Leu Lys Leu Ala Ser Pro Pro
            260                 265                 270

Glu Glu Asn Ile Gln His Gly Pro Met Ala Ala Val Phe Arg Asn Ala
        275                 280                 285

Gly Ala Gly Leu Phe Leu Trp Pro Ala Met Arg Ala Ala Phe Glu Glu
290                 295                 300

Arg Asp Lys Arg Leu Leu Arg Ala Cys Leu Ser Ser Leu Asp Ile Met
305                 310                 315                 320

Asp Ala Ala Val Leu Ala Ser Phe Pro Phe Tyr Trp Arg Gly Val Gln
                325                 330                 335

Asp Thr Ser Arg Phe Glu Pro Ala Leu Gly Cys Leu Ser Glu Tyr Phe
            340                 345                 350

Ala Leu Val Val Leu Leu Ala Glu Thr Val Leu Ala Thr Met Phe Asp
        355                 360                 365

His Ala Leu Val Phe Met Arg Ala Leu Ala Asp Gly Asn Phe Asp Asp
370                 375                 380

Tyr Asp Glu Thr Arg Tyr Ile Asp Pro Val Lys Asn Glu Tyr Leu Asn
385                 390                 395                 400

Gly Ala Glu Gly Thr Leu Leu Arg Gly Ile Val Ala Ser Asn Thr Ala
                405                 410                 415

Leu Ala Val Val Cys Ala Asn Thr Tyr Ser Thr Ile Arg Lys Leu Pro
            420                 425                 430

Ser Val Ala Thr Ser Ala Cys Asn Val Ala Tyr Arg Thr Glu Thr Leu
        435                 440                 445

Lys Ala Arg Arg Pro Gly Met Ser Asp Ile Tyr Arg Ile Leu Gln Lys
450                 455                 460

Glu Phe Phe Tyr Ile Ala Trp Leu Gln Arg Val Ala Thr His Ala
465                 470                 475                 480

Asn Phe Cys Leu Asn Ile Leu Lys Arg Ser Val Asp Thr Gly Ala Pro
                485                 490                 495

Pro Phe Leu Phe Arg Ala Ser Ser Glu Lys Arg Leu Gln Gln Leu Asn
            500                 505                 510

Lys Met Leu Cys Pro Leu Leu Val Pro Ile Gln Tyr Glu Asp Phe Ser
        515                 520                 525

Lys Ala Met Gly Ser Glu Leu Lys Arg Glu Lys Leu Glu Thr Phe Val
530                 535                 540

Lys Ala Ile Ser Ser Asp Arg Asp Pro Arg Gly Ser Leu Arg Phe Leu
```

```
                545                 550                 555                 560
Ile Ser Asp His Ala Arg Glu Ile Ile Ala Asp Gly Val Arg Phe Lys
                565                 570                 575

Pro Val Ile Asp Glu Pro Val Arg Ala Ser Val Ala Leu Ser Thr Ala
                580                 585                 590

Ala Ala Gly Lys Val Lys Ala Arg Arg Leu Thr Ser Val Arg Ala Pro
                595                 600                 605

Val Pro Gly Ala Gly Ala Val Ser Ala Arg Arg Lys Ser Glu Ile
    610                 615                 620

<210> SEQ ID NO 65
<211> LENGTH: 292
<212> TYPE: PRT
<213> ORGANISM: Infectious Laryngotracheitis Virus

<400> SEQUENCE: 65

Met Ser Gly Phe Ser Asn Ile Gly Ser Ile Ala Thr Val Ser Leu Val
1               5                   10                  15

Cys Ser Leu Leu Cys Ala Ser Val Leu Gly Ala Pro Val Leu Asp Gly
                20                  25                  30

Leu Glu Ser Ser Pro Phe Pro Phe Gly Gly Lys Ile Ile Ala Gln Ala
            35                  40                  45

Cys Asn Arg Thr Thr Ile Glu Val Thr Val Pro Trp Ser Asp Tyr Ser
50                  55                  60

Gly Arg Thr Glu Gly Val Ser Val Glu Val Lys Trp Phe Tyr Gly Asn
65                  70                  75                  80

Ser Asn Pro Glu Ser Phe Val Phe Gly Val Asp Ser Glu Thr Gly Ser
                85                  90                  95

Gly His Glu Asp Leu Ser Thr Cys Trp Ala Leu Ile His Asn Leu Asn
            100                 105                 110

Ala Ser Val Cys Arg Ala Ser Asp Ala Gly Ile Pro Asp Phe Asp Lys
        115                 120                 125

Gln Cys Glu Lys Val Gln Arg Arg Leu Arg Ser Gly Val Glu Leu Gly
    130                 135                 140

Ser Tyr Val Ser Gly Asn Gly Ser Leu Val Leu Tyr Pro Gly Met Tyr
145                 150                 155                 160

Asp Ala Gly Ile Tyr Ala Tyr Gln Leu Ser Val Gly Gly Lys Gly Tyr
                165                 170                 175

Thr Gly Ser Val Tyr Leu Asp Val Gly Pro Asn Pro Gly Cys His Asp
            180                 185                 190

Gln Tyr Gly Tyr Thr Tyr Tyr Ser Leu Ala Asp Glu Ala Ser Asp Leu
        195                 200                 205

Ser Ser Tyr Asp Val Ala Ser Pro Glu Leu Asp Gly Pro Met Glu Glu
    210                 215                 220

Asp Tyr Ser Asn Cys Leu Asp Met Pro Pro Leu Arg Pro Trp Thr Thr
225                 230                 235                 240

Val Cys Ser His Asp Val Glu Glu Gln Glu Asn Ala Thr Asp Glu Leu
                245                 250                 255

Tyr Leu Trp Asp Glu Glu Cys Ala Gly Pro Leu Asp Glu Tyr Val Asp
            260                 265                 270

Glu Arg Ser Glu Thr Met Pro Arg Met Val Val Phe Ser Pro Pro Ser
        275                 280                 285

Thr Leu Gln Gln
    290
```

<210> SEQ ID NO 66
<211> LENGTH: 985
<212> TYPE: PRT
<213> ORGANISM: Infectious Laryngotracheitis Virus

<400> SEQUENCE: 66

```
Met Gly Thr Met Leu Val Leu Arg Leu Phe Leu Leu Ala Val Ala Asp
1               5                   10                  15

Ala Ala Leu Pro Thr Gly Arg Phe Cys Arg Val Trp Lys Val Pro Pro
            20                  25                  30

Gly Gly Thr Ile Gln Glu Asn Leu Ala Val Leu Ala Glu Ser Pro Val
        35                  40                  45

Thr Gly His Ala Thr Tyr Pro Pro Glu Gly Ala Val Ser Phe Gln
    50                  55                  60

Ile Phe Ala Asp Thr Pro Thr Leu Arg Ile Arg Tyr Gly Ala Thr Glu
65                  70                  75                  80

Asp Glu Leu Ala Leu Glu Arg Gly Thr Ser Ala Ser Asp Ala Asp Asn
                85                  90                  95

Val Thr Phe Ser Leu Ser Tyr Arg Pro Arg Pro Glu Ile His Gly Ala
            100                 105                 110

Tyr Phe Thr Ile Gly Val Phe Ala Thr Gly Gln Ser Thr Glu Ser Ser
        115                 120                 125

Tyr Ser Val Ile Ser Arg Val Leu Val Asn Ala Ser Leu Glu Arg Ser
    130                 135                 140

Val Arg Leu Glu Thr Pro Cys Asp Glu Asn Phe Leu Gln Asn Glu Pro
145                 150                 155                 160

Thr Trp Gly Ser Lys Arg Trp Leu Gly Pro Pro Ser Pro Tyr Val Arg
                165                 170                 175

Asp Asn Asp Val Ala Val Leu Thr Lys Ala Gln Tyr Ile Gly Glu Cys
            180                 185                 190

Tyr Ser Asn Ser Ala Ala Gln Thr Gly Leu Thr Ser Leu Asn Met Thr
        195                 200                 205

Phe Phe Tyr Ser Pro Lys Arg Ile Val Asn Val Thr Trp Thr Thr Gly
    210                 215                 220

Gly Pro Ser Pro Ser Arg Ile Thr Val Tyr Ser Ser Arg Glu Asn Gly
225                 230                 235                 240

Gln Pro Val Leu Arg Asn Val Ser Asp Gly Phe Leu Val Lys Tyr Thr
                245                 250                 255

Pro Asp Ile Asp Gly Arg Ala Met Ile Asn Val Ile Ala Asn Tyr Ser
            260                 265                 270

Pro Ala Asp Ser Gly Ser Val Leu Ala Phe Thr Ala Phe Arg Glu Gly
        275                 280                 285

Lys Leu Pro Ser Ala Ile Gln Leu His Arg Ile Asp Met Ser Gly Thr
    290                 295                 300

Glu Pro Pro Gly Thr Glu Thr Thr Phe Asp Cys Gln Lys Met Ile Glu
305                 310                 315                 320

Thr Pro Tyr Arg Ala Leu Gly Ser Asn Val Pro Arg Asp Asp Ser Ile
                325                 330                 335

Arg Pro Gly Ala Thr Leu Pro Pro Phe Asp Thr Ala Ala Pro Asp Phe
            340                 345                 350

Asp Thr Gly Thr Ser Pro Thr Pro Thr Thr Val Pro Glu Pro Ala Ile
        355                 360                 365

Thr Thr Leu Ile Pro Arg Ser Ser Ser Asp Met Gly Phe Phe Ser Thr
    370                 375                 380
```

-continued

```
Ala Arg Ala Thr Gly Ser Glu Thr Leu Ser Val Pro Val Gln Glu Thr
385                 390                 395                 400

Asp Arg Thr Leu Ser Thr Thr Pro Leu Thr Leu Pro Leu Thr Pro Gly
            405                 410                 415

Glu Ser Glu Asn Thr Leu Phe Pro Thr Thr Ala Pro Gly Ile Ser Thr
                420                 425                 430

Glu Thr Pro Ser Ala Ala His Glu Thr Thr Gln Thr Gln Ser Ala Glu
            435                 440                 445

Thr Val Val Phe Thr Gln Ser Pro Ser Thr Glu Ser Glu Thr Ala Arg
        450                 455                 460

Ser Gln Ser Gln Glu Pro Trp Tyr Phe Thr Gln Thr Pro Ser Thr Glu
465                 470                 475                 480

Gln Ala Ala Leu Thr Gln Thr Gln Ile Ala Glu Thr Glu Ala Leu Phe
                485                 490                 495

Thr Gln Thr Pro Ser Ala Glu Gln Met Thr Phe Thr Gln Thr Pro Gly
            500                 505                 510

Ala Glu Thr Glu Ala Pro Ala Gln Thr Pro Ser Thr Ile Pro Glu Ile
        515                 520                 525

Phe Thr Gln Ser Arg Ser Thr Pro Pro Glu Thr Ala Arg Ala Pro Ser
530                 535                 540

Ala Ala Pro Glu Val Phe Thr Gln Ser Ser Thr Val Thr Glu Val
545                 550                 555                 560

Phe Thr Gln Thr Pro Ser Thr Val Pro Lys Thr Thr Leu Ser Ser Ser
                565                 570                 575

Thr Glu Pro Ala Ile Phe Thr Arg Thr Gln Ser Ala Gly Thr Glu Ala
            580                 585                 590

Phe Thr Gln Thr Ser Ser Ala Glu Pro Asp Thr Met Arg Thr Gln Ser
        595                 600                 605

Thr Glu Thr His Phe Phe Thr Gln Ala Pro Ser Thr Val Pro Lys Ala
610                 615                 620

Thr Gln Thr Pro Ser Thr Glu Pro Glu Val Leu Thr Gln Ser Pro Ser
625                 630                 635                 640

Thr Glu Pro Val Pro Phe Thr Arg Thr Leu Gly Ala Glu Pro Glu Ile
                645                 650                 655

Thr Gln Thr Pro Ser Ala Ala Pro Glu Val Tyr Thr Arg Ser Ser Ser
            660                 665                 670

Thr Met Pro Glu Thr Ala Gln Ser Thr Pro Leu Ala Ser Gln Asn Pro
        675                 680                 685

Thr Ser Ser Gly Thr Gly Thr His Asn Thr Glu Pro Arg Thr Tyr Pro
690                 695                 700

Val Gln Thr Thr Pro His Thr Gln Lys Leu Tyr Thr Glu Asn Lys Thr
705                 710                 715                 720

Leu Ser Phe Pro Thr Val Val Ser Glu Phe His Glu Met Ser Thr Ala
                725                 730                 735

Glu Ser Gln Thr Pro Leu Leu Asp Val Lys Ile Val Glu Val Lys Phe
            740                 745                 750

Ser Asn Asp Gly Glu Val Thr Ala Thr Cys Val Ser Thr Val Lys Ser
        755                 760                 765

Pro Tyr Arg Val Glu Thr Asn Trp Lys Val Asp Leu Val Asp Val Met
770                 775                 780

Asp Glu Ile Ser Gly Asn Ser Pro Ala Gly Val Phe Asn Ser Asn Glu
785                 790                 795                 800
```

```
Lys Trp Gln Lys Gln Leu Tyr Tyr Arg Val Thr Asp Gly Arg Thr Ser
                805                 810                 815
Val Gln Leu Met Cys Leu Ser Cys Thr Ser His Ser Pro Glu Pro Tyr
            820                 825                 830
Cys Leu Phe Asp Thr Ser Leu Ile Ala Arg Glu Lys Asp Ile Ala Pro
        835                 840                 845
Glu Leu Tyr Phe Thr Ser Asp Pro Gln Thr Ala Tyr Cys Thr Ile Thr
    850                 855                 860
Leu Pro Ser Gly Val Val Pro Arg Phe Glu Trp Ser Leu Asn Asn Val
865                 870                 875                 880
Ser Leu Pro Glu Tyr Leu Thr Ala Thr Val Val Ser His Thr Ala
                885                 890                 895
Gly Gln Ser Thr Val Trp Lys Ser Ser Ala Arg Ala Gly Glu Ala Trp
            900                 905                 910
Ile Ser Gly Arg Gly Gly Asn Ile Tyr Glu Cys Thr Val Leu Ile Ser
        915                 920                 925
Asp Gly Thr Arg Val Thr Thr Arg Lys Glu Arg Cys Leu Thr Asn Thr
    930                 935                 940
Trp Ile Ala Val Glu Asn Gly Ala Ala Gln Ala Gln Leu Tyr Ser Leu
945                 950                 955                 960
Phe Ser Gly Leu Val Ser Gly Leu Cys Gly Ser Ile Ser Ala Leu Tyr
                965                 970                 975
Ala Thr Leu Trp Thr Ala Ile Tyr Phe
            980                 985

<210> SEQ ID NO 67
<211> LENGTH: 434
<212> TYPE: PRT
<213> ORGANISM: Infectious Laryngotracheitis Virus

<400> SEQUENCE: 67

Met His Arg Pro His Leu Arg Arg His Ser Arg Tyr Tyr Ala Lys Gly
1               5                   10                  15
Glu Val Leu Asn Lys His Met Asp Cys Gly Gly Lys Arg Cys Cys Ser
            20                  25                  30
Gly Ala Ala Val Phe Thr Leu Phe Trp Thr Cys Val Arg Ile Met Arg
        35                  40                  45
Glu His Ile Cys Phe Val Arg Asn Ala Met Asp Arg His Leu Phe Leu
    50                  55                  60
Arg Asn Ala Phe Trp Thr Ile Val Leu Leu Ser Ser Phe Ala Ser Gln
65                  70                  75                  80
Ser Thr Ala Ala Val Thr Tyr Asp Tyr Ile Leu Gly Arg Arg Ala Leu
                85                  90                  95
Asp Ala Leu Thr Ile Pro Ala Val Gly Pro Tyr Asn Arg Tyr Leu Thr
            100                 105                 110
Arg Val Ser Arg Gly Cys Asp Val Val Glu Leu Asn Pro Ile Ser Asn
        115                 120                 125
Val Asp Asp Met Ile Ser Ala Ala Lys Glu Lys Glu Lys Gly Gly Pro
    130                 135                 140
Phe Glu Ala Ser Val Val Trp Phe Tyr Val Ile Lys Gly Asp Asp Gly
145                 150                 155                 160
Glu Asp Lys Tyr Cys Pro Ile Tyr Arg Lys Glu Tyr Arg Glu Cys Gly
                165                 170                 175
Asp Val Gln Leu Leu Ser Glu Cys Ala Val Gln Ser Ala Gln Met Trp
            180                 185                 190
```

-continued

```
Ala Val Asp Tyr Val Pro Ser Thr Leu Val Ser Arg Asn Gly Ala Gly
        195                 200                 205

Leu Thr Ile Phe Ser Pro Thr Ala Ala Leu Ser Gly Gln Tyr Leu Leu
    210                 215                 220

Thr Leu Lys Ile Gly Arg Phe Ala Gln Thr Ala Leu Val Thr Leu Glu
225                 230                 235                 240

Val Asn Asp Arg Cys Leu Lys Ile Gly Ser Gln Leu Asn Phe Leu Pro
                245                 250                 255

Ser Lys Cys Trp Thr Thr Glu Gln Tyr Gln Thr Gly Phe Gln Gly Glu
            260                 265                 270

His Leu Tyr Pro Ile Ala Asp Thr Asn Thr Arg His Ala Asp Asp Val
        275                 280                 285

Tyr Arg Gly Tyr Glu Asp Ile Leu Gln Arg Trp Asn Asn Leu Leu Arg
    290                 295                 300

Lys Lys Asn Pro Ser Ala Pro Asp Pro Arg Pro Asp Ser Val Pro Gln
305                 310                 315                 320

Glu Ile Pro Ala Val Thr Lys Lys Ala Glu Gly Arg Thr Pro Asp Ala
                325                 330                 335

Glu Ser Ser Glu Lys Lys Ala Pro Pro Glu Asp Ser Glu Asp Asp Met
            340                 345                 350

Gln Ala Glu Ala Ser Gly Glu Asn Pro Ala Ala Leu Pro Glu Asp Asp
        355                 360                 365

Glu Val Pro Glu Asp Thr Glu His Asp Asp Pro Asn Ser Asp Pro Asp
    370                 375                 380

Tyr Tyr Asn Asp Met Pro Ala Val Ile Pro Val Glu Glu Thr Thr Lys
385                 390                 395                 400

Ser Ser Asn Ala Val Ser Met Pro Ile Phe Ala Ala Phe Val Ala Cys
                405                 410                 415

Ala Val Ala Leu Val Gly Leu Leu Val Trp Ser Ile Val Lys Cys Ala
            420                 425                 430

Arg Ser
```

<210> SEQ ID NO 68
<211> LENGTH: 362
<212> TYPE: PRT
<213> ORGANISM: Infectious Laryngotracheitis Virus

<400> SEQUENCE: 68

```
Met Ala Ser Leu Leu Gly Thr Leu Ala Leu Leu Ala Ala Thr Leu Ala
1               5                   10                  15

Pro Phe Gly Ala Met Gly Ile Val Ile Thr Gly Asn His Val Ser Ala
            20                  25                  30

Arg Ile Asp Asp Asp His Ile Val Ile Val Ala Pro Arg Pro Glu Ala
        35                  40                  45

Thr Ile Gln Leu Gln Leu Phe Phe Met Pro Gly Gln Arg Pro His Lys
    50                  55                  60

Pro Tyr Ser Gly Thr Val Arg Val Ala Phe Arg Ser Asp Ile Thr Asn
65                  70                  75                  80

Gln Cys Tyr Gln Glu Leu Ser Glu Glu Arg Phe Glu Asn Cys Thr His
                85                  90                  95

Arg Ser Ser Ser Val Phe Val Gly Cys Lys Val Thr Glu Tyr Thr Phe
            100                 105                 110

Ser Ala Ser Asn Arg Leu Thr Gly Pro Pro His Pro Phe Lys Leu Thr
        115                 120                 125
```

Ile Arg Asn Pro Arg Pro Asn Asp Ser Gly Met Phe Tyr Val Ile Val
    130                 135                 140

Arg Leu Asp Asp Thr Lys Glu Pro Ile Asp Val Phe Ala Ile Gln Leu
145                 150                 155                 160

Ser Val Tyr Gln Phe Ala Asn Thr Ala Ala Thr Arg Gly Leu Tyr Ser
                    165                 170                 175

Lys Ala Ser Cys Arg Thr Phe Gly Leu Pro Thr Val Gln Leu Glu Ala
                180                 185                 190

Tyr Leu Arg Thr Glu Glu Ser Trp Arg Asn Trp Gln Ala Tyr Val Ala
            195                 200                 205

Thr Glu Ala Thr Thr Thr Ser Ala Glu Ala Thr Thr Pro Thr Pro Val
    210                 215                 220

Thr Ala Thr Ser Ala Ser Glu Leu Glu Ala Glu His Phe Thr Phe Pro
225                 230                 235                 240

Trp Leu Glu Asn Gly Val Asp His Tyr Glu Pro Thr Pro Ala Asn Glu
                    245                 250                 255

Asn Ser Asn Val Thr Val Arg Leu Gly Thr Met Ser Pro Thr Leu Ile
                260                 265                 270

Gly Val Thr Ala Ala Val Ser Ala Thr Ile Gly Leu Val Ile
            275                 280                 285

Val Ile Ser Ile Val Thr Arg Asn Met Cys Thr Pro His Arg Lys Leu
    290                 295                 300

Asp Thr Val Ser Gln Asp Asp Glu Glu Arg Ser Gln Thr Arg Arg Glu
305                 310                 315                 320

Ser Arg Lys Phe Gly Pro Met Val Ala Cys Glu Ile Asn Lys Gly Ala
                    325                 330                 335

Asp Gln Asp Ser Glu Leu Val Glu Leu Val Ala Ile Val Asn Pro Ser
                340                 345                 350

Ala Leu Ser Ser Pro Asp Ser Ile Lys Met
            355                 360

<210> SEQ ID NO 69
<211> LENGTH: 499
<212> TYPE: PRT
<213> ORGANISM: Infectious Laryngotracheitis Virus

<400> SEQUENCE: 69

Met Asn Met Leu Val Ile Val Leu Ala Ser Cys Leu Ala Arg Leu Thr
1               5                   10                  15

Phe Ala Thr Arg His Val Leu Phe Leu Glu Gly Thr Gln Ala Val Leu
                20                  25                  30

Gly Glu Asp Asp Pro Arg Asn Val Pro Glu Gly Thr Val Ile Lys Trp
            35                  40                  45

Thr Lys Val Leu Arg Asn Ala Cys Lys Met Lys Ala Ala Asp Val Cys
50                  55                  60

Ser Ser Pro Asn Tyr Cys Phe His Asp Leu Ile Tyr Asp Gly Gly Lys
65                  70                  75                  80

Lys Asp Cys Pro Pro Ala Gly Pro Leu Ser Ala Asn Leu Val Ile Leu
                85                  90                  95

Leu Lys Arg Gly Glu Ser Phe Val Leu Gly Ser Gly Leu His Asn
            100                 105                 110

Ser Asn Ile Thr Asn Ile Met Trp Thr Glu Tyr Gly Gly Leu Leu Phe
        115                 120                 125

Asp Pro Val Thr Arg Ser Asp Glu Gly Ile Tyr Phe Arg Arg Ile Ser

```
                130                 135                 140
Gln Pro Asp Leu Ala Met Glu Thr Thr Ser Tyr Asn Val Ser Val Leu
145                 150                 155                 160

Ser His Val Asp Glu Lys Ala Pro Ala Pro His Glu Val Glu Ile Asp
                165                 170                 175

Thr Ile Lys Pro Ser Glu Ala His Ala His Val Glu Leu Gln Met Leu
                180                 185                 190

Pro Phe His Glu Leu Asn Asp Asn Ser Pro Thr Tyr Val Thr Pro Val
                195                 200                 205

Leu Arg Val Phe Pro Pro Thr Glu His Val Lys Phe Asn Val Thr Tyr
210                 215                 220

Ser Trp Tyr Gly Phe Asp Val Lys Glu Glu Cys Glu Glu Val Lys Leu
225                 230                 235                 240

Phe Glu Pro Cys Val Tyr His Pro Thr Asp Gly Lys Cys Gln Phe Pro
                245                 250                 255

Ala Thr Asn Gln Arg Cys Leu Ile Gly Ser Val Leu Met Ala Glu Phe
                260                 265                 270

Leu Gly Ala Ala Ser Leu Leu Asp Cys Ser Arg Asp Thr Leu Glu Asp
                275                 280                 285

Cys His Glu Asn Arg Val Pro Asn Leu Arg Phe Asp Ser Arg Leu Ser
                290                 295                 300

Glu Ser Arg Ala Gly Leu Val Ile Ser Pro Leu Ile Ala Ile Pro Lys
305                 310                 315                 320

Val Leu Ile Ile Val Ser Asp Gly Asp Ile Leu Gly Trp Ser Tyr
                325                 330                 335

Thr Val Leu Gly Lys Arg Asn Ser Pro Arg Val Val Val Glu Thr His
                340                 345                 350

Met Pro Ser Lys Val Pro Met Asn Lys Val Val Ile Gly Ser Pro Gly
                355                 360                 365

Pro Met Asp Glu Thr Gly Asn Tyr Lys Met Tyr Phe Val Val Ala Gly
                370                 375                 380

Val Ala Ala Thr Cys Val Ile Leu Thr Cys Ala Leu Leu Val Gly Lys
385                 390                 395                 400

Lys Lys Cys Pro Ala His Gln Met Gly Thr Phe Ser Lys Thr Glu Pro
                405                 410                 415

Leu Tyr Ala Pro Leu Pro Lys Asn Glu Phe Glu Ala Gly Gly Leu Thr
                420                 425                 430

Asp Asp Glu Glu Val Ile Tyr Asp Glu Val Tyr Glu Pro Leu Phe Arg
                435                 440                 445

Gly Tyr Cys Lys Gln Glu Phe Arg Glu Asp Val Asn Thr Phe Phe Gly
                450                 455                 460

Ala Val Val Glu Gly Glu Arg Ala Leu Asn Phe Lys Ser Ala Ile Ala
465                 470                 475                 480

Ser Met Ala Asp Arg Ile Leu Ala Asn Lys Ser Gly Arg Arg Asn Met
                485                 490                 495

Asp Ser Tyr

<210> SEQ ID NO 70
<211> LENGTH: 260
<212> TYPE: PRT
<213> ORGANISM: Infectious Laryngotracheitis Virus

<400> SEQUENCE: 70

Met Pro Phe Lys Thr Arg Gly Ala Glu Asp Ala Ala Ala Gly Lys Asn
```

-continued

```
1               5                   10                  15
Arg Phe Lys Lys Ser Arg Asn Arg Glu Ile Leu Pro Thr Arg Leu Arg
            20                  25                  30

Gly Thr Gly Lys Lys Thr Ala Gly Leu Ser Asn Tyr Thr Gln Pro Ile
        35                  40                  45

Pro Trp Asn Pro Lys Phe Cys Ser Ala Arg Gly Glu Ser Asp Asn His
    50                  55                  60

Ala Cys Lys Asp Thr Phe Tyr Arg Arg Thr Cys Cys Ala Ser Arg Ser
65                  70                  75                  80

Thr Val Ser Ser Gln Pro Asp Ser Pro His Thr Pro Met Pro Thr Glu
                85                  90                  95

Tyr Gly Arg Val Pro Ser Ala Lys Arg Lys Lys Leu Ser Ser Ser Asp
            100                 105                 110

Cys Glu Gly Ala His Gln Pro Leu Val Ser Cys Lys Leu Pro Asp Ser
        115                 120                 125

Gln Ala Ala Pro Ala Arg Thr Tyr Ser Ser Ala Gln Arg Tyr Thr Val
    130                 135                 140

Asp Glu Val Ser Ser Pro Thr Pro Pro Gly Val Asp Ala Val Ala Asp
145                 150                 155                 160

Leu Glu Thr Arg Ala Glu Leu Pro Gly Ala Thr Thr Glu Gln Thr Glu
                165                 170                 175

Ser Lys Asn Lys Leu Pro Asn Gln Gln Ser Arg Leu Lys Pro Lys Pro
            180                 185                 190

Thr Asn Glu His Val Gly Gly Glu Arg Cys Pro Ser Glu Gly Thr Val
        195                 200                 205

Glu Ala Pro Ser Leu Gly Ile Leu Ser Arg Val Gly Ala Ala Ile Ala
    210                 215                 220

Asn Glu Leu Ala Arg Met Arg Arg Ala Cys Leu Pro Leu Ala Ala Ser
225                 230                 235                 240

Ala Ala Ala Ala Gly Ile Val Ala Trp Ala Ala Ala Arg Ala Leu Gln
                245                 250                 255

Lys Gln Gly Arg
            260

<210> SEQ ID NO 71
<211> LENGTH: 294
<212> TYPE: PRT
<213> ORGANISM: Infectious Laryngotracheitis Virus

<400> SEQUENCE: 71

Met Ser Lys Cys Tyr Cys Leu Ala Arg His Leu Tyr Lys Ser Pro Arg
1               5                   10                  15

Cys Val Gly Arg Arg Val Ala Phe Gly Gly Leu Ala Thr Met Ser Arg
            20                  25                  30

Pro Pro Thr Ser His Leu Asp Leu Ala Phe Ser Ala Ala Phe Arg Gly
        35                  40                  45

Thr Asp Leu Pro Gly Gly Arg Phe Trp Arg Ala Ser Gln Ser Cys Asp
    50                  55                  60

Ile Phe Phe Trp Pro Asp Leu Ala Ala Val Ile Val Gln Ala Ala Arg
65                  70                  75                  80

Ala Tyr Phe Glu Gly Lys Glu Arg Leu Gly Ser Leu Gln Val Ala Glu
                85                  90                  95

Asp Ile Thr Ala His Asp Pro Arg Ile Ala Pro Ala Ala Lys Arg Ala
            100                 105                 110

-continued

```
Val Ala Ala Ala Val Gly Leu Trp Thr Ala Leu Ser Glu Leu Val Gly
            115                 120                 125

Gly Pro Asn Gly Glu Leu Glu Ser Lys Val Trp Gly Lys Gln Ile Pro
        130                 135                 140

Arg Ala Ala Ala Trp Glu Ile Arg Asp Val Pro Lys Val Pro Val Ile
145                 150                 155                 160

Gly Pro Asp Ile Leu Ser Phe Phe Ser Ala Val Glu Leu Pro Val
                165                 170                 175

Leu Tyr Ile Arg Ala Arg Gly Gly Ala His Ser Arg Ser Ala His Trp
                180                 185                 190

Asn Asn Gln Ser Ser Ala Pro Ala Gly Leu Ala Ala Ile Arg Ile
            195                 200                 205

Gly Met Glu Met Val Arg Ser Leu Leu Val Ile Ala Leu Pro Leu Ser
        210                 215                 220

Asn Phe Thr Leu Pro Glu Asp Leu Pro Glu Gly Ser Gln Asn Ser Ile
225                 230                 235                 240

Arg Ala Phe Val Ala His Leu Met Asn Cys Val Ala Thr Asp Lys Ile
                245                 250                 255

Met Ser Pro Asp Val Arg Val Pro Val Glu Ser Phe Tyr Ser His
                260                 265                 270

Cys Leu Arg Glu Ile Ile Met Cys Glu Arg Ala Phe Cys Tyr Pro Cys
                275                 280                 285

Asn Pro Pro Lys Trp
    290

<210> SEQ ID NO 72
<211> LENGTH: 278
<212> TYPE: PRT
<213> ORGANISM: Infectious Laryngotracheitis Virus

<400> SEQUENCE: 72

Met Glu Asn Met Leu Asp Gly Cys Tyr Pro Leu Ala Leu Met Asp Ser
1               5                   10                  15

Asp His Ile Thr Ala His Ala Val Pro Arg Gly Glu Arg Arg Gln
            20                  25                  30

Gly Ala Ala Val Ala Ser Ser Glu Ser Ala Asp Ser Val Asp Pro Cys
        35                  40                  45

Ile Arg Ile Ala Ser Arg Leu Trp Arg Glu Leu Val Glu Ile Ser Ser
    50                  55                  60

Glu Leu Lys Asp Gly Tyr Gly Phe Thr Ser Ala Arg Asp Arg Arg
65                  70                  75                  80

Asn Ala Leu Ile Ala Ala Asn Glu Arg Leu Arg Ser Ala Phe Leu Gly
                85                  90                  95

Ala Ser Arg Ala Thr Arg Gly Leu Gly Leu Arg Pro Arg Trp Ala Ser
            100                 105                 110

Thr Glu Ser Val Ala Asn Ser Pro Thr Asp Pro Asn Asn Gly Asn Gly
        115                 120                 125

Leu Gly Glu Leu Glu Ala Met Glu Gly Ile Glu Gly Asp Phe Trp
    130                 135                 140

Leu Asp Ser Leu Asp Gly Asp Arg Phe Glu Asp Glu Ser Arg Thr Met
145                 150                 155                 160

Gln Ser Glu Asn Met Arg Phe Val Ile Glu Lys Glu Leu Leu Ser Trp
                165                 170                 175

Leu Ser Arg His Leu Pro Ala Asp Leu Ala Ser Ala Glu Arg Glu Thr
            180                 185                 190
```

```
Ser Arg Ser Leu Leu Ala Ala Gly His Trp Cys Cys Leu Trp His Pro
        195                 200                 205

Arg Pro Cys Arg Glu Ala Cys Leu Tyr Asp Ser Ile Tyr Val Gln Ser
    210                 215                 220

Leu Phe Cys Val Gly Thr Gly Arg Val Pro Gln Ser Glu Met Arg Arg
225                 230                 235                 240

Arg Glu Tyr Leu Ala Ala Leu Arg Ala Gly Ala Ala Ala Asn Ser
                245                 250                 255

Pro Glu Val Ser Ala Ser Ile Phe Ala Arg Asp Ala Gly Ile Ala Leu
        260                 265                 270

Ala Leu Ala Arg Arg
        275

<210> SEQ ID NO 73
<211> LENGTH: 52
<212> TYPE: PRT
<213> ORGANISM: Infectious Laryngotracheitis Virus

<400> SEQUENCE: 73

Gln His Gly Pro Met Ala Ala Val Phe Arg Asn Ala Gly Ala Gly Leu
1               5                   10                  15

Phe Leu Trp Pro Ala Met Arg Ala Ala Phe Glu Glu Arg Asp Lys Arg
            20                  25                  30

Leu Leu Arg Ala Cys Leu Ser Ser Leu Asp Ile Met Asp Ala Val
        35                  40                  45

Leu Ala Ser Phe
    50

<210> SEQ ID NO 74
<211> LENGTH: 52
<212> TYPE: PRT
<213> ORGANISM: herpes simplex virus

<400> SEQUENCE: 74

Gln Ser Gly Pro Asp Ala Ala Val Phe Arg Ser Ser Leu Gly Ser Leu
1               5                   10                  15

Leu Tyr Trp Pro Gly Val Arg Ala Leu Leu Asp Arg Asp Cys Arg Val
            20                  25                  30

Ala Ala Arg Tyr Ala Gly Arg Met Thr Tyr Leu Ala Thr Gly Ala Leu
        35                  40                  45

Leu Ala Arg Phe
    50

<210> SEQ ID NO 75
<211> LENGTH: 52
<212> TYPE: PRT
<213> ORGANISM: Equine herpesvirus

<400> SEQUENCE: 75

Leu Arg Thr Pro Asn Ser Ala Val Phe Arg Ala Phe Phe Gly Ser Leu
1               5                   10                  15

Val Tyr Trp Ala Glu Leu Arg Leu Ala Leu Arg Asp Pro Ala Ser Ile
            20                  25                  30

Asn Cys Arg Tyr Val Gly Phe His Leu Gln Thr Ser Glu Ile Tyr Leu
        35                  40                  45

Leu Ala Arg Ala
    50
```

```
<210> SEQ ID NO 76
<211> LENGTH: 52
<212> TYPE: PRT
<213> ORGANISM: Marek's disease virus

<400> SEQUENCE: 76

Met Arg Asp Pro Met Ala Ser Ala Ala Arg Ala Ser Tyr Gly Ser Leu
1               5                   10                  15

Ala Tyr Trp Pro Glu Leu Arg Cys Ala Leu Gly Ser Glu Asn Lys Arg
            20                  25                  30

Ile Val Arg Tyr Ala Ile Val Ala Met Leu Gln Ala Glu Ile Tyr Leu
        35                  40                  45

Leu Thr Arg Ile
    50
```